United States Patent
Zanin-Zhorov et al.

(10) Patent No.: US 11,311,541 B2
(45) Date of Patent: Apr. 26, 2022

(54) TREATMENT OF GVHD

(71) Applicants: KADMON CORPORATION, LLC, New York, NY (US); REGENTS OF THE UNIVERSITY OF MINNESOTA, Minneapolis, MN (US)

(72) Inventors: Alexandra Zanin-Zhorov, Staten Island, NY (US); Bruce Robert Blazar, Golden Valley, MN (US); Ryan Flynn, Minneapolis, MN (US)

(73) Assignees: KADMON CORPORATION, LLC, New York, NY (US); REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 15/303,420

(22) PCT Filed: Apr. 9, 2015

(86) PCT No.: PCT/US2015/025176
§ 371 (c)(1),
(2) Date: Oct. 11, 2016

(87) PCT Pub. No.: WO2015/157556
PCT Pub. Date: Oct. 15, 2015

(65) Prior Publication Data
US 2017/0112832 A1 Apr. 27, 2017

Related U.S. Application Data

(60) Provisional application No. 61/977,564, filed on Apr. 9, 2014.

(51) Int. Cl.
| | |
|---|---|
| *A61K 31/50* | (2006.01) |
| *A61K 31/506* | (2006.01) |
| *C07D 401/12* | (2006.01) |
| *C07D 239/42* | (2006.01) |
| *C07D 491/052* | (2006.01) |
| *C07D 413/14* | (2006.01) |
| *C07D 403/14* | (2006.01) |
| *C07D 498/04* | (2006.01) |
| *C07D 495/04* | (2006.01) |
| *C07D 239/30* | (2006.01) |
| *C07D 403/12* | (2006.01) |
| *C07D 401/14* | (2006.01) |
| *C07D 417/14* | (2006.01) |
| *C07D 491/048* | (2006.01) |
| *C07D 471/04* | (2006.01) |
| *C07D 519/00* | (2006.01) |
| *C07D 513/04* | (2006.01) |
| *C07D 487/04* | (2006.01) |
| *C07D 409/14* | (2006.01) |
| *C07D 239/48* | (2006.01) |
| *C07D 239/47* | (2006.01) |
| *A61K 31/519* | (2006.01) |
| *A61K 31/517* | (2006.01) |
| *A61K 31/53* | (2006.01) |
| *A61K 31/5377* | (2006.01) |
| *A61K 31/541* | (2006.01) |
| *A61K 31/551* | (2006.01) |

(52) U.S. Cl.
CPC .......... *A61K 31/506* (2013.01); *A61K 31/517* (2013.01); *A61K 31/519* (2013.01); *A61K 31/53* (2013.01); *A61K 31/5377* (2013.01); *A61K 31/541* (2013.01); *A61K 31/551* (2013.01); *C07D 239/30* (2013.01); *C07D 239/42* (2013.01); *C07D 239/47* (2013.01); *C07D 239/48* (2013.01); *C07D 401/12* (2013.01); *C07D 401/14* (2013.01); *C07D 403/12* (2013.01); *C07D 403/14* (2013.01); *C07D 409/14* (2013.01); *C07D 413/14* (2013.01); *C07D 417/14* (2013.01); *C07D 471/04* (2013.01); *C07D 487/04* (2013.01); *C07D 491/048* (2013.01); *C07D 491/052* (2013.01); *C07D 495/04* (2013.01); *C07D 498/04* (2013.01); *C07D 513/04* (2013.01); *C07D 519/00* (2013.01)

(58) Field of Classification Search
CPC ... A61K 31/506; A61K 31/517; C07D 401/14
See application file for complete search history.

(56) References Cited

U.S. PATENT DOCUMENTS

| | | | |
|---|---|---|---|
| 2004/0002508 A1 | 1/2004 | Nagarathnam et al. | |
| 2012/0202793 A1 | 8/2012 | Sweetnam et al. | |
| 2012/0283229 A1 | 11/2012 | Glick | |
| 2015/0252025 A1* | 9/2015 | Poyurovsky | A61K 31/506 514/218 |
| 2017/0000884 A1* | 1/2017 | Betts | A61K 45/06 |

OTHER PUBLICATIONS

Goodman & Gilman, The Pharmacological Basis of Therapeutics, (9th ed, 1996) p. 51.*

* cited by examiner

*Primary Examiner* — Shobha Kantamneni
(74) *Attorney, Agent, or Firm* — Fox Rothschild LLP

(57) ABSTRACT

The invention relates to treatment of graft versus host disease (GVHD) using compounds that inhibit ROCK2. In preferred aspects, the present invention provides methods for the treatment of GVHD, including chronic GVHD (cGVHD) using compounds having the formulae 1-XXV, as set forth herein.

2 Claims, 42 Drawing Sheets

A.

B.

B.

C.

A.

B.

B) Weight measures

C) Survival curve

TREATMENT OF GVHD

CROSS-REFERENCE TO RELATED APPLICATIONS

This application claims priority to U.S. Application No. 61/977,564, filed on Apr. 9, 2014, which is incorporated herein by reference in its entirety.

FIELD OF THE INVENTION

The invention relates to treatment of graft versus host disease (GVHD) using compounds that inhibit ROCK2.

BACKGROUND OF THE INVENTION

Rho-associated protein kinase (ROCK) is a key intracellular regulator of cytoskeletal dynamics and cell motility. Rho-kinase regulates a number of downstream targets of RhoA through phosphorylation, including, for example, myosin light chain, the myosin light chain phosphatase binding subunit and LIM-kinase 2. These substrates regulate actin filament organization and contractility. In smooth muscle cells Rho-kinase mediates calcium sensitization and smooth muscle contraction. Inhibition of Rho-kinase blocks 5-HT and phenylephrine agonist induced muscle contraction. When introduced into non-smooth muscle cells, Rho kinase induces stress fiber formation and is required for the cellular transformation mediated by RhoA. Rho kinase participates in a variety of cellular processes, including but not limited to cell adhesion, cell motility and migration, growth control, cell contraction, and cytokinesis. Rho kinase is also involved in Na/H exchange transport system activation, stress fiber formation, adducin activation, and physiological processes such as vasoconstriction, bronchial smooth muscle constriction, vascular smooth muscle and endothelial cell proliferation, platelet aggregation, and others.

Inhibition of Rho-kinase activity in animal models has demonstrated a number of benefits of Rho-kinase inhibition for the treatment of human diseases. These include models of cardiovascular diseases such as hypertension, atherosclerosis, restenosis, cardiac hypertrophy, ocular hypertension, cerebral ischemia, cerebral vasospasm, penile erectile dysfunction, central nervous system disorders such as neuronal degeneration and spinal cord injury, and in neoplasias. Inhibition of Rho-kinase activity has been shown to inhibit tumor cell growth and metastasis, angiogenesis, arterial thrombotic disorders such as platelet aggregation and leukocyte aggregation, asthma, regulation of intraoccular pressure, and bone resorption. The inhibition of Rho-kinase activity in patients has benefits for controlling cerebral vasospasms and ischemia following subarachnoid hemorrhage, reduction of intraocular pressure, increase in ocular aqueous outflow by relaxation of trabecular meshwork tissue, improving blood flow to the optic nerve, and protection of healthy ganglion cells.

In mammals, Rho-kinase consists of two isoforms, ROCK1 (ROCKβ; p160-ROCK) and ROCK2 (ROCKα). ROCK1 and ROCK2 are differentially expressed and regulated in specific tissues. For example, ROCK1 is ubiquitously expressed at relatively high levels, whereas ROCK2 is preferentially expressed in cardiac and brain and skeletal muscle. The isoforms are also expressed in some tissues and in a developmental stage specific manner. ROCK1 is a substrate for cleavage by caspase-3 during apoptosis, whereas ROCK2 is not. Smooth muscle specific basic calponin is phosphorylated only by ROCK2.

Given the extent of involved cellular processes and diseases, compounds that selectively inhibit one rho kinase, or inhibit ROCK1 and ROCK2, are desired.

SUMMARY OF THE INVENTION

The present invention relates to treatment of graft versus host disease (GVHD), including chronic GVHD (cGVHD) using compounds having the formulae I-XXV, as set forth herein. In certain embodiments, the invention provides a compound of formula I:

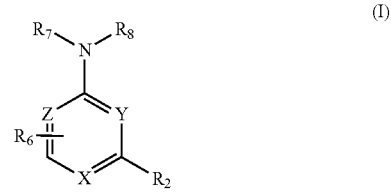

or a pharmaceutically acceptable salt thereof, wherein:
X is selected from N or C—$R_1$;
Y is selected from N or C—$R_5$;
Z is selected from N or C—$R_3$;
$R_1$ is selected from the group consisting of H, lower alkyl, CN, halo, hydroxy, lower alkoxy, amino, perfluoro lower alkyl, and (lower alkyl)-O-(lower alkyl);
$R_2$ is a group having the formula -A-$R_{10}$;
A is selected from the group consisting of a covalent bond, aryl, heteroaryl, cycloalkyl, and heterocyclyl;
$R_{10}$ is selected from the group consisting of H, CN, halo, hydroxy, lower alkoxy, amino, perfluoro lower alkyl, $C_1$-$C_{10}$ alkyl, $C_2$-$C_{10}$ alkenyl, and -(M)$_x$-(CH$_2$)$_y$—$R_{11}$;
M is selected from the group consisting of N—$R_{20}$, C$R_{21}R_{22}$, and C=O;
x is 0 or 1;
$R_{20}$ is selected from H and $C_{1-5}$ alkyl;
$R_{21}$ and $R_{22}$ are independently selected from the group consisting of H, halogen, and lower alkyl, or alternatively $R_{21}$ and $R_{22}$ may be taken together with the atom to which they are attached to form a $C_{3-6}$ cycloalkyl;
y is 0, 1, 2, 3, 4, 5, or 6;
$R_{11}$ is selected from the group consisting of H, $C_{1-6}$ alkyl, optionally substituted $C_{3-6}$ cycloalkyl, optionally substituted aryl, optionally substituted heteroaryl, optionally substituted heterocyclyl, wherein the optional substituents are selected from the group consisting of lower alkyl, $C_{1-6}$ cycloalkyl, oxo, CN, halo, hydroxy, lower alkoxy, amino, perfluoro lower alkyl, and (lower alkyl)-O-(lower alkyl);
alternatively $R_{11}$ is selected from the group consisting of —N$R_{13}R_{14}$, —C(=O)N$R_{13}R_{14}$, and —C(=O)$R_{12}$, and —CO$_2R_{12}$;
$R^{12}$ is selected from the group consisting of $C_1$-$C_{10}$ alkyl, aryl, heteroaryl, —($C_1$-$C_6$ alkyl)-O—($C_1$-$C_6$ alkyl), aralkyl, $C_3$-$C_7$ cycloalkyl, a three to twelve membered heterocyclic ring containing up to 3 heteroatoms, each of which may be optionally substituted by from 1 to 3 substituents independently selected from halo, oxo, $C_1$-$C_6$ alkyl, $C_3$-$C_6$ cycloalkyl, $C_1$-$C_6$ alkoxy, ($C_1$-$C_6$ alkyl)-O—($C_1$-$C_6$ alkyl), hydroxy, cyano and $C_1$-$C_3$ perfluoro alkyl;

$R^{13}$ and $R^{14}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), aryl, aralkyl, heteroaryl, $C_3$-$C_6$ cycloalkyl, a three to twelve membered heterocyclic ring containing up to 3 heteroatoms, each of which may be optionally substituted by from 1 to 3 substituents independently selected from halo, oxo, $C_1$-$C_6$ alkyl, $C_2$-$C_6$ alkenyl, $C_3$-$C_7$ cycloalkyl, $C_1$-$C_6$ alkoxy, ($C_1$-$C_6$ alkyl)-O—($C_1$-$C_6$ alkyl), hydroxy, amino, cyano and $C_1$-$C_3$ perfluoro alkyl;

or $R^{13}$ and $R^{14}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_7$ cycloalkyl, ($C_1$-$C_6$ alkyl)-O—($C_1$-$C_6$ alkyl), oxo, hydroxy, cyano and $C_1$-$C_3$ perfluoro alkyl;

$R_3$ is selected from the group consisting of H, lower alkyl, CN, halo, hydroxy, lower alkoxy, amino, perfluoro lower alkyl, and (lower alkyl)-O-(lower alkyl);

$R_5$ is selected from the group consisting of H, lower alkyl, CN, halo, hydroxy, lower alkoxy, amino, perfluoro lower alkyl, and (lower alkyl)-O-(lower alkyl);

$R_6$ is selected from the group consisting of H, lower alkyl, CN, halo, hydroxy, lower alkoxy, amino, perfluoro lower alkyl, and (lower alkyl)-O-(lower alkyl);

$R_7$ is selected from the group consisting of H and lower alkyl; and $R_8$ is a nitrogen-containing heterocyclic ring system ring which may comprise 0-2 additional ring heteroatoms selected from N, O and S, and may be unsubstituted or may be substituted with 1 to 3 substituents selected from halo, CN, oxo, hydroxy, amino, lower alkyl, perfluoro lower alkyl, and lower alkoxy.

In further embodiments, the present invention relates to treatment of GVHD, such as cGVHD using a compound having the formulae XXVI:

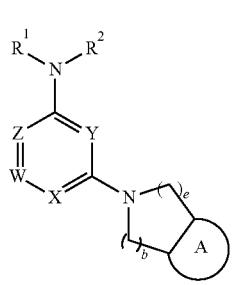

(XXVI)

or pharmaceutically acceptable salt thereof, wherein:

$R^1$ is selected from the group consisting of H or $C_1$-$C_6$ alkyl;

$R^2$ is selected from the group consisting of aryl, heteroaryl, $C_3$-$C_7$ cycloalkyl, a three to twelve membered heterocyclic ring containing up to 3 heteroatoms, each of which may be optionally substituted from 1 to 3 substituents independently selected from halo and $C_1$-$C_6$ alkyl;

X is selected from N or $CR^3$;
Y is selected from N or $CR^3$;
Z is selected from N or $CR^4$;
W is selected from $CR^5$;
wherein X, Y, and Z are independently selected and at least one of which is N;

wherein each $R^3$ is independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —$NR^{31}R^{32}$, and —($C_1$-$C_6$ alkyl)-O—($C_1$-$C_6$ alkyl);

$R^{31}$ and $R^{32}$ are independently selected from the group consisting of H, $C_1$-$C_8$ alkyl, $C_2$-$C_8$ alkenyl, $C_2$-$C_8$ alkynyl, and —($C_1$-$C_6$ alkyl)-O—($C_1$-$C_6$ alkyl);

$R^4$ and $R^5$ are independently selected from the group consisting of H, halo, $C_1$-$C_8$ alkyl, $C_2$-$C_8$ alkenyl, $C_2$-$C_8$ alkynyl, $C_1$-$C_6$ alkoxy, —($C_1$-$C_6$ alkyl)-O—($C_1$-$C_6$ alkyl), —$NR^{41}R^{42}$, —$(CH_2)_xNR^{41}R^{42}$ and —O—($C_1$-$C_6$ alkyl)-O—($C_1$-$C_6$ alkyl;

$R^{41}$ and $R^{42}$ are independently selected from the group consisting of H, $C_1$-$C_8$ alkyl, $C_2$-$C_8$ alkenyl, $C_2$-$C_8$ alkynyl, and —($C_1$-$C_6$ alkyl)-O—($C_1$-$C_6$ alkyl);

or $R^{41}$ and $R^{42}$ may be taken together to form a three to twelve membered cycloalkyl or heterocyclic ring having up to 3 heteroatoms which is optionally substituted from 1 to 3 substituents independently selected from halo, $C_1$-$C_6$ alkyl, and $C_1$-$C_6$ alkoxy;

x is selected from 0 to 6;

or $R^4$ and $R^5$ may be taken together to form a three to twelve membered heterocyclic or aromatic ring having up to 3 heteroatoms which is optionally substituted from 1 to 3 substituents independently selected from halo and $C_1$-$C_6$ alkyl and $C_1$-$C_6$ alkoxy;

a is selected from 0 to 2;
b is selected from 0 to 2;
wherein a or b are independently selected and one of which is at least 1

A is a three to twelve membered heterocyclic or aromatic ring having up to 3 heteroatoms which is optionally substituted from 1 to 3 substituents independently selected from halo, $C_1$-$C_6$ alkyl, $C_2$-$C_6$ alkenyl, $C_1$-$C_6$ alkoxy, $C_3$-$C_7$ cycloalkyl, oxo, acyl, —S—($C_1$-$C_6$ alkyl), OH, $NH_2$, CN and $C_1$-$C_3$ perfluroalkyl.

In other embodiments, the present invention relates to treatment of GVHD, such as cGVHD using a compound having the formula XXXI:

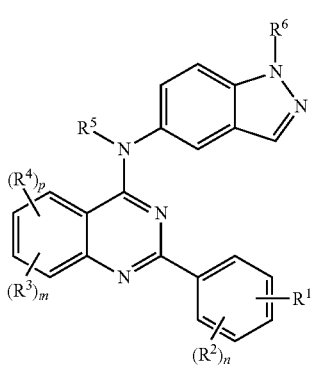

(XXXI)

or pharmaceutically acceptable salt, wherein:

$R^1$ is selected from the group consisting of —O—$(CH_2)_y$—$CO_2R^{12}$, —O—$(CH_2)_y$—C(=O)$NR^{13}R^{14}$, —O—$(CH_2)_y$-heteroaryl, —O—$(CH_2)_y$-cycloalkyl, —O—C(=O)—$(CH_2)_y$—$NR^{13}R^{14}$, —O—$(CH_2)_z$—$NR^{13}R^{14}$, —NH—C(=O)—$(CH_2)_y$—$NR^{13}R^{14}$, —NH—C(=O)—X—$R^{15}$, —NH—$(CH_2)_y$—$NR^{13}R^{14}$;

$R^{12}$ is selected from the group consisting of $C_1$-$C_6$ alkyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, —($C_1$-$C_6$ alkyl)-O—($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted at one or more carbon atoms by from 1 to 3 substituents independently selected from halo, $C_1$-$C_6$ alkoxy, hydroxy, amino, cyano and $C_1$-$C_3$ perfluoro alkyl;

$R^{13}$ and $R^{14}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;

or $R^{13}$ and $R^{14}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_7$ cycloalkyl, oxo, OH, $NH_2$, CN and $C_1$-$C_3$ perfluoro alkyl;

X is selected from a covalent bond, O, NH, and $C_1$-$C_6$ alkyl;

$R^{15}$ is selected from the group consisting of heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, OH, $NH_2$, CN and $C_1$-$C_3$ perfluoro alkyl;

or $R^{15}$ is selected from —($C_1$-$C_6$ alkyl)-O—($C_1$-$C_6$ alkyl), —($C_1$-$C_6$ alkyl)-$NR^{16}R^{17}$, —$CO_2R^{18}$, —O—$(CH_2)_x$—$CO_2R^{18}$, and —C(=O)$NR^{16}R^{17}$;

$R^{16}$ and $R^{17}$ independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, OH, $NH_2$, CN and $C_1$-$C_3$ perfluoro alkyl;

or $R^{16}$ and $R^{17}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

$R^{18}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

x is selected from 0 to 6;
y is selected from 0 to 6;
z is selected from 2 to 6;

each $R^2$ is independently selected from the group consisting of lower alkyl, CN, halo, hydroxy, lower alkoxy, amino, and perfluoro lower alkyl;

each $R^3$ is independently selected from the group consisting of lower alkyl, CN, halo, hydroxy, lower alkoxy, amino, and perfluoro lower alkyl;

$R^4$ is selected from —$(CH_2)_a$—$NR^{43}R^{44}$, —Y—$R^{42}$, —O—$(CH_2)_a$—$CO_2R^{42}$, —O—$(CH_2)_a$—C(=O)$NR^{43}R^{44}$, —O—$(CH_2)_a$-heteroaryl, —O—$(CH_2)_a$-cycloalkyl, —O—C(=O)—$(CH_2)_a$—$NR^{43}R^{44}$, —O—$(CH_2)_c$—$NR^{43}R^{44}$, —NH—C(=O)—$(CH_2)_a$—$NR^{43}R^{44}$, —NH—C(=O)—Y—$R^{45}$, —NH—C(=O)—$(CH_2)_a$—$NR^{43}R^{44}$;

$R^{42}$ is selected from the group consisting of $C_1$-$C_6$ alkyl, —($C_1$-$C_6$ alkyl)-O—($C_1$-$C_6$ alkyl), —($C_1$-$C_6$ alkyl)-$NR^{46}R^{47}$, —($C_1$-$C_6$ alkyl)-C(=O)$NR^{46}R^{47}$, —($C_1$-$C_6$ alkyl)-O—($C_1$-$C_6$ alkyl)-O—($C_1$-$C_6$ alkyl), each of which may be optionally substituted at one or more carbon atoms by from 1 to 3 substituents independently selected from halo, $C_1$-$C_6$ alkoxy, hydroxy, amino, cyano and $C_1$-$C_3$ perfluoro alkyl;

$R^{43}$ and $R^{44}$ are independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), —($C_1$-$C_6$ alkyl)-$NR^{46}R^{47}$, —($C_1$-$C_6$ alkyl)-C(=O)$NR^{46}R^{47}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;

or $R^{43}$ and $R^{44}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

Y is selected from a covalent bond, O, NH, and $C_1$-$C_6$ alkyl;

$R^{45}$ is selected from the group consisting of H, aryl, —($C_1$-$C_6$ alkyl)-O—($C_1$-$C_6$ alkyl), —($C_1$-$C_6$ alkyl)-$NR^{46}R^{47}$, —$CO_2R^{48}$, —O—$(CH_2)_b$—$CO_2R^{48}$, and —C(=O)$NR^{46}R^{47}$, $R^{46}$ and $R^{47}$ independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;

or $R^{46}$ and $R^{47}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

$R^{48}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-$NR^{46}R^{47}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

a is selected from 0 to 6;
b is selected from 0 to 6;
c is selected from 2 to 6;

$R^5$ is selected from the group consisting of H, $C_1$-$C_6$ alkyl, —$(CH_2)_d$—C(=O)—$NR^{53}R^{54}$, —C(=O)—$(CH_2)_d$—$NR^{53}R^{54}$, —C(=O)—X—$R^{55}$, and —C(=O)—$(CH_2)_d$—$NR^{53}R^{54}$;

$R^{53}$ and $R^{54}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-$NR^{56}R^{57}$, —($C_1$-$C_6$ alkyl)-C(=O)$NR^{56}R^{57}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;

or $R^{53}$ and $R^{54}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_7$ cycloalkyl, oxo, hydroxy, amino, cyano and $C_1$-$C_3$ perfluoro alkyl;

$R^{55}$ is selected from the group consisting of H, aryl, —($C_1$-$C_6$ alkyl)-O—($C_1$-$C_6$ alkyl), —($C_1$-$C_6$ alkyl)-$NR^{56}R^{57}$, —$CO_2R^{58}$, —O—$(CH_2)_e$—$CO_2R^{58}$, and —C(=O)$NR^{56}R^{57}$, $R^{56}$ and $R^{57}$ independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;

or $R^{56}$ and $R^{57}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

$R^{58}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-$NR^{56}R^{57}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

d is selected from 0 to 6;

e is selected from 0 to 6;

$R^6$ is selected from the group consisting of H, $C_1$-$C_6$ alkyl, —$(CH_2)_r$—C(=O)—$NR^{63}R^{64}$, —C(=O)—$(CH_2)_r$—$NR^{63}R^{64}$, —C(=O)—X—$R^{65}$, and —C(=O)—$(CH_2)_r$—$NR^{63}R^{64}$;

$R^{63}$ and $R^{64}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-$NR^{66}R^{67}$, —($C_1$-$C_6$ alkyl)-C(=O)$NR^{66}R^{67}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;

or $R^{63}$ and $R^{64}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_7$ cycloalkyl, oxo, hydroxy, amino, cyano and $C_1$-$C_3$ perfluoro alkyl;

$R^{65}$ is selected from the group consisting of H, aryl, —($C_1$-$C_6$ alkyl)-O—($C_1$-$C_6$ alkyl), —($C_1$-$C_6$ alkyl)-$NR^{66}R^{67}$, —$CO_2R^{68}$, —O—$(CH_2)_s$—$CO_2R^{68}$, and —C(=O)$NR^{66}R^{67}$, $R^{66}$ and $R^{67}$ independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;

or $R^{66}$ and $R^{67}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

$R^{68}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-$NR^{66}R^{67}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

r is selected from 0 to 6;
s is selected from 0 to 6;
n is selected from 0 to 4;
m is selected from 0 to 3; and
p is selected from 0 and 1.

DETAILED DESCRIPTION

Figure 1:
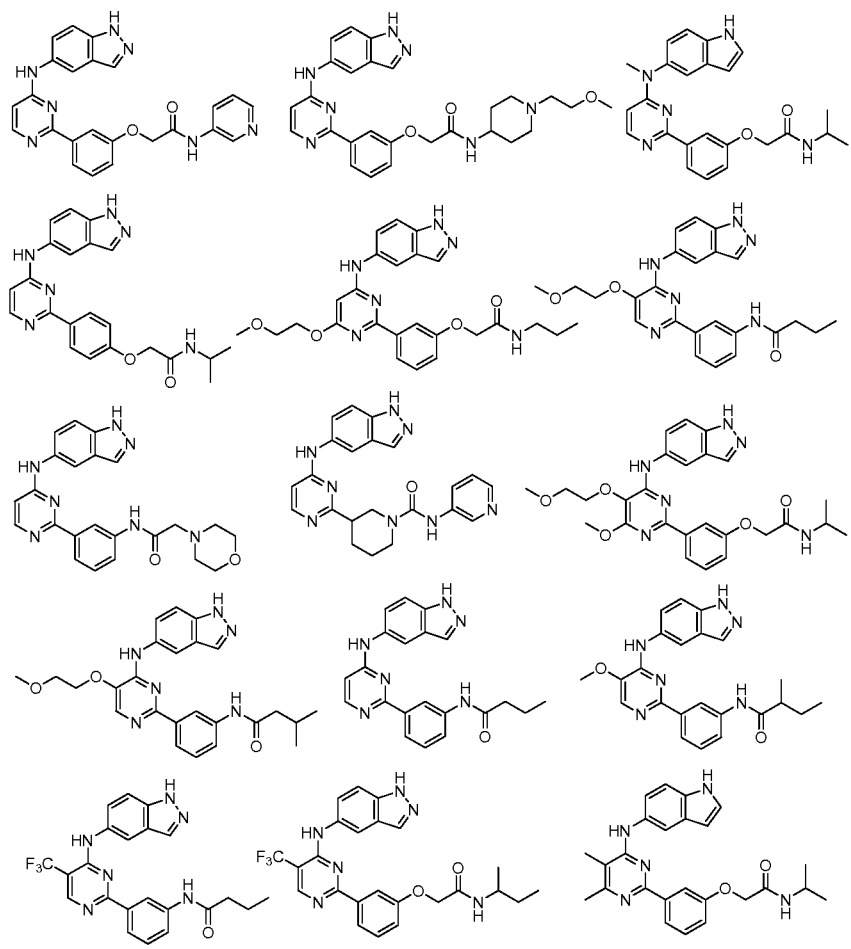
FIG. 1 shows compounds of the invention.

The present invention relates to compounds having the formula I:

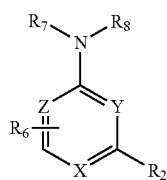
(I)

wherein:
- X is selected from N or C—R$_1$;
- Y is selected from N or C—R$_5$;
- Z is selected from N or C—R$_3$;
- R$_1$ is selected from the group consisting of H, lower alkyl, CN, halo, hydroxy, lower alkoxy, amino, perfluoro lower alkyl, and (lower alkyl)-O-(lower alkyl);
- R$_2$ is a group having the formula -A-R$_{10}$;
- A is selected from the group consisting of a covalent bond, aryl, heteroaryl, cycloalkyl, and heterocyclyl;
- R$_{10}$ is selected from the group consisting of H, CN, halo, hydroxy, lower alkoxy, amino, perfluoro lower alkyl, C$_1$-C$_{10}$ alkyl, C$_2$-C$_{10}$ alkenyl, and -(M)$_x$-(CH$_2$)$_y$—R$_{11}$
- M is selected from the group consisting of N—R$_{20}$, CR$_{21}$R$_{22}$, and C=O;
- x is 0 or 1;
- R$_{20}$ is selected from H and C$_{1-5}$ alkyl;
- R$_{21}$ and R$_{22}$ are independently selected from the group consisting of H, halogen, and lower alkyl, or alternatively R$_{21}$ and R$_{22}$ may be taken together with the atom to which they are attached to form a C$_{3-6}$ cycloalkyl;
- y is 0, 1, 2, 3, 4, 5, or 6;
- R$_{11}$ is selected from the group consisting of H, C$_{1-6}$ alkyl, optionally substituted C$_{3-6}$ cycloalkyl, optionally substituted aryl, optionally substituted heteroaryl, optionally substituted heterocyclyl, wherein the optional substituents are selected from the group consisting of lower alkyl, C$_{1-6}$ cycloalkyl, oxo, CN, halo, hydroxy, lower alkoxy, amino, perfluoro lower alkyl, and (lower alkyl)-O-(lower alkyl);
- alternatively R$_{11}$ is selected from the group consisting of —NR$_{13}$R$_{14}$, —C(=O)NR$_{13}$R$_{14}$, and —C(=O)R$_{12}$, and —CO$_2$R$_{12}$;
- R$^{12}$ is selected from the group consisting of C$_1$-C$_{10}$ alkyl, aryl, heteroaryl, —(C$_1$-C$_6$ alkyl)-O—(C$_1$-C$_6$ alkyl), aralkyl, C$_3$-C$_7$ cycloalkyl, a three to twelve membered heterocyclic ring containing up to 3 heteroatoms, each of which may be optionally substituted by from 1 to 3 substituents independently selected from halo, oxo, C$_1$-C$_6$ alkyl, C$_3$-C$_6$ cycloalkyl, C$_1$-C$_6$ alkoxy, (C$_1$-C$_6$ alkyl)-O—(C$_1$-C$_6$ alkyl), hydroxy, cyano and C$_1$-C$_3$ perfluoro alkyl;
- R$^{13}$ and R$^{14}$ are independently selected from the group consisting of H, C$_1$-C$_8$ alkyl, C$_2$-C$_8$ alkenyl, C$_2$-C$_8$ alkynyl, —(C$_1$-C$_6$ alkyl)-O—(C$_1$-C$_6$ alkyl), aryl, aralkyl, heteroaryl, C$_3$-C$_6$ cycloalkyl, a three to twelve membered heterocyclic ring containing up to 3 heteroatoms, each of which may be optionally substituted by from 1 to 3 substituents independently selected from halo, oxo, C$_1$-C$_6$ alkyl, C$_2$-C$_6$ alkenyl, C$_3$-C$_7$ cycloalkyl, C$_1$-C$_6$ alkoxy, (C$_1$-C$_6$ alkyl)-O—(C$_1$-C$_6$ alkyl), hydroxy, amino, cyano and C$_1$-C$_3$ perfluoro alkyl;
- or R$^{13}$ and R$^{14}$ may be taken together form a three to twelve membered heterocyclic ring having up to 3 heteroatoms which is optionally substituted by from 1 to 3 substituents independently selected from halo, C$_1$-C$_6$ alkyl, C$_2$-C$_6$ alkenyl, C$_1$-C$_6$ alkoxy, C$_3$-C$_7$ cycloalkyl, (C$_1$-C$_6$ alkyl)-O—(C$_1$-C$_6$ alkyl), oxo, hydroxy, cyano and C$_1$-C$_3$ perfluoroalkyl;
- R$_3$ is selected from the group consisting of H, lower alkyl, CN, halo, hydroxy, lower alkoxy, amino, perfluoro lower alkyl, and (lower alkyl)-O-(lower alkyl);
- R$_5$ is selected from the group consisting of H, lower alkyl, CN, halo, hydroxy, lower alkoxy, amino, perfluoro lower alkyl, and (lower alkyl)-O-(lower alkyl);
- R$_6$ is selected from the group consisting of H, lower alkyl, CN, halo, hydroxy, lower alkoxy, amino, perfluoro lower alkyl, and (lower alkyl)-O-(lower alkyl);
- R$_7$ is selected from the group consisting of H and lower alkyl; and
- R$_8$ is a nitrogen-containing heterocyclic ring system ring which may comprise 0-2 additional ring heteroatoms selected from N, O and S, and may be unsubstituted or may be substituted with 1 to 3 substituents selected from halo, CN, oxo, hydroxy, amino, lower alkyl, perfluoro lower alkyl, and lower alkoxy.

In certain embodiments of the invention, the ring system of R$_8$ is saturated, contains one or more double bonds, or is aromatic. The ring system than comprises R$_8$ is preferably a monocyclic or a bicyclic ring system having 4 to 10 ring atoms. In certain aspects of the invention, R$_8$ is selected from:

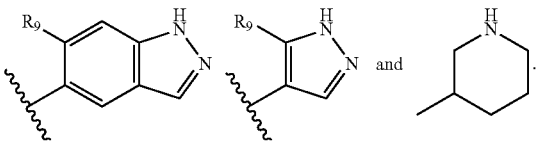

wherein R$_9$ is selected from H, halogen and lower alkyl.

In certain embodiments, R$_2$ is a substituted aryl group and is preferably a substituted phenyl group.

In certain aspects of the invention, the compounds useful according to the present invention include those having the formula II, III or IV:

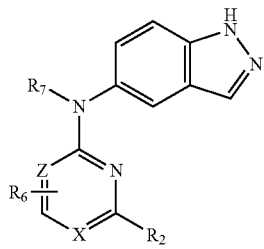
(II)

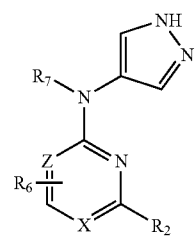
(III)

-continued

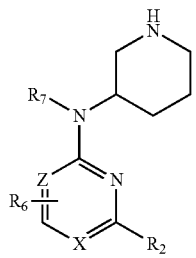
(IV)

wherein $R_2$, $R_6$, $R_7$, X and Z are as defined above for formula I.

In other aspects of the invention, the compounds useful according to the present invention include those having the formula V or VI:

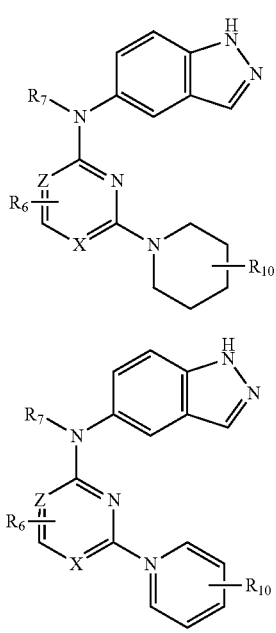
(V)

(VI)

wherein $R_6$, $R_7$, X, Z and $R_{10}$ are as defined above for formula I.

In other aspects of the invention, the compounds useful according to the present invention include those having the formula VII:

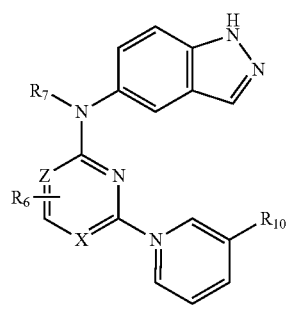
(VII)

wherein $R_6$, $R_7$, X, Z, and $R_{10}$ are as defined above for formula I.

In other aspects of the invention, the compounds useful according to the present invention include those having the formula IX:

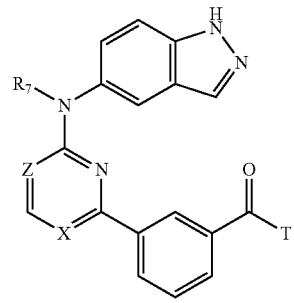
(IX)

wherein $R_6$, $R_7$, X and Z are as defined above for formula I, and T is $-(CH_2)_y-R_{11}$ wherein y and $R_{11}$ are as defined above for formula I.

In other aspects of the invention, the compounds useful according to the present invention include those having the formula X:

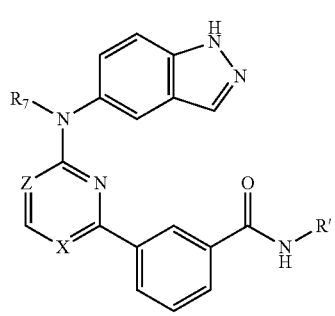
(X)

wherein $R_6$, $R_7$, X and Z are as defined above for formula I, and R' is $R_{13}$ as defined above for formula I.

In other aspects of the invention, the compounds useful according to the present invention include those having the formula XI:

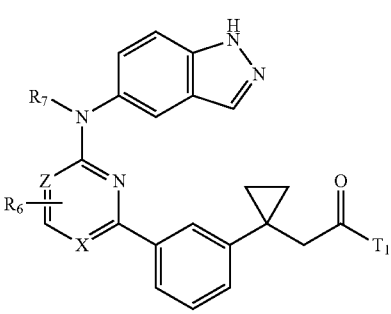
(XI)

wherein $R_6$, $R_7$, X and Z are as defined above for formula I, and $T_1$ is $R_{12}$ as defined above for formula I.

In other aspects of the invention, the compounds useful according to the present invention include those having the formula XII:

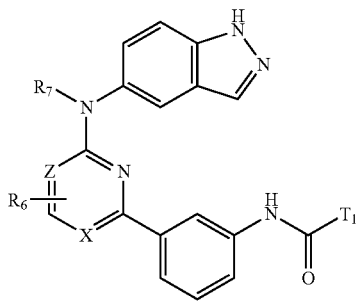

(XII)

wherein $R_6$, $R_7$, X and Z are as defined above for formula I, and $T_1$ is $R_{12}$ as defined above for formula I.

In other aspects of the invention, the compounds useful according to the present invention include those having the formula XIII:

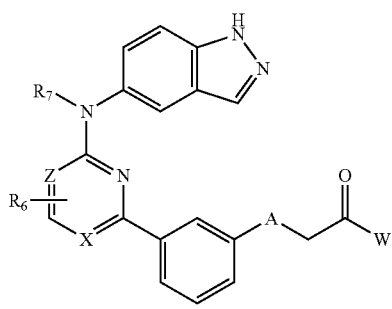

(XIII)

wherein $R_6$, $R_7$, X and Z are as defined above for formula I, A is M as defined above for formula 1 and W is $R_{12}$ as defined above for formula I.

In other aspects of the invention, the compounds useful according to the present invention include those having the formula XIV:

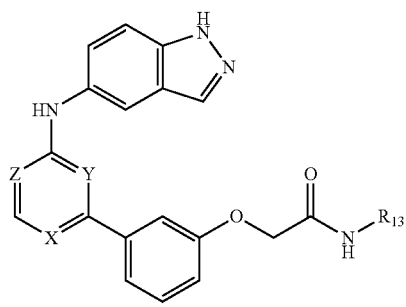

(XIV)

wherein X, Z and $R^{13}$ are as defined above for formula I.

In certain aspects of the invention, for each of the compounds depicted above, the moiety

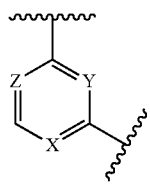

may be selected from a heteroaromatic group such that Y is N. In other aspects of the invention, both Y and X are N, and in still other aspects X, Y and Z are each N. In preferred aspects of the invention, this heteroaromatic group is selected from any one of the following groups:

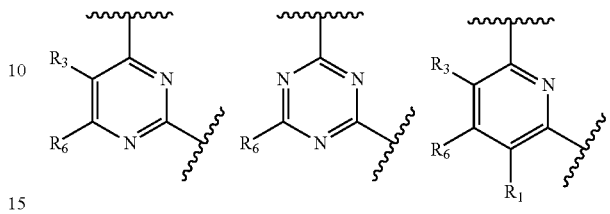

In other aspects of the invention, the compounds useful according to the present invention include those having the formula XV:

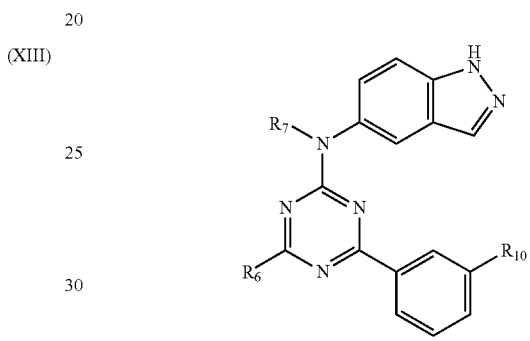

wherein $R_6$, $R_7$, and $R_{10}$ are as defined above for formula I.

In other aspects of the invention, the compounds useful according to the present invention include those having the formula XVI:

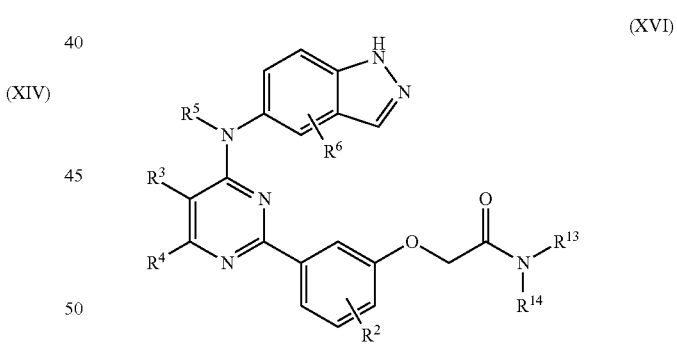

(XVI)

or pharmaceutically acceptable salt or stereoisomer thereof, wherein:

$R^{13}$ and $R^{14}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), heteroaryl, $C_3$-$C_7$ cycloalkyl, a three to twelve membered heterocyclic or aromatic ring containing up to 3 heteroatoms, each of which may be optionally substituted by from 1 to 3 substituents independently selected from halo, oxo, $C_1$-$C_6$ alkyl, $C_2$-$C_6$ alkenyl, $C_3$-$C_7$ cycloalkyl, $C_1$-$C_6$ alkoxy, CN and $C_1$-$C_3$ perfluoro alkyl;

or $R^{13}$ and $R^{14}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_7$ cycloalkyl, oxo, —OH, —$NH_2$, CN and $C_1$-$C_3$ perfluoro alkyl;

$R^2$ is selected from H and halo;

each $R^3$ and $R^4$ is independently selected from the group consisting of H, $C_1$-$C_8$ alkyl, —CN, halo, —OH, —O—($C_1$-$C_6$ alkyl), —O—($C_1$-$C_6$ alkyl)-O—($C_1$-$C_6$ alkyl), —$NR^{31}R^{32}$, $C_1$-$C_3$ perfluoro alkyl, —O—$(CH_2)_a NR^{31}R^{32}$, —$NR^{31}$—$(CH_2)_a NR^{33}R^{34}$, —$NR^{31}$—$(CH_2)_a OR^{33}$, aryl, $C_3$-$C_7$ cycloalkyl, a three to twelve membered heterocyclic ring having up to 3 heteroatoms which is optionally substituted from 1 to 3 substituents independently selected from halo, $C_1$-$C_6$ alkyl, and —($C_1$-$C_6$ alkyl)-O—($C_1$-$C_6$ alkyl);

$R^{31}$ and $R^{32}$ are independently selected from the group consisting of H, $C_1$-$C_8$ alkyl, $C_2$-$C_8$ alkenyl, $C_2$-$C_8$ alkynyl, and —($C_1$-$C_6$ alkyl)-O—($C_1$-$C_6$ alkyl);

or $R^{31}$ and $R^{32}$ may be taken together to form a three to twelve membered heterocyclic ring having up to 3 heteroatoms which is optionally substituted from 1 to 3 substituents independently selected from halo and $C_1$-$C_6$ alkyl;

$R^{33}$ and $R^{34}$ are independently selected from the group consisting of H and $C_1$-$C_8$ alkyl;

a is selected from 0 to 6;

$R^5$ is selected from H and $C_1$-$C_6$ alkyl;

$R^6$ is selected from the group consisting of H, halo, and $C_1$-$C_6$ alkyl.

In an embodiment of the invention $R^{13}$ is selected from the group consisting of $C_1$-$C_8$ alkyl, $C_3$-$C_7$ cycloalkyl and a three to twelve-membered heterocyclic ring. In an another embodiment of the invention $R^{13}$ is selected from the group consisting of isopropyl, cycloalkyl, N-morpholino and 3-pyridine. In an embodiment of the invention $R^{14}$ is H. In an embodiment of the invention $R^2$ is H. In another embodiment of the invention $R^2$ is F. In an embodiment of the invention $R^3$ is selected from the group consisting of H, $C_1$-$C_8$ alkyl and $C_1$-$C_3$ perfluoro alkyl. In an another embodiment of the invention $R^3$ is selected from the group consisting of H, $CH_3$ and $CF_3$. In an embodiment of the invention $R^4$ is selected from the group consisting of H, $C_1$-$C_8$ alkyl, $C_1$-$C_3$ perfluoro alkyl and a three to twelve-membered heterocyclic ring. In an another embodiment of the invention $R^4$ is selected from the group consisting of H, $CH_3$, $CF_3$, piperazinyl and N-morpholino.

In aspects of the invention, the compounds useful according to the present invention include those having the formula XVII:

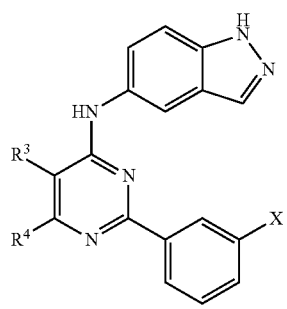

(XVII)

or pharmaceutically acceptable salt or stereoisomer thereof, wherein:

X is selected from the group consisting of —NH—C(=O)—$CHR^{13}R^{14}$; —NH—C(=O)—$(CH_2)_b$—$NR^{13}R^{14}$; —C(=O)—$NR^{13}R^{14}$;

$R^{13}$ and $R^{14}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), aryl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, oxo, $C_1$-$C_6$ alkyl, $C_2$-$C_6$ alkenyl, $C_3$-$C_7$ cycloalkyl, $C_1$-$C_6$ alkoxy, CN and $C_1$-$C_3$ perfluoro alkyl;

each $R^3$ and $R^4$ is independently selected from the group consisting of H, $C_1$-$C_8$ alkyl, —CN, halo, —OH, —O—($C_1$-$C_6$ alkyl), —O—($C_1$-$C_6$ alkyl)-O—($C_1$-$C_6$ alkyl), —$NR^{31}R^{32}$, $C_1$-$C_3$ perfluoro alkyl, —O—$(CH_2)_a NR^{31}R^{32}$, aryl, $C_3$-$C_7$ cycloalkyl, a three to twelve membered heterocyclic ring having up to 3 heteroatoms which is optionally substituted from 1 to 3 substituents independently selected from halo and $C_1$-$C_6$ alkyl;

$R^{31}$ and $R^{32}$ are independently selected from the group consisting of H, $C_1$-$C_8$ alkyl, $C_2$-$C_8$ alkenyl, $C_2$-$C_8$ alkynyl, and —($C_1$-$C_6$ alkyl)-O—($C_1$-$C_6$ alkyl);

a is selected from 0 to 6;

b is selected from 0 to 1.

In an embodiment of the invention $R^{13}$ is a three to twelve-membered heterocyclic ring. In an another embodiment of the invention $R^{13}$ is selected from the group consisting of isopropyl, cycloalkyl, N-morpholino, 3-pyridinyl, tetrahydropyranyl, piperdinyl, and tetrahydrothiopyranyl dioxide. In an another embodiment of the invention $R^{13}$ is selected from the group consisting of:

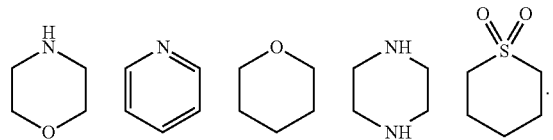

In an embodiment of the invention $R^{14}$ is H. In an embodiment of the invention $R^3$ and $R^4$ are each H.

In another aspect of the invention, the compounds useful according to the present invention include those having the formula XVIII:

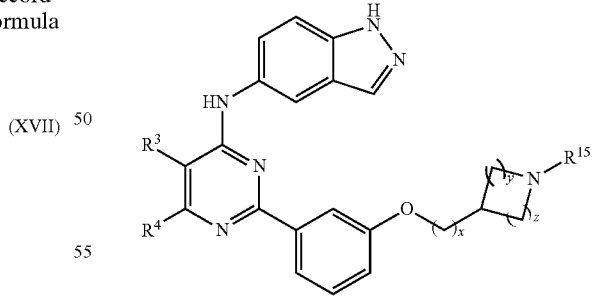

(XVIII)

or pharmaceutically acceptable salt or stereoisomer thereof, wherein:

each $R^3$ and $R^4$ is independently selected from the group consisting of H, $C_1$-$C_8$ alkyl, —CN, halo, —OH, —O—($C_1$-$C_6$ alkyl), —O—($C_1$-$C_6$ alkyl)-O—($C_1$-$C_6$ alkyl), —$NR^{31}R^{32}$, $CF_3$, —O—$(CH_2)_a NR^{31}R^{32}$, aryl, $C_3$-$C_7$ cycloalkyl, a three to twelve membered heterocyclic ring having up to 3 heteroatoms which is optionally substituted from 1 to 3 substituents independently selected from halo and $C_1$-$C_6$ alkyl;

R$^{31}$ and R$^{32}$ are independently selected from the group consisting of H, C$_1$-C$_8$ alkyl, C$_2$-C$_8$ alkenyl, C$_2$-C$_8$ alkynyl, and —(C$_1$-C$_6$ alkyl)-O—(C$_1$-C$_6$ alkyl);

a is selected from 0 to 6;

R$^{15}$ is selected from the group consisting of H, C$_1$-C$_8$ alkyl, —CN, halo, —OH, —O—(C$_1$-C$_6$ alkyl), —O—(C$_1$-C$_6$ alkyl)-O—(C$_1$-C$_6$ alkyl), —C(=O)—O—C(R)$_3^{31}$, CF$_3$, C$_3$-C$_7$ cycloalkyl, a three to twelve membered heterocyclic or aromatic ring having up to 3 heteroatoms which is optionally substituted from 1 to 3 substituents independently selected from halo and C$_1$-C$_6$ alkyl;

x is selected from 1 to 3;
y is selected from 0 to 3;
z is selected from 0 to 3;
wherein y or z are independently selected and one of which is at least 1.

In aspects of the invention, the compounds useful according to the present invention include those having the formula XIX:

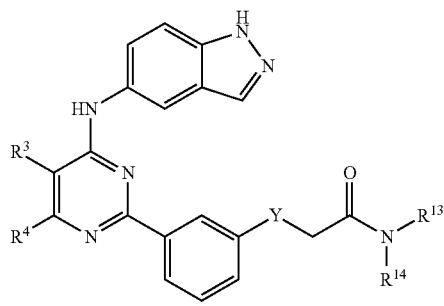

(XIX)

or pharmaceutically acceptable salt or stereoisomer thereof, wherein:

R$^{13}$ and R$^{14}$ are independently selected from the group consisting of H, C$_1$-C$_8$ alkyl, C$_2$-C$_8$ alkenyl, C$_2$-C$_8$ alkynyl, —(C$_1$-C$_6$ alkyl)-O—(C$_1$-C$_6$ alkyl), heteroaryl, C$_3$-C$_7$ cycloalkyl, a three to twelve membered heterocyclic or aromatic ring containing up to 3 heteroatoms, each of which may be optionally substituted by from 1 to 3 substituents independently selected from halo, oxo, C$_1$-C$_6$ alkyl, C$_2$-C$_6$ alkenyl, C$_3$-C$_7$ cycloalkyl, C$_1$-C$_6$ alkoxy, CN and C$_1$-C$_3$ perfluoro alkyl;

or R$^{13}$ and R$^{14}$ may be taken together form a three to twelve membered heterocyclic ring having up to 3 heteroatoms which is optionally substituted by from 1 to 3 substituents independently selected from halo, C$_1$-C$_6$ alkyl, C$_2$-C$_6$ alkenyl, C$_1$-C$_6$ alkoxy, C$_3$-C$_7$ cycloalkyl, oxo, —OH, —NH$_2$, CN and C$_1$-C$_3$ perfluoro alkyl;

Y is selected from the group consisting of S, CH$_2$, and —CR$^{31}$R$^{32}$—

R$^2$ is selected from H and halo;

each R$^3$ and R$^4$ is independently selected from the group consisting of H, C$_1$-C$_8$ alkyl, —CN, halo, —OH, —O—(C$_1$-C$_6$ alkyl), —O—(C$_1$-C$_6$ alkyl)-O—(C$_1$-C$_6$ alkyl), —NR$^{31}$R$^{32}$, C$_1$-C$_3$ perfluoro alkyl, —O—(CH$_2$)$_a$NR$^{31}$R$^{32}$, —NR$^{31}$—(CH$_2$)$_a$NR$^{33}$R$^{34}$, —NR$^{31}$—(CH$_2$)$_a$OR$^{33}$, aryl, C$_3$-C$_7$ cycloalkyl, a three to twelve membered heterocyclic ring having up to 3 heteroatoms which is optionally substituted from 1 to 3 substituents independently selected from halo, C$_1$-C$_6$ alkyl, and —(C$_1$-C$_6$ alkyl)-O—(C$_1$-C$_6$ alkyl);

R$^{31}$ and R$^{32}$ are independently selected from the group consisting of H, halo, C$_1$-C$_8$ alkyl, C$_2$-C$_8$ alkenyl, C$_2$-C$_8$ alkynyl, and —(C$_1$-C$_6$ alkyl)-O—(C$_1$-C$_6$ alkyl);

or R$^{31}$ and R$^{32}$ may be taken together to form a three to twelve membered cycloalkyl or heterocyclic ring having up to 3 heteroatoms which is optionally substituted from 1 to 3 substituents independently selected from halo and C$_1$-C$_6$ alkyl;

R$^{33}$ and R$^{34}$ are independently selected from the group consisting of H and C$_1$-C$_8$ alkyl;

a is selected from 0 to 6.

In an embodiment of the invention Y forms a three-membered cycloalkane. In an another embodiment of the invention Y is fluoro;

In another aspect of the invention, the compounds useful according to the present invention include those having the formula XX:

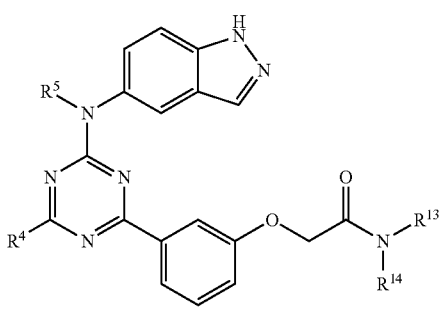

(XX)

or pharmaceutically acceptable salt or stereoisomer thereof, wherein:

R$^{13}$ and R$^{14}$ are independently selected from the group consisting of H, C$_1$-C$_8$ alkyl, C$_2$-C$_8$ alkenyl, C$_2$-C$_8$ alkynyl, —(C$_1$-C$_6$ alkyl)-O—(C$_1$-C$_6$ alkyl), heteroaryl, C$_3$-C$_7$ cycloalkyl, a three to twelve membered heterocyclic or aromatic ring containing up to 3 heteroatoms, each of which may be optionally substituted by from 1 to 3 substituents independently selected from halo, oxo, C$_1$-C$_6$ alkyl, C$_2$-C$_6$ alkenyl, C$_3$-C$_7$ cycloalkyl, C$_1$-C$_6$ alkoxy, CN and C$_1$-C$_3$ perfluoro alkyl;

or R$^{13}$ and R$^{14}$ may be taken together form a three to twelve membered heterocyclic ring having up to 3 heteroatoms which is optionally substituted by from 1 to 3 substituents independently selected from halo, C$_1$-C$_6$ alkyl, C$_2$-C$_6$ alkenyl, C$_1$-C$_6$ alkoxy, C$_3$-C$_7$ cycloalkyl, oxo, —OH, —NH$_2$, CN and C$_1$-C$_3$ perfluoro alkyl;

R$^4$ is selected from the group consisting of H, C$_1$-C$_8$ alkyl, —CN, halo, —OH, —O—(C$_1$-C$_6$ alkyl), —O—(C$_1$-C$_6$ alkyl)-O—(C$_1$-C$_6$ alkyl), —NR$^{31}$R$^{32}$, CF$_3$, —O—(CH$_2$)$_a$NR$^{31}$R$^{32}$, aryl, C$_3$-C$_7$ cycloalkyl, a three to twelve membered heterocyclic ring having up to 3 heteroatoms which is optionally substituted from 1 to 3 substituents independently selected from halo and C$_1$-C$_6$ alkyl;

R$^{31}$ and R$^{32}$ are independently selected from the group consisting of H, C$_1$-C$_8$ alkyl, C$_2$-C$_8$ alkenyl, C$_2$-C$_8$ alkynyl, and —(C$_1$-C$_6$ alkyl)-O—(C$_1$-C$_6$ alkyl);

or R$^{31}$ and R$^{32}$ may be taken together to form a three to twelve membered heterocyclic ring having up to 3 heteroatoms which is optionally substituted from 1 to 3 substituents independently selected from halo and C$_1$-C$_6$ alkyl;

R$^5$ is selected from H and C$_1$-C$_6$ alkyl.

In another aspect of the invention, the compounds useful according to the present invention include those having the formula XXI:

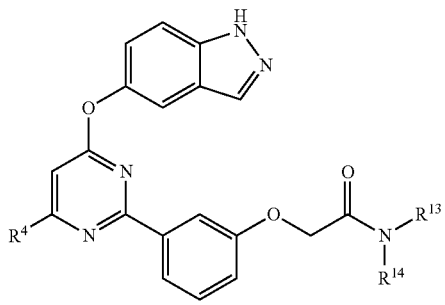

(XXI)

or pharmaceutically acceptable salt or stereoisomer thereof, wherein:
$R^{13}$ and $R^{14}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), heteroaryl, $C_3$-$C_7$ cycloalkyl, a three to twelve membered heterocyclic or aromatic ring containing up to 3 heteroatoms, each of which may be optionally substituted by from 1 to 3 substituents independently selected from halo, oxo, $C_1$-$C_6$ alkyl, $C_2$-$C_6$ alkenyl, $C_3$-$C_7$ cycloalkyl, $C_1$-$C_6$ alkoxy, CN and $C_1$-$C_3$ perfluoro alkyl;

or $R^{13}$ and $R^{14}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_7$ cycloalkyl, oxo, —OH, —$NH_2$, CN and $C_1$-$C_3$ perfluoro alkyl;

$R^4$ is selected from the group consisting of H, $C_1$-$C_8$ alkyl, —CN, halo, —OH, —O—($C_1$-$C_6$ alkyl), —O—($C_1$-$C_6$ alkyl)-O—($C_1$-$C_6$ alkyl), —$NR^{31}R^{32}$, $C_1$-$C_3$ perfluoro alkyl, —O—$(CH_2)_a NR^{31}R^{32}$, aryl, $C_3$-$C_7$ cycloalkyl, a three to twelve membered heterocyclic ring having up to 3 heteroatoms which is optionally substituted from 1 to 3 substituents independently selected from halo and $C_1$-$C_6$ alkyl;

$R^{31}$ and $R^{32}$ are independently selected from the group consisting of H, $C_1$-$C_8$ alkyl, $C_2$-$C_8$ alkenyl, $C_2$-$C_8$ alkynyl, and —($C_1$-$C_6$ alkyl)-O—($C_1$-$C_6$ alkyl);

or $R^{31}$ and $R^{32}$ may be taken together to form a three to twelve membered heterocyclic ring having up to 3 heteroatoms which is optionally substituted from 1 to 3 substituents independently selected from halo and $C_1$-$C_6$ alkyl;

a is selected from 0 to 6.

In another aspect of the invention, the compounds useful according to the present invention include those having the formula XXII:

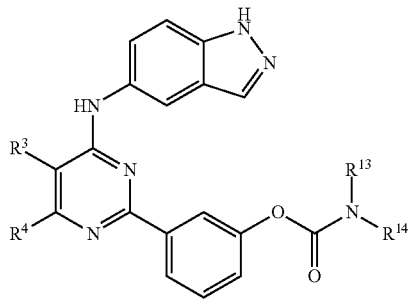

(XXII)

or pharmaceutically acceptable salt or stereoisomer thereof, wherein:
$R^{13}$ and $R^{14}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), heteroaryl, $C_3$-$C_7$ cycloalkyl, a three to twelve membered heterocyclic or aromatic ring containing up to 3 heteroatoms, each of which may be optionally substituted by from 1 to 3 substituents independently selected from halo, oxo, $C_1$-$C_6$ alkyl, $C_2$-$C_6$ alkenyl, $C_3$-$C_7$ cycloalkyl, $C_1$-$C_6$ alkoxy, CN and $C_1$-$C_3$ perfluoro alkyl;

or $R^{13}$ and $R^{14}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_7$ cycloalkyl, oxo, —OH, —$NH_2$, CN and $C_1$-$C_3$ perfluoro alkyl;

$R^3$ is H;
$R^4$ is selected from the group consisting of H, $C_1$-$C_8$ alkyl, —CN, halo, —OH, —O—($C_1$-$C_6$ alkyl), —O—($C_1$-$C_6$ alkyl)-O—($C_1$-$C_6$ alkyl), —$NR^{31}R^{32}$, $C_1$-$C_3$ perfluoro alkyl, —O—$(CH_2)_a NR^{31}R^{32}$, aryl, $C_3$-$C_7$ cycloalkyl, a three to twelve membered heterocyclic ring having up to 3 heteroatoms which is optionally substituted from 1 to 3 substituents independently selected from halo and $C_1$-$C_6$ alkyl;

$R^{31}$ and $R^{32}$ are independently selected from the group consisting of H, $C_1$-$C_8$ alkyl, $C_2$-$C_8$ alkenyl, $C_2$-$C_8$ alkynyl, and —($C_1$-$C_6$ alkyl)-O—($C_1$-$C_6$ alkyl);

or $R^{31}$ and $R^{32}$ may be taken together to form a three to twelve membered heterocyclic ring having up to 3 heteroatoms which is optionally substituted from 1 to 3 substituents independently selected from halo and $C_1$-$C_6$ alkyl;

a is selected from 0 to 6.

In another aspect of the invention, the compounds useful according to the present invention include those having the formula XXIII:

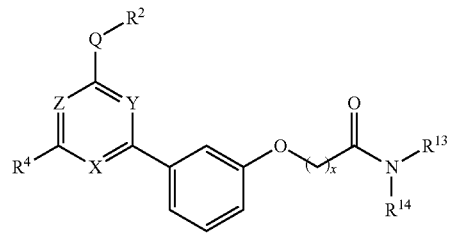

(XXIII)

or pharmaceutically acceptable salt or stereoisomer thereof, wherein:
$R^{13}$ and $R^{14}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), heteroaryl, $C_3$-$C_7$ cycloalkyl, a three to twelve membered heterocyclic or aromatic ring containing up to 3 heteroatoms, each of which may be optionally substituted by from 1 to 3 substituents independently selected from halo, oxo, $C_1$-$C_6$ alkyl, $C_2$-$C_6$ alkenyl, $C_3$-$C_7$ cycloalkyl, $C_1$-$C_6$ alkoxy, CN and $C_1$-$C_3$ perfluoro alkyl;

or $R^{13}$ and $R^{14}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_7$ cycloalkyl, oxo, —OH, —$NH_2$, CN and $C_1$-$C_3$ perfluoro alkyl;

x is selected from 0 to 1;
$R^2$ is selected from the group consisting of cyclohexylpyridine, 1H-pyrazole, and pyridine;

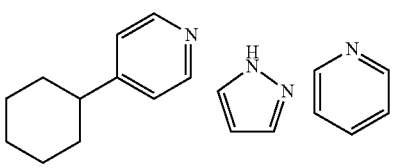

X is selected from N or CR$^3$;
Y is selected from N or CR$^3$;
Z is selected from N or CR$^4$;
wherein at least one of X, Y, and Z is N;
R$^4$ is selected from the group consisting of H, C$_1$-C$_8$ alkyl, —CN, halo, —OH, —O—(C$_1$-C$_6$ alkyl), —O—(C$_1$-C$_6$ alkyl)-O—(C$_1$-C$_6$ alkyl), —NR$^{31}$R$^{32}$, CF$_3$, —O—(CH$_2$)$_a$NR$^{31}$R$^{32}$, —NR$^{31}$—(CH$_2$)$_a$NR$^{33}$R$^{34}$, —NR$^{31}$—(CH$_2$)$_a$OR$^{33}$, aryl, C$_3$-C$_7$ cycloalkyl, a three to twelve membered heterocyclic ring having up to 3 heteroatoms which is optionally substituted from 1 to 3 substituents independently selected from halo, C$_1$-C$_6$ alkyl, and —(C$_1$-C$_6$ alkyl)-O—(C$_1$-C$_6$ alkyl);
R$^{31}$ and R$^{32}$ are independently selected from the group consisting of H, C$_1$-C$_8$ alkyl, C$_2$-C$_8$ alkenyl, C$_2$-C$_8$ alkynyl, and —(C$_1$-C$_6$ alkyl)-O—(C$_1$-C$_6$ alkyl);
or R$^{31}$ and R$^{32}$ may be taken together to form a three to twelve membered heterocyclic ring having up to 3 heteroatoms which is optionally substituted from 1 to 3 substituents independently selected from halo and C$_1$-C$_6$ alkyl;
a is selected from 0 to 6;
Q is selected from the group NR$^5$ and 0;
R$^5$ is selected from H and C$_1$-C$_6$ alkyl.

In another aspect of the invention, the compounds useful according to the present invention include those having the formula XXIV:

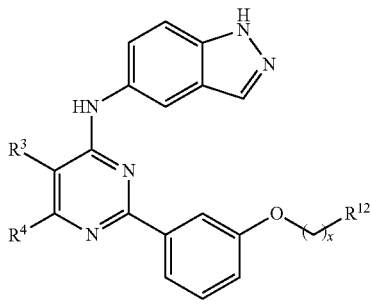

(XXIV)

or pharmaceutically acceptable salt or stereoisomer thereof, wherein:
R$^{12}$ is selected from the group consisting of H, C$_1$-C$_8$ alkyl, C$_2$-C$_8$ alkenyl, C$_2$-C$_8$ alkynyl, —(C$_1$-C$_6$ alkyl)-O—(C$_1$-C$_6$ alkyl), amino, NR$^{31}$R$^{32}$, heteroaryl, C$_3$-C$_7$ cycloalkyl, a three to twelve membered heterocyclic or aromatic ring containing up to 3 heteroatoms, each of which may be optionally substituted by from 1 to 3 substituents independently selected from halo, oxo, C$_1$-C$_6$ alkyl, C$_2$-C$_6$ alkenyl, C$_3$-C$_7$ cycloalkyl, C$_1$-C$_6$ alkoxy, CN and C$_1$-C$_3$ perfluoro alkyl;
x is selected from 0 to 2;
each R$^3$ and R$^4$ is independently selected from the group consisting of H, C$_1$-C$_8$ alkyl, —CN, halo, —OH, —O—(C$_1$-C$_6$ alkyl), —O—(C$_1$-C$_6$ alkyl)-O—(C$_1$-C$_6$ alkyl), —NR$^{31}$R$^{32}$, CF$_3$, —O—(CH$_2$)$_a$NR$^{31}$R$^{32}$, aryl, C$_3$-C$_7$ cycloalkyl, a three to twelve membered heterocyclic ring having up to 3 heteroatoms which is optionally substituted from 1 to 3 substituents independently selected from halo and C$_1$-C$_6$ alkyl;
R$^{31}$ and R$^{32}$ are independently selected from the group consisting of H, C$_1$-C$_8$ alkyl, C$_2$-C$_8$ alkenyl, C$_2$-C$_8$ alkynyl, C$_3$-C$_7$ cycloalkyl and —(C$_1$-C$_6$ alkyl)-O—(C$_1$-C$_6$ alkyl);
or R$^{31}$ and R$^{32}$ may be taken together to form a three to twelve membered heterocyclic ring having up to 3 heteroatoms which is optionally substituted from 1 to 3 substituents independently selected from halo and C$_1$-C$_6$ alkyl;
a is selected from 1 to 6.

In another aspect of the invention, the compounds useful according to the present invention include those having the formula XXV:

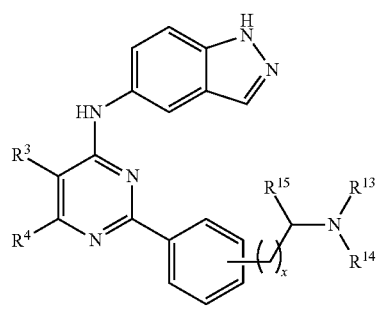

(XXV)

or pharmaceutically acceptable salt or stereoisomer thereof, wherein:
R$^{13}$ and R$^{14}$ are independently selected from the group consisting of H, C$_1$-C$_8$ alkyl, C$_2$-C$_8$ alkenyl, C$_2$-C$_8$ alkynyl, —(C$_1$-C$_6$ alkyl)-O—(C$_1$-C$_6$ alkyl), heteroaryl, C$_3$-C$_7$ cycloalkyl, a three to twelve membered heterocyclic or aromatic ring containing up to 3 heteroatoms, each of which may be optionally substituted by from 1 to 3 substituents independently selected from halo, oxo, C$_1$-C$_6$ alkyl, C$_2$-C$_6$ alkenyl, C$_3$-C$_7$ cycloalkyl, C$_1$-C$_6$ alkoxy, CN and C$_1$-C$_3$ perfluoro alkyl;
or R$^{13}$ and R$^{14}$ may be taken together form a three to twelve membered heterocyclic ring having up to 3 heteroatoms which is optionally substituted by from 1 to 3 substituents independently selected from halo, C$_1$-C$_6$ alkyl, C$_2$-C$_6$ alkenyl, C$_1$-C$_6$ alkoxy, C$_3$-C$_7$ cycloalkyl, oxo, —OH, —NH$_2$, CN and C$_1$-C$_3$ perfluoro alkyl;
x is selected from 0 to 3;
R$^{15}$ is selected from the group consisting of H, C$_1$-C$_8$ alkyl, C$_2$-C$_8$ alkenyl, C$_2$-C$_8$ alkynyl, aryl, heteroaryl, heterocyclic ring, and C$_3$-C$_7$ cycloalkyl;
each R$^3$ and R$^4$ is independently selected from the group consisting of H, C$_1$-C$_8$ alkyl, —CN, halo, —OH, —O—(C$_1$-C$_6$ alkyl), —O—(C$_1$-C$_6$ alkyl)-O—(C$_1$-C$_6$ alkyl), —NR$^{31}$R$^{32}$, CF$_3$, —O—(CH$_2$)$_a$NR$^{31}$R$^{32}$, aryl, C$_3$-C$_7$ cycloalkyl, a three to twelve membered heterocyclic ring having up to 3 heteroatoms which is optionally substituted from 1 to 3 substituents independently selected from halo and C$_1$-C$_6$ alkyl;
R$^{31}$ and R$^{32}$ are independently selected from the group consisting of H, C$_1$-C$_8$ alkyl, C$_2$-C$_8$ alkenyl, C$_2$-C$_8$ alkynyl, and —(C$_1$-C$_6$ alkyl)-O—(C$_1$-C$_6$ alkyl);
or R$^{31}$ and R$^{32}$ may be taken together to form a three to twelve membered heterocyclic ring having up to 3 heteroatoms which is optionally substituted from 1 to 3 substituents independently selected from halo and $C_1$-$C_6$ alkyl;

a is selected from 1 to 6.

The present invention relates to compounds having the formula XXVI:

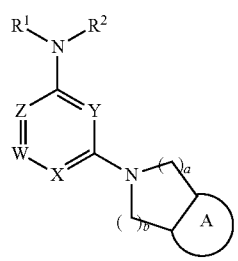

(XXVI)

or pharmaceutically acceptable salt thereof, wherein:
$R^1$ is selected from the group consisting of H or $C_1$-$C_6$ alkyl;
$R^2$ is selected from the group consisting of aryl, heteroaryl, $C_3$-$C_7$ cycloalkyl, a three to twelve membered heterocyclic ring containing up to 3 heteroatoms, each of which may be optionally substituted from 1 to 3 substituents independently selected from halo and $C_1$-$C_6$ alkyl;
X is selected from N or $CR^3$;
Y is selected from N or $CR^3$;
Z is selected from N or $CR^4$;
W is selected from $CR^5$;
wherein X, Y, and Z are independently selected and at least one of which is N;
wherein each $R^3$ is independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —$NR^{31}R^{32}$, and —($C_1$-$C_6$ alkyl)-O—($C_1$-$C_6$ alkyl);
$R^{31}$ and $R^{32}$ are independently selected from the group consisting of H, $C_1$-$C_8$ alkyl, $C_2$-$C_8$ alkenyl, $C_2$-$C_8$ alkynyl, and —($C_1$-$C_6$ alkyl)-O—($C_1$-$C_6$ alkyl);
$R^4$ and $R^5$ are independently selected from the group consisting of H, halo, $C_1$-$C_8$ alkyl, $C_2$-$C_8$ alkenyl, $C_2$-$C_8$ alkynyl, $C_1$-$C_6$ alkoxy, —($C_1$-$C_6$ alkyl)-O—($C_1$-$C_6$ alkyl), —$NR^{41}R^{42}$, —$(CH_2)_xNR^{41}R^{42}$ and —O—($C_1$-$C_6$ alkyl)-O—($C_1$-$C_6$ alkyl);
$R^{41}$ and $R^{42}$ are independently selected from the group consisting of H, $C_1$-$C_8$ alkyl, $C_2$-$C_8$ alkenyl, $C_2$-$C_8$ alkynyl, and —($C_1$-$C_6$ alkyl)-O—($C_1$-$C_6$ alkyl);
or $R^{41}$ and $R^{42}$ may be taken together to form a three to twelve membered cycloalkyl or heterocyclic ring having up to 3 heteroatoms which is optionally substituted from 1 to 3 substituents independently selected from halo, $C_1$-$C_6$ alkyl, and $C_1$-$C_6$ alkoxy;
x is selected from 0 to 6;
or $R^4$ and $R^5$ may be taken together to form a three to twelve membered heterocyclic or aromatic ring having up to 3 heteroatoms which is optionally substituted from 1 to 3 substituents independently selected from halo and $C_1$-$C_6$ alkyl and $C_1$-$C_6$ alkoxy;
a is selected from 0 to 2;
b is selected from 0 to 2;
wherein a or b are independently selected and one of which is at least 1
A is a three to twelve membered heterocyclic or aromatic ring having up to 3 heteroatoms which is optionally substituted from 1 to 3 substituents independently selected from halo, $C_1$-$C_6$ alkyl, $C_2$-$C_6$ alkenyl, $C_1$-$C_6$ alkoxy, $C_3$-$C_7$ cycloalkyl, oxo, acyl, —S—($C_1$-$C_6$ alkyl), OH, $NH_2$, CN and $C_1$-$C_3$ perfluroalkyl.

In an embodiment of the invention, $R^1$ is H;
In an embodiment of the invention, $R^2$ is selected from indazole, cyclohexylpyridine, phenylpyridine, phenyl-1H-pyrazole, 1H-pyrrolo[2,3-b]pyridine, 1H-pyrazole, pyridine, isoquinoline, quinoline and 1,3-thiazolyl pyridine;
In an embodiment of the invention, $R^2$ is selected from:

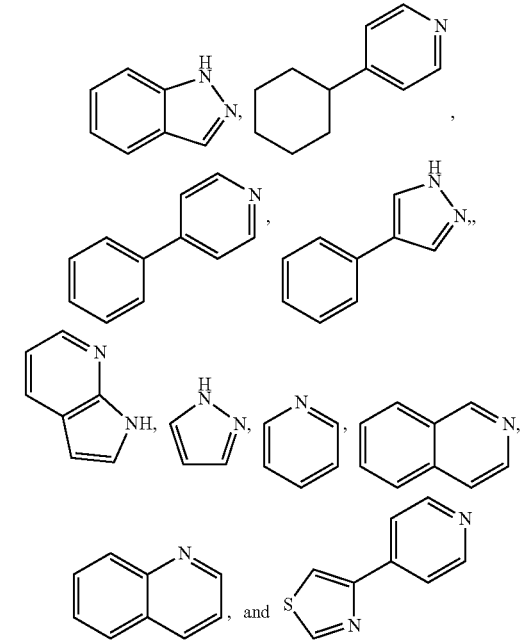

In an embodiment of the invention $R^2$ is selected from:
X, Z=N; W=$CR^3$
X, Y=N; Z=$CR^4$
In an embodiment of the invention $R^4$ and $R^5$ are each H;
In another embodiment $R^4$ and $R^5$ are each —$CH_3$;
In still another embodiment $R^4$ and $R^5$ are taken together to form a five-membered ring including, without limitation, dihydrofuran;
In other aspects of the invention, the ROCK2 inhibiting compound may be selected from the ROCK2 compounds disclosed in PCT/US2006/011271, filed Mar. 27, 2006, which is incorporated herein in its entirety. Thus, the ROCK2 inhibiting compound may have the formula XXXI:

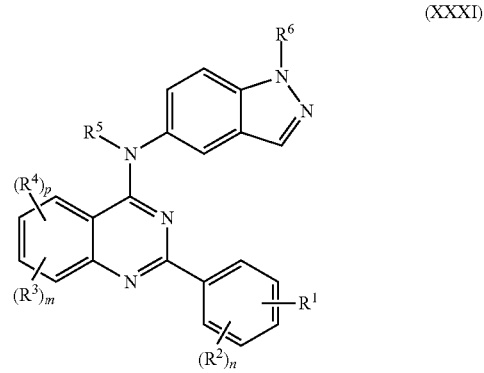

(XXXI)

or pharmaceutically acceptable salt, wherein:
$R_1$ is selected from the group consisting of —O—$(CH_2)_y$—$CO_2R^{12}$, —O—$(CH_2)_y$—C(=O)$NR^{13}R^{14}$, —O—$(CH_2)_y$-heteroaryl, —O—$(CH_2)_y$-cycloalkyl, —O—C(=O)—

$(CH_2)_y$—$NR^{13}R^{14}$, —O—$(CH_2)_z$—$NR^{13}R^{14}$, —NH—C(=O)—$(CH_2)$—$NR^{13}R^{14}$, —NH—C(=O)—X—$R^{15}$, —NH—$(CH_2)_y$—$NR^{13}R^{14}$;

$R^{12}$ is selected from the group consisting of $C_1$-$C_6$ alkyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, —($C_1$-$C_6$ alkyl)-O—($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted at one or more carbon atoms by from 1 to 3 substituents independently selected from halo, $C_1$-$C_6$ alkoxy, hydroxy, amino, cyano and $C_1$-$C_3$ perfluoro alkyl;

$R^{13}$ and $R^{14}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;

or $R^{13}$ and $R^{14}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_7$ cycloalkyl, oxo, OH, $NH_2$, CN and $C_1$-$C_3$ perfluoro alkyl;

X is selected from a covalent bond, O, NH, and $C_1$-$C_6$ alkyl;

$R^{15}$ is selected from the group consisting of heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, OH, $NH_2$, CN and $C_1$-$C_3$ perfluoro alkyl;

or $R^{15}$ is selected from —($C_1$-$C_6$ alkyl)-O—($C_1$-$C_6$ alkyl), —($C_1$-$C_6$ alkyl)-$NR^{16}R^{17}$, —$CO_2R_8$, —O—$(CH_2)_x$—$CO_2R^{18}$, and —C(=O)$NR^{16}R^{17}$;

$R^{16}$ and $R^{17}$ independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, OH, $NH_2$, CN and $C_1$-$C_3$ perfluoro alkyl;

or $R^{16}$ and $R^{17}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

$R^{18}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

x is selected from 0 to 6;
y is selected from 0 to 6;
z is selected from 2 to 6;

each $R^2$ is independently selected from the group consisting of lower alkyl, CN, halo, hydroxy, lower alkoxy, amino, and perfluoro lower alkyl;

each $R^3$ is independently selected from the group consisting of lower alkyl, CN, halo, hydroxy, lower alkoxy, amino, and perfluoro lower alkyl;

$R^4$ is selected from —$(CH_2)_a$—$NR^{43}R^{44}$, —Y—$R^{42}$, —O—$(CH_2)_a$—$CO_2R^{42}$, —O—$(CH_2)_a$—C(=O)$NR^{43}R^{44}$, —O—$(CH_2)_a$-heteroaryl, —O—$(CH_2)_a$-cycloalkyl, —O—C(=O)—$(CH_2)_a$—$NR^{43}R^{44}$, —O—$(CH_2)_c$—$NR^{43}R^{44}$, —NH—C(=O)—$(CH_2)_a$—$NR^{43}R^{44}$, —NH—C(=O)—Y—$R^{45}$, —NH—C(=O)—$(CH_2)_a$—$NR^{43}R^{44}$;

$R^{42}$ is selected from the group consisting of $C_1$-$C_6$ alkyl, —($C_1$-$C_6$ alkyl)-O—($C_1$-$C_6$ alkyl), —($C_1$-$C_6$ alkyl)-$NR^{46}R^{47}$, —($C_1$-$C_6$ alkyl)-C(=O)$NR^{46}R^{47}$, —($C_1$-$C_6$ alkyl)-O—($C_1$-$C_6$ alkyl)-O—($C_1$-$C_6$ alkyl), each of which may be optionally substituted at one or more carbon atoms by from 1 to 3 substituents independently selected from halo, $C_1$-$C_6$ alkoxy, hydroxy, amino, cyano and $C_1$-$C_3$ perfluoro alkyl;

$R^{43}$ and $R^{44}$ are independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), —($C_1$-$C_6$ alkyl)-$NR^{46}R^{47}$, —($C_1$-$C_6$ alkyl)-C(=O)$NR^{46}R^{47}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;

or $R^{43}$ and $R^{44}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

Y is selected from a covalent bond, O, NH, and $C_1$-$C_6$ alkyl;

$R^{45}$ is selected from the group consisting of H, aryl, —($C_1$-$C_6$ alkyl)-O—($C_1$-$C_6$ alkyl), —($C_1$-$C_6$ alkyl)-$NR^{46}R^{47}$, —$CO_2R^{48}$, —O—$(CH_2)_b$—$CO_2R^{48}$, and —C(=O)$NR^{46}R^{47}$;

$R^{46}$ and $R^{47}$ independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;

or $R^{46}$ and $R^{47}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

$R^{48}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-$NR^{46}R^{47}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

a is selected from 0 to 6;
b is selected from 0 to 6;
c is selected from 2 to 6;

$R^5$ is selected from the group consisting of H, $C_1$-$C_6$ alkyl, —$(CH_2)_d$—C(=O)—$NR^{53}R^{54}$, —C(=O)—$(CH_2)_d$—$NR^{53}R^{54}$, —C(=O)—X—$R^{55}$, and —C(=O)—$(CH_2)_d$—$NR^{53}R^{54}$;

$R^{53}$ and $R^{54}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-$NR^{56}R^{57}$, —($C_1$-$C_6$ alkyl)-C(=O)$NR^{56}R^{57}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;

or $R^{53}$ and $R^{54}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_7$ cycloalkyl, oxo, hydroxy, amino, cyano and $C_1$-$C_3$ perfluoro alkyl;

$R^{55}$ is selected from the group consisting of H, aryl, —($C_1$-$C_6$ alkyl)-O—($C_1$-$C_6$ alkyl), —($C_1$-$C_6$ alkyl)-$NR^{56}R^{57}$, —$CO_2R^{58}$, —O—$(CH_2)_e$—$CO_2R^{58}$, and —C(=O)$NR^{56}R^{57}$, $R^{56}$ and $R^{57}$ independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;

or $R^{56}$ and $R^{57}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

$R^{58}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-$NR^{56}R^{57}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

d is selected from 0 to 6;
e is selected from 0 to 6;

$R^6$ is selected from the group consisting of H, $C_1$-$C_6$ alkyl, —$(CH_2)_r$—C(=O)—$NR^{63}R^{64}$, —C(=O)—$(CH_2)_r$—$NR^{63}R^{64}$, —C(=O)—X—$R^{65}$, and —C(=O)—$(CH_2)_r$—$NR^{63}R^{64}$;

$R^{63}$ and $R^{64}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-$NR^{66}R^{67}$, —($C_1$-$C_6$ alkyl)-C(=O)$NR^{66}R^{67}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;

or $R^{63}$ and $R^{64}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_7$ cycloalkyl, oxo, hydroxy, amino, cyano and $C_1$-$C_3$ perfluoro alkyl;

$R^{65}$ is selected from the group consisting of H, aryl, —($C_1$-$C_6$ alkyl)-O—($C_1$-$C_6$ alkyl), —($C_1$-$C_6$ alkyl)-$NR^{66}R^{67}$, —$CO_2R^{68}$, —O—$(CH_2)_s$—$CO_2R^{68}$, and —C(=O)$NR^{66}R^{67}$, $R^{66}$ and $R^{67}$ independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;

or $R^{66}$ and $R^{67}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

$R^{68}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-$NR^{66}R^{67}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

r is selected from 0 to 6;
s is selected from 0 to 6;
n is selected from 0 to 4;
m is selected from 0 to 3; and
p is selected from 0 and 1.

In one embodiment of Formula XXXI, $R^4$ and $R^5$ are independently selected from H and $C_1$-$C_6$ alkyl. In another embodiment, $R^4$ and $R^5$ are H.

In an embodiment of the invention, the compound of formula XXXI has the formula XXXII:

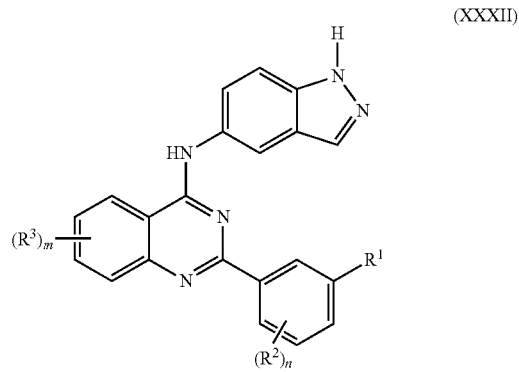

(XXXII)

or a pharmaceutically acceptable salt thereof, wherein $R^1$, $R^2$, $R^3$, n and m are as for the compound of the formula I.

In an embodiment of the invention, the compound of formula XXXI has the formula XXXIII:

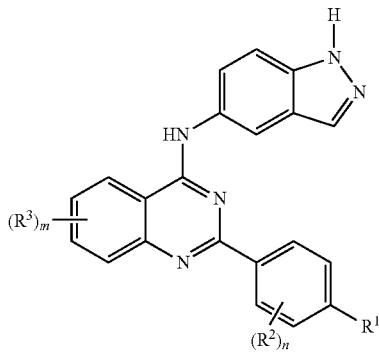

(XXXIII)

or a pharmaceutically acceptable salt thereof, wherein $R^1$, $R^2$, $R^3$, n and m are as for the compound of the formula I.

In an embodiment of the invention, the compound of formula XXXI has the formula XXXIV:

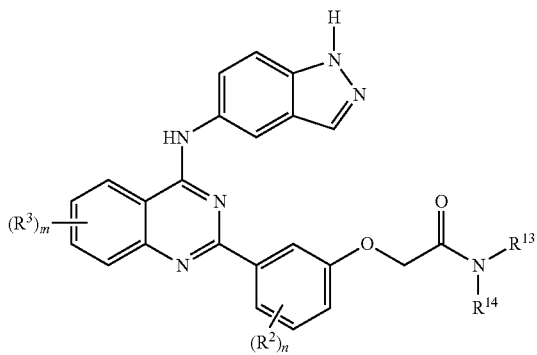

(XXXIV)

or a pharmaceutically acceptable salt thereof, wherein:
$R^{13}$ and $R^{14}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;
or $R^{13}$ and $R^{14}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_7$ cycloalkyl, oxo, hydroxy, amino, cyano and $C_1$-$C_3$ perfluoro alkyl;
X is selected from a covalent bond, O, NH, and $C_1$-$C_6$ alkyl;
$R^{16}$ and $R^{17}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;
or $R^{16}$ and $R^{17}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;
each $R^2$ is independently selected from the group consisting of lower alkyl, CN, halo, hydroxy, lower alkoxy, amino, and perfluoro lower alkyl;
each $R^3$ is independently selected from the group consisting of lower alkyl, CN, halo, hydroxy, lower alkoxy, amino, and perfluoro lower alkyl;
n is selected from 0 to 4; and
m is selected from 0 to 3.

In an embodiment of the invention, the compound of formula XXXI has the formula $XXXIV_a$:

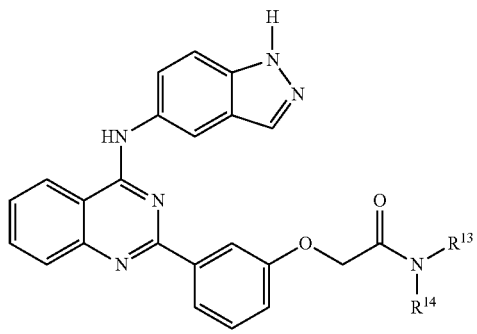

($XXXIV_a$)

or a pharmaceutically acceptable salt thereof, wherein:
$R^{13}$ and $R^{14}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;
or $R^{13}$ and $R^{14}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;
$R^{16}$ and $R^{17}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;
or $R^{16}$ and $R^{17}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl.

In an embodiment of the invention, the compound of formula XXXI has the formula XXXV:

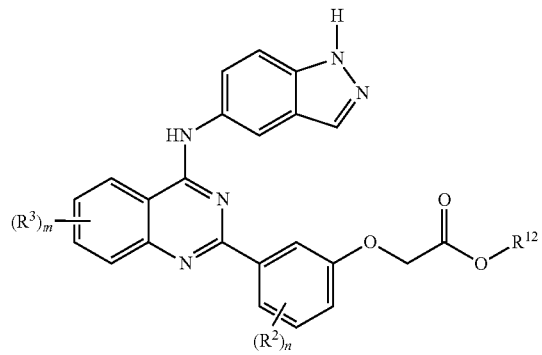

(XXXV)

or a pharmaceutically acceptable salt thereof, wherein:
$R^{12}$ is selected from the group consisting of $C_1$-$C_6$ alkyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, —($C_1$-$C_6$ alkyl)-O—($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted at one or more carbon atoms by from 1 to 3 substituents independently selected from halo, $C_1$-$C_6$ alkoxy, hydroxy, amino, cyano and $C_1$-$C_3$ perfluoro alkyl;
each $R^2$ is independently selected from the group consisting of lower alkyl, CN, halo, hydroxy, lower alkoxy, amino, and perfluoro lower alkyl;
each $R^3$ is independently selected from the group consisting of lower alkyl, CN, halo, hydroxy, lower alkoxy, amino, and perfluoro lower alkyl;
n is selected from 0 to 4; and
m is selected from 0 to 3.

In an embodiment of the invention, the compound of formula XXXI has the formula XXXV$_a$:

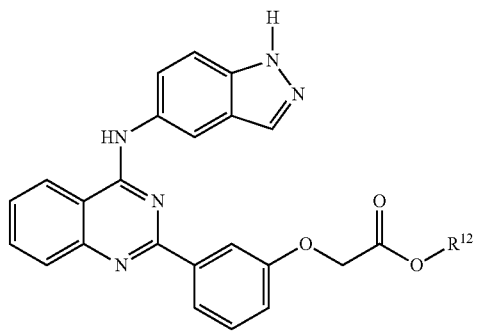

(XXXV$_a$)

or a pharmaceutically acceptable salt thereof, wherein:
$R^{12}$ is selected from the group consisting of $C_1$-$C_6$ alkyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, —($C_1$-$C_6$ alkyl)-O—($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted at one or more carbon atoms by from 1 to 3 substituents independently selected from halo, $C_1$-$C_6$ alkoxy, hydroxy, amino, cyano and $C_1$-$C_3$ perfluoro alkyl.

In another embodiment of the invention, the rho kinase inhibitor has the XXXVI:

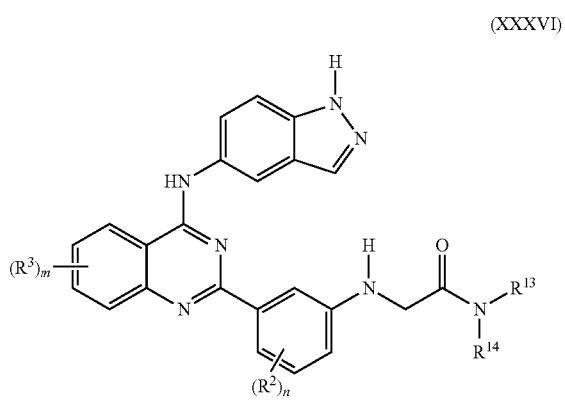

(XXXVI)

or a pharmaceutically acceptable salt thereof, wherein:
$R^{13}$ and $R^{14}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;
or $R^{13}$ and $R^{14}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_7$ cycloalkyl, oxo, hydroxy, amino, cyano and $C_1$-$C_3$ perfluoro alkyl;
$R^{16}$ and $R^{17}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;
or $R^{16}$ and $R^{17}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;
each $R^2$ is independently selected from the group consisting of lower alkyl, CN, halo, hydroxy, lower alkoxy, amino, and perfluoro lower alkyl;
each $R^3$ is independently selected from the group consisting of lower alkyl, CN, halo, hydroxy, lower alkoxy, amino, and perfluoro lower alkyl;
n is selected from 0 to 4; and
m is selected from 0 to 3.

In an embodiment of the invention, the compound of formula XXXVI has the formula XXXVI$_a$:

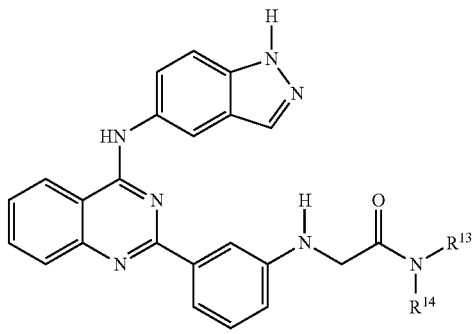

(XXXVI$_a$)

or a pharmaceutically acceptable salt thereof, wherein:
$R^{13}$ and $R^{14}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-NR$^{16}$R$^{17}$, —($C_1$-$C_6$ alkyl)-C(=O)NR$^{16}$R$^{17}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;
or $R^{13}$ and $R^{14}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_7$ cycloalkyl, oxo, hydroxy, amino, cyano and $C_1$-$C_3$ perfluoro alkyl;
$R^{16}$ and $R^{17}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;
or $R^{16}$ and $R^{17}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl.

In further aspects of the invention, the compound of formula XXXI is SLx-2119:

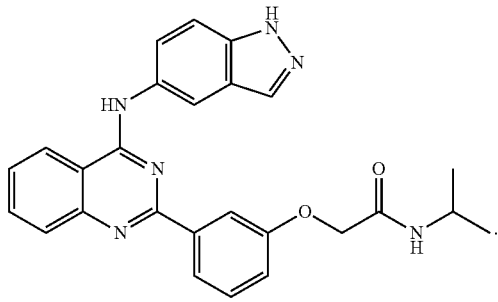

(SLx-2119)

In further aspects of the invention, the rho kinase inhibitor is selected from the group consisting of:

2-(3-(4-(1H-indazol-5-ylamino)quinazolin-2-yl)phenoxy)-N-isopropylacetamide, 2-(3-(4-(1H-indazol-5-ylamino)quinazolin-2-yl)phenoxy)-N-(2-methoxyethyl)acetamide, 2-(3-(4-(1H-indazol-5-ylamino)quinazolin-2-yl)phenoxy)-N-(pyridin-3-yl)acetamide, 2-(3-(4-(1H-indazol-5-ylamino)quinazolin-2-yl)phenoxy)-1-(4-methylpiperazin-1-yl)ethanone, 2-(3-(4-(1H-indazol-5-ylamino)quinazolin-2-yl)phenoxy)-1-morpholinoethanone, 2-(3-(4-(1H-indazol-5-ylamino)quinazolin-2-yl)phenoxy)-N-methylacetamide, 2-(3-(4-(1H-indazol-5-ylamino)quinazolin-2-yl)phenoxy)-N—((R)-pyrrolidin-3-yl)acetamide, 2-(3-(4-(1H-indazol-5-ylamino)quinazolin-2-yl)phenoxy)-N—((S)-pyrrolidin-3-yl)acetamide, 2-(3-(4-(1H-indazol-5-ylamino)quinazolin-2-yl)phenoxy)-N—((R)-tetrahydrofuran-3-yl)acetamide, 2-(3-(4-(1H-indazol-5-ylamino)quinazolin-2-yl)phenoxy)-1-(piperidin-1-yl)ethanone, 2-(3-(4-(1H-indazol-5-ylamino)quinazolin-2-yl)phenoxy)-N-tert-butylacetamide, 2-(3-(4-(1H-indazol-5-ylamino)quinazolin-2-yl)phenoxy)-N-ethylacetamide, 2-(3-(4-(1H-indazol-5-ylamino)quinazolin-2-yl)phenoxy)-N-(cyanomethyl)acetamide, 2-(3-(4-(1H-indazol-5-ylamino)quinazolin-2-yl)phenoxy)-N-cyclobutylacetamide, 2-(3-(4-(1H-indazol-5-ylamino)quinazolin-2-yl)phenoxy)-N-isobutylacetamide, 2-(3-(4-(1H-indazol-5-ylamino)quinazolin-2-yl)phenoxy)-N-(2,2,2-trifluoroethyl)acetamide, 2-(3-(4-(1H-indazol-5-ylamino)quinazolin-2-yl)phenoxy)-N-cyclohexylacetamide, 2-(3-(4-(1H-indazol-5-ylamino)quinazolin-2-yl)phenoxy)-N-neopentylacetamide, 2-(3-(4-(1H-indazol-5-ylamino)quinazolin-2-yl)phenoxy)-N-(prop-2-ynyl)acetamide, N-(3-(4-(1H-indazol-5-ylamino)quinazolin-2-yl)phenyl)-4-methylpiperazine-1-carboxamide, 3-(3-(4-(1H-indazol-5-ylamino)quinazolin-2-yl)phenyl)-1,1-dimethylurea, N-(3-(4-(1H-indazol-5-ylamino)quinazolin-2-yl)phenyl)-2-methoxyacetamide, methyl 2-(3-(4-(1H-indazol-5-ylamino)quinazolin-2-yl)phenylamino)-2-oxoacetate, 1-(3-(4-(1H-indazol-5-ylamino)quinazolin-2-yl)phenyl)-3-(2-(dimethylamino)ethyl)urea, N-(3-(4-(1H-indazol-5-ylamino)quinazolin-2-yl)phenyl)-2-morpholinoacetamide, N-(3-(4-(1H-indazol-5-ylamino)quinazolin-2-yl)phenyl)-3-(4-isopropylpiperazin-1-yl)propanamide, N-(3-(4-(1H-indazol-5-ylamino)quinazolin-2-yl)phenyl)piperidine-4-carboxamide, and N-(3-(4-(1H-indazol-5-ylamino)-6-(2-methoxyethoxy)quinazolin-2-yl)phenyl)butyramide.

In further aspects of the invention, the rho kinase inhibitor is

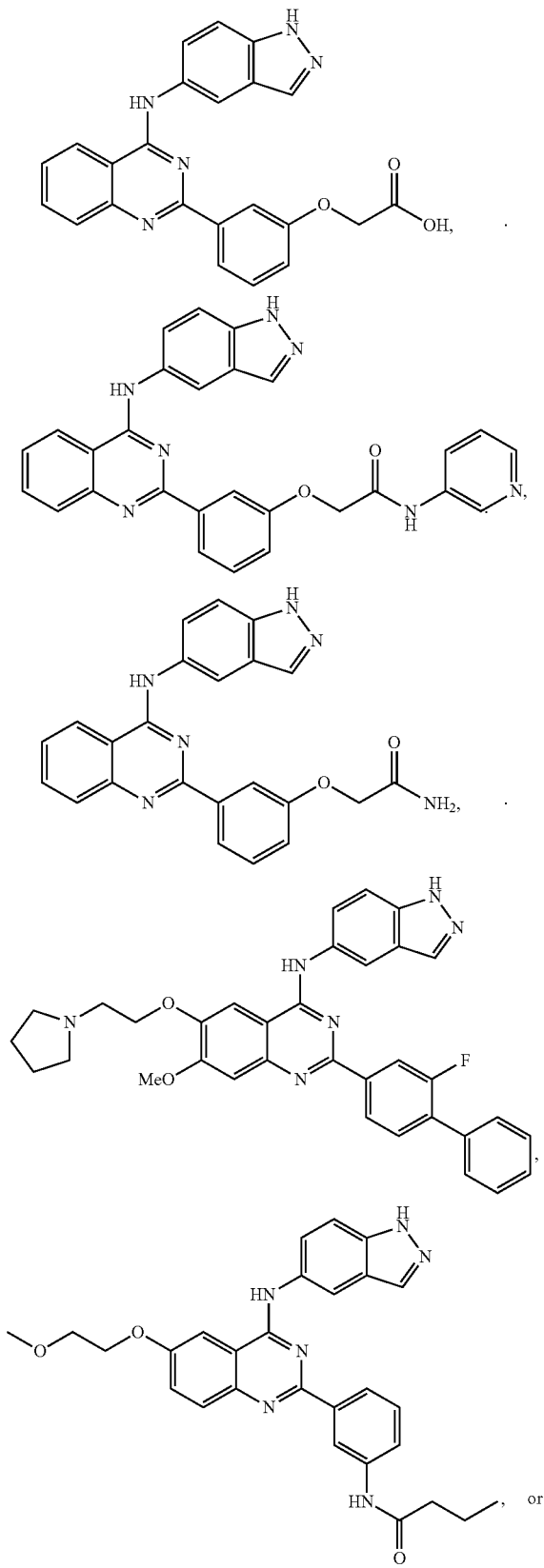

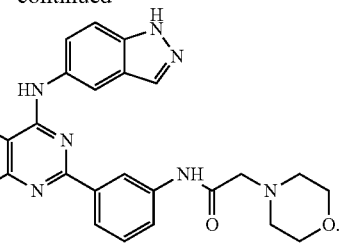

The term "heteroatom" as used herein means an atom of any element other than carbon or hydrogen. Preferred heteroatoms are nitrogen, oxygen, and sulfur.

The term "alkyl" refers to the radical of saturated aliphatic groups, including straight-chain alkyl groups and branched-chain alkyl groups. In preferred embodiments, a straight chain or branched chain alkyl has 10 or fewer carbon atoms in its backbone (e.g., $C_1$-$C_{10}$ for straight chain, $C_3$-$C_{10}$ for branched chain). Likewise, preferred cycloalkyls have from 3-10 carbon atoms in their ring structure, and more preferably have 3 to 6 carbons in the ring structure.

Unless the number of carbons is otherwise specified, "lower alkyl" as used herein means an alkyl group, as defined above, but having from one to six carbons, and more preferably from one to four carbon atoms. Likewise, "lower alkenyl" and "lower alkynyl" have similar chain lengths ($C_2$-$C_6$). Preferred alkyl groups are lower alkyls. In preferred embodiments, a substituent designated herein as alkyl is a lower alkyl.

The term "cycloalkyl" refers to saturated, carbocyclic groups having from 3 to 7 carbons in the ring. Preferred cycloalkyl groups include cyclopropyl, cyclobutyl, cyclopentyl and cyclohexyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5- and 6-membered single-ring aromatic groups that may include from zero to four heteroatoms, for example, benzene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles", "heteroaromatics" or "heteroaryl". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, aryls and/or heterocyclic groups.

The terms "heterocyclyl" or "heterocyclic group" refer to 3- to 10-membered ring structures, more preferably 5- or 6-membered rings, whose ring structures include one to four heteroatoms. Heterocycles can also be polycycles. Heterocyclic groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" refer to two or more rings (e.g., cycloalkyls, cycloalkenyls, aryls and/or heterocyclyls) in which two or more carbons are common to two adjoining rings, e.g., the rings are "fused rings". Rings that are joined through non-adjacent atoms are termed "bridged" rings. Each of the rings of the polycyclic group can be substituted with such substituents as described above, for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

As used herein, the term "nitro" means —NO$_2$. The term "halogen" or "halo" designates —F, —Cl, —Br or —I. The term "hydroxyl" means —OH.

The terms "amine" and "amino" refer to both unsubstituted and substituted amines, e.g., a moiety that can be represented by the general formula:

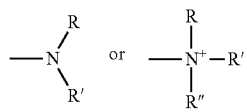

wherein R, R' and R" each independently represent H, alkyl, alkenyl, alkynyl, aralkyl, aryl, and heterocyclic groups, and most preferably H or lower alkyl.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. The term lower alkoxy refers to an alkoxy group having from 1 to 6 carbon atoms.

The term "oxo" as used herein refers to an oxygen atom that has a double bond to a another atom, particularly to carbon or sulfur.

As used herein, the definition of each expression, e.g. alkyl, m, n, R, etc., when it occurs more than once in any structure, is intended to be independent of its definition elsewhere in the same structure.

It will be understood that "substituted", "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. Illustrative substituents include, for example, those described herein above.

Certain compounds of the present invention may exist in particular geometric or stereoisomeric forms. The present invention contemplates all such compounds, including cis- and trans-isomers, R- and S-enantiomers, diastereomers, the racemic mixtures thereof, and other mixtures thereof, as falling within the scope of the invention. Additional asymmetric carbon atoms may be present in a substituent such as an alkyl group. All such isomers, as well as mixtures thereof, are included in this invention.

Certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this context, refers to the relatively non-toxic, inorganic and organic acid addition salts of compounds of the present invention. Representative salts include the hydrochloride, hydrobromide, sulfate, bisulfate, phosphate, nitrate, acetate, stearate, laurate, benzoate, lactate, phosphate, tosylate, citrate, maleate, fumarate, succinate, tartrate, napthylate, and mesylate salts and the like. (See, for example, Berge et al. "Pharmaceutical Salts", *J. Pharm. Sci.* (1977) 66:1-19).

In other cases, the compounds of the present invention may contain one or more acidic functional groups and, thus, are capable of forming pharmaceutically-acceptable salts with pharmaceutically-acceptable bases. Representative salts include alkali or alkaline earth salts such as lithium, sodium, potassium, calcium, magnesium salts and the like. Representative organic amines useful for the formation of base addition salts include ethylamine, diethylamine, ethylenediamine, ethanolamine, diethanolamine, piperazine and the like. (See, for example, Berge et al., supra).

In one aspect, the present invention provides compounds of Formula I that are inhibitors of Rho-kinase. Rho kinase (ROCK), a serine/threonine kinase, serves as a target protein for small GTP-binding protein Rho, and is an important mediator of numerous cellular functions, including focal adhesions, motility, smooth muscle contraction, and cytokinesis. In smooth muscle, ROCK plays an important role in Ca$^{2+}$ sensitization and the control of vascular tone. It modulates the level of phosphorylation of the myosin II light chain of myosin II, mainly through inhibition of myosin phosphatase, and contributes to agonist-induced Ca$^{2+}$ sensitization in smooth muscle contraction.

Rho kinase is found in two forms, ROCK 1 (ROCKβ; p160-ROCK) and ROCK 2 (ROCKα). In some embodiments, the compound of Formula I is selectively inhibits ROCK1. In some embodiments, the compound of Formula I selectively inhibits ROCK2. In some embodiments, the compound of Formula I is non-selective with respect to inhibition of ROCK1 and ROCK2.

Methods of determining kinase inhibition are well known in the art. For example, kinase activity of an enzyme and the inhibitory capacity of a test compound can be determined by measuring enzyme specific phosphorylation of a substrate. Commercial assays and kits can be employed. For example, kinase inhibition can be determined using an IMAP® assay (Molecular Devices). This assay method involves the use of a fluorescently-tagged peptide substrate. Phosphorylation of the tagged peptide by a kinase of interest promotes binding of the peptide to a trivalent metal-based nanoparticle via the specific, high affinity interaction between the phospho-group and the trivalent metal. Proximity to the nanoparticle results in increased fluorescence polarization. Inhibition of the kinase by a kinase inhibitor prevents phosphorylation of the substrate and thereby limits binding of the fluorescently-tagged substrate to the nanoparticle. Such an assay can be compatible with a microwell assay format, allowing simultaneous determination of $IC_{50}$ of multiple compounds.

In another aspect of the present invention there is provided a method of treating a patient suffering from a disease comprising administering to a patient in need of such treatment a therapeutically effective amount of a compound of the present invention. The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment, e.g. reasonable side effects applicable to any medical treatment.

Compounds of the invention that inhibit Rho-kinase and or Rho-kinase mediated phosphorylation are useful for treatment of patients suffering from cardiovascular and non-cardiovascular diseases involving Rho-kinase function, such as hypertension, pulmonary hypertension, atherosclerosis, restenosis, coronary heart disease, cardiac hypertrophy, ocular hypertension, retinopathy, ischemic diseases, cerebral ischemia, cerebral vasospasm, penile erectile dysfunction, peripheral circulatory disorder, peripheral artery occlusive disease, glaucoma, (e.g., regulating intraoccular pressure), fibroid lung, fibroid liver, fibroid kidney, chronic obstructive pulmonary disease (COPD), adult respiratory distress syndrome, central nervous system disorders such as neuronal degeneration and spinal cord injury. Further, Rho-kinase inhibitors of the invention can be used to treat arterial thrombotic disorders such as platelet aggregation and leukocyte aggregation, and bone resorption.

In certain embodiments, a Rho-kinase inhibitor of the invention is used to treat inflammation, including, but not limited to asthma, cardiovascular inflammation, renal inflammation, and arteriosclerosis.

Rho-kinase inhibitors of the invention inhibit tumor cell growth and metastasis, and angiogenesis, and are useful for treating neoplastic diseases. Neoplastic diseases include any malignant growth or tumor caused by abnormal or uncontrolled cell division, and may spread to other parts of the body through the lymphatic system or the blood stream. Neoplastic disease includes, without limitation, lymphoma (a neoplasm of lymph tissue that is usually malignant), carcinoma (any malignant tumor derived from epithelial tissue), leukemia (malignant neoplasm of blood-forming tissues; characterized by abnormal proliferation of leukocytes), sarcoma (a usually malignant tumor arising from connective tissue (bone or muscle etc.), and blastoma (malignancy in precursor cells). Nonlimiting examples include squamous cell cancer, small-cell lung cancer, pituitary cancer, esophageal cancer, astrocytoma, soft tissue sarcoma, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, and various types of head and neck cancer.

According to the invention, ROCK inhibitors are used to effect weight loss and/or limit weight gain. In a preferred embodiment, the ROCK inhibitor is ROCK2 selective. ROCK-2 inhibitors promote weight loss in normal subjects, and limit weight gain in subjects prone to obesity.

In an embodiment of the invention, a ROCK inhibitor is used to reduce or prevent insulin resistance or restore insulin sensitivity. Accordingly, in one embodiment, the compounds of the invention are used to promote or restore insulin-dependent glucose uptake. In another embodiment of the invention, a ROCK-inhibitors of the invention is used to promote or restore glucose tolerance. In another embodiment of the invention, a ROCK inhibitor of the invention is used to treat metabolic syndrome. In another embodiment, a ROCK-inhibitors of the invention is used to reduce or prevent hyperinsulinemia. In an embodiment of the invention, a ROCK inhibitor is used to treat diabetes (particularly type 2 diabetes). ROCK inhibitors of the invention may also be used to promote or restore insulin-mediated relaxation of vascular smooth muscle cells (VSMCs). In preferred embodiments, the ROCK inhibitor is ROCK2 selective.

In certain embodiments, compounds of the invention are used for treatment of central nervous system disorders. Such disorders may involve neuronal degeneration or physical injury to neural tissue, including without limitation, Huntington's disease, Parkinson's Disease, Alzheimer's, Amyotrophic lateral sclerosis (ALS), or multiple sclerosis. In certain embodiments, compounds of the invention have properties particularly useful for treatment of such disorders, such as beneficial tissue distribution to tissues of the central nervous system, and ability to cross the blood brain barrier.

The invention provides pan-ROCK inhibitors (i.e., compounds that inhibit ROCK1 and ROCK1) as well as ROCK inhibitors that are isoform selective. As discussed above, in certain embodiments of the invention, a ROCK2-selective inhibitor may be preferred. For example, one study observed that ROCK2 is frequently over expressed in hepatocellular cancer compared to non-timorous livers while ROCK1 expression is unaltered. Other cancers which may benefit from treatment with a ROCK2 selective inhibitor include, but are not limited to, colon and bladder cancer. In contrast, ROCK1 expression levels have been observed to be higher in mammary tumors. Any cancer may be tested to determine whether there is overexpression of ROCK1 and/or ROCK2 and treated accordingly. In certain circumstances, ROCK 1 and ROCK2 isoforms show similarity in regulating certain downstream targets, In another aspect, the present invention provides pharmaceutically acceptable compositions which comprise a therapeutically-effective amount of one or more of the compounds of Formula I, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3)

topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals with toxicity, irritation, allergic response, or other problems or complications, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

In certain embodiments, a dose of a compound or a composition is administered to a subject every day, every other day, every couple of days, every third day, once a week, twice a week, three times a week, or once every two weeks. If desired, the effective daily dose of the active compound may be administered as two, three, four, five, six or more sub-doses administered separately at appropriate intervals throughout the day, optionally, in unit dosage forms. In some embodiments, a dose(s) of a compound or a composition is administered for 2 days, 3 days, 5 days, 7 days, 14 days, or 21 days. In certain embodiments, a dose of a compound or a composition is administered for 1 month, 1.5 months, 2 months, 2.5 months, 3 months, 4 months, 5 months, 6 months or more.

The above-described administration schedules are provided for illustrative purposes only and should not be considered limiting. A person of ordinary skill in the art will readily understand that all doses are within the scope of the invention.

While it is possible for a compound of the present invention to be administered alone, it is preferable to administer the compound as a pharmaceutical formulation (composition).

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" O and B books, Corvallis, Oreg., U.S.A., 1977).

Microemulsification technology may be employed to improve bioavailability of lipophilic (water insoluble) pharmaceutical agents. Examples include Trimetrine (Dordunoo, S. K., et al., Drug Development and Industrial Pharmacy, 17(12), 1685-1713, 1991) and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

In one aspect of invention, the formulations contain micelles formed from a compound of the present invention and at least one amphiphilic carrier, in which the micelles have an average diameter of less than about 100 nm. More preferred embodiments provide micelles having an average diameter less than about 50 nm, and even more preferred embodiments provide micelles having an average diameter less than about 30 nm, or even less than about 20 nm.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Particularly preferred amphiphilic carriers are saturated and monounsaturated polyethyleneglycolyzed fatty acid glycerides, such as those obtained from fully or partially hydrogenated various vegetable oils. Such oils may advantageously consist of tri-. di- and mono-fatty acid glycerides and di- and mono-polyethyleneglycol esters of the corresponding fatty acids, with a particularly preferred fatty acid composition including capric acid 4-10, capric acid 3-9, lauric acid 40-50, myristic acid 14-24, palmitic acid 4-14 and stearic acid 5-15%. Another useful class of amphiphilic carriers includes partially esterified sorbitan and/or sorbitol, with saturated or mono-unsaturated fatty acids (SPAN-series) or corresponding ethoxylated analogs (TWEEN-series).

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG(750)). The polymers used in the present invention have a significantly smaller molecular weight, approximately 100 daltons, compared to the large MW of 5000 daltons or greater that used in standard pegylation techniques. Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween®. and Pluronic®. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

The above-described administration schedules are provided for illustrative purposes only and should not be considered limiting. A person of ordinary skill in the art will readily understand that all doses are within the scope of the invention.

Compounds of the invention can be advantageously administered with second agents to patients in need thereof. When a rho-kinase inhibitor is administered with a second agent, the rho-kinase inhibitor and the second agent can be adminstered sequentially or concomitantly. Sequentially means that one agent is administered for a time followed by administration of the second agent, which may be followed by administration of the first agent. When agents are administered sequentially, the level or one agent may not be maintained at a therapeutically effective level when the second agent is administered, and vice versa. Concomitantly means that the first and second agent are administered according to a schedule that maintains both agents at an substantially therapeutically effective level, even though the agents are not administered simultaneously. Each agent can be administered in single or multiple doses, and the doses can be administered on any schedule, including, without limitation, twice daily, daily, weekly, every two weeks, and monthly.

The invention also includes adjunctive administration. Adjunctive administration means that a second agent is administered to a patient in addition to a first agent that is already being administered to treat a disease or disease symptom. In some embodiments, adjunctive administration involves administering a second agent to a patient in which administration of the first agent did not sufficiently treat a disease or disease symptom. In other embodiments, adjunctive administration involves administration of the second agent to a patient whose disease has been effectively treated by administration of the first agent, with the expectation that the adjunctive treatment improves the outcome of the treatment. In some embodiments, the effect of administering the first and second agents is synergistic. In some embodiments, administration of the first and second agents prevents or lengthens the time until relapse, compared to administration of either of the agents alone. In some embodiments, administration of the first and second agents allows for reduced dosage and/or frequency of administration of the first and second agent.

In an embodiment of the invention, a rho-kinase inhibitor of the invention is administered and an anti-neoplastic agent are administered to a subject in need thereof. In another embodiment, a rho-kinase inhibitor of the invention and an angiogenesis inhibitor are administered to a subject in need thereof. In another embodiment, a rho-kinase inhibitor of the invention and an anti-inflammatory agent are administered to a subject in need thereof. In yet another embodiment, a rho-kinase inhibitor of the invention and an immunosuppressant are administered. The second agent can be, without limitation, a small molecule, an antibody or antigen binding fragment thereof, or radiation.

Antineoplastic agents include, without limitation, cytotoxic chemotherapeutic agents, targeted small molecules and biological molecules, and radiation. Compounds and agents that can be administered for oncological treatment, in addition to a rho kinase inhibitor of the invention, include the following: irinotecan, etoposide, camptothecin, 5-fluorouracil, hydroxyurea, tamoxifen, paclitaxel, capcitabine, carboplatin, cisplatin, bleomycin, dactomycin, gemcitabine, doxorubicin, danorubicin, cyclophosphamide, and radiotherapy, which can be external (e.g., external beam radiation therapy (EBRT)) or internal (e.g., brachytherapy (BT)).

Targeted small molecules and biological molecules include, without limitation, inhibitors of components of signal transduction pathways, such as modulators of tyrosine kinases and inhibitors of receptor tyrosine kinases, and agents that bind to tumor-specific antigens. Examples include inhibitors of epidermal growth factor receptor (EGFR), including gefitinib, erlotinib, and cetuximab, inhibitors of HER2 (e.g., trastuzumab, trastuzumab emtansine (trastuzumab-DM1; T-DM1) and pertuzumab), anti-VEGF antibodies and fragments (e.g., bevacizumab), antibodies that inhibit CD20 (e.g., rituximab, ibritumomab), anti-VEGFR antibodies (e.g., ramucirumab (IMC-1121B), IMC-1C11, and CDP791), anti-PDGFR antibodies, and imatinib. Small molecule kinase inhibitors can be specific for a particular tyrosine kinase or be inhibitors of two or more kinases. For example, the compound N-(3,4-dichloro-2-fluorophenyl)-7-({[(3 aR,6aS)-2-methyloctahydrocyclopenta[c]pyrrol-5-yl]methyl}oxy)-6-(methyloxy)quinazolin-4-amine (also known as XL647, EXEL-7647 and KD-019) is an in vitro inhibitor of several receptor tyrosine kinases (RTKs), including EGFR, EphB4, KDR (VEGFR), Flt4 (VEGFR3) and ErbB2, and is also an inhibitor of the SRC kinase, which is involved in pathways that result in nonresponsiveness of tumors to certain TKIs. In an embodiment of the invention, treatment of a subject in need comprises administration of a rho-kinase inhibitor of Formula I and administration of KD-019.

Dasatinib (BMS-354825; Bristol-Myers Squibb, New York) is another orally bioavailable, ATP-site competitive Src inhibitor. Dasatanib also targets Bcr-Abl (FDA-approved for use in patients with chronic myelogenous leukemia (CML) or Philadelphia chromosome positive (Ph+) acute lymphoblastic leukemia (ALL)) as well as c-Kit, PDGFR, c-FMS, EphA2, and Src family kinases. Two other oral tyrosine kinase inhibitor of Src and Bcr-Abl are bosutinib (SKI-606) and saracatinib (AZD0530).

According to the invention, angiogenesis inhibitors can be administered to a subject in conjunction with compounds of the invention. Angiogenesis inhibitors include any substance that inhibits the growth of new blood vessels. For example, angiogenesis inhibitors include antagonists of VEGF, PlGF, and VEGF receptors, including the antibodies disclosed herein. By inhibitor is meant an inhibitor of a biological process or inhibitor of a target. In this regard, an angiogenesis inhibitor is an agent that reduces angiogenesis. A Rho-kinase inhibitor is an agent, such as a competitive inhibitor of ATP binding, that inhibits an intrinsic activity or blocks an interaction of Rho-kinase. By antagonist is meant a substance that reduces or inhibits an activity or function in a cell associated with a target. For example, a VEGF antagonist reduces or blocks a function in a cell that is associated with VEGF. A VEGF antagonist may act on VEGF, by binding to VEGF and blocking binding to its receptors and/or may act on another cellular component involved in VEGF-mediated signal transduction. Similarly, a VEGFR2 antagonist is an agent that reduces or blocks VEGFR2-mediated signal transduction by binding to VEGFR2 and blocking ligand binding or interaction with a VEGFR2 substrate, or acts on another cellular component to reduce or block VEGFR2-mediated signal transduction. Thus, angiogenesis inhibitors include antagonists of, without limitation, VEGF, VEGFR1, VEGFR2, PDGF, PDGFR-β, neuropilin-1 (NRP1), and complement.

Non-limiting examples of VEGF-binding agents include VEGF antibodies and VEGF traps (i.e., ligand binding domains of VEGF receptors. In general, a VEGF trap is a protein that comprises VEGF binding domains of one or more VEGF receptor protein. VEGF-traps include, without limitation, soluble VEGFR-1, soluble neuropilin 1 (NRP1), soluble VEGFR-3 (which binds VEGF-C and VEGF-D), and aflibercept (Zaltrap; Eyelea; VEGF Trap R1R2), comprised of segments of the extracellular domains of human vascular endothelial growth factor receptors VEGFR1 and VEGFR2 fused to the constant region (Fc) of human IgG1. Conbercept (KH902) is a fusion protein which contains the extracellular domain 2 of VEGFR-1 (Flt-1) and extracellular domain 3, 4 of VEGFR-2 (KDR) fused to the Fc portion of human IgG1. Several VEGF traps containing KDR and FLT-1 Ig-like domains in various combinations are disclosed in U.S. Pat. No. 8,216,575. DARPins (an acronym for designed ankyrin repeat proteins) are genetically engineered antibody mimetic proteins typically exhibiting highly specific and high-affinity target protein binding. DARPin® MP0112 is a vascular endothelial growth factor (VEGF) inhibitor and has entered clinical trials for the treatment of wet macular degeneration and diabetic macular edema.

According to the invention, VEGF expression can be targeted. For example, VEGF inhibitor PTC299 targets VEGF post-transcriptionally by selectively binding the 5'- and 3'-untranslated regions (UTR) of VEGF messenger RNA (mRNA), thereby preventing translation of VEGF. Pegaptanib (Macugen) is an RNA aptamer directed against VEGF-165.

Placental growth factor (PlGF) has been implicated in pathological angiogenesis. PlGF is structurally related to VEGF and is also a ligand for VEGFR-1. Consequently, VEGF traps comprising the extracellular domain of VEGFR1 (see above) are useful for targeting PlGF.

PDGF is composed of four polypeptide chains that form homodimers PDGF-AA, BB, CC, and DD as well as the heterodimer PDGF-AB. The PDGF receptors (PDGFR)-α and -β mediate PDGF functions. Specifically, PDGFRα binds to PDGF-AA, -BB, -AB, and -CC, whereas PDGFRβ interacts with -BB and -DD. Non-limiting examples of PDGF-binding agents include anti-PDGF antibodies and PDGF traps. Agents that target PDGF include Fovista™ (E10030, Ophthotech), a pegylated aptamer targeting PDGF-B, and AX102 (Sennino et al., 2007, Cancer Res. 75(15):7359-67), a DNA oligonucleotide aptamer that binds PDGF-B.

Agents that target PDGF receptors include ramucirumab (IMC-3G3, human IgG$_1$) an anti-PDGFRα antibody, crenolanib (CP-868596), a selective inhibitor of PDGFRα (IC$_{50}$=0.9 nM) and PDGFRβ (IC$_{50}$=1.8 nM), and nilotinib (Tasigna®), an inhibitor of PDGFRα and PDGFRβ and other tyrosine kinases.

Angiogenesis inhibitors include intracellular agents that block signal transduction mediated by, for example, VEGF, PDGF, ligands of VEGF or PDGF receptors, or complement. Intracellular agents that inhibit angiogenesis inhibitors include the following, without limitation. Sunitinib (Sutent; SU11248) is a panspecific small-molecule inhibitor of VEGFR1-VEGFR3, PDGFRα and PDGFRβ, stem cell factor receptor (cKIT), Flt-3, and colony-stimulating factor-1 receptor (CSF-1R). Axitinib (AG013736; Inlyta) is another small molecule tyrosine kinase inhibitor that inhibits VEGFR-1-VEGFR-3, PDGFR, and cKIT. Cediranib (AZD2171) is an inhibitor of VEGFR-1-VEGFR-3, PDGFRβ, and cKIT. Sorafenib (Nexavar) is another small molecular inhibitor of several tyrosine protein kinases, including VEGFR, PDGFR, and Raf kinases. Pazopanib (Votrient; GW786034) inhibits VEGFR-1, -2 and -3, cKIT and PDGFR. Foretinib (GSK1363089; XL880) inhibits VEGFR2 and MET. CP-547632 is as a potent inhibitor of the VEGFR-2 and basic fibroblast growth factor (FGF) kinases. E-3810 ((6-(7-((1-aminocyclopropyl) methoxy)-6-methoxyquinolin-4-yloxy)-N-methyl-1-naphthamide) inhibits VEGFR-1, -2, and -3 and FGFR-1 and -2 kinases in the nanomolar range. Brivanib (BMS-582664) is a VEGFR-2 inhibitor that also inhibits FGF receptor signaling. CT-322 (Adnectin) is a small protein based on a human fibronectin domain and binds to and inhibits activation of VEGFR2. Vandetanib (Caprelas; Zactima; ZD6474) is an inhibitor of VEGFR2, EGFR, and RET tyrosine kinases. X-82 (Xcovery) is a small molecule indolinone inhibitor of signaling through the growth factor receptors VEGFR and PDGFR Anti-inflammatories and immunosuppressants include steroid drugs such as glucocorticoids (e.g., dexamethasone), FK506 (tacrolimus), ciclosporin, fingolimod, interferon, such as IFNβ or IFNγ, a tumor necrosis factor-alpha (TNF-α) binding protein such as infliximab (Remicade), etanercept (Enbrel), or adalimumab (Humira), and mycophenolic acid.

In certain embodiments, ROCK inhibitors of the invention are coadministered with agents used to treat metabolic disorders. For example, for treatment of obesity, the ROCK inhibitors may be combined with weight loss drugs such as, but not limited to, phentermine, fat adsorption inhibitors (e.g., Xenical), appetite suppressants, and the like. Procedures used to assist weight loss include, for example, stomach bands, stomach bypass or stapling. For insulin resistance or metabolic syndrome or hyperinsulinemia, ROCK inhibitors of the invention can be coadministered with compounds that lower cholesterol levels, for example, one or more medicines such as statins, fibrates, or nicotinic acid. For high blood pressure associated with such diseases, ROCK inhibitors of the invention can be coadministered with, for example, one or more antihypertensive medicines such as diuretics or angiotensin-converting enzyme (ACE) inhibitors. ROCK inhibitors of the invention can be administered in a treatment program that includes lifestyle changes such as increased physical activity, an improved diet, and/or quitting smoking. In certain embodiments, the ROCK inhibitor is ROCK2 selective.

Th17 cells are novel subset of helper $CD4^+$ T cells that secrete IL-17, IL-21 and IL-22. The pro-inflammatory activity of Th17 cells can be beneficial to the host during infection, but uncontrolled Th17 function has been linked and actively involved in several autoimmune pathologies. Indeed, high levels of IL-17 are detected in the sera and biopsies of rheumatoid arthritis (RA) and systemic lupus erythematosus (SLE) patients which correlates with destruction of synovial tissue and disease activity. The pathological role of IL-17 in arthritic joints is associated with its stimulation of pro-inflammatory cytokine production and increased recruitment of T cells and innate immune cells. Moreover, numbers of Th17 cells are significantly increased in the peripheral blood of RA patients as well as elevated concentrations of IL-17 were seen in supernatants of their PBMCs after stimulation with anti-CD3/CD28 antibodies ex vivo. In addition, in multiple sclerosis (MS) patients, myelin reactive Th17 cells are also enriched and produce high amounts of IL-22 and IFN-γ. Further, a significantly higher number of $IL-17^+$ cells is detected in disease-affected gut areas compared to healthy areas of the same subjects with Crohn's disease (CD).

The development and function of Th17 cells depends on activation of specific intracellular signaling pathways. The steroid receptor-type nuclear receptor RORγt is selectively expressed in Th17 cells and appears to be required for IL-17 production. The induction of RORγt has been observed to be mediated by IL-6, IL-21 and IL-23 via a STAT3-dependent mechanism. STAT3 also binds directly to the IL-17 and IL-21 promoters. In addition to RORγt and STAT3, the interferon regulatory factor 4 (IRF4) is required for the differentiation of Th17 cells since IRF4 KO mice failed to mount Th17 response and were resistant to development of autoimmune responses. Recent studies have demonstrated that phosphorylation of IRF4 by Rho-kinase 2 (ROCK2) regulates IL-17 and IL-21 production and development of autoimmunity in mice.

According to the invention, targeting Th17 (IL-17-secreting) cells by rho-kinase inhibition provides a method for treating Th17 cell-mediated diseases, including but not limited to autoimmune disorders such as rheumatoid arthritis (RA) multiple sclerosis (MS), systemic luypus srythematosus (SLE), psoriasis, Crohn's disease, atopic dermatitis, eczema, and GVHD in humans. In an embodiment of the invention, the Rho-kinase inhibitor is a compound of Formula I. In some embodiments, the rho-kinase inhibitor inhibits ROCK1 and ROCK2. In some embodiments, the rho-kinase inhibitor selectively inhibits ROCK2. Selective inhibition of ROCK2 provides for treatment of Th17 cell-mediated diseases and reduces or prevents toxicities associated with complete inhibition of ROCK activity.

Regulatory T cells (Tregs) play a critical role in the maintenance of immunological tolerance to self-antigens and inhibition of autoimmune responses, but, at the same time, prevent an effective immune response against tumor cells. Indeed, Tregs isolated from the peripheral blood of patients with autoimmune disease, such as rheumatoid arthritis (RA) and multiple sclerosis (MS), show a defect in their ability to suppress effector T cell function, while increased accumulation of Tregs correlates with a poor prognosis in many cancers. Thus, the level of Treg function effects a balance between effective immunity and avoidance of pathological autoreactivity.

The development and function of Tregs depend on activation of specific signaling transduction pathways. TGF-β and IL-2 activate expression of Foxp3 and STAT5 transcription factors that both play an essential role in the control of Treg suppressive function. On the other hand, pro-inflammatory cytokines inhibit Foxp3 expression via up-regulation of STAT3 phosphorylation. As shown herein, pharmacological inhibition of ROCK2 (e.g., with selective ROCK2 inhibitors such as KD025, ROCK2-specific siRNA-mediated inhibition of ROCK2), but not ROCK1, leads to downregulation of STAT3 phosphorylation, interferon regulatory factor 4 (IRF4) and steroid receptor-type nuclear receptor RORγt protein levels in human T cells.

Furthermore, as demonstrated herein, targeting ROCK2 with a selective inhibitor (e.g., KD025) leads to an increased proportion of $Foxp3^+$ T cells via a STAT5-dependent mechanism and positively regulates their suppressive activity towards autoreactive lymphocytes. This effect of ROCK2 inhibition on Tregs is critical to limiting or preventing the onset of aberrant self-immune responses. This effect may be shown, for example, by assaying the ability of Tregs treated with a ROCK2 inhibitor to inhibit proliferation and cytokine secretion in target cells in vitro.

Accordingly, ROCK2 inhibitors of the invention effectively reduce or prevent chronic GVHD pathologies. As shown herein, the compounds of the invention reduce or prevent cGVHD pathologies in target organs. For example, a selective ROCK2 inhibitor administered to a transplant patient maintains or restores pulmonary function. The maintenance or restoration of pulmonary function correlates with reduced germinal center activity which would otherwise lead to production of autoreactive antibodies, and with reduced collagen deposition and antibody deposition in affected tissues. These pathologies are common to other targets of cGVHD as well, e.g., skin, gut, and liver, which would be similarly reduced or prevented.

It is to be understood and expected that variations in the principles of invention herein disclosed may be made by one skilled in the art and it is intended that such modifications are to be included within the scope of the present invention.

Throughout this application, various publications are referenced. These publications are hereby incorporated into this application by reference in their entireties to more fully describe the state of the art to which this invention pertains. The following examples further illustrate the invention, but should not be construed to limit the scope of the invention in any way.

EXAMPLES

Abbreviations used in the following examples and preparations include:
Ac₂O acetic anhydride
AcOH acetic acid
Bn Benzyl
Celite® diatomaceous earth
DCM dichloromethane
DIEA di-isopropylethylamine
DMAP 4-dimethylamino pyridine
DME 1,2-dimethoxyethane
DMF dimethylformamide
DMSO dimethyl sulfoxide
EDC 1-(3-dimethylaminopropyl)-3-ethylcarbodiimide hydrochloride
EtOAc ethyl acetate
EtOH ethyl alcohol or ethanol
Et₂O ethyl ether
Et₃N triethylamine
g grams
HOBt 1-hydroxybenzotriazole
HPLC high pressure liquid chromatography
h hour(s)
MeCN acetonitrile
min minute(s)
MeOH methyl alcohol or methanol
mL milliliter
mmol millimoles
MS mass spectrometry
NMR nuclear magnetic resonance
iPrOH iso-propanol
PyBOP® benzotriazol-1-yl-oxytripyrrolidinophosphonium
rt room temperature
s singlet
t triplet
THF tetrahydrofuran Mass spectrometry was conducted by: SynPep Co., 6905 Ct. Dublin, Calif. 94568, or it was recorded on an LC-MS: Waters 2695 Separations Module with a Waters ZQ2000 single quadrapole MS detector. Unless stated all mass spectrometry was run in ESI mode. ¹H NMR spectra were recorded on a Varian 400 MHz machine using Mercury software. In sofar the synthesis of the following examples of compounds of the present invention is not explicitly described in such example, the synthesis is as described herein in general terms and the appropriate starting material can be easily selected for synthesizing the compound of the example.

Example 1

2-Bromo-N-isoopropylacetamide

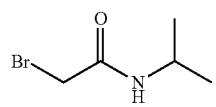

A solution of iso-propyl amine (5.0 g, 7.20 mL, 84.6 mmol) in 63 mL of DCM was cooled to −10° C. To this was added a solution of α-bromoacetylbromide (8.53 g, 3.68 mL, 42.3 mmol) in 10.5 mL of DCM. The reaction mixture was stirred for 10 min. The iso-propylammonium hydrobromide was filtered from the mixture and the filtrate then concentrated in vacuo to give the title compound as a white solid (5.30 g, 70%).

Example 2

N-isopropyl-2-(3-(4,4,5,5-tetramethyl-1,3,2-dioxaborolan-2-yl)phenoxy)acetamide

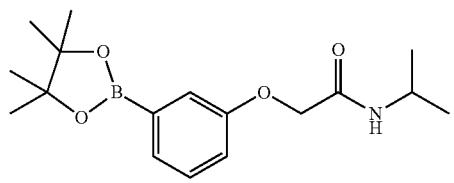 [SMILES: CC(C)NC(=O)COc1cccc(B2OC(C)(C)C(C)(C)O2)c1]

A mixture of 3-(4,4,5,5-tetramethyl-1,3,2-dioxaborolan-2-yl)phenol (0.50 g, 2.27 mmol), 2-bromo-N-isoopropylacetamide (0.61 g, 3.41 mmol), and K₂CO₃ (0.47 g, 3.41 mmol) in DMF (3 mL) was stirred at rt followed by addition of ice water. The precipitate was filtered and washed with water and dried to provide the title compound (0.32 g, 44%).

Example 3 tert-Butyl 5-((2-chloropyrimidin-4-yl)amino)-1H-indazole-1-carboxylate

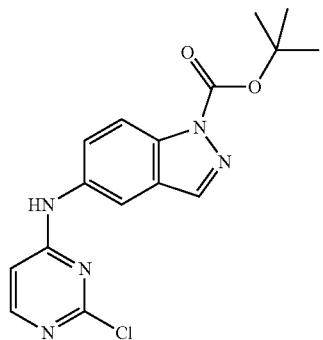 [SMILES: CC(C)(C)OC(=O)n1ncc2cc(Nc3ccnc(Cl)n3)ccc21]

A mixture of 2,4-dichloropyrimidine (1.99 g, 13.4 mmol), tert-butyl 5-amino-1H-indazole-1-carboxylate (3.4 g, 14.7 mmol), DIEA (3 mL), and DMF (13 mL) was stirred at 65° C. for 7 h, concentrated in vacuo, and titurated with Et₂O. The precipitate was filtered and washed with IPA and dried to provide the title compound (1.83 g, 40%).

Example 4 tert-Butyl 5-((2-(3-(2-(isopropylamino)-2-oxoethoxy)phenyl)pyrimidin-4-yl)amino)-1H-indazole-1-carboxylate

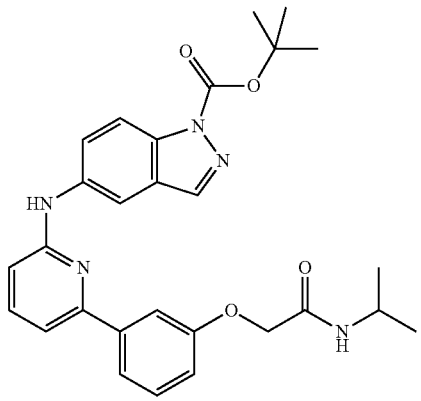 [SMILES: CC(C)NC(=O)COc1cccc(-c2cccc(Nc3ccc4c(cnn4C(=O)OC(C)(C)C)c3)n2)c1]

A mixture of tert-butyl 5-((2-chloropyrimidin-4-yl)amino)-1H-indazole-1-carboxylate (100 mg, 0.29 mmol), N-isopropyl-2-(3-(4,4,5,5-tetramethyl-1,3,2-dioxaborolan-2-yl)phenoxy)acetamide (130 mg, 0.41 mmol), Pd(dppf)Cl$_2$.CH$_2$Cl$_2$ (20 mg, 0.02 mmol), and K$_2$CO$_3$ (80 mg, 0.58 mmol) in dioxane/water (10 and 2 mL) was heated in microwave for 30 min. The reaction was worked up and purified by chromatography to provide the title compound (176 mg, 35%).

Example 5

2-(3-(4-((1H-indazol-5-yl)amino)pyrimidin-2-yl)phenoxy)-N-isopropylacetamide HCl salt

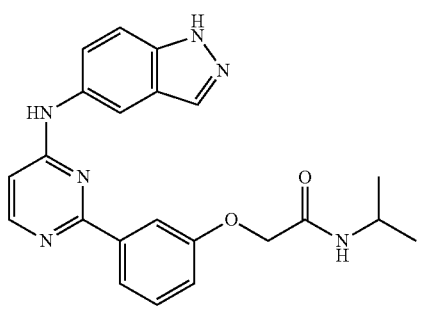

tert-Butyl 5-((2-(3-(2-(isopropylamino)-2-oxoethoxy)phenyl)pyrimidin-4-yl)amino)-1H-indazole-1-carboxylate was taken up in 4 M HCl in dioxane and stirred at rt for 2 h. The volatiles were removed in vacuo to give the title compound as HCl salt. $^1$H NMR (400 MHz, DMSO-d$_6$) δ12.6 (d, J=6.8 Hz, 6H), 3.93 (m, 1H), 4.51 (s, 2H), 6.75 (d, J=6 Hz, 1H), 7.14 (d, J=7.6 Hz, 1H), 7.44-7.59 (m, 3H), 7.87-7.91 (m, 3H), 8.09 (s, 1H), 8.18 (s, 1H), 8.31 (d, J=6.4 Hz, 1H), 10.19 (d, J=0.8 Hz, 1H), 13.10 (s, 1H). MS (ES+) m/e 403 (M+H)$^+$.

Example 6 tert-butyl 2-(3-(4,4,5,5-tetramethyl-1,3,2-dioxaborolan-2-yl)phenoxy)acetate

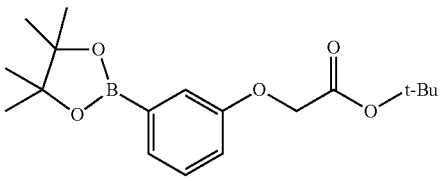 [SMILES: CC(C)(C)OC(=O)COc1cccc(B2OC(C)(C)C(C)(C)O2)c1]

3-(4,4,5,5-tetramethyl-1,3,2-dioxaborolan-2-yl)phenol, tert-butyl 2-bromoacetate A mixture of 3-(4,4,5,5-tetramethyl-1,3,2-dioxaborolan-2-yl)phenol (4 g, 18.2 mmol), tert-butyl 2-bromoacetate (5.7 g, 27.3 mmol) and K$_2$CO$_3$ (3.44 g, 27.3 mmol) in CH$_3$CN (100 mL) was stirred at 70° C. overnight. The reaction mixture was poured into water and extracted with EtOAc. The organic layer was dried over Na$_2$SO$_4$ and removed to give a residue. The residue was purified by column chromatograph to give the title compound (4 g, 67%) as a white solid.

Example 7

N-(2-chloropyrimidin-4-yl)-1H-indazol-5-amine

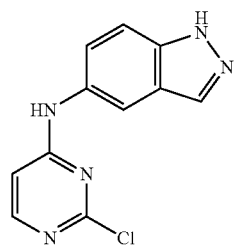 [SMILES: Clc1nccc(Nc2ccc3[nH]ncc3c2)n1]

A mixture of compound 2,4-dichloropyrimidine (14.8 g, 0.1 mol), 1H-indazol-5-amine (14.6 g, 110 mmol) and Et$_3$N (15 g, 150 mmol) in EtOH (200 mL) was stirred at 80° C. for 3 hrs. The reaction mixture was cooled and filtered. The filtered cake was collected and dried to give compound 5 (15 g, 60%) as a solid.

Example 8 tert-butyl 5-((tert-butoxycarbonyl)(2-chloropyrimidin-4-yl)amino)-1H-indazole-1-carboxylate

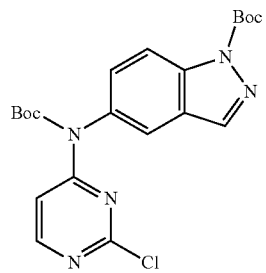 [SMILES: CC(C)(C)OC(=O)N(c1ccc2c(cnn2C(=O)OC(C)(C)C)c1)c1ccnc(Cl)n1]

To a mixture of N-(2-chloropyrimidin-4-yl)-1H-indazol-5-amine (7.35 g, 30 mmol), Boc$_2$O (18.9 g, 90 mmol) in CH$_2$Cl$_2$ (150 mL) was added DMAP (3.6 g, 30 mmol) at 0° C. during 5 min. After 0.5 hr, the reaction was completed. The reaction mixture was washed with water, dried over Na$_2$SO$_4$ and removed to give a residue, which was purified by gel column chromatograph to give the title compound (6 g, 67%) as a white solid.

Example 9 tert-butyl 5-((2-(3-(2-(tert-butoxy)-2-oxoethoxy) phenyl)pyrimidin-4-yl)(tert-butoxycarbonyl)amino)-1H-indazole-1-carboxylate

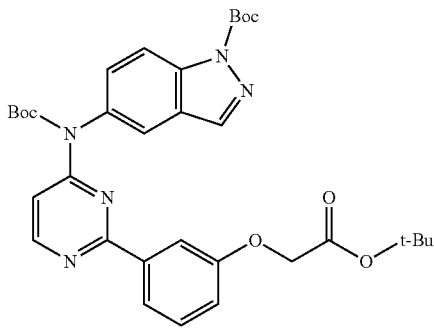 [SMILES: CC(C)(C)OC(=O)COc1cccc(-c2nccc(N(C(=O)OC(C)(C)C)c3ccc4c(cnn4C(=O)OC(C)(C)C)c3)n2)c1]

A mixture of tert-butyl 5-((tert-butoxycarbonyl)(2-chloropyrimidin-4-yl)amino)-1H-indazole-1-carboxylate (4 g, 8.9 mmol), tert-butyl 2-(3-(4,4,5,5-tetramethyl-1,3,2-dioxaborolan-2-yl)phenoxy)acetate (3.3 g, 10 mmol), KOAc (35 g, 360 mmol), Pd(dppf)$_2$Cl$_2$ (400 mg) and Boc$_2$O (3.9 g, 18 mmol) in dioxane/water (10/1, 100 mL) was stirred at 100° C. for 3 days. The reaction mixture was poured into water and extracted with EtOAc. The organic layer was dried over Na$_2$SO$_4$ and removed to give a residue, which was purified by gel column chromatograph to give the title compound (3 g, 54%) as a solid.

Example 10

2-(3-(4-((1H-indazol-5-yl)amino)pyrimidin-2-yl) phenoxy)acetic acid

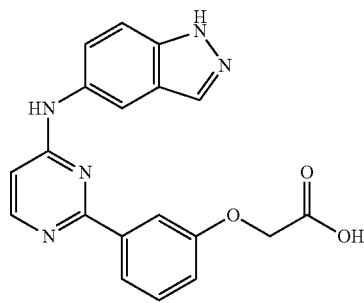 [SMILES: O=C(O)COc1cccc(-c2nccc(Nc3ccc4[nH]ncc4c3)n2)c1]

A mixture of compound tert-butyl 5-((2-(3-(2-(tert-butoxy)-2-oxoethoxy)phenyl)pyrimidin-4-yl)(tert-butoxycarbonyl)amino)-1H-indazole-1-carboxylate (2 g) and CF$_3$COOH (20 mL) in DCM (20 mL) was stirred at 25° C. for 2 hrs. The solvent was removed to give the title compound (1.5 g) as a yellow solid.

Example 11

(S)-tert-butyl 3-(2-(3-(4-((1H-indazol-5-yl)amino) pyrimidin-2-yl)phenoxy)acetamido)pyrrolidine-1-carboxylate

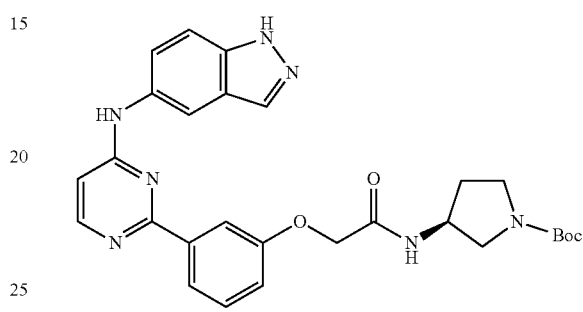

A mixture of 2-(3-(4-((1H-indazol-5-yl)amino)pyrimidin-2-yl)phenoxy)acetic acid (600 mg, 1.66 mmol), 3-aminopyrrolidine-1-carboxylic acid tert-butyl ester (300 mg, 1.62 mmol), HATU (760 mg, 2 mmol) and Et$_3$N (250 mg, 2 mmol) in DMF (18 mL) was stirred at 25° C. overnight. The reaction mixture was poured into water and extracted with EtOAc. The organic layer was dried over Na$_2$SO$_4$ and concentrated to give a residue, which was purified by HPLC to provide the title compound (300 mg, 50%) as a solid.

Example 12

(R)-2-(3-(4-((1H-indazol-5-yl)amino)pyrimidin-2-yl) phenoxy)-N-(pyrrolidin-3-yl)acetamide HCl salt

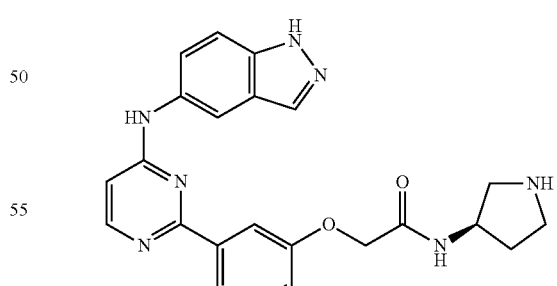

$^1$H NMR (400 MHz, DMSO-d$_6$) δ1.84-1.96 (m, 1H), 2.07-2.19 (m, 1H), 3.07-3.38 (m, 4H), 4.40-4.42 (m, 1H), 4.65 (s, 2H), 7.36 (d, J=6.4 Hz, 1H), 7.56 (t, J=8.0 Hz, 1H), 7.65 (d, J=8.0 Hz, 1H), 7.90-7.94 (m, 2H), 8.14-8.29 (m, 2H), 8.66 (d, J=6.8 Hz, 1H), 9.39-9.80 (m, 3H), 11.87 (s, 1H). MS (ES+) m/e 430 (M+H)$^+$.

Example 13

(R)-2-(3-(4-((1H-indazol-5-yl)amino)pyrimidin-2-yl)phenoxy)-N-(pyrrolidin-3-yl)acetamide HCl salt

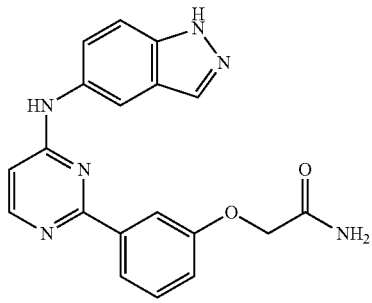 [SMILES: NC(=O)COc1cccc(-c2nccc(Nc3ccc4[nH]ncc4c3)n2)c1]

A mixture of compound 2-(3-(4-((1H-indazol-5-yl)amino)pyrimidin-2-yl)phenoxy)acetic acid (500 mg, 1.39 mmol), NH$_4$Cl (125 mg, 2 mmol), HATU (720 mg, 1.89 mmol) and Et$_3$N (200 mg, 2 mmol) in DMF (15 mL) was stirred at 25° C. overnight. The reaction mixture was poured into water and extracted with EtOAc. The organic layer was dried over Na$_2$SO$_4$ and concentrated to give a residue, which was purified by HPLC to provide the title compound (60.1 mg, 12%) as a solid. $^1$H NMR (400 MHz, DMSO-d$_6$) δ4.52 (s, 2H), 6.78 (d, J=6.4 Hz, 1H), 7.19 (dd, J=9.6 and 1.6 Hz, 1H), 7.40-7.62 (m, 5H), 7.84-7.87 (m, 2H), 8.11 (s, 1H), 8.15 (s, 1H), 8.33 (d, J=6.4 Hz, 1H), 10.35 (s, 1H). MS (ES+) m/e 361 (M+H)$^+$.

Example 14

2-(3-(4-((1H-indazol-5-yl)amino)pyrimidin-2-yl)phenoxy)-1-(1,1-dioxidothiomorpholino)ethanone TFA salt

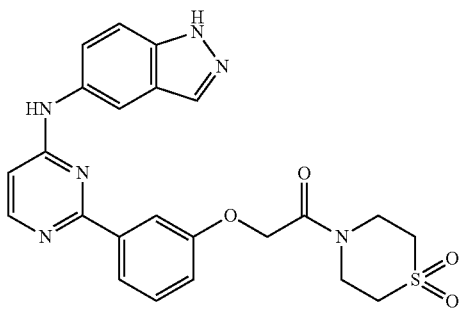 [SMILES: O=C(COc1cccc(-c2nccc(Nc3ccc4[nH]ncc4c3)n2)c1)N1CCS(=O)(=O)CC1]

A mixture of compound 2-(3-(4-((1H-indazol-5-yl)amino)pyrimidin-2-yl)phenoxy)acetic acid (500 mg, 1.39 mmol), thiomorpholine 1,1-dioxide (375 mg, 2.2 mmol), HATU (720 mg, 1.89 mmol) and Et3N (200 mg, 2 mmol) in DMF (15 mL) was stirred at 25° C. overnight. The reaction mixture was poured into water and extracted with EtOAc. The organic layer was dried over Na2SO4 and concentrated to give a residue, which was purified by pre-HPLC to give the title compound (54.6 mg, 10%) as a solid. 1H NMR (400 MHz, DMSO-d6) δ3.11 (b, 2H), 3.30 (b, 2H), 3.85 (b, 4H), 5.00 (s, 2H), 6.76 (d, J=6.4 Hz, 1H), 6.91 (s, 1H), 7.09 (s, 1H), 7.16 (dd, J=8.0 and 2.4 Hz, 1H), 7.45 (t, J=8.0 Hz, 1H), 7.47-7.50 (m, 2H), 7.81 (s, 1H), 7.86 (d, J=8.0 Hz, 1H), 8.08 (s, 1H), 8.12 (b, 1H), 8.33 (d, J=6.4 Hz, 1H), 10.26 (s, 1H). MS (ES+) m/e 479 (M+H)$^+$.

Example 15

N-(3-(4,4,5,5-tetramethyl-1,3,2-dioxaborolan-2-yl)phenyl)morpholine-4-carboxamide

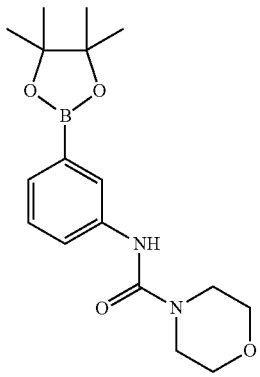 [SMILES: CC1(C)OB(c2cccc(NC(=O)N3CCOCC3)c2)OC1(C)C]

To a mixture of triphosgene (600 mg, 2 mmol) in THF (10 mL) was dropped a solution of 3-(4,4,5,5-tetramethyl-1,3,2-dioxaborolan-2-yl)aniline (836 mg, 4 mmol) and Et$_3$N (1.2 g, 12 mmol) in THF (10 mL) during 10 min at 40° C. After 0.5 hr, morpholine (435 mg, 5 mmol) was added to the reaction mixture. After 15 min, the reaction mixture was quenched with saturated NH$_4$Cl, extracted with EtOAc. The organic layer was dried over Na$_2$SO$_4$ and concentrated to give a residue, which was purified by gel column chromatography to give the title compound (530 mg, 50%) as a white solid.

Example 16 tert-butyl 5-((tert-butoxycarbonyl)(2-(3-(morpholine-4-carboxamido)phenyl)pyrimidin-4-yl)amino)-1H-indazole-1-carboxylate

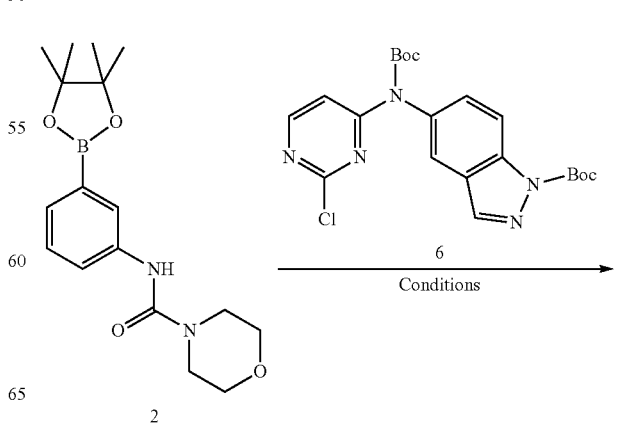

-continued

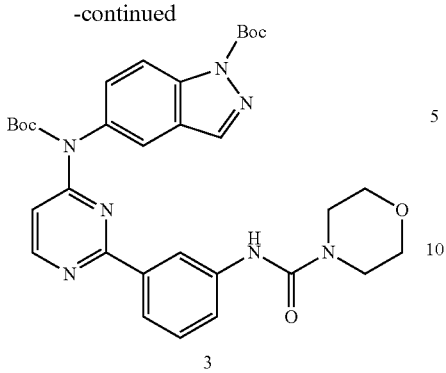

A mixture of tert-butyl 5-((tert-butoxycarbonyl)(2-chloropyrimidin-4-yl)amino)-1H-indazole-1-carboxylate (300 mg, 0.7 mmol), N-(3-(4,4,5,5-tetramethyl-1,3,2-dioxaborolan-2-yl)phenyl)morpholine-4-carboxamide (250 mg, 0.8 mmol), CsF (510 mg, 3 mmol), Pd(PPh$_3$)$_4$ (120 mg) and Boc$_2$O (432 mg, 2 mmol) in dioxane/water (10/1, 10 mL) was stirred at 130° C. under microwave for 20 min. Three pots were combined. The reaction mixture was diluted with water and extracted with EtOAc. The organic layer was dried over Na$_2$SO$_4$ and concentrated to give a residue, which was purified by column chromatograph to give the title compound (360 mg).

Example 17

N-(3-(4-((1H-indazol-5-yl)amino)pyrimidin-2-yl)phenyl)morpholine-4-carboxamide HCl salt

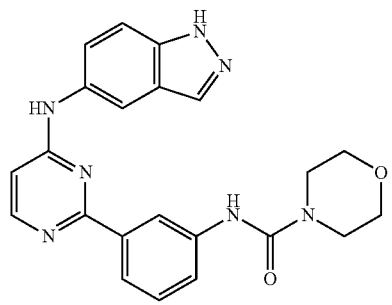 [SMILES: O=C(Nc1cccc(-c2nccc(Nc3ccc4[nH]ncc4c3)n2)c1)N1CCOCC1]

A mixture of tert-butyl 5-((tert-butoxycarbonyl)(2-(3-(morpholine-4-carboxamido)phenyl)pyrimidin-4-yl)amino)-1H-indazole-1-carboxylate (360 mg, crude) in MeOH/HCl (4M, 20 mL) was stirred at 25° C. overnight. The reaction mixture was concentrated to give title compound (68 mg) as an HCl salt. $^1$H NMR (400 MHz, DMSO-d$_6$) δ3.49 (s, 4H), 3.62 (s, 4H), 7.14 (b, 1H), 7.50 (t, J=7.6 Hz, 1H), 7.60-7.65 (m, 3H), 7.88 (d, J=6.8 Hz, 1H), 8.22 (s, 1H), 8.28 (d, J=5.6 Hz, 1H), 8.46 (b, 1H), 8.68 (s, 1H), 9.00 (s, 1H), 11.77 (s, 1H). MS (ES+) m/e 416 (M+H)$^+$.

Example 18

Methyl 3-(4-((1H-indazol-5-yl)amino)pyrimidin-2-yl)benzoate

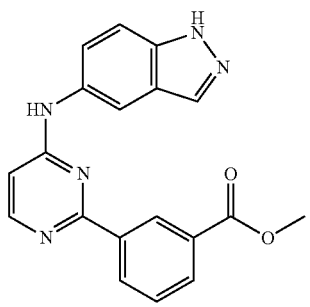 [SMILES: COC(=O)c1cccc(-c2nccc(Nc3ccc4[nH]ncc4c3)n2)c1]

A mixture of N-(2-chloropyrimidin-4-yl)-1H-indazol-5-amine (3.7 g, 15 mmol), 3-methoxycarbonylphenylboronic acid (3.3 g, 18 mmol), K$_2$CO$_3$ (4.14 g, 30 mmol) and Pd(dppf)$_2$Cl$_2$ (700 mg) in dioxane/water (4/1, 75 mL) was stirred at 100° C. for 16 hrs. The reaction mixture was concentrated to give the title compound (7 g, crude) which was carried out directly for next step reaction without further purification.

Example 19

3-(4-((1H-indazol-5-yl)amino)pyrimidin-2-yl)benzoic acid

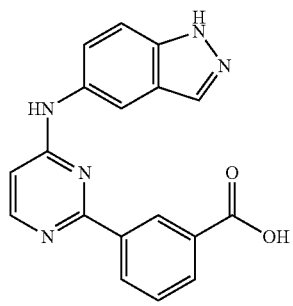 [SMILES: O=C(O)c1cccc(-c2nccc(Nc3ccc4[nH]ncc4c3)n2)c1]

To a mixture of methyl 3-(4-((1H-indazol-5-yl)amino)pyrimidin-2-yl)benzoate (7 g, crude) in dioxane (120 mL) was added NaOH (2M, 120 mL). The reaction mixture was refluxed for 1.5 h and was then cooled to rt and extracted with EtOAc (100 mL). The aqueous phase was separated and acidified with HCl (6M). The mixture was filtered and the filter cake was collected, dried to give the title compound (1.3 g, crude) used for the next step reaction directly.

Example 20

3-(4-((1H-indazol-5-yl)amino)pyrimidin-2-yl)-N-(1,1-dioxidotetrahydro-2H-thiopyran-4-yl)benzamide TFA salt

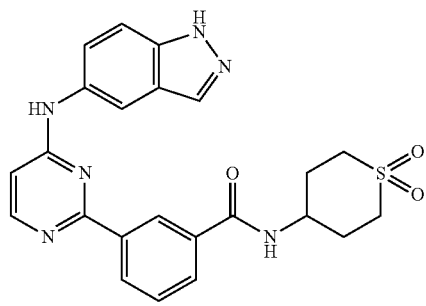 [SMILES: O=C(NC1CCS(=O)(=O)CC1)c1cccc(-c2nccc(Nc3ccc4[nH]ncc4c3)n2)c1]

To the mixture of 3-(4-((1H-indazol-5-yl)amino)pyrimidin-2-yl)benzoic acid (400 mg, 1.2 mmol), 4-aminotetrahydro-2H-thiopyran 1,1-dioxide (300 mg, 1.4 mmol), HATU (720 mg, 1.89 mmol) and Et$_3$N (200 mg, 2 mmol) in DMF (15 mL) was stirred at 25° C. overnight. The reaction mixture was poured into water and extracted with EtOAc. The organic layer was dried over Na$_2$SO$_4$ and concentrated to give a residue, which was purified by HPLC to give the title compound (81 mg, 20%) as a solid. $^1$H NMR (400 MHz, CD$_3$OD) δ2.19-2.24 (m, 2H), 2.31-2.33 (m, 2H), 3.12-3.15 (m, 2H), 3.34-3.38 (m, 2H), 4.23-4.28 (m, 1H), 6.93 (d, J=6.8 Hz, 1H), 7.58-7.76 (m, 3H), 8.12 (s, 1H), 8.14 (s, 1H), 8.24 (d, J=7.2 Hz, 1H), 8.31 (d, J=8.0 Hz, 1H), 8.65 (s, 1H). MS (ES+) m/e 463 (M+H)$^+$.

Example 21 tert-Butyl 4-(3-(4-((1H-indazol-5-yl)amino)pyrimidin-2-yl)benzamido)piperidine-1-carboxylate

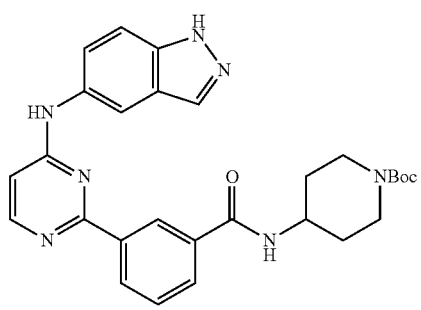 [SMILES: CC(C)(C)OC(=O)N1CCC(NC(=O)c2cccc(-c3nccc(Nc4ccc5[nH]ncc5c4)n3)c2)CC1]

A mixture of 3-(4-((1H-indazol-5-yl)amino)pyrimidin-2-yl)benzoic acid (400 mg, 1.2 mmol), 4-amino-piperidine-1-carboxylic acid tert-butyl ester (300 mg, 1.5 mmol), HATU (720 mg, 1.89 mmol) and Et$_3$N (200 mg, 2 mmol) in DMF (15 mL) was stirred at 25° C. overnight. The reaction mixture was poured into water and extracted with EtOAc. The organic layer was dried over Na$_2$SO$_4$ and concentrated to give a residue, which was purified by HPLC to provide the title compound (200 mg, 30%) as a solid.

Example 22

3-(4-((1H-indazol-5-yl)amino)pyrimidin-2-yl)-N-(piperidin-4-yl)benzamide HCl salt

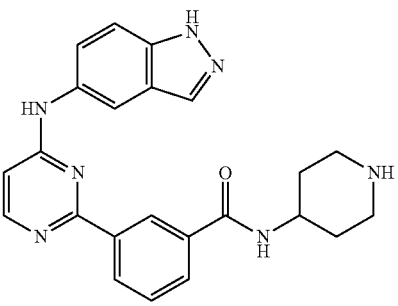 [SMILES: O=C(NC1CCNCC1)c1cccc(-c2nccc(Nc3ccc4[nH]ncc4c3)n2)c1]

A mixture of tert-butyl 4-(3-(4-((1H-indazol-5-yl)amino)pyrimidin-2-yl)benzamido)piperidine-1-carboxylate (200 mg) in HCl in MeOH (5 mL) was stirred at 25° C. for 3 h. The solvent was removed to provide the title compound (150 mg) as a yellow solid. $^1$H NMR (400 MHz, DMSO-d$_6$) δ1.79-1.87 (m, 2H), 1.98-2.01 (m, 2H), 3.01-3.04 (m, 2H), 3.32-3.36 (m, 2H), 3.64-3.69 (m, 1H), 7.10-7.15 (m, 1H), 7.66 (d, J=8.0 Hz, 1H), 7.75 (t, J=8 Hz, 1H), 8.16 (s, 1H), 8.20 (s, 1H), 8.36 (d, J=6.8 Hz, 1H), 8.42 (d, J=7.6 Hz, 1H), 8.78 (d, J=7.2 Hz, 1H), 8.90 (s, 1H), 8.96 (s, 1H), 11.73 (s, 1H). MS (ES+) m/e 414 (M+H)$^+$.

Example 23

N-(2-chloro-5-methylpyrimidin-4-yl)-1H-indazol-5-amine

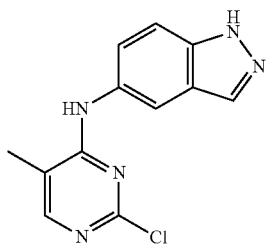 [SMILES: Cc1cnc(Cl)nc1Nc1ccc2[nH]ncc2c1]

To a mixture of compound 2,4-dichloro-5-methylpyrimidine (5 g, 30.8 mmol) and 5-aminoindazole (4.1 g, 30.8 mmol) in anhydrous ethanol (100 mL) was added Na$_2$CO$_3$ (16 g, 154 mmol). The resulting mixture was heated at 80° C. overnight under N$_2$. After cooling to room temperature, the mixture was diluted with water and extracted with EtOAc. The organic phase was dried over anhydrous Na$_2$SO$_4$ and concentrated in vacuo followed by column chromatography on silica gel (eluted with DCM:MeOH=50:1) to provide the title compound (7 g, yield 87%) as a brown solid.

Example 24 tert-butyl 5-((tert-butoxycarbonyl)(2-chloro-5-methylpyrimidin-4-yl)amino)-1H-indazole-1-carboxylate

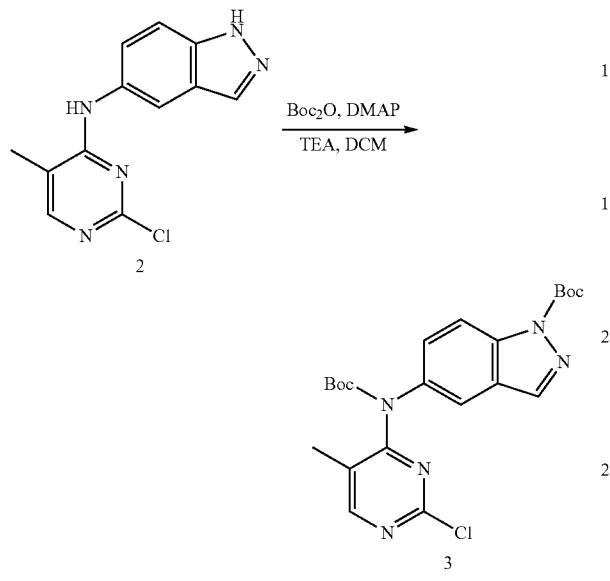

To a solution of N-(2-chloro-5-methylpyrimidin-4-yl)-1H-indazol-5-amine (5 g, 19.3 mmol) in anhydrous DCM (100 mL) was added Boc₂O (12.6 g, 57.9 mmol), TEA (5.85 g, 57.9 mmol) and DMAP (1.17 g, 9.56 mmol). The resulting mixture was stirred at room temperature for 4 h. The mixture was diluted with water and extracted with DCM. The organic phase was dried over anhydrous Na₂SO₄, and the solvent was removed in vacuo followed by purification by column chromatograph on silica gel (eluted with PE:EA=10:1) to give compound the title compound (5 g, yield 56%) as a white solid.

Example 25 tert-butyl 5-((tert-butoxycarbonyl)(2-(3-(2-(cyclopropylamino)-2-oxoethoxy)phenyl)-5-methylpyrimidin-4-yl)amino)-1H-indazole-1-carboxylate

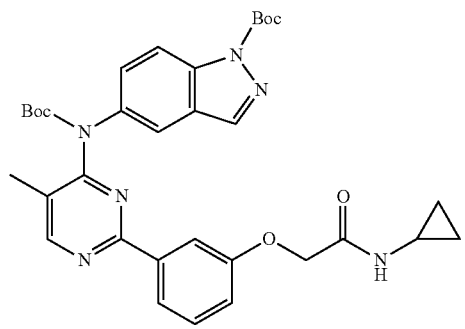 [SMILES: Cc1cnc(-c2cccc(OCC(=O)NC3CC3)c2)nc1N(C(=O)OC(C)(C)C)c1ccc2c(cnn2C(=O)OC(C)(C)C)c1]

To a mixture of compound tert-butyl 5-((tert-butoxycarbonyl)(2-chloro-5-methylpyrimidin-4-yl)amino)-1H-indazole-1-carboxylate (1.9 g, 4.14 mmol), compound N-cyclopropyl-2-(3-(4,4,5,5-tetramethyl-1,3,2-dioxaborolan-2-yl)phenoxy)acetamide (1.57 g, 4.97 mmol) and CsF (1.89 g, 12.42 mmol) in 1,4-dioxane (20 mL) and water (5 mL) was added Pd(PPh₃)₄ (239 mg, 0.21 mmol). The resulting mixture was heated at 100° C. overnight under N₂. After cooling to room temperature, the mixture was diluted with water and extracted with EtOAc, the organic phase was dried over anhydrous Na₂SO₄ and concentrated under reduced pressure to give a residue, which was purified by column chromatography on silica gel (eluted with PE:EA=5:1) to provide the title compound (1.6 g, yield 62%) as a yellow solid.

Example 26

2-(3-(4-((1H-indazol-5-yl)amino)-5-methylpyrimidin-2-yl)phenoxy)-N-cyclopropylacetamide hydrochloride

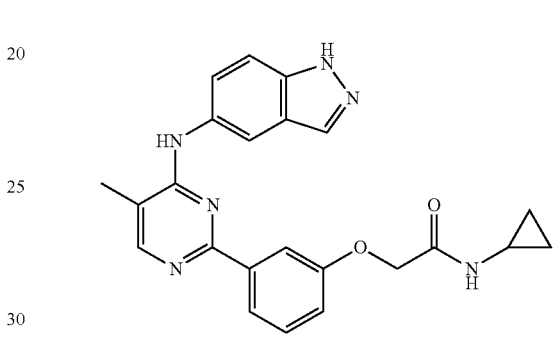

To a solution of compound tert-butyl 5-((tert-butoxycarbonyl)(2-(3-(2-(cyclopropylamino)-2-oxoethoxy)phenyl)-5-methylpyrimidin-4-yl)amino)-1H-indazole-1-carboxylate (500 mg, 0.81 mmol) in EtOAc (2 mL) was added HCl/EtOAc (10 mL) and stirred at room temperature overnight. The formed precipitated was filtered and washed with EtOAc, dried in vacuo to afford the title compound (300 mg, yield 89%) as a yellow solid. $^1$H NMR (400 MHz, CD₃OD) δ0.50-0.54 (m, 2H), 0.70-0.75 (m, 2H), 2.42 (s, 3H), 2.66-2.71 (m, 1H), 4.51 (s, 2H), 7.27 (dd, J=8.4 and 2.4 Hz, 1H), 7.49 (t, J=8.0 Hz, 1H), 7.64-7.68 (m, 2H), 7.72 (s, 1H), 8.04 (s, 2H), 8.20 (s, 1H), 8.28 (s, 1H). MS (ES+) m/e 451 (M+H)⁺.

Example 27 tert-butyl 5-((tert-butoxycarbonyl)(2-(3-(2-((1-(tert-butoxycarbonyl)piperidin-4-yl)amino)-2-oxoethoxy)phenyl)-5-methylpyrimidin-4-yl)amino)-1H-indazole-1-carboxylate

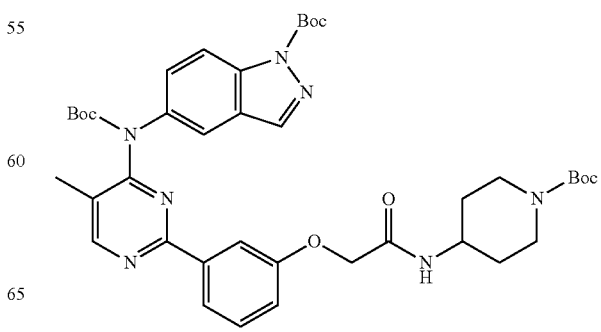

To a mixture of tert-butyl 5-((tert-butoxycarbonyl)(2-chloro-5-methylpyrimidin-4-yl)amino)-1H-indazole-1-carboxylate (1.4 g, 3.05 mmol), tert-butyl 4-(2-(3-(4,4,5,5-tetramethyl-1,3,2-dioxaborolan-2-yl)phenoxy)acetamido)piperidine-1-carboxylate (1.68 g, 3.66 mmol) and CsF (1.39 g, 9.15 mmol) in 1,4-dioxane (20 mL) and water (5 mL) was added Pd(PPh₃)₄ (176 mg, 0.15 mmol). The resulting mixture was heated at 100° C. overnight under N₂. After cooling to room temperature, the mixture was diluted with water and extracted with EtOAc, the organic phase was dried over anhydrous Na₂SO₄ and concentrated under reduced pressure to give a residue, which was purified by column chromatography on silica gel (eluted with PE:EA=1:1) to afford the title compound (1.1 g, yield 47%) as a yellow solid.

Example 28

2-(3-(4-((1H-indazol-5-yl)amino)-5-methylpyrimidin-2-yl)phenoxy)-N-(piperidin-4-yl)acetamide hydrochloride

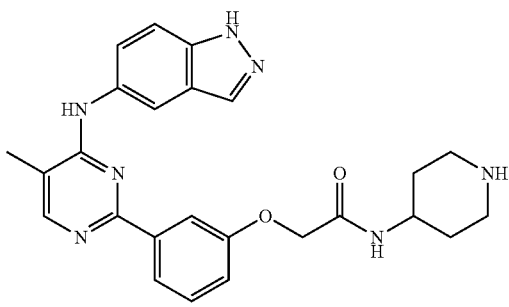 [SMILES: Cc1cnc(-c2cccc(OCC(=O)NC3CCNCC3)c2)nc1Nc1ccc2[nH]ncc2c1]

To a solution of tert-butyl 5-((tert-butoxycarbonyl)(2-(3-(2-((1-(tert-butoxycarbonyl)piperidin-4-yl)amino)-2-oxoethoxy)phenyl)-5-methylpyrimidin-4-yl)amino)-1H-indazole-1-carboxylate (700 mg, 0.92 mmol) in EtOAc (2 mL) was added HCl/EtOAc (10 mL) and stirred at room temperature overnight. The formed precipitated was filtered and washed with EtOAc, dried in vacuo to afford the title compound (230 mg, yield 54%) as a yellow solid. ¹H NMR (400 MHz, CD₃OD) δ1.73-1.84 (m, 2H), 2.01-2.05 (m, 2H), 2.42 (s, 3H), 3.02-3.09 (m, 2H), 3.39-3.43 (m, 2H), 3.99-4.05 (m, 1H), 4.57 (s, 2H), 7.30 (dd, J=8.4 and 2.4 Hz, 1H), 7.51 (t, J=8.4 Hz, 1H), 7.67-7.74 (m, 4H), 8.05 (s, 1H), 8.20 (s, 1H), 8.24 (s, 1H). MS (ES+) m/e 494 (M+H)⁺.

Example 29 tert-butyl 2-(3-bromophenoxy)acetate

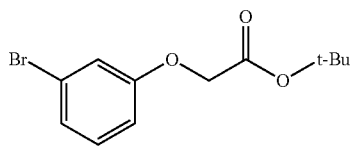 [SMILES: CC(C)(C)OC(=O)COc1cccc(Br)c1]

To a solution of 3-bromophenol (5 g, 28.9 mmol) in MeCN (100 mL) was added t-butyl bromoacetate (6.76 g, 34.7 mmol) and K₂CO₃ (5.98 g, 43.3 mmol). The resulting mixture was heated at 80° C. overnight under nitrogen. After cooling to room temperature, the mixture was diluted with water and extracted with EtOAc. The organic layer was washed with brine and dried over Na₂SO₄, filtrated and concentrated to give the residue, which was purified by column chromatography on silica gel (PE:EA=50:1) to give the title compound (7 g, yield 84%) as a oil liquid.

Example 30

2-(3-bromophenoxy)acetyl chloride

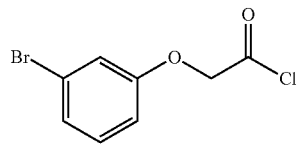 [SMILES: O=C(Cl)COc1cccc(Br)c1]

To a solution of tert-butyl 2-(3-bromophenoxy)acetate (4.6 g, 16 mmol) in anhydrous DCM (50 mL) was added TFA (18 g, 0.16 mol) and stirred at room temperature overnight. After TLC showed the reaction was completed, the mixture was concentrated under reduced pressure to get a crude acid. The acid was dissolved in anhydrous DCM (50 mL), oxalyl chloride (2.44 g, 19.2 mmol) and DMF (0.2 mL) were added into the solution. The mixture was stirred at room temperature for 4 h. The mixture was concentrated under reduced pressure to provide a white solid, which was used for next step reaction without further purification.

Example 31

2-(3-bromophenoxy)-N-cyclopropylacetamide

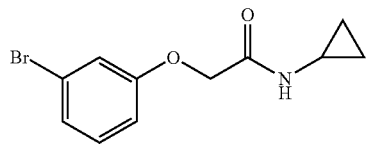

To a solution of 2-(3-bromophenoxy)acetyl chloride (2.3 g, 9.24 mmol) in anhydrous DCM (30 mL) was added triethylamine (2.8 g, 27.7 mmol) and cyclopropylamine (632 mg, 11.1 mmol) at 0° C. Then the resulting mixture was stirred at room temperature overnight. The reaction was diluted with water and extracted with EtOAc. The organic layer was dried over anhydrous Na₂SO₄ and concentrated under reduced pressure to give a residue, which was purified by column chromatography on silica gel (eluted with PE:EA=5:1) to give the title compound (1.95 g, yield 78%) as a white solid.

Example 32

N-cyclopropyl-2-(3-(4,4,5,5-tetramethyl-1,3,2-dioxaborolan-2-yl)phenoxy)acetamide

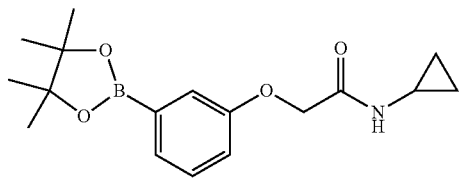 [SMILES: CC1(C)OB(c2cccc(OCC(=O)NC3CC3)c2)OC1(C)C]

To a mixture of 2-(3-bromophenoxy)-N-cyclopropylacetamide (1.95 g, 7.25 mmol), bis(pinacolato)diboron (2.76 g, 10.87 mmol) and KOAc (2.13 g, 21.7 mmol) in DMSO (20 mL) was added Pd(dppf)Cl$_2$-DCM (265 mg, 0.36 mmol). The resulting mixture was heated at 100° C. overnight under N$_2$. After cooling to room temperature, the mixture was diluted with water and extracted with EtOAc, the organic phase was dried over anhydrous Na$_2$SO$_4$ and concentrated under reduced pressure to give a residue, which was purified by column chromatography on silica gel (eluted with PE:EA=10:1) to provide the title compound (1.4 g, yield 60%) as a white solid.

Example 33 tert-butyl 4-(2-(3-bromophenoxy)acetamido)piperidine-1-carboxylate

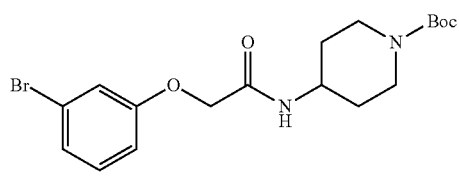 [SMILES: CC(C)(C)OC(=O)N1CCC(NC(=O)COc2cccc(Br)c2)CC1]

To a solution of 2-(3-bromophenoxy)acetyl chloride (2.1 g, 8.43 mmol) in anhydrous DCM (30 mL) was added triethylamine (2.56 g, 25.3 mmol) and 4-amino-1-Boc-piperidine (2.02 g, 10.1 mmol) at 0° C. Then the resulting mixture was stirred at room temperature overnight. The reaction was diluted with water and extracted with EtOAc. The organic layer was dried over anhydrous Na$_2$SO$_4$ and concentrated under reduced pressure to give a residue, which was purified by column chromatography on silica gel (eluted with PE:EA=5:1) to give the tile compound (2.8 g, yield 80%) as a white solid.

Example 34 tert-butyl 4-(2-(3-(4,4,5,5-tetramethyl-1,3,2-dioxaborolan-2-yl)phenoxy)acetamido)piperidine-1-carboxylate

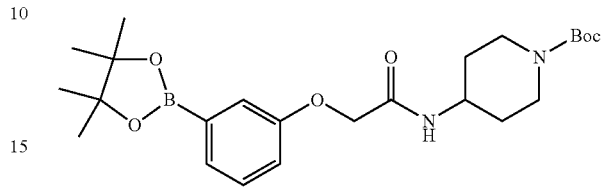

To a mixture of tert-butyl 4-(2-(3-bromophenoxy)acetamido)piperidine-1-carboxylate (2.8 g, 6.79 mmol), bis(pinacolato)diboron (2.59 g, 10.2 mmol), and KOAc (1.99 g, 20.4 mmol) in DMSO (30 mL) was added Pd(dppf)Cl$_2$-DCM (249 mg, 0.34 mmol). The resulting mixture was heated to 100° C. overnight under N$_2$. After cooling to room temperature, the mixture was diluted with water and extracted with EtOAc, the organic phase was dried over anhydrous Na$_2$SO$_4$ and concentrated under reduced pressure to give a residue, which was purified by column chromatography on silica gel (eluted with PE:EA=5:1) to provide the title compound (1.7 g, yield 54%) as a white solid.

Example 35

N-(2-chloropyrimidin-4-yl)-6-fluoro-1H-indazol-5-amine

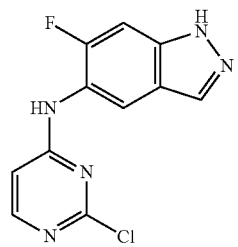 [SMILES: Fc1cc2[nH]ncc2cc1Nc1ccnc(Cl)n1]

To a mixture of 2,4-dichloropyrimidine (730 mg, 4.89 mmol) and 6-fluoro-5-aminoindazole (740 mg, 4.89 mmol) in anhydrous ethanol (15 mL) was added Na$_2$CO$_3$ (1.56 g, 14.7 mmol). The resulting mixture was heated at 80° C. overnight under N$_2$. After cooling to room temperature, the mixture was diluted with water and extracted with EtOAc, the organic phase was dried over anhydrous Na$_2$SO$_4$ and concentrated under reduced pressure to give a residue, which was purified by column chromatography on silica gel (eluted with PE:EA=3:1) to provide the title compound (750 mg, yield 58%) as a brown solid.

Example 36 tert-butyl 5-((tert-butoxycarbonyl)(2-chloropyrimidin-4-yl)amino)-6-fluoro-1H-indazole-1-carboxylate

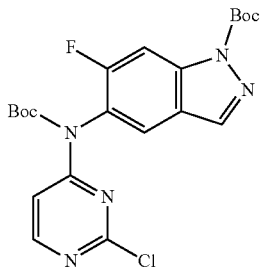 [SMILES: CC(C)(C)OC(=O)N(c1ccnc(Cl)n1)c1cc2cnn(C(=O)OC(C)(C)C)c2cc1F]

To a solution of N-(2-chloropyrimidin-4-yl)-6-fluoro-1H-indazol-5-amine (750 mg, 2.85 mmol) in anhydrous DCM (10 mL) was added Boc$_2$O (1.86 g, 8.55 mmol), TEA (864 mg, 8.55 mmol) and DMAP (173 mg, 1.42 mmol). The resulting mixture was stirred at room temperature for 4 hrs. The mixture was diluted with water and extracted with DCM. The organic phase was dried over anhydrous Na$_2$SO$_4$, and the solvent was removed in vacuum to give a residue, which was purified by column chromatograph on silica gel (eluted with PE:EA=20:1) to give the title compound (800 g, yield 60%) as a white solid.

Example 37 tert-butyl 5-((tert-butoxycarbonyl)(2-(3-(2-(isopropylamino)-2-oxoethoxy)phenyl)pyrimidin-4-yl)amino)-6-fluoro-1H-indazole-1-carboxylate

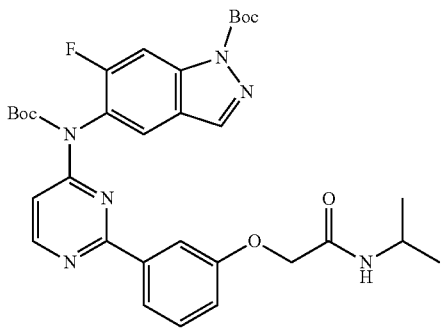 [SMILES: CC(C)NC(=O)COc1cccc(-c2nccc(N(C(=O)OC(C)(C)C)c3cc4cnn(C(=O)OC(C)(C)C)c4cc3F)n2)c1]

To a mixture of tert-butyl 5-((tert-butoxycarbonyl)(2-chloropyrimidin-4-yl)amino)-6-fluoro-1H-indazole-1-carboxylate (920 mg, 1.98 mmol) in 1,4-dioxane (16 mL) and water (4 mL) was added N-isopropyl-2-(3-(4,4,5,5-tetramethyl-1,3,2-dioxaborolan-2-yl)phenoxy)acetamide (760 mg, 2.38 mmol), Pd(PPh$_3$)$_4$ (115 mg, 0.1 mmol) and CsF (906 mg, 5.96 mmol). The resulting mixture was heated at 100° C. overnight under N$_2$. After cooling to room temperature, the mixture was diluted with water and extracted with EtOAc, the organic phase was dried over anhydrous Na$_2$SO$_4$ and concentrated under reduced pressure to give a residue, which was purified by column chromatography on silica gel (eluted with PE:EA=3:1) to provide the title compound (600 mg, yield 48%) as a yellow solid.

Example 38

2-(3-(4-((6-fluoro-1H-indazol-5-yl)amino)pyrimidin-2-yl)phenoxy)-N-isopropylacetamide hydrochloride

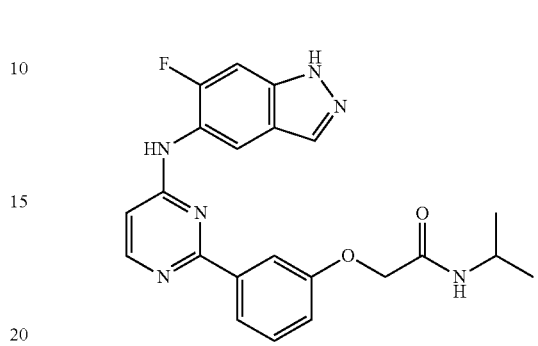

To a mixture of tert-butyl 5-((tert-butoxycarbonyl)(2-(3-(2-(isopropylamino)-2-oxoethoxy)phenyl)pyrimidin-4-yl)amino)-6-fluoro-1H-indazole-1-carboxylate (520 mg, 0.84 mmol) in EtOAc (2 mL) was added HCl/EtOAc (10 mL) and stirred at room temperature overnight. The formed precipitate was filtered and washed with EtOAc, dried in vacuo to afford the title compound (200 mg, yield 56%) as a yellow solid. $^1$H NMR (400 MHz, DMSO-d$_6$) δ1.04 (d, J=6.4 Hz, 6H), 3.88-3.93 (m, 1H), 4.51 (s, 2H), 7.00 (b, 1H), 7.22 (d, J=7.6 Hz, 1H), 7.49 (t, J=7.6 Hz, 1H), 7.56 (d, J=10.4 Hz, 1H), 7.75-7.79 (m, 2H), 7.93 (d, J=7.2 Hz, 1H), 8.09 (d, J=6.4 Hz, 1H), 8.16 (s, 1H), 8.36 (d, J=6.4 Hz, 1H), 11.09 (s, 1H). MS (ES+) m/e 457 (M+H)$^+$.

Example 39

N-(2-chloro-5-methoxypyrimidin-4-yl)-1H-indazol-5-amine

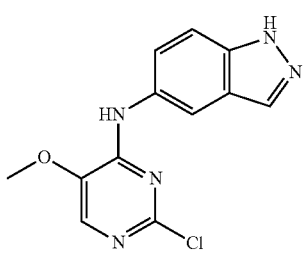 [SMILES: COc1cnc(Cl)nc1Nc1ccc2[nH]ncc2c1]

To the mixture of 2,4-dichloro-5-methoxypyrimidine (3.56 g, 0.02 mol) in EtOH (80 mL) was added 1H-indazol-5-amine (2.66 g, 0.02 mol), and then DIEA (7.8 g, 0.06 mol). The resulting mixture was stirred at 45° C. overnight. The reaction mixture was cooled to room temperature and filtered. The cake was rinsed by MTBE and collected to give the title compound (4.4 g, yield 81%) as brown solid.

Example 40 tert-butyl 5-((tert-butoxycarbonyl)(2-chloro-5-methoxypyrimidin-4-yl)amino)-1H-indazole-1-carboxylate

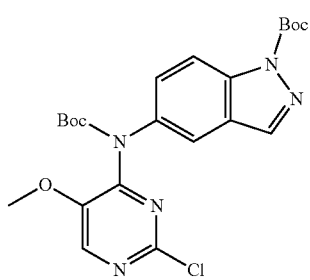 [SMILES: COc1cnc(Cl)nc1N(C(=O)OC(C)(C)C)c1ccc2c(cnn2C(=O)OC(C)(C)C)c1]

To the mixture of N-(2-chloro-5-methoxypyrimidin-4-yl)-1H-indazol-5-amine (4.2 g, 15.3 mmol) in DCM (50 mL) were added TEA (4.6 g, 45.9 mmol), (Boc)$_2$O (8.32 g, 38.2 mmol), and DMAP (0.2 g). The resulting mixture was stirred at room temperature for 1 h and concentrated followed by purification by column chromatograph to provide the title compound (5.5 g, yield 76%) as light yellow solid.

Example 41 tert-butyl 5-((tert-butoxycarbonyl)(2-(3-(2-(isopropylamino)-2-oxoethoxy)phenyl)-5-methoxypyrimidin-4-yl)amino)-1H-indazole-1-carboxylate

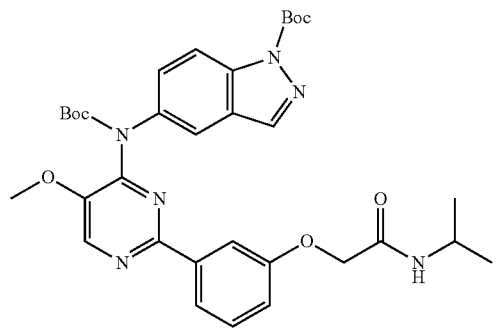 [SMILES: COc1cnc(-c2cccc(OCC(=O)NC(C)C)c2)nc1N(C(=O)OC(C)(C)C)c1ccc2c(cnn2C(=O)OC(C)(C)C)c1]

To the solution of tert-butyl 5-((tert-butoxycarbonyl)(2-chloro-5-methoxypyrimidin-4-yl)amino)-1H-indazole-1-carboxylate (1.5 g, 3.16 mmol) in the solvents (dioxane:water=10:1, 33 ml) were added N-isopropyl-2-(3-(4,4,5,5-tetramethyl-1,3,2-dioxaborolan-2-yl) phenoxy)acetamide (1.2 g, 3.79 mmol), (Boc)$_2$O (1.38 g, 6.32 mmol), CsF (1.4 g, 9.48 mmol), and then Pd(PPh$_3$)$_4$ (0.11 g, 0.095 mmol) under N$_2$. The resulting mixture was stirred at 90° C. for 24 hrs. The mixture was purified by column chromatograph to give the title compound (0.98 g, yield 49%) as white solid.

Example 42

2-(3-(4-((1H-indazol-5-yl)amino)-5-hydroxypyrimidin-2-yl)phenoxy)-N-isopropylacetamide

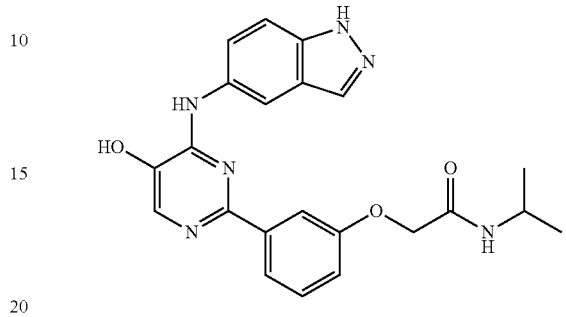

The mixture of tert-butyl 5-((tert-butoxycarbonyl)(2-(3-(2-(isopropylamino)-2-oxoethoxy)phenyl)-5-methoxypyrimidin-4-yl)amino)-1H-indazole-1-carboxylate (1.2 g, 2 mmol) and pyridine hydrochloride (7.8 g) was stirred at 140° C. for 1 hr. The reaction cooled to room temperature. Water (20 mL) was added followed by NH$_3$.H$_2$O to adjust the pH to 6-7. The mixture was filtered. The cake was collected and dried to give the title compound (0.46 g, yield 55%) as gray solid.

Example 43

2-(3-(4-((1H-indazol-5-yl)amino)-5-(2-(dimethylamino)ethoxy)pyrimidin-2-yl)phenoxy)-N-isopropylacetamide TFA salt

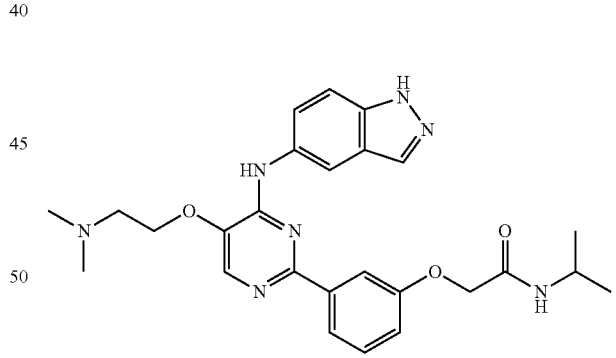

To the mixture of 2-(3-(4-((1H-indazol-5-yl)amino)-5-hydroxypyrimidin-2-yl)phenoxy)-N-isopropylacetamide (450 mg, 1.07 mmol) in THF (45 mL) were added 2-(dimethylamino) ethanol (115 mg, 1.29 mmol), and then PPh$_3$ (563 mg, 2.15 mmol) was added. The resulting mixture was stirred at room temperature for 0.5 hr. Then DEAD (374 mg, 2.15 mmol) was added. The resulting mixture was heated at reflux overnight. The solvent was removed under reduced pressure followed by addition of 10 mL EtOAc and 10 mL water. TFA was added to adjust pH=4-5. The aqueous solution was concentrated and purified by Prep HPLC to give the title compound (0.1 g, yield 10%) as yellow solid. ¹H NMR (400 MHz, DMSO-d₆) δ1.07 (d, J=6.4 Hz, 6H), 2.94 (d, J=4.0 Hz, 6H), 3.64-3.65 (m, 2H), 3.92-3.94 (m, 1H), 4.48 (s, 2H), 4.52-4.53 (m, 2H), 7.02 (dd, J=9.2 and 1.6 Hz, 1H), 7.37 (t, J=7.2 Hz, 1H), 7.60-7.89 (m, 5H), 8.12-8.19 (m, 3H), 8.90 (s, 1H), 9.60 (b, 1H). MS (ES+) m/e 490 (M+H)⁺.

Example 44

N-(2,6-dichloropyrimidin-4-yl)-1H-indazol-5-amine

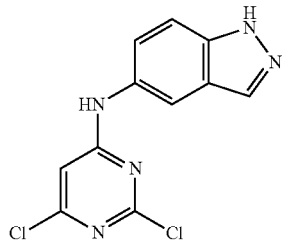 [SMILES: Clc1cc(Nc2ccc3[nH]ncc3c2)nc(Cl)n1]

A solution of 2,4,6-trichloropyrimidine (3.67 g, 20 mmol), 1H-indazol-5-amine (2.66 g, 20 mmol) and TEA (3.03 g, 30 mmol) in EtOH (75 mL) was heated at reflux overnight. After removing the solvent, the residue was re-crystallized in MeOH to provide the title compound (4.2 g, yield 50%) as a solid.

Example 45

N-(2-chloro-6-(4-methylpiperazin-1-yl)pyrimidin-4-yl)-1H-indazol-5-amine

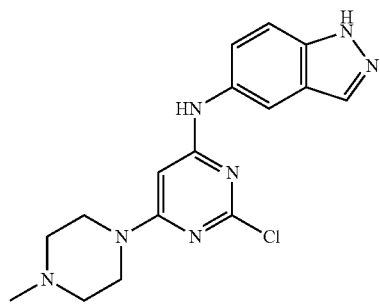 [SMILES: CN1CCN(c2cc(Nc3ccc4[nH]ncc4c3)nc(Cl)n2)CC1]

A solution of N-(2,6-dichloropyrimidin-4-yl)-1H-indazol-5-amine (4.2 g, 15 mmol), 1-methylpiperazine (2.0 g, 20 mmol) and TEA (3.03 g, 30 mmol) in MeOH (75 mL) was refluxed overnight. After removing the solvent, the residue was re-crystallized in DCM to give the title compound (3 g, yield 58%) as a solid.

Example 46 tert-butyl 5-((tert-butoxycarbonyl)(2-chloro-6-(4-methylpiperazin-1-yl)pyrimidin-4-yl)amino)-1H-indazole-1-carboxylate

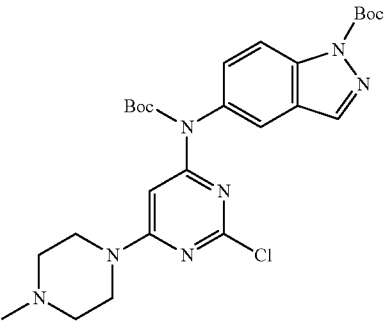 [SMILES: CN1CCN(c2cc(N(C(=O)OC(C)(C)C)c3ccc4c(cnn4C(=O)OC(C)(C)C)c3)nc(Cl)n2)CC1]

To a solution of N-(2-chloro-6-(4-methylpiperazin-1-yl)pyrimidin-4-yl)-1H-indazol-5-amine (1.5 g, 4.4 mmol) in DCM (20 mL) were added TEA (0.93 g, 9.2 mmol), (Boc)₂O (3 g, 13.9 mmol) and DMAP (1.1 g, 9.2 mmol). The resulting mixture was stirred at room temperature for 3 hrs. After removing the solvent, the residue was purified by column chromatography on silica gel (eluting with petroleum ether:ethyl acetate=50:1-10:1) to give the title (1.2 g, yield 50%) as a solid.

Example 47 tert-butyl 5-((tert-butoxycarbonyl)(2-(3-(2-(isopropylamino)-2-oxoethoxy)phenyl)-6-(4-methylpiperazin-1-yl)pyrimidin-4-yl)amino)-1H-indazole-1-carboxylate

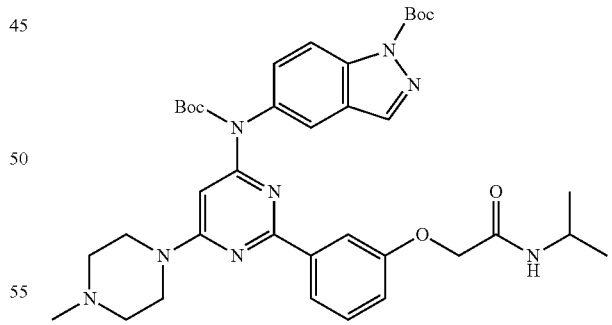

To a solution of tert-butyl 5-((tert-butoxycarbonyl)(2-chloro-6-(4-methylpiperazin-1-yl)pyrimidin-4-yl)amino)-1H-indazole-1-carboxylate (0.600 g, 1.1 mmol), Pd(dppf)Cl₂ (50 mg), CsF (0.501 g, 3.3 mmol) and N-isopropyl-2-(3-(4,4,5,5-tetramethyl-1,3,2-dioxaborolan-2-yl)phenoxy)acetamide (0.640 g, 2 mmol) in dioxane/water (10:1, 10 mL) was stirred at 100° C. overnight. After removing the solvent, the residue was purified by HPLC to give the title compound (250 mg, yield 32%).

Example 48

2-(3-(4-((1H-indazol-5-yl)amino)-6-(4-methylpiperazin-1-yl)pyrimidin-2-yl)phenoxy)-N-isopropylacetamide TFA salt

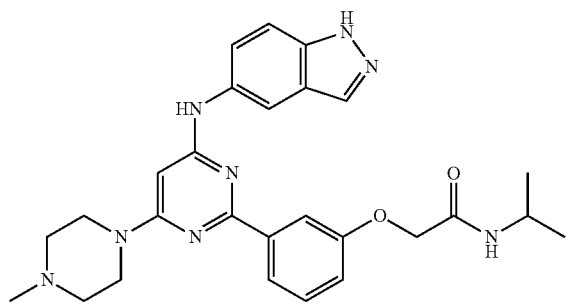 [SMILES: CC(C)NC(=O)COc1cccc(-c2nc(Nc3ccc4[nH]ncc4c3)cc(N3CCN(C)CC3)n2)c1]

A solution of tert-butyl 5-((tert-butoxycarbonyl)(2-(3-(2-(isopropylamino)-2-oxoethoxy)phenyl)-6-(4-methylpiperazin-1-yl)pyrimidin-4-yl)amino)-1H-indazole-1-carboxylate (250 mg, 0.36 mmol) in DCM (10 mL) and TFA (3.0 mL) was stirred at room temperature for 3 hrs. The mixture was concentrated in vacuo to provide the title compound (150 mg, yield 70%) as a solid. $^1$H NMR (400 MHz, DMSO-$d_6$) δ1.02 (d, J=6.4 Hz, 6H), 2.79 (s, 3H), 3.04 (b, 2H), 3.20-3.27 (m, 2H), 3.47-3.50 (m, 2H), 3.85-3.93 (m, 1H), 4.45 (s, 2H), 4.71-4.75 (m, 2H), 6.56 (s, 1H), 7.01 (dd, J=8.4 and 2.4 Hz, 1H), 7.36 (t, J=8.0 Hz, 1H), 7.41-7.52 (m, 4H), 7.88 (d, J=7.6 Hz, 1H), 7.98 (s, 2H), 9.53 (s, 1H), 10.00 (s, 1H). MS (ES+) m/e 501 (M+H)$^+$.

Example 49

N-(2-chloropyrimidin-4-yl)-6-methyl-1H-indazol-5-amine

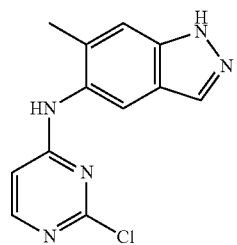

A solution of 2,4-dichloropyrimidine (0.69 g, 4.6 mmol), 6-methyl-1H-indazol-5-ylamine hydrochloride (0.85 g, 4.6 mmol) and TEA (1.4 g, 13.8 mmol) in EtOH (16 mL) was heated at reflux overnight. The volatiles were removed to give the crude title compound (1.7 g), which was used for the next step reaction without purification.

Example 50 tert-butyl 5-((tert-butoxycarbonyl)(2-chloropyrimidin-4-yl)amino)-6-methyl-1H-indazole-1-carboxylate

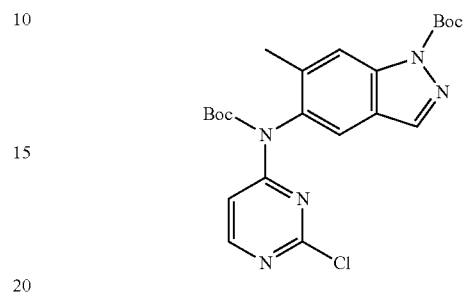

To a solution of N-(2-chloropyrimidin-4-yl)-6-methyl-1H-indazol-5-amine (1.7 g, crude) in DCM (20 mL) were added TEA (0.93 g, 9.2 mmol), (Boc)$_2$O (3 g, 13.9 mmol) and DMAP (1.1 g, 9.2 mmol). The resulting mixture was stirred at room temperature for 3 hrs. After removal of the solvent, the residue was purified by column chromatography on silica gel (eluting with petroleum ether:ethyl acetate=50:1-10:1) to give the title compound (0.45 g, yield 21.1% for 2 steps) as a solid.

Example 51 tert-butyl 5-((tert-butoxycarbonyl)(2-(3-(2-(isopropylamino)-2-oxoethoxy)phenyl)pyrimidin-4-yl)amino)-6-methyl-1H-indazole-1-carboxylate

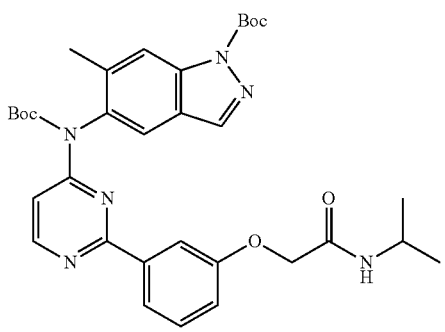 [SMILES: Cc1cc2c(cnn2C(=O)OC(C)(C)C)cc1N(C(=O)OC(C)(C)C)c1ccnc(-c2cccc(OCC(=O)NC(C)C)c2)n1]

A solution of tert-butyl 5-((tert-butoxycarbonyl)(2-chloropyrimidin-4-yl)amino)-6-methyl-1H-indazole-1-carboxylate (0.45 g, 1.67 mmol), Pd(dppf)Cl$_2$ (50 mg), Na$_2$CO$_3$ (0.35 g, 3.34 mmol) and N-isopropyl-2-(3-(4,4,5,5-tetramethyl-1,3,2-dioxaborolan-2-yl)phenoxy)acetamide (0.64 g, 2 mmol) in dioxane/water (10:1, 10 mL) was stirred at 100° C. overnight. After removing the solvent, the residue was purified by HPLC to give the title compound (180 mg, yield 17%).

Example 52

N-isopropyl-2-(3-(4-((6-methyl-1H-indazol-5-yl)amino)pyrimidin-2-yl)phenoxy)acetamide TFA salt

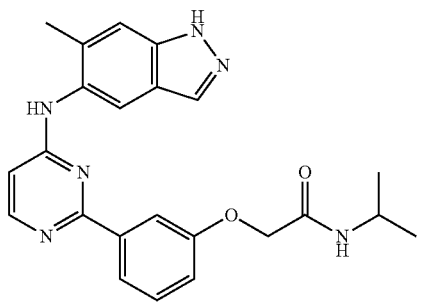 [SMILES: Cc1cc2[nH]ncc2cc1Nc1ccnc(-c2cccc(OCC(=O)NC(C)C)c2)n1]

To a solution of tert-butyl 5-((tert-butoxycarbonyl)(2-(3-(2-(isopropylamino)-2-oxoethoxy)phenyl)pyrimidin-4-yl)amino)-6-methyl-1H-indazole-1-carboxylate (180 mg, 0.29 mmol) in DCM (10 mL) was added TFA (1.5 mL) was added. The mixture was stirred at room temperature overnight and concentrated in vacuo to provide the title compound (170 mg, yield 96%). MS (ES+) m/e 417 (M+H)+.

Example 53

N-(2-chloropyrimidin-4-yl)-N-methyl-1H-indazol-5-amine

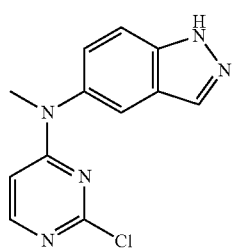 [SMILES: CN(c1ccc2[nH]ncc2c1)c1ccnc(Cl)n1]

To a solution of 2,4-dichloropyrimidine (1.0 g, 6.7 mmol) in EtOH (20 mL) was added (1H-Indazol-5-yl)-methylamine (1.0 g, 6.8 mmol) and TEA (2.02 g, 20 mmol). The resulting mixture was refluxed overnight. The solvent was removed to give the crude title compound (2.5 g), which was used for the next step reaction without purification.

Example 54 tert-butyl 5-((2-chloropyrimidin-4-yl)(methyl)amino)-1H-indazole-1-carboxylate

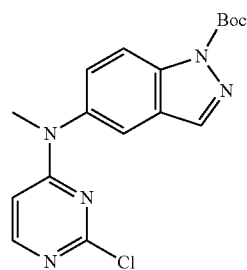 [SMILES: CN(c1ccc2c(cnn2C(=O)OC(C)(C)C)c1)c1ccnc(Cl)n1]

To a solution of N-(2-chloropyrimidin-4-yl)-N-methyl-1H-indazol-5-amine (2.5 g, crude) in DCM (50 mL) were added TEA (2.0 g, 20 mmol), (Boc)₂O (4.2 g, 19.2 mmol), and DMAP (1.0 g) was added. The resulting mixture was stirred at room temperature for 1 hr. The mixture was concentrated in vacuo and purified by column chromatograph to give the title compound (0.95 g, yield 38.8% for 2 steps) as a solid.

Example 55 tert-butyl 5-((2-(3-(2-(isopropylamino)-2-oxoethoxy)phenyl)pyrimidin-4-yl)(methyl)amino)-1H-indazole-1-carboxylate

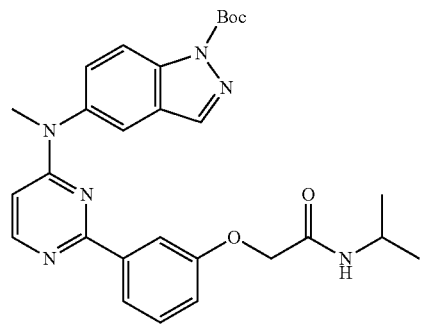 [SMILES: CC(C)NC(=O)COc1cccc(-c2nccc(N(C)c3ccc4c(cnn4C(=O)OC(C)(C)C)c3)n2)c1]

To a solution of tert-butyl 5-((2-chloropyrimidin-4-yl)(methyl)amino)-1H-indazole-1-carboxylate (0.6 g, 1.67 mmol) in the solvent (dioxane:water=4:1, 20 mL) were added N-isopropyl-2-[3-(4,4,5,5-tetramethyl-[1,3,2]dioxaborolan-2-yl)-phenoxy]-acetamide (0.6 g, 1.88 mmol), (Boc)₂O (1.09 g, 5 mmol), K₃PO₄ (1.06 g, 5 mmol), t-Bu₃P (0.4 g, 2 mmol) and Pd₂(dba)₃ (0.1 g) under N₂. The resulting mixture was stirred at 100° C. for 24 hrs and concentrated in vacuo to provide the crude material which was carried out for the next step reaction without further purification.

Example 56

2-(3-(4-((1H-indazol-5-yl)(methyl)amino)pyrimidin-2-yl)phenoxy)-N-isopropylacetamide TFA salt

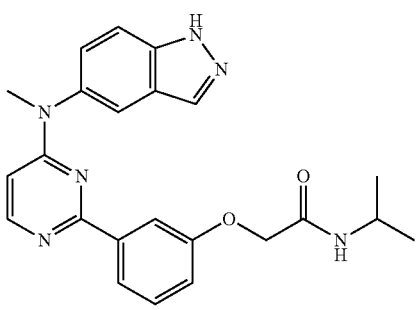 [SMILES: CC(C)NC(=O)COc1cccc(-c2nccc(N(C)c3ccc4[nH]ncc4c3)n2)c1]

To tert-butyl 5-((2-(3-(2-(isopropylamino)-2-oxoethoxy)phenyl)pyrimidin-4-yl)(methyl)amino)-1H-indazole-1-carboxylate as above was added HCl/MeOH (4M, 5 mL) and the mixture was stirred for 2.0 hr. The solvent was removed in vacuo and the residue was purified by HPLC to give the title compound (120 mg) as a TFA salt. $^1$H NMR (400 MHz, CD3OD) δ1.20 (d, J=6.8 Hz, 6H), 3.85 (s, 3H), 4.07-4.13 (m, 1H), 4.62 (s, 2H), 6.37-6.45 (m, 1H), 7.39 (dd, J=10.4 and 2.0 Hz, 1H), 7.43 (d, J=2.0 Hz, 1H), 7.60 (t, J=7.6 Hz, 1H), 7.79 (d, J=8.8 Hz, 1H), 7.86-7.89 (m, 2H), 7.91 (s, 1H), 8.05 (b, 1H), 8.18 (s, 1H). MS (ES+) m/e 417 (M+H)$^+$.

Example 57

2-chloro-N-(1H-pyrazol-4-yl)pyrimidin-4-amine

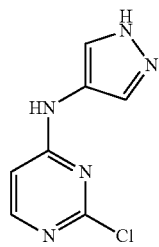 [SMILES: Clc1nccc(Nc2cn[nH]c2)n1]

The mixture of 2, 4-dichloro-pyrimidine (200 mg, 2.41 mmol), 1H-pyrazol-4-ylamine (431 mg, 2.89 mmol), and TEA (730 mg, 7.23 mmol) in i-PrOH (8 mL) was stirred at 50° overnight. After cooling, the reaction mixture was concentrated. The crude product was used directly for the next step without purification.

Example 58 tert-butyl 4-((tert-butoxycarbonyl)(2-chloropyrimidin-4-yl)amino)-1H-pyrazole-1-carboxylate

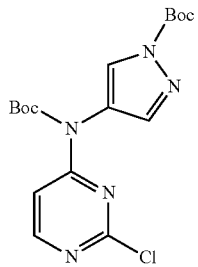

To a mixture of (2-chloro-pyrimidin-4-yl)-(1H-pyrazol-4-yl)-amine (470 mg, 2.41 mmol), TEA (730 mg, 7.23 mmol) and DMAP (607 mg, 4.82 mmol) in dry DCM (15 mL), Boc$_2$O (1040 mg, 4.82 mmol) was added slowly. The reaction mixture was stirred at room temperature for 3 h, and concentrated. The residue was purified by column chromatography on silica gel to give the title compound (200 mg, 0.5 mmol, 21% yield) as a white solid.

Example 59 tert-butyl 4-((2-(3-(2-(isopropylamino)-2-oxoethoxy)phenyl)pyrimidin-4-yl)amino)-1H-pyrazole-1-carboxylate

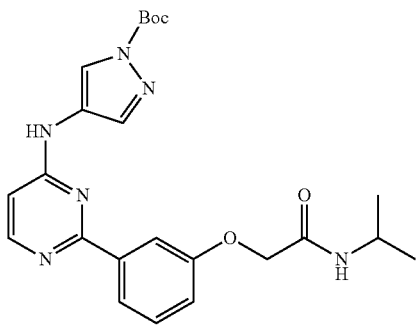 [SMILES: CC(C)NC(=O)COc1cccc(-c2nccc(Nc3cnn(C(=O)OC(C)(C)C)c3)n2)c1]

To a mixture of 4-[tert-butoxycarbonyl-(2-chloro-pyrimidin-4-yl)-amino]-pyrazole-1-carboxylic acid tert-butyl ester (118.5 mg, 0.3 mmol), N-isopropyl-2-(3-(4, 4, 5, 5-tetramethyl-1, 3, 2-dioxaborolan-2-yl) phenoxy) acetamide (134 mg, 0.42 mmol), Na$_2$CO$_3$ (64 mg, 0.6 mmol), and Boc$_2$O (130 mg, 0.6 mmol) in EtOH (3 mL) and H$_2$O (0.3 mL), Pd(dppf)$_2$Cl$_2$ (21 mg, 0.03 mmol) was added. The mixture was stirred at 1300 under N$_2$ protection under microwave for 30 minutes. After cooling, the mixture was concentrated. The residue was purified by flash column chromatograph on silica gel, and then purified by P-HPLC to give the title compound (30 mg, 0.066 mmol, 22% yield) as a white solid.

Example 60

2-(3-(4-((1H-pyrazol-4-yl)amino)pyrimidin-2-yl)phenoxy)-N-isopropylacetamide TFA salt

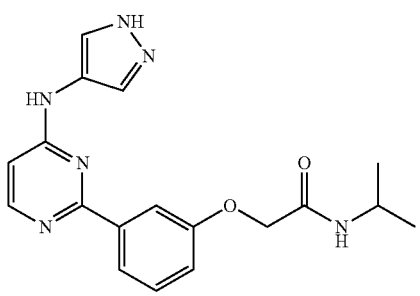 [SMILES: CC(C)NC(=O)COc1cccc(-c2nccc(Nc3cn[nH]c3)n2)c1]

To a solution of tert-butyl 4-((2-(3-(2-(isopropylamino)-2-oxoethoxy) phenyl) pyrimidin-4-yl) amino)-1H-pyrazole-1-carboxylate (167 mg, 0.369 mmol) in DCM (20 mL) TFA (2 mL) was added. The mixture was stirred at room temperature for 5 hrs, and then concentrated to give the title compound (170 mg, 0.364 mmol, 98% yield) as a yellow solid. $^1$H NMR (400 MHz, CD3OD) δ 8.20-8.18 (d, J=7.2 Hz, 1H), 8.07 (s 2H), 7.80-7.78 (d, 2H), 7.64-7.60 (t, J=8.8 Hz, 1H), 7.40-7.40 (dd, J=9.6, 2.4 Hz, 1H), 6.91-6.89 (d, J=7.2 Hz, 1H), 4.63 (s, 2H), 4.13-4.09 (m, 1H) 1.18-1.16 (d, J=6.4 Hz 6H). MS (ES+) m/e 353 (M+H)$^+$.

Example 61

5-((2-chloropyrimidin-4-yl)oxy)-1H-indazole

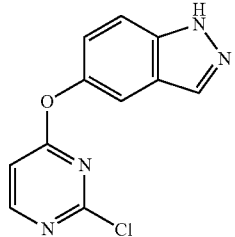 [SMILES: Clc1nccc(Oc2ccc3[nH]ncc3c2)n1]

The mixture of 2, 4-dichloro-pyrimidine (184 mg, 1.232 mmol), 1H-indazol-5-ol (150 mg, 1.12 mmol), and TEA (340 mg, 3.36 mmol) in EtOH (5 mL) was stirred at 800 overnight. After cooling, the reaction mixture was concentrated. The crude product was used directly for the next step without purification.

Example 62 tert-butyl 5-((2-chloropyrimidin-4-yl)oxy)-1H-indazole-1-carboxylate

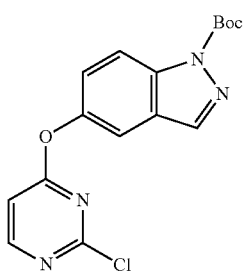 [SMILES: CC(C)(C)OC(=O)n1ncc2cc(Oc3ccnc(Cl)n3)ccc21]

To a stirred mixture of 5-((2-chloropyrimidin-4-yl)oxy)-1H-indazole (275 mg, 1.12 mmol), TEA (340 mg, 3.36 mmol) and DMAP (28 mg, 0.224 mmol) in dry DCM (5 mL), Boc$_2$O (484 mg, 2.24 mmol) was added slowly. The reaction mixture was stirred at room temperature for 2 hrs, and then concentrated. The residue was purified by column chromatography on silica gel to give the title compound (200 mg, 0.57 mmol, 50% yield) as a white solid.

Example 63 tert-butyl 5-((2-(3-(2-(isopropylamino)-2-oxoethoxy)phenyl)pyrimidin-4-yl)oxy)-1H-indazole-1-carboxylate

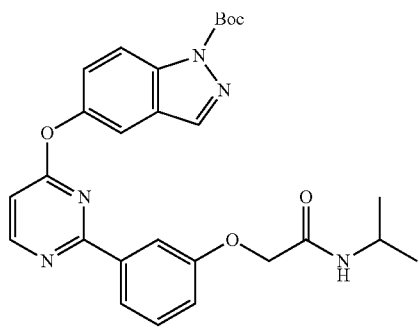 [SMILES: CC(C)NC(=O)COc1cccc(-c2nccc(Oc3ccc4c(cnn4C(=O)OC(C)(C)C)c3)n2)c1]

To a mixture of tetr-butyl-5-((2-chloropyrimidin-4-yl)oxy)-1H-indazole-1-carboxylate (104 mg, 0.3 mmol), N-isopropyl-2-(3-(4, 4, 5, 5-tetramethyl-1, 3, 2-dioxaborolan-2-yl) phenoxy) acetamide (134 mg, 0.42 mmol), t-Bu$_3$P (61 mg, 0.3 mmol), K$_3$PO$_4$.3H$_2$O (160 mg, 0.6 mmol), and Boc$_2$O (130 mg, 0.6 mmol) in dioxane (3 mL) and H$_2$O (0.4 mL), Pd$_2$(dba)$_3$ (27 mg, 0.03 mmol) was added. The mixture was stirred at 800 under N$_2$ protection overnight. After cooling, the mixture was concentrated. The residue was purified by reverse-phase HPLC to give the title compound (58 mg, 0.115 mmol, 38% yield) as a white solid.

Example 64

2-(3-(4-((1H-indazol-5-yl)oxy)pyrimidin-2-yl)phenoxy)-N-isopropylacetamide HCl salt

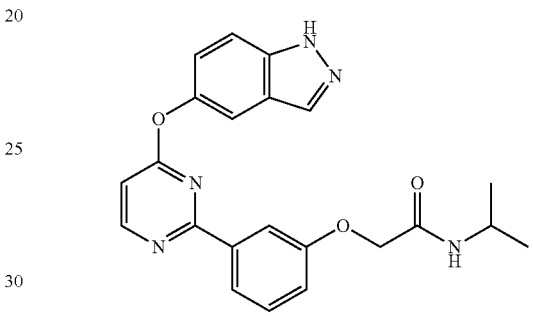

The solution of tert-butyl 5-((2-(3-(2-(isopropylamino)-2-oxoethoxy) phenyl) pyrimidin-4-yl) oxy)-1H-indazole-1-carboxylate (340 mg, 0.675 mmol) HCl (g)/EtOAc (40 mL) was stirred at room temperature for 3 hrs, and then concentrated to provide the title compound (272 mg, 0.621 mmol, 92% yield) as a white solid. $^1$H NMR (400 MHz, CD3OD) δ 8.87-8.85 (d, J=6.4 Hz, 1H), 8.25 (s 1H), 7.78-7.71 (m, 2H), 7.69-7.65 (m, 2H), 7.50-7.43 (m, 3H), 7.30-727 (dd, J=8.0, 2.4 Hz, 1H), 4.48 (s, 2H), 4.06-4.00 (m, 1H), 1.14-1.12 (d, J=6.4 Hz 6H). MS (ES+) m/e 404 (M+H)$^+$.

Example 65

2-(3-(4-((1H-indazol-5-yl)amino)pyrimidin-2-yl)phenoxy)-1-(piperazin-1-yl)ethanone HCl salt

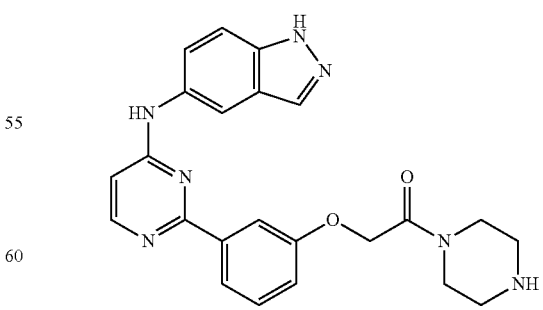

The title compound was prepared using essentially the same procedure described for example 12. $^1$H NMR (400 MHz, CD3OD) δ 3.24 (b, 4H), 3.82 (b, 4H), 5.00 (s, 2H), 6.93 (b, 1H), 7.33 (dd, J=7.6 and 1.6 Hz, 1H), 7.56 (t, J=8.4

Hz, 1H), 7.68 (d, J=8.4 Hz, 2H), 7.79 (b, 2H), 8.15 (s, 1H), 8.22 (d, J=7.2 Hz, 2H). (ES+) m/e 430 (M+H)+.

Example 66

2-(3-(4-amino-6-chloropyrimidin-2-yl)phenoxy)-N-isopropylacetamide

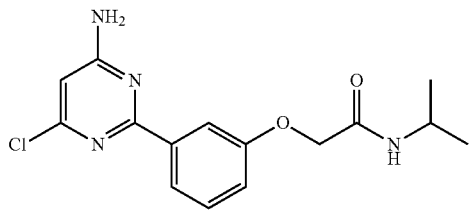 [SMILES: CC(C)NC(=O)COc1cccc(-c2nc(N)cc(Cl)n2)c1]

Example 67

2-(3-(6-amino-2-chloropyrimidin-4-yl)phenoxy)-N-isopropylacetamide

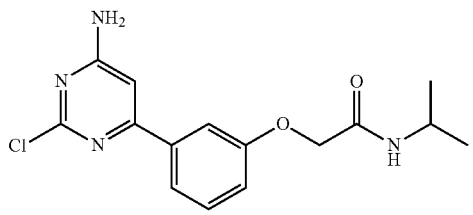 [SMILES: CC(C)NC(=O)COc1cccc(-c2cc(N)nc(Cl)n2)c1]

To a mixture of 4-amino-2, 6-dichloropyrimidine (1.016 g, 6.72 mmol), N-isopropyl-2-(3-(4,4,5,5-tetramethyl-1,3,2-dioxaborolan-2-yl)phenoxy)acetamide (2.032 g, 6.37 mmol) and CsF (2.858 g, 18.803 mmol) in 1,4-dioxane (31.2 mL) and H₂O (6.3 mL) was added Pd(PPh₃)₄ (0.362 g, 0.313 mmol). The resulting mixture was stirred at 100° C. overnight under N₂. After cooling to room temperature, the mixture was concentrated under reduced pressure to give a residue, which was purified by column chromatography on silica gel (eluted with PE:EtOAc=2:1) to obtain compound 2-(3-(4-amino-6-chloropyrimidin-2-yl)phenoxy)-N-isopropylacetamide (670 mg, yield 33%) as a white powder and 2-(3-(6-amino-2-chloropyrimidin-4-yl)phenoxy)-N-isopropylacetamide (460 mg, yield 22%) as a white powder.

Example 68

2-(3-(4-amino-6-(4-methylpiperazin-1-yl)pyrimidin-2-yl)phenoxy)-N-isopropylacetamide

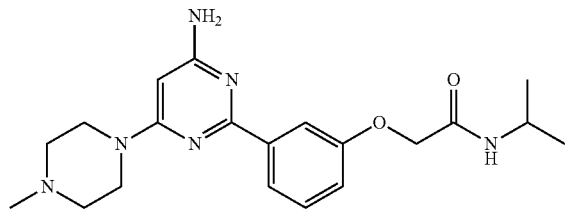 [SMILES: CC(C)NC(=O)COc1cccc(-c2nc(N)cc(N3CCN(C)CC3)n2)c1]

To a solution of compound 2-(3-(4-amino-6-chloropyrimidin-2-yl)phenoxy)-N-isopropylacetamide (0.97 g, 3.031 mmol) in n-BuOH (15 mL) was added 1-methylpiperazine (1.5 g, 15 mmol) and stirred at 120° C. overnight under N₂. After cooling to room temperature, the mixture was concentrated under reduced pressure to give a residue, which was purified by column chromatography on silica gel (eluted with EtOAc:MeOH=20:1) to obtain the title compound (460 mg, yield 39%) as a light yellow powder.

Example 69

2-(3-(6-amino-2-(4-methylpiperazin-1-yl)pyrimidin-4-yl)phenoxy)-N-isopropylacetamide

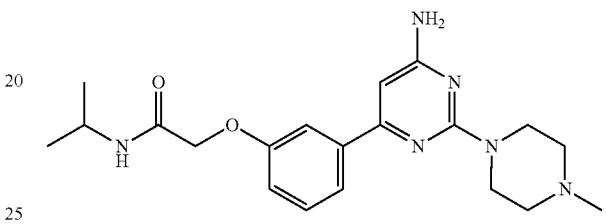

To a solution of compound 2-(3-(6-amino-2-chloropyrimidin-4-yl)phenoxy)-N-isopropylacetamide (0.436 g, 1.363 mmol) in n-BuOH (10 mL) was added 1-methylpiperazine (0.682 g, 6.815 mmol) and stirred at 120° C. overnight under N₂. After cooling to room temperature, the mixture was concentrated under reduced pressure to give a residue, which was purified by column chromatography on silica gel (eluted with EtOAc:MeOH=20:1) to obtain the title compound (0.273 g, yield 52%) as a light yellow powder.

Example 70

N-isopropyl-2-(3-(4-(4-methylpiperazin-1-yl)-6-(pyridin-4-ylamino)pyrimidin-2-yl)phenoxy)acetamide

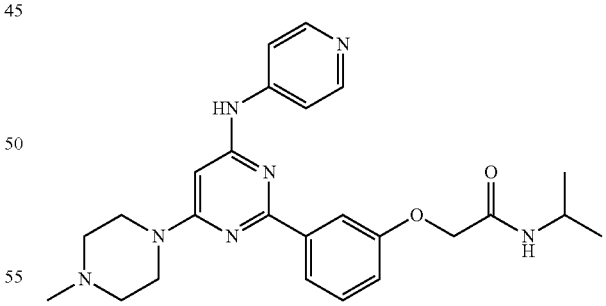

To a mixture of compound 2-(3-(4-amino-6-(4-methylpiperazin-1-yl)pyrimidin-2-yl)phenoxy)-N-isopropylacetamide (460 mg, 1.199 mmol), 4-iodopyridine (319.5 mg, 1.559 mmol), Pd₂(dba)₃ (109.8 mg, 0.12 mmol) and X-Phos (57 mg, 0.12 mmol) in anhydrous 1,4-dioxane (15 mL) was added Cs₂CO₃ (1.17 g, 3.3 mmol). The resulting mixture was heated to 120° C. overnight under N₂. After cooling to room temperature, the mixture was diluted with 1,4-dioxane and filtered through celite pad. The filtrate was concentrated and the residue was washed with EtOAc and dried in vacuo to obtain the title compound (173 mg, yield 31.3%) as a white solid. $^1$H NMR (400 MHz, CD3OD) δ 1.17 (d, J=6.4 Hz, 6H), 2.36 (s, 3H), 2.55 (t, J=5.2 Hz, 4H), 3.72 (t, J=4.8 Hz, 4H), 4.06-4.16 (m, 1H), 4.56 (s, 2H), 5.97 (s, 1H), 7.19 (dd, J=8.0 and 2.4 Hz, 1H), 7.39 (t, J=8.0 Hz, 1H), 7.78 (d, J=6.4 Hz, 2H), 7.98 (s, 1H), 8.02 (d, J=8.0 Hz, 1H), 8.32 (d, J=5.6 Hz, 1H). m/e 462 (M+H)$^+$.

Example 71

N-isopropyl-2-(3-(2-(4-methylpiperazin-1-yl)-6-(pyridin-4-ylamino)pyrimidin-4-yl)phenoxy)acetamide

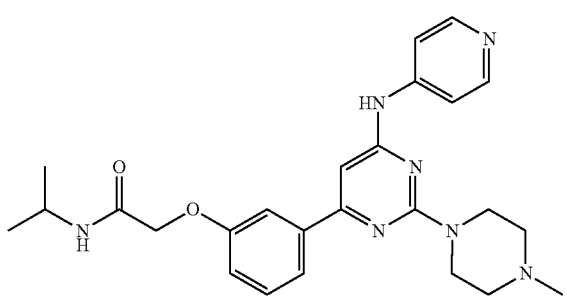 [SMILES: CC(C)NC(=O)COc1cccc(-c2cc(Nc3ccncc3)nc(N3CCN(C)CC3)n2)c1]

To a mixture of compound 2-(3-(6-amino-2-(4-methylpiperazin-1-yl)pyrimidin-4-yl)phenoxy)-N-isopropylacetamide (493 mg, 1.286 mmol), 4-iodopyridine (290 mg, 1.415 mmol), Pd$_2$(dba)$_3$ (117.8 mg, 0.129 mmol) and X-Phos (61.4 mg, 0.129 mmol) in anhydrous 1,4-dioxane (15 mL) was added Cs$_2$CO$_3$ (1258 mg, 3.858 mmol). The resulting mixture was heated to 120° C. overnight under N$_2$. After cooling to room temperature, the mixture was diluted with 1,4-dioxane and filtered through celite pad. The filtrate was concentrated and the residue was washed with EtOAc and dried in vacuo to obtain the title compound (184 mg, yield 31.0%) as a white solid. $^1$H NMR (400 MHz, CD3OD) δ 1.17 (d, J=6.4 Hz, 6H), 2.36 (s, 3H), 2.57 (t, J=4.8 Hz, 4H), 3.65 (b, 4H), 4.08-4.14 (m, 1H), 4.54 (s, 2H), 6.57 (s, 1H), 7.08 (dd, J=8.0 and 2.4 Hz, 1H), 7.39 (t, J=8.4 Hz, 1H), 7.62 (d, J=7.6 Hz, 1H), 7.69-7.73 (m, 3H), 8.31 (d, J=6.4 Hz, 1H). m/e 462 (M+H)$^+$.

Example 72 tert-Butyl 4-((3-bromophenoxy)methyl)piperidine-1-carboxylate

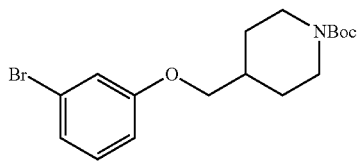 [SMILES: CC(C)(C)OC(=O)N1CCC(COc2cccc(Br)c2)CC1]

A solution of tert-butyl 4-(hydroxymethyl)piperidine-1-carboxylate (1.5 g, 7.0 mmol), 3-bromophenol (1.5 g, 7.0 mmol) and PPh$_3$ (2.7 g, 10.5 mmol) was stirred in dry THF (30 mL) was stirred at 0° C. under a nitrogen atmosphere. To this mixture was added DEAD (1.8 g, 10.5 mmol) dropwise over a period of 5 min, and the reaction was monitored by TLC. After complete disappearance of the starting material, the solvent was evaporated under reduced pressure and the resulting oil purified by column chromatography (PE/EA, 9/1) to provide the title compound (2.4 g crude) which was used directly without further purification. m/e 372 (M+H)$^+$.

Example 73 tert-butyl 4-((3-(4,4,5,5-tetramethyl-1,3,2-dioxaborolan-2-yl)phenoxy)methyl) piperidine-1-carboxylate

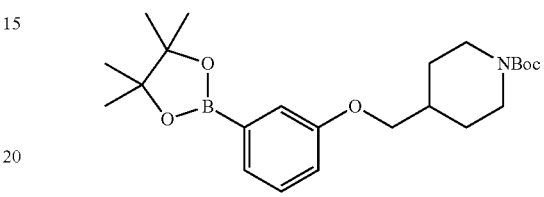

A solution of tert-butyl 4-((3-bromophenoxy)methyl)piperidine-1-carboxylate (2.4 g, 6.5 mmol), Pin$_2$B$_2$ (2.5 g, 9.7 mmol), Pd(dppf)Cl$_2$ (250 mg) and potassium acetate (1.9 g, 19.4 mmol) in 50 mL of dioxane was degassed and flushed with N$_2$, heated at 80° C. for 14 h. The mixture was concentrated to give a residue, which was diluted with EtOAc (300 µL), filtered, concentrated and was purified by chromatography (EA:PE, 1:10) to give the title compound (600 mg, 22%) as a yellow solid. $^1$H NMR (300 MHz, CDCl$_3$) δ 7.38 (1H, m), 7.27 (2H, m), 6.96 (1H, m), 3.82 (2H, d, J=6.0 Hz), 2.76 (1H, m), 1.73 (4H, m), 1.84 (4H, m).

Example 74 tert-Butyl 5-(tert-butoxycarbonyl(2-(3-((1-(tert-butoxycarbonyl)piperidin-4-yl) methoxy)phenyl)pyrimidin-4-yl)amino)-1H-indazole-1-carboxylate

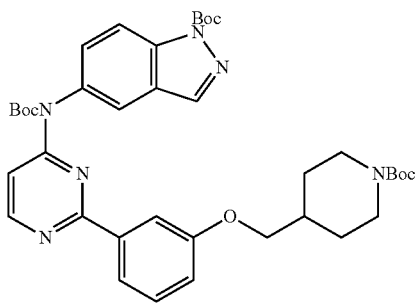 [SMILES: CC(C)(C)OC(=O)N1CCC(COc2cccc(-c3nccc(N(C(=O)OC(C)(C)C)c4ccc5c(cnn5C(=O)OC(C)(C)C)c4)n3)c2)CC1]

A mixture of tert-butyl 5-(tert-butoxycarbonyl(2-chloropyrimidin-4-yl)amino)-1H-indazole-1-carboxylate (642 mg, 1.44 mmol), tert-butyl 4-((3-(4,4,5,5-tetramethyl-1,3,2-dioxaborolan-2-yl)phenoxy)methyl) piperidine-1-carboxylate (600 mg, 1.44 mmol), KOAc (564 mg, 5.76 mmol), Boc$_2$O (604 mg, 2.88 mmol) and Pd(dppf)Cl$_2$ (70 mg) in dioxane/water (30 mL/3 mL) was degassed and flushed with N$_2$, heated at 100° C. 16 h. The mixture was concentrated to give a residue, which was diluted with DCM, filtered, concentrated and purified by chromatography (PE/EA, 5/1) to give the title compound (300 mg, crude) as a yellow oil. m/e 701 (M+H)$^+$.

Example 75

N-(2-(3-(piperidin-4-ylmethoxy)phenyl)pyrimidin-4-yl)-1H-indazol-5-amine

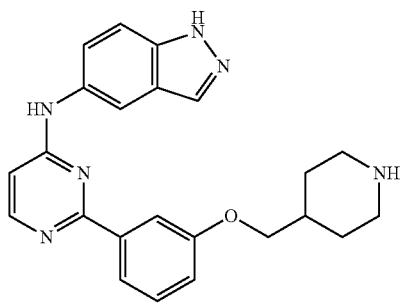 [SMILES: c1cc(OCC2CCNCC2)cc(-c2nccc(Nc3ccc4[nH]ncc4c3)n2)c1]

tert-Butyl-5-(tert-butoxycarbonyl(2-(3-((1-(tert-butoxycarbonyl)piperidin-4-yl) methoxy)phenyl)pyrimidin-4-yl)amino)-1H-indazole-1-carboxylate (250 mg, 0.36 mmol) was dissolved in 30 mL HCl/Et$_2$O (saturated). It was stirred at room temperature over night. The mixture was concentrated to give a residue, which was diluted with water, and extracted by EA. The water phase was adjusted to 11 using saturated NaHCO$_3$ solution. It was concentrated and the residue was further purified by preparative TLC to provide the title compound as a yellow solid (50 mg, 35%). $^1$H NMR (300 MHz, CD3OD) δ 8.24 (2H, m), 8.04 (1H, s), 7.90 (2H, m), 7.56 (2H, m), 7.38 (1H, t, J=6.0 Hz), 7.04 (1H, dd, J=9.0 Hz, J=3.0 Hz), 6.65 (1H, d, J=6.0 Hz), 3.95 (2H, d, J=6.0 Hz), 3.42 (2H, d, J=3.0 Hz), 2.15 (2H, t, J=3.0 Hz), 2.12 (1H, m), 2.07 (2H, q, J=3.0 Hz), 1.69 (2H, q, J=3.0 Hz); m/e 401 (M+H)$^+$.

Example 76 tert-Butyl 4-(3-bromophenoxy)piperidine-1-carboxylate

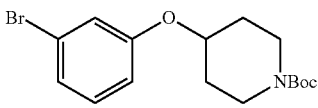

A solution of tert-butyl 4-hydroxypiperidine-1-carboxylate (1.4 g, 7.0 mmol), 3-bromophenol (1.2 g, 7.0 mmol) and PPh$_3$ (2.7 g, 10.4 mmol) was stirred in dry THF (35 mL) at 0° C. under a nitrogen atmosphere. To this mixture was added DEAD (1.8 g, 10.4 mmol) dropwise over a period of 5 min, and the reaction was monitored by TLC. After complete disappearance of starting material, the solvent was evaporated under reduced pressure and the resulting oil purified by column chromatography (PE/EA, 9/1) to provide the title compound (1.3 g, 52%). m/e 357 (M+H)$^+$.

Example 77 tert-Butyl-4-(3-(4,4,5,5-tetramethyl-1,3,2-dioxaborolan-2-yl)phenoxy)piperidine-1-carboxylate

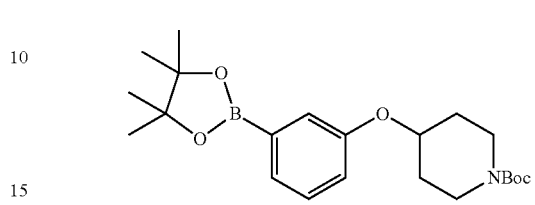

A solution of tert-butyl 4-(3-bromophenoxy) piperidine-1-carboxylate (1.3 g, 3.5 mmol), Pin$_2$B$_2$ (1.4 g, 5.3 mmol), Pd(dppf)Cl$_2$ (135 mg) and potassium acetate (1.0 g, 10.6 mmol) in 20 mL of dioxane was degassed, flushed with N$_2$, and heated at 80° C. for 14 h. The mixture was concentrated to give a residue, which was diluted with EtOAc (200 mL), filtered, concentrated and purified by chromotography (EA: PE, 1:10) to give the title compound (500 mg, 36%) as a yellow solid. $^1$H NMR (300 MHz, CDCl$_3$) δ 7.38 (1H, m), 7.32 (1H, m), 7.27 (1H, m), 7.25 (1H, m), 7.38 (1H, m), 4.51 (1H, m), 3.69 (2H, m), 3.36 (2H, m), 1.88 (2H, m), 1.74 (2H, m), 1.34 (2H, m).

Example 78 tert-Butyl-5-(tert-butoxycarbonyl(2-(3-(1-(tert-butoxycarbonyl)piperidin-4-yloxy)phenyl)pyrimidin-4-yl)amino)-1H-indazole-1-carboxylate

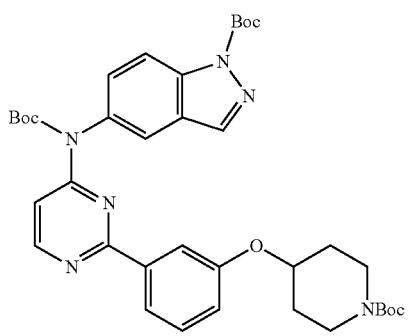 [SMILES: CC(C)(C)OC(=O)N1CCC(Oc2cccc(-c3nccc(N(C(=O)OC(C)(C)C)c4ccc5c(cnn5C(=O)OC(C)(C)C)c4)n3)c2)CC1]

A mixture of tert-butyl 5-(tert-butoxycarbonyl(2-chloropyrimidin-4-yl)amino)-1H-indazole-1-carboxylate (221 mg, 0.5 mmol), tert-butyl 4-(3-(4,4,5,5-tetramethyl-1,3,2-dioxaborolan-2-yl)phenoxy)piperidine-1-carboxylate (200 mg, 0.5 mmol), KOAc (196 mg, 2.0 mmol), Boc$_2$O (210 mg, 1.0 mmol) and Pd(dppf)Cl$_2$ (40 mg) in dioxane/water (30 mL/3 mL) was degassed and flushed with N$_2$, heated at 100° C. 16 h. The mixture was concentrated to give a residue, which was diluted with DCM, filtered, concentrated and purified by chromatography (PE/EA, 5/1) to provide the title compound (180 mg, crude) as a yellow oil. m/e 687 (M+H)$^+$.

Example 79

N-(2-(3-(Piperidin-4-yloxy)phenyl)pyrimidin-4-yl)-1H-indazol-5-amine

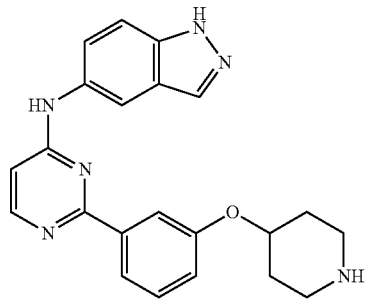 [SMILES: c1cc(OC2CCNCC2)cc(-c2nccc(Nc3ccc4[nH]ncc4c3)n2)c1]

tert-Butyl-5-(tert-butoxycarbonyl(2-(3-(1-(tert-butoxycarbonyl)piperidin-4-yloxy)phenyl)pyrimidin-4-yl)amino)-1H-indazole-1-carboxylate (170 mg, 0.25 mmol) was dissolved in 30 mL HCl/Et$_2$O (saturated). It was stirred at room temperature overnight. The mixture was concentrated to give a residue, which was diluted with water, and extracted by EA. The water phase was adjusted to 11 using saturated NaHCO$_3$ solution. It was concentrated and the residue was further purified by preparative TLC to provide the title compound (20 mg, 21%) as a yellow solid. $^1$H NMR (300 MHz, CD$_3$OD) δ 8.26 (1H, d, J=6.0 Hz), 8.18 (1H, s), 8.04 (1H, s), 7.96 (1H, s), 7.93 (1H, t, J=3.0 Hz), 7.56 (2H, m), 7.42 (1H, t, J=9.0 Hz), 7.14 (1H, dd, J=9.0 Hz, J=3.0 Hz), 6.87 (1H, d, J=6.0 Hz), 5.80 (1H, m), 3.38 (2H, m), 3.30 (2H, m), 2.16 (2H, m), 2.11 (2H, m); m/e 387 (M+H)$^+$.

Example 80

2-(3-Bromo-4-fluorophenoxy)-N-cyclopropylacetamide

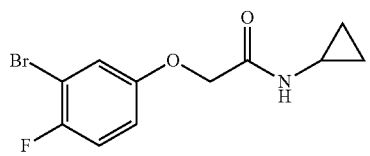 [SMILES: O=C(COc1ccc(F)c(Br)c1)NC1CC1]

A solution of 2-chloro-N-cyclopropylacetamide (1.7 g, 13.1 mmol), 3-bromo-4-fluorophenol (2.5 g, 13.1 mmol) and K$_2$CO$_3$ (2.7 g, 19.6 mmol) in 20 mL of acetone was heated at 60° C. for 16 h. The mixture was filtered and concentrated to give a residue, which was purified by column chromatography (PE/EA, 3/1) to give the title compound (2.5 g, 66%) as a yellow solid. m/e 289 (M+H)$^+$.

Example 81

N-Cyclopropyl-2-(4-fluoro-3-(4,4,5,5-tetramethyl-1,3,2-dioxaborolan-2-yl)phenoxy)acetamide

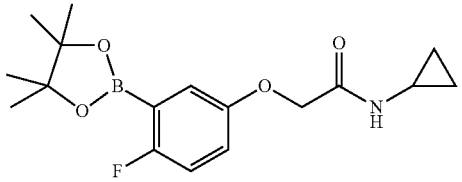 [SMILES: CC1(C)OB(c2cc(OCC(=O)NC3CC3)ccc2F)OC1(C)C]

A solution of 2-(3-bromo-4-fluorophenoxy)-N-cyclopropylacetamide (2.5 g, 8.7 mmol), Pin$_2$B$_2$ (3.3 g, 13.0 mmol), Pd(dppf)Cl$_2$ (330 mg) and potassium acetate (2.6 g, 26.0 mmol) in 35 mL of dioxane was degassed and flushed with N$_2$, heated at 80° C. for 14 h. The mixture was concentrated to give a residue, which was diluted with EtOAc (200 mL), filtered, concentrated and purified by chromatography (EA: PE, 1:5) to give the title compound (600 mg, 21%) as a yellow solid. m/e 336 (M+H)$^+$.

Example 82

2-(3-(4-(1H-indazol-5-ylamino)pyrimidin-2-yl)-4-fluorophenoxy)-N-cyclopropylacetamide

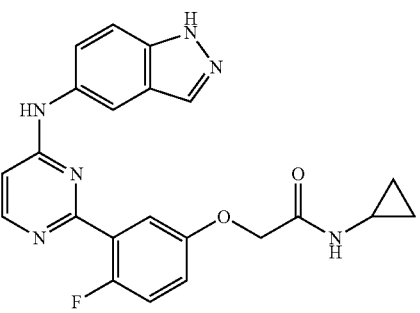 [SMILES: O=C(COc1ccc(F)c(-c2nccc(Nc3ccc4[nH]ncc4c3)n2)c1)NC1CC1]

A mixture of N-(2-chloropyrimidin-4-yl)-1H-indazol-5-amine (150 mg, 0.61 mmol), N-cyclopropyl-2-(4-fluoro-3-(4,4,5,5-tetramethyl-1,3,2-dioxaborolan-2-yl)phenoxy)acetamide (205 mg, 0.61 mmol), KOAc (240 mg, 2.45 mmol) and Pd(dppf)Cl$_2$ (60 mg) in dioxane/water (20 mL/3 mL) was degassed and flushed with N$_2$, heated at 100° C. 16 h. The mixture was concentrated to give a residue, which was diluted with DCM, filtered, concentrated and purified by chromatography (DCM/MeOH, 20/1) followed by further purification by preparative TLC to give the title compound (35 mg, 14%) as a yellow solid. $^1$H NMR (300 MHz, CD$_3$OD) δ 8.26 (1H, d, J=6.0 Hz), 8.17 (1H, s), 8.03 (1H, s), 7.52 (3H, m), 7.13 (2H, m), 6.70 (1H, d, J=6.0 Hz), 4.53 (2H, s), 2.72 (1H, t, J=3.0 Hz), 0.75 (2H, t, J=3.0 Hz), 0.57 (2H, t, J=3.0 Hz); m/e 419 (M+H)$^+$.

Example 83

2-(3-(4-(1H-indazol-5-ylamino)-5-methylpyrimidin-2-yl)-4-fluorophenoxy)-N-cyclopropylacetamide

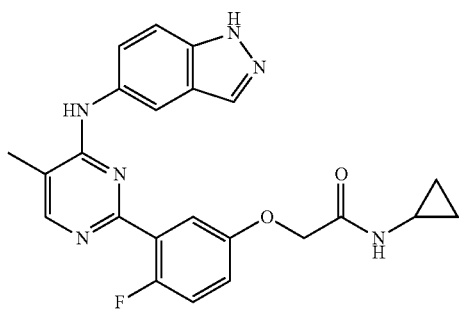 [SMILES: Cc1cnc(-c2cc(OCC(=O)NC3CC3)ccc2F)nc1Nc1ccc2[nH]ncc2c1]

A mixture of N-(2-chloro-5-methylpyrimidin-4-yl)-1H-indazol-5-amine (209 mg, 0.80 mmol), N-cyclopropyl-2-(4-fluoro-3-(4,4,5,5-tetramethyl-1,3,2-dioxaborolan-2-yl)phenoxy)acetamide (270 mg, 0.80 mmol), KOAc (316 mg, 3.22 mmol) and Pd(dppf)Cl$_2$ (60 mg) in dioxane/water (20 mL/3 mL) was degassed and flushed with N$_2$, heated at 100° C. 16 h. The mixture was concentrated to give a residue, which was diluted with DCM, filtered, concentrated and purified by chromatography (DCM/MeOH, 20/1) followed by further purification by preparative TLC to give the title compound (35 mg, 10%) as a yellow solid. $^1$H NMR (300 MHz, CD$_3$OD) δ 8.16 (1H, s), 8.12 (1H, s), 8.02 (1H, s), 7.70 (1H, dd, J=9.0 Hz, J=3.0 Hz), 7.54 (1H, d, J=9.0 Hz), 7.44 (1H, m), 7.10 (2H, m), 4.46 (2H, s), 2.69 (1H, m), 2.31 (3H, s), 0.73 (2H, t, J=3.0 Hz), 0.55 (2H, t, J=3.0 Hz); m/e 433 (M+H)$^+$.

Example 84

2-(3-Bromo-5-fluorophenoxy)-N-cyclopropylacetamide

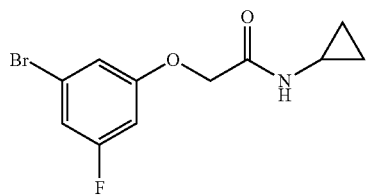 [SMILES: O=C(COc1cc(F)cc(Br)c1)NC1CC1]

A solution of 2-chloro-N-cyclopropylacetamide (2.8 g, 20.9 mmol), 3-bromo-5-fluorophenol (4.0 g, 20.9 mmol) and K$_2$CO$_3$ (4.3 g, 31.4 mmol) in 40 mL of acetone was heated at 60° C. for 16 h. The mixture was filtered and concentrated to give a residue, which was purified by column chromatography (PE/EA, 3/1) to give the title compound (4.3 g, 71%) as a yellow solid. m/e 288 (M+H)$^+$.

Example 85

N-cyclopropyl-2-(3-fluoro-5-(4,4,5,5-tetramethyl-1,3,2-dioxaborolan-2-yl)phenoxy)acetamide

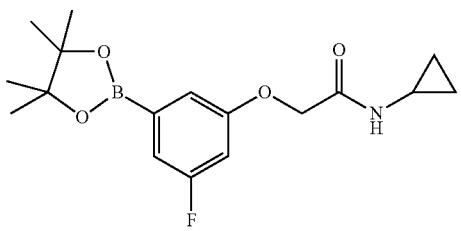 [SMILES: CC1(C)OB(c2cc(F)cc(OCC(=O)NC3CC3)c2)OC1(C)C]

A solution of 2-(3-bromo-5-fluorophenoxy)-N-cyclopropylacetamide (4.3 g, 14.9 mmol), Pin$_2$B$_2$ (5.7 g, 22.4 mmol), Pd(dppf)Cl$_2$ (600 mg) and potassium acetate (4.4 g, 44.8 mmol) in 50 mL of dioxane was degassed and flushed with N$_2$, heated at 80° C. for 14 h. The mixture was concentrated to give a residue, which was diluted with EtOAc (200 mL), filtered, concentrated and purified by chromatography (EA:PE, 1:5) to give the title compound (3.2 g, 64%) as a yellow solid. m/e 336 (M+H)$^+$.

Example 86

2-(3-(4-(1H-indazol-5-ylamino)pyrimidin-2-yl)-5-fluorophenoxy)-N-cyclopropylacetamide

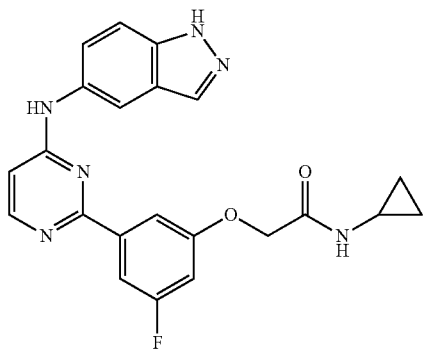 [SMILES: O=C(COc1cc(F)cc(-c2nccc(Nc3ccc4[nH]ncc4c3)n2)c1)NC1CC1]

A mixture of N-(2-chloropyrimidin-4-yl)-1H-indazol-5-amine (340 mg, 1.4 mmol), N-cyclopropyl-2-(3-fluoro-5-(4,4,5,5-tetramethyl-1,3,2-dioxaborolan-2-yl)phenoxy)acetamide (650 mg, 1.9 mmol), CsF (835 mg, 5.5 mmol) and Pd(dppf)Cl$_2$ (200 mg) in dioxane/water (20 mL/3 mL) was degassed and flushed with N$_2$, heated at 100° C. 16 h. The mixture was concentrated to give a residue, which was diluted with DCM, filtered, concentrated and purified by chromatography (DCM/MeOH, 20/1) to give the title compound (80 mg, 14%) as a yellow solid. $^1$H NMR (300 MHz, CD$_3$OD) δ 8.26 (1H, d, J=6.0 Hz), 8.08 (1H, s), 8.06 (1H, s), 7.78 (1H, s), 7.65 (1H, dd, J=9.0 Hz, J=3.0 Hz), 7.58 (2H, s), 6.89 (1H, dt, J=9.0 Hz, J=3.0 Hz), 6.66 (1H, d, J=6.0 Hz), 4.58 (2H, s), 2.74 (1H, m), 0.76 (2H, t, J=3.0 Hz), 0.58 (2H, t, J=3.0 Hz); m/e 419 (M+H)$^+$.

Example 87

2-(3-(4-(1H-indazol-5-ylamino)-5-methylpyrimidin-2-yl)-5-fluorophenoxy)-N-cyclopropylacetamide

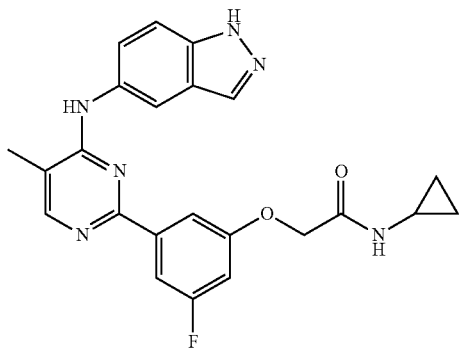 [SMILES: Cc1cnc(-c2cc(F)cc(OCC(=O)NC3CC3)c2)nc1Nc1ccc2[nH]ncc2c1]

A mixture of N-(2-chloro-5-methylpyrimidin-4-yl)-1H-indazol-5-amine (360 mg, 1.4 mmol), N-cyclopropyl-2-(3-fluoro-5-(4,4,5,5-tetramethyl-1,3,2-dioxaborolan-2-yl)phenoxy)acetamide (650 mg, 1.9 mmol), CsF (835 mg, 5.5 mmol) and Pd(dppf)Cl$_2$ (200 mg) in dioxane/water (20 mL/3 mL) was degassed and flushed with N$_2$, heated at 100° C. 16 h. The mixture was concentrated to give a residue, which was diluted with DCM, filtered, concentrated and purified by chromatography (DCM/MeOH, 20/1) to give the title compound (60 mg, 10%) as a yellow solid. $^1$H NMR (300 MHz, CD$_3$OD) δ 8.14 (1H, s), 8.04 (2H, m), 7.70 (2H, m), 7.57 (2H, m), 6.81 (1H, dt, J=9.0 Hz, J=3.0 Hz), 4.51 (2H, s), 2.72 (1H, m), 2.29 (3H, s), 0.72 (2H, t, J=3.0 Hz), 0.57 (2H, t, J=3.0 Hz); m/e 433 (M+H)$^+$.

Example 88 tert-Butyl 3-((3-bromophenoxy)methyl)piperidine-1-carboxylate

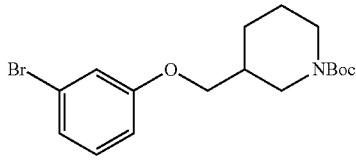 [SMILES: CC(C)(C)OC(=O)N1CCCC(COc2cccc(Br)c2)C1]

A solution of tert-butyl 3-(hydroxymethyl)piperidine-1-carboxylate (935 mg, 4.35 mmol), 3-bromophenol (753 mg, 4.35 mmol) and PPh$_3$ (1.71 mg, 6.53 mmol) was stirred in dry THF (30 mL) at 0° C. under a nitrogen atmosphere. To this mixture was added dropwise DEAD (1.14 g, 6.53 mmol) over a period of 5 min, and the reaction was monitored by TLC. After complete disappearance of starting material, the mixture was poured to EA (50 mL), washed with brine (3×20 mL), dried over Na$_2$SO$_4$ and filtered. The filtrate was evaporated under reduced pressure and the resulting oil was purified by column chromatography (PE/EA, 10/1) to get the title compound (0.8 g, crude). m/e 370 (M+H)$^+$.

Example 89 tert-Butyl 3-((3-(4,4,5,5-tetramethyl-1,3,2-dioxaborolan-2-yl)phenoxy)methyl) piperidine-1-carboxylate

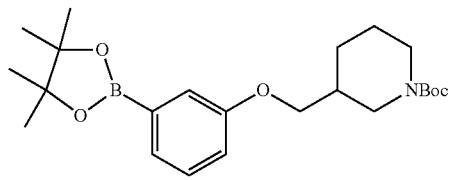 [SMILES: CC(C)(C)OC(=O)N1CCCC(COc2cccc(B3OC(C)(C)C(C)(C)O3)c2)C1]

A solution of tert-butyl 3-((3-bromophenoxy)methyl)piperidine-1-carboxylate (0.7 g, 1.9 mmol), Pin$_2$B$_2$ (0.72 g, 2.8 mmol), Pd(dppf)Cl$_2$ (154 mg) and potassium acetate (556 mg, 5.67 mmol) in dioxane (50 mL) was degassed and flushed with N$_2$, heated at 80° C. for 14 h. The mixture was concentrated to give a residue, which was diluted with EtOAc (100 mL), washed with brine (3×30 mL), dried over Na$_2$SO$_4$ and filtered. The filtrate was evaporated under reduced pressure and the resulting oil was purified by column chromatography (EA:PE, 1:5) to give the title compound (0.9 g, crude). m/e 418 (M+H)$^+$.

Example 90 tert-Butyl-5-(tert-butoxycarbonyl(2-(3-((1-(tert-butoxycarbonyl)piperidin-3-yl) methoxy)phenyl)pyrimidin-4-yl)amino)-1H-indazole-1-carboxylate

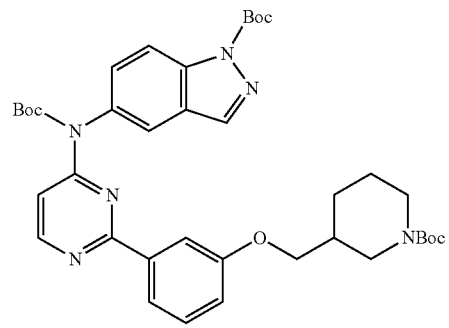 [SMILES: CC(C)(C)OC(=O)N1CCCC(COc2cccc(-c3nccc(N(C(=O)OC(C)(C)C)c4ccc5c(cnn5C(=O)OC(C)(C)C)c4)n3)c2)C1]

A mixture of tert-butyl 5-(tert-butoxycarbonyl(2-chloropyrimidin-4-yl)amino)-1H-indazole-1-carboxylate (240 mg, 0.54 mmol), tert-butyl 3-((3-(4,4,5,5-tetramethyl-1,3,2-dioxaborolan-2-yl)phenoxy)methyl) piperidine-1-carboxylate (270 mg, 0.65 mmol), CsF (788 mg, 5.4 mmol), Boc$_2$O (353 mg, 1.62 mmol) and Pd(dppf)Cl$_2$ (88 mg) in dioxane/water (20 mL/2 mL) was degassed and flushed with N$_2$, heated at 100° C. for 16 h. The mixture was concentrated to give a residue, which was diluted with EtOAc (100 mL), washed with brine (30 mL×3), dried over Na$_2$SO$_4$ and filtered. The filtrate was evaporated under reduced pressure and the resulting oil was purified by column chromatography (DCM:MeOH, 50:1) to give the title compound (0.1 g) as a yellow oil. m/e 701 (M+H)$^+$.

Example 91

N-(2-(3-(piperidin-3-ylmethoxy)phenyl)pyrimidin-4-yl)-1H-indazol-5-amine

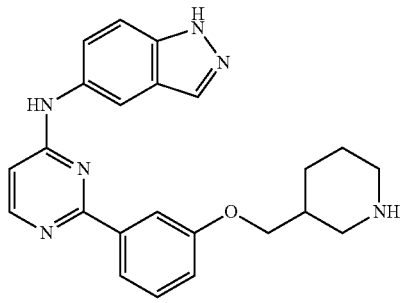 [SMILES: c1cc(OCC2CCCNC2)cc(-c2nccc(Nc3ccc4[nH]ncc4c3)n2)c1]

tert-Butyl-5-(tert-butoxycarbonyl(2-(3-((1-(tert-butoxycarbonyl)piperidin-3-yl) methoxy)phenyl)pyrimidin-4-yl)amino)-1H-indazole-1-carboxylate (100 mg, 0.14 mmol) was dissolved in HFIP (3 mL), the solution was stirred at 150° C. for 1 h with M.W. The mixture was concentrated to give a residue, which was purified by pre-TLC (DCM:MeOH, 4:1) to give the title compound as a yellow solid (40 mg, 70%). $^1$H NMR (400 MHz, CD$_3$OD) δ 8.26 (d, J=8.4 Hz, 1H), 8.21 (s, 1H), 8.07 (s, 1H), 7.91-7.88 (m, 2H), 7.61-7.52 (m, 2H), 7.44 (t, J=8.0 Hz, 1H), 7.14-7.12 (m, 1H), 6.74 (d, J=6.4 Hz, 1H), 4.11-4.07 (m, 1H), 3.97-3.93 (m, 1H), 3.58-3.54 (m, 1H), 3.41-3.31 (m, 1H), 3.00-2.89 (m, 2H), 2.36-2.27 (m, 1H), 2.04-1.97 (m, 1H), 1.85-1.78 (m, 1H), 1.56-1.45 (m, 1H); m/e 401 (M+H)$^+$.

Example 92 tert-Butyl 3-(3-bromophenoxy)pyrrolidine-1-carboxylate

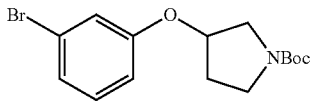

A solution of tert-butyl 3-hydroxypyrrolidine-1-carboxylate (1.0 g, 5.8 mmol), 3-bromophenol (1.08 g, 5.8 mmol) and PPh$_3$ (2.28 g, 8.7 mmol) in dry THF (35 mL) was stirred at 0° C. under a nitrogen atmosphere. To this mixture was added DEAD (1.51 g, 8.7 mmol) dropwise over a period of 5 min, and the reaction was monitored by TLC. After complete disappearance of starting material, the mixture was poured to EA (50 mL), washed with brine (20 mL×3), dried over Na$_2$SO$_4$ and filtered. The filtrate was evaporated under reduced pressure and the resulting oil was purified by column chromatography (PE/EA, 10/1) to afford the title compound (0.8 g, crude). m/e 342 (M+H)$^+$.

Example 93 tert-Butyl 3-(3-(4,4,5,5-tetramethyl-1,3,2-dioxaborolan-2-yl)phenoxy)pyrrolidine-1-carboxylate

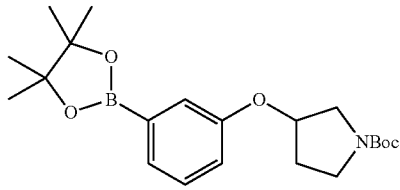 [SMILES: CC(C)(C)OC(=O)N1CCC(Oc2cccc(B3OC(C)(C)C(C)(C)O3)c2)C1]

A solution of tert-butyl 3-(3-bromophenoxy)pyrrolidine-1-carboxylate (0.8 g, 2.3 mmol), Pin$_2$B$_2$ (1.91 g, 7.5 mmol), Pd(dppf)Cl$_2$ (408 mg) and potassium acetate (1.47 g, 15 mmol) in dioxane (50 mL) was degassed and flushed with N$_2$, heated at 80° C. for 14 h. The mixture was concentrated to give a residue, which was diluted with EtOAc (100 mL), washed with brine (3×30 mL), dried over Na$_2$SO$_4$ and filtered. The filtrate was evaporated under reduced pressure and the resulting oil was purified by column chromatography (EA:PE, 1:5) to give the title compound as a yellow oil (450 mg, crude). m/e 390 (M+H)$^+$.

Example 94 tert-Butyl-5-(tert-butoxycarbonyl(2-(3-(1-(tert-butoxycarbonyl)pyrrolidin-3-yloxy)phenyl)pyrimidin-4-yl)amino)-1H-indazole-1-carboxylate

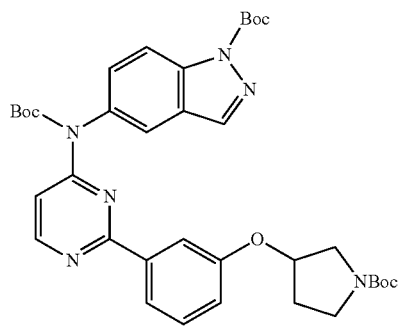 [SMILES: CC(C)(C)OC(=O)N1CCC(Oc2cccc(-c3nccc(N(C(=O)OC(C)(C)C)c4ccc5c(cnn5C(=O)OC(C)(C)C)c4)n3)c2)C1]

A mixture of tert-butyl 5-(tert-butoxycarbonyl(2-chloropyrimidin-4-yl)amino)-1H-indazole-1-carboxylate (466 mg, 1.05 mmol), tert-butyl 3-(3-(4,4,5,5-tetramethyl-1,3,2-dioxaborolan-2-yl)phenoxy)pyrrolidine-1-carboxylate (488 mg, 1.25 mmol), CsF (1.53 g, 10.5 mmol), Boc$_2$O (687 mg, 3.15 mmol) and Pd(dppf)Cl$_2$ (172 mg) in dioxane/water (30 mL/3 mL) was degassed and flushed with N$_2$, heated at 100° C. for 16 h. The mixture was concentrated to give a residue, which was diluted with EtOAc (100 mL), washed with brine (3×30 mL), dried over Na$_2$SO$_4$ and filtered. The filtrate was evaporated under reduced pressure and the resulting oil was purified by column chromatography (PE/EA, 5/1) to give the title compound as a yellow solid (200 mg, 28.5%). m/e 673 (M+H)⁺.

Example 95

N-(2-(3-(pyrrolidin-3-yloxy)phenyl)pyrimidin-4-yl)-1H-indazol-5-amine

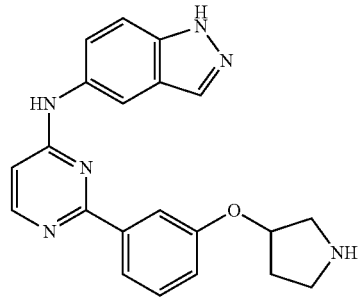 [SMILES: c1cc(OC2CCNC2)cc(-c2nccc(Nc3ccc4[nH]ncc4c3)n2)c1]

tert-Butyl-5-(tert-butoxycarbonyl(2-(3-(1-(tert-butoxycarbonyl)pyrrolidin-3-yloxy)phenyl)pyrimidin-4-yl)amino)-1H-indazole-1-carboxylate (135 mg, 0.25 mmol) was dissolved in 2 mL of con. HCl. It was stirred for 5 minutes at room temperature. 10 mL of water was added and then adjust pH 9-10 by 1N NaOH. Extracted with EA (30 mL×3), dried over Na$_2$SO$_4$ and filtered. The filtrate was evaporated under reduced pressure and the resulting oil was purified by pre-TLC (DCM/MeOH, 5/1) to give the title compound as a yellow solid (45 mg, 62.5%). $^1$H NMR (400 MHz, CD$_3$OD) δ 8.27 (d, J=6.0 Hz, 1H), 8.17 (s, 1H), 8.05 (s, 1H), 7.98 (d, J=7.6 Hz, 1H), 7.90-7.86 (m, 1H), 7.59-7.53 (m, 2H), 7.44 (t, J=8.0 Hz, 1H), 7.11 (dd, J=2.0 Hz, J=2.4 Hz, 1H), 6.67 (d, J=6.0 Hz, 1H), 5.28-5.26 (m, 1H), 3.62-3.31 (m, 4H), 2.40-2.25 (m, 2H); m/e 373 (M+H)⁺.

Example 96

2-(5-Bromo-2-fluorophenoxy)-N-cyclopropylacetamide

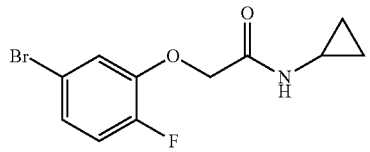 [SMILES: O=C(COc1cc(Br)ccc1F)NC1CC1]

A solution of 2-chloro-N-cyclopropylacetamide (1.0 g, 7.5 mmol), 5-bromo-2-fluorophenol (1.44 g, 7.5 mmol) and K$_2$CO$_3$ (1.55 g, 11.25 mmol) in 30 mL of acetone was heated at 60° C. for 16 h. The mixture was filtered and concentrated to give a residue, which was purified by column chromatography (PE/EA, 2/1) to give the title as a yellow solid (1.2 g, 55.3%). m/e 288 (M+H)⁺.

Example 97

N-cyclopropyl-2-(2-fluoro-5-(4,4,5,5-tetramethyl-1,3,2-dioxaborolan-2-yl)phenoxy)acetamide

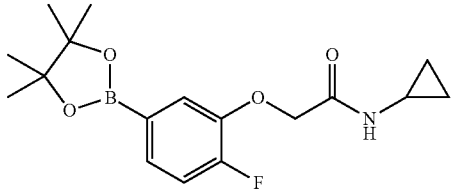 [SMILES: CC1(C)OB(c2ccc(F)c(OCC(=O)NC3CC3)c2)OC1(C)C]

A solution of 2-(5-bromo-2-fluorophenoxy)-N-cyclopropylacetamide (0.83 g, 2.88 mmol), Pin$_2$B$_2$ (1.1 g, 4.33 mmol), Pd(dppf)Cl$_2$ (120 mg) and potassium acetate (0.85 g, 8.64 mmol) in 35 mL of dioxane was degassed and flushed with N$_2$, heated at 80° C. for 14 h. The mixture was concentrated to give a residue, which was diluted with EtOAc (100 mL), washed with brine (3×30 mL), dried over Na$_2$SO$_4$ and filtered. The filtrate was evaporated under reduced pressure and the resulting oil was purified by column chromatography (PE/EA, 2/1) to give the title compound as an oil (600 mg, 21%). m/e 336 (M+H)⁺.

Example 98

2-(5-(4-(1H-indazol-5-ylamino)pyrimidin-2-yl)-2-fluorophenoxy)-N-cyclopropylacetamide

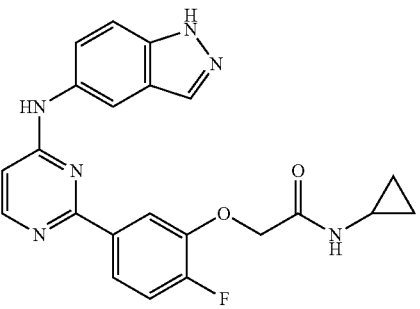 [SMILES: O=C(COc1cc(-c2nccc(Nc3ccc4[nH]ncc4c3)n2)ccc1F)NC1CC1]

A mixture of N-(2-chloropyrimidin-4-yl)-1H-indazol-5-amine (147 mg, 0.6 mmol), N-cyclopropyl-2-(2-fluoro-5-(4,4,5,5-tetramethyl-1,3,2-dioxaborolan-2-yl)phenoxy)acetamide (300 mg, 0.89 mmol), KOAc (235 mg, 2.4 mmol) and Pd(dppf)Cl$_2$ (70 mg) in dioxane/water (20 mL/3 mL) was degassed and flushed with N$_2$, heated at 100° C. for 16 h. The mixture was concentrated to give a residue, which was diluted with DCM (30 mL) and filtered. The filtrate was concentrated and purified by column chromatography (DCM/MeOH, 10/1) to give the title compound as a yellow solid (35 mg, 14%). $^1$H NMR (400 MHz, DMSO) δ 13.01 (s, 1H), 9.65 (s, 1H), 8.33 (d, J=5.6 Hz, 1H), 8.21-8.20 (m, 1H), 8.09-7.96 (m, 3H), 7.62-7.55 (m, 2H), 7.39-7.34 (m, 1H), 6.68 (d, J=6.0 Hz, 1H), 4.64 (s, 2H), 2.70-2.65 (m, 1H), 0.63-0.59 (m, 2H), 0.48-0.43 (m, 2H); m/e 419 (M+H)⁺.

Example 99

2-(5-(4-(1H-indazol-5-ylamino)-5-methylpyrimidin-2-yl)-2-fluorophenoxy)-N-cyclopropylacetamide

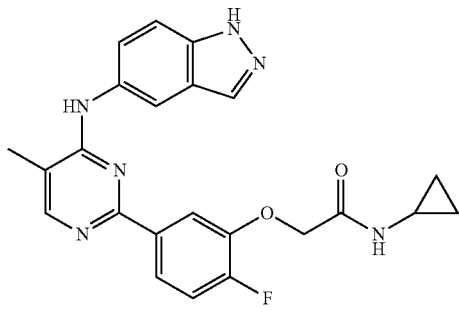 [SMILES: Cc1cnc(-c2ccc(F)c(OCC(=O)NC3CC3)c2)nc1Nc1ccc2[nH]ncc2c1]

A mixture of N-(2-chloro-5-methylpyrimidin-4-yl)-1H-indazol-5-amine (100 mg, 0.38 mmol), N-cyclopropyl-2-(2-fluoro-5-(4,4,5,5-tetramethyl-1,3,2-dioxaborolan-2-yl)phenoxy)acetamide (130 mg, 0.38 mmol), KOAc (151 mg, 1.55 mmol) and Pd(dppf)Cl$_2$ (50 mg) in dioxane/water (20 mL/3 mL) was degassed and flushed with N$_2$, heated at 100° C. for 16 h. The mixture was concentrated to give a residue, which was diluted with DCM (30 mL) and filtered. The filtrate was concentrated and purified by column chromatography (DCM/MeOH, 10/1) to give the title compound as a yellow solid (10 mg, 2.9%). $^1$H NMR (400 MHz, DMSO) δ 13.01 (s, 1H), 8.62 (s, 1H), 8.21 (s, 1H), 8.17 (d, J=4.0 Hz, 1H), 8.11-8.09 (m, 2H), 7.97-7.94 (m, 1H), 7.85-7.82 (m, 1H), 7.71-7.68 (m, 1H), 7.59-7.56 (m, 1H), 7.31-7.26 (m, 1H), 4.58 (s, 2H), 2.68-2.63 (m, 1H), 2.25 (s, 3H), 0.66-0.58 (m, 2H), 0.47-0.43 (m, 2H); m/e 433 (M+H)$^+$.

Example 100

N-(6-chloro-2-(pyrrolidin-1-yl)pyrimidin-4-yl)-1H-indazol-5-amine

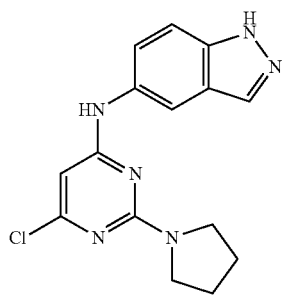 [SMILES: Clc1cc(Nc2ccc3[nH]ncc3c2)nc(N2CCCC2)n1]

A mixture of N-(2,6-dichloropyrimidin-4-yl)-1H-indazol-5-amine (0.88 g, 3.17 mol), pyrrolidine (225 mg, 3.17 mmol) and DIPEA (818 mg, 6.34 mmol) in BuOH (30 mL) was stirred at 120° C. for 12 h. The mixture was concentrated to give a residue, which was purified by pre-HPLC to give the title compound as a white solid (0.8 g, 80%). m/e 315 (M+H)$^+$.

Example 101 tert-butyl-5-(6-(3-(2-(cyclopropylamino)-2-oxoethoxy)phenyl)-2-(pyrrolidin-1-yl) pyrimidin-4-ylamino)-1H-indazole-1-carboxylate

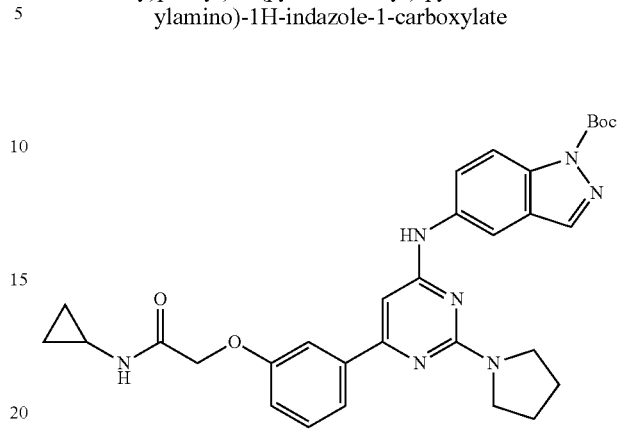

A mixture of N-(6-chloro-2-(pyrrolidin-1-yl)pyrimidin-4-yl)-1H-indazol-5-amine (300 mg, 0.95 mmol), N-cyclopropyl-2-(3-(4,4,5,5-tetramethyl-1,3,2-dioxaborolan-2-yl)phenoxy)acetamide (452 mg, 1.43 mmol), CsF (1.38 g, 1.55 mmol) and Pd(dppf)Cl$_2$ (150 mg) in dioxane/water (30 mL/3 mL) was degassed and flushed with N$_2$, heated at 100° C. for 16 h. The mixture was concentrated to give a residue, which was diluted with DCM (50 mL) and filtered. The filtrate was concentrated and purified by column chromatography (DCM/MeOH, 10/1) to give the title compound as a yellow solid (90 mg, 16%). m/e 570 (M+H)$^+$.

Example 102

2-(3-(6-(1H-indazol-5-ylamino)-2-(pyrrolidin-1-yl)pyrimidin-4-yl)phenoxy)-N-cyclopropylacetamide

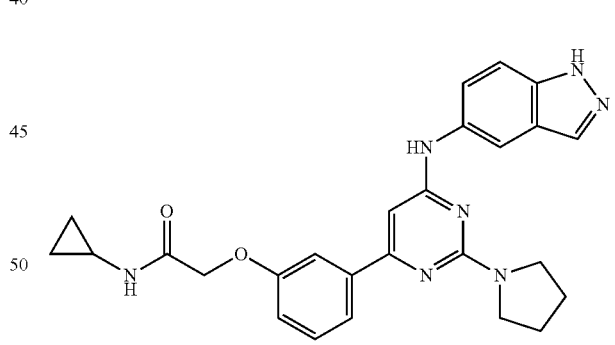

tert-Butyl 5-(6-(3-(2-(cyclopropylamino)-2-oxoethoxy)phenyl)-2-(pyrrolidin-1-yl) pyrimidin-4-ylamino)-1H-indazole-1-carboxylate (90 mg, 0.16 mmol) was dissolved in HFIP (2 mL), the solution was stirred at 150° C. for 1 h with M.W. The mixture was concentrated to give a residue, which was purified by pre-TLC (DCM:MeOH, 4:1) to give the title compound as a yellow solid (35 mg, 46.7%). $^1$H NMR (400 MHz, DMSO) δ 12.92 (s, 1H), 9.27 (s, 1H), 8.32 (s, 1H), 8.19 (d, J=4.4 Hz, 1H), 7.99 (s, 1H), 7.60 (s, 1H), 7.56-7.47 (m, 3H), 7.39 (t, J=8.0 Hz, 1H), 7.02 (dd, J=2.0 Hz, J=2.0 Hz, 1H), 6.47 (s, 1H), 4.50 (s, 2H), 3.63-3.60 (m, 4H), 2.73-2.66 (m, 1H), 1.95-1.98 (m, 4H), 0.66-0.61 (m, 2H), 0.51-0.47 (m, 2H); m/e 470 (M+H)$^+$.

Example 103

3-(3-bromophenyl)-N-cyclopropylpropanamide

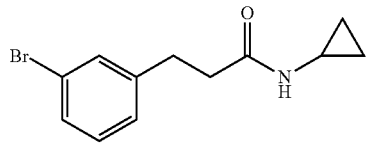

3-(3-Bromophenyl) propanoic acid (3.0 g, 13.1 mmol) was added to a solution of SOCl2 (10 ml) and was stirred for 2 hours at 70° C. The mixture was concentrated under reduced pressure. The residue was dissolved in CH2Cl2 (20 ml), then was added dropwise into the mixture of cyclopropanamine (1.17 g, 19.6 mmol) and triethylamine (4.0 g, 39.3 mmol) at 0° C., then the reaction mixture was stirred overnight at ambient temperature. The reaction mixture was quenched with 1N HCl and the organic layer was washed with brine, dried, concentrated to residue. The residue was purified by chromatography (PE/EA: 1/1 to 1/2) to give the title compound as white solid (2.8 g, 79%). $^1$H NMR (400 MHz, CDCl$_3$) δ7.36 (m, 2H), 7.15 (m, 2H), 5.53 (s, 1H), 2.94 (t, 2H), 2.68 (s, 1H), 2.41 (t, 2H), 0.77 (m, 2H), 0.44 (m, 2H). m/e 268 (M+H)$^+$.

Example 104

N-Cyclopropyl-3-(3-(4,4,5,5-tetramethyl-1,3,2-dioxaborolan-2-yl)phenyl)propanamide

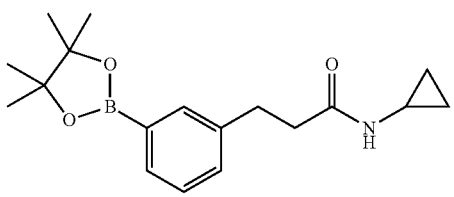 [SMILES: CC1(C)OB(c2cccc(CCC(=O)NC3CC3)c2)OC1(C)C]

PdCl$_2$(dppf) (420 mg, 0.5 mmol) was added into the mixture of 3-(3-bromophenyl)-N-cyclopropylpropanamide (2.8 g, 10.3 mmol), 4,4,4',4',5,5,5',5'-octamethyl-2,2'-bi(1,3,2-dioxaborolane) (3.9 g, 15.5 mmol) and KOAc (2.5 g, 25.7 mmol) in dioxane (80 ml). The mixture was stirred overnight at 100° C. under nitrogen. The reaction mixture was then concentrated in vacuo, and the residue was purified by chromatography (PE/EA: 5/1 to 1/1) to give the title compound as an off-white solid (3.0 g, 92%). $^1$H NMR (300 MHz, CDCl$_3$) δ 7.60-7.67 (m, 2H), 7.27-7.33 (m, 2H), 5.47 (s, 1H), 2.92-2.97 (m, 2H), 2.41 (t, 2H), 2.04 (s, 1H), 1.34 (s, 12H), 0.70-0.72 (m, 2H), 0.38-0.40 (m, 2H); m/e 316 (M+H)$^+$.

Example 105 tert-Butyl 5-(tert-butoxycarbonyl(2-(3-(3-(cyclopropylamino)-3-oxopropyl)phenyl) pyrimidin-4-yl) amino)-1H-indazole-1-carboxylate

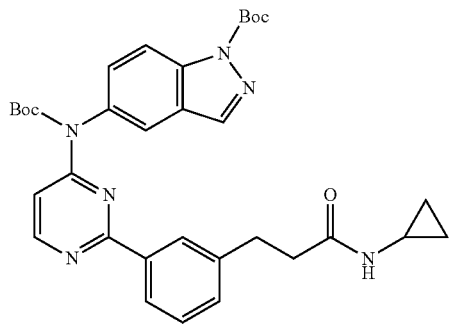 [SMILES: CC(C)(C)OC(=O)N(c1ccc2c(cnn2C(=O)OC(C)(C)C)c1)c1ccnc(-c2cccc(CCC(=O)NC3CC3)c2)n1]

PdCl$_2$(dppf) (165 mg, 0.21 mmol) was added into the mixture of N-cyclopropyl-3-(3-(4,4,5,5-tetramethyl-1,3,2-dioxaborolan-2-yl)phenyl)propanamide (380 mg, 1.2 mmol), Boc2O (650 mg, 3.0 mmol), CsF (600 mg, 4.0 mmol) and tert-butyl 5-(tert-butoxycarbonyl(2-chloropyrimidin-4-yl)amino)-1H-indazole-1-carboxylate (446 mg, 1.0 mmol) in dioxane/H$_2$O (30 ml, 10/1) under N$_2$ flow. The mixture was stirred for 24 h at 100° C. under nitrogen. The reaction mixture was extracted with EA (60 ml) and washed with brine, dried, concentrated in vacuo, and the residue was purified by chromatography (PE/EA: 5/1 to 1/5) to give the title compound product (240 mg) as a yellow oil. m/e 599 (M+H)$^+$.

Example 106

3-(3-(4-(1H-indazol-5-ylamino)pyrimidin-2-yl)phenyl)-N-cyclopropylpropanamide

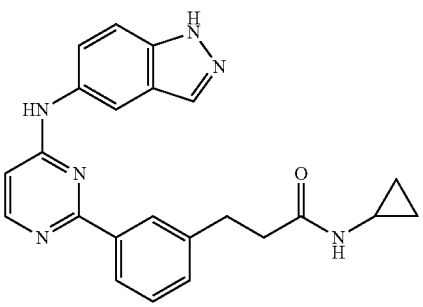 [SMILES: O=C(CCc1cccc(-c2nccc(Nc3ccc4[nH]ncc4c3)n2)c1)NC1CC1]

tert-Butyl-5-(tert-butoxycarbonyl(2-(3-(3-(cyclopropylamino)-3-oxopropyl)phenyl)pyrimidin-4-yl)amino)-1H-indazole-1-carboxylate (220 mg, 0.367 mmol) was added to a mixture of saturated HCl in ethyl ether (30 mL). The mixture was stirred for 3 hours at ambient temperature. Then the mixture was filtered and the yellow solid was added to HCl (5 ml), then was stirred for 10 minutes and diluted with H2O (50 ml), filtered. The obtained off-white crystals as hydrochloride salt was added to saturated NaHCO₃ (10 ml) and was stirred for 2 h. The mixture was filtered and the solid was washed with H₂O (10 ml), dried to give the title compound (50 mg, 34%) as an off-white solid. ¹H NMR (300 MHz, DMSO) δ13.00 (s, 1H), 9.62 (s, 1H), 8.34-8.32 (m, 3H), 8.22 (m, 1H), 8.06 (s, 1H), 7.85 (s, 1H), 7.55 (m, 1H), 7.40 (m, 3H), 6.66 (d, 1H), 2.90 (m, 2H), 2.60 (m, 1H), 2.40 (m, 2H), 0.57 (m, 2H), 0.33 (m, 2H). m/e 399 (M+H)⁺.

Example 107

2-(3-bromophenylthio)-N-cyclopropylacetamide

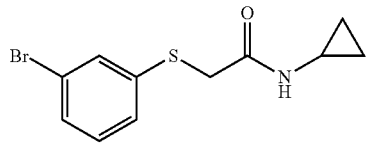 [SMILES: O=C(CSc1cccc(Br)c1)NC1CC1]

A solution of 2-chloro-N-cyclopropylacetamide (1.33 g, 10 mmol), 3-bromobenzenethiol (1.6 g, 8.5 mmol) and K₂CO₃ (4.8 g, 35 mmol) in 30 mL of acetone was heated at 70° C. overnight. The mixture was filtered and concentrated to give a residue, which was purified by column chromatography (PE/EA, 1/1) to give the title compound (2.4 g, 96%) as a white solid. ¹H NMR δ (300 MHz, CDCl3) 7.39 (1H, m), 7.31 (1H, m), 7.14 (2H, m), 6.71 (1H, s), 3.58 (2H, s), 2.64-2.77 (1H, m), 0.73-0.84 (2H, m), 0.41 (2H, m); m/e 286 (M+H)⁺.

Example 108

N-cyclopropyl-2-(3-(4,4,5,5-tetramethyl-1,3,2-dioxaborolan-2-yl)phenylthio)acetamide

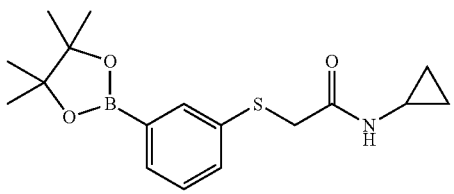 [SMILES: CC1(C)OB(c2cccc(SCC(=O)NC3CC3)c2)OC1(C)C]

A solution of 2-(3-bromophenylthio)-N-cyclopropylacetamide (2.43 g, 9.1 mmol), Pin₂B₂ (3.5 g, 13.7 mmol), Pd(dppf)Cl₂ (730 mg) and potassium acetate (2.67 g, 27.3 mmol) in 30 mL of dioxane was degassed and flushed with N₂, heated at 95° C. for 12 h. The mixture was concentrated to give a residue, which was diluted with EtOAc (200 mL), filtered, concentrated and purified by chromatography (EA: PE, 1:1) to give the title compound (2.4 g, 82%) as a yellow oil. m/e 286 (M+H)⁺.

Example 109 tert-Butyl 5-(tert-butoxycarbonyl(2-(3-(2-(cyclopropylamino)-2-oxoethylthio)phenyl)pyrimidin-4-yl)amino)-1H-indazole-1-carboxylate

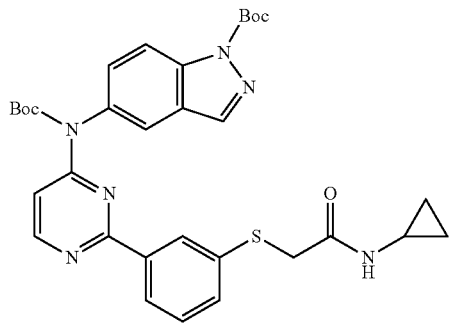 [SMILES: CC(C)(C)OC(=O)N(c1ccc2c(cnn2C(=O)OC(C)(C)C)c1)c1ccnc(-c2cccc(SCC(=O)NC3CC3)c2)n1]

A mixture of N-cyclopropyl-2-(3-(4,4,5,5-tetramethyl-1,3,2-dioxaborolan-2-yl)phenylthio)acetamide (380 mg, 1.1 mmol), N-(2-chloropyrimidin-4-yl)-1H-indazol-5-amine (246 mg, 1.0 mmol), CsF (730 mg, 5.0 mmol), Boc₂O (650 mg, 3.0 mmol), and Pd(dppf)Cl₂ (1700 mg) in dioxane/water (27 mL/3 mL) was degassed and flushed with N₂, heated at 100° C. 24 h. The mixture was concentrated to give a residue, which was diluted with DCM, filtered, concentrated and purified by chromatography (DCM/MeOH, 20/1) to give the crude title compound (200 mg) as a yellow solid. m/e 617 (M+H)⁺.

Example 110

2-(3-(4-(1H-indazol-5-ylamino)pyrimidin-2-yl)phenylthio)-N-cyclopropylacetamide

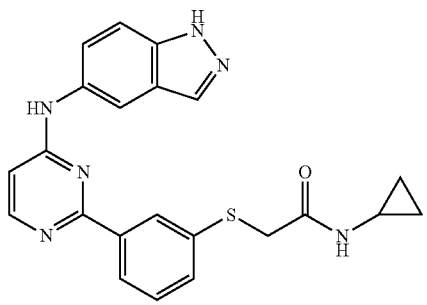 [SMILES: O=C(CSc1cccc(-c2nccc(Nc3ccc4[nH]ncc4c3)n2)c1)NC1CC1]

A mixture of tert-butyl 5-(tert-butoxycarbonyl(2-(3-(2-(cyclopropylamino)-2-oxoethylthio)phenyl)pyrimidin-4-yl)amino)-1H-indazole-1-carboxylate (209 mg, 0.80 mmol) in con. HCl (3 mL) was stirred for 10 minutes followed by addition of ice. The reaction mixture was adjusted to pH 10 with NaHCO₃ solution and extracted with CH₂Cl₂/MeOH (1/1, 20 ml). Filtered and the filtrate was concentrated to give a residue, which was purified by chromatography (DCM/MeOH, 20/1) followed by further purification by pre-TLC to give the title compound (25 mg, 18%) as a yellow solid. ¹H NMR (300 MHz, CD₃OD) δ 8.36 (1H, m), 8.24 (1H, d, J=6 Hz), 8.14 (2H, m), 8.05 (1H, s), 7.56 (2H, s), 7.49 (1H, m), 7.41 (1H, d, J=6 Hz), 6.63 (1H, d, J=6 Hz), 3.60 (2H, s), 2.58 (1H, m), 0.61 (2H, m), 0.36 (2H, m); m/e 417 (M+H)+.

Example 111

2-(3-(4-aminopyrimidin-2-yl)phenoxy)-N-isopropylacetamide

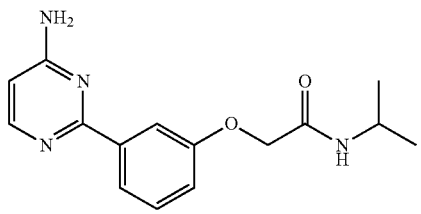 [SMILES: CC(C)NC(=O)COc1cccc(-c2nccc(N)n2)c1]

A mixture of 2-chloropyrimidin-4-amine (0.50 g, 3.8 mmol), N-isopropyl-2-(3-(4,4,5,5-tetramethyl-1,3,2-dioxaborolan-2-yl)phenoxy)acetamide (1.46 g, 4.6 mmol), CsF (1.75 g, 11.4 mmol), and Pd(PPh₃)₄ (0.2 g, 0.2 mmol) in a mixture of dioxane (8 mL) and H₂O (2 mL) was stirred at 100° C. overnight under N₂. After cooling to room temperature, the mixture was concentrated under reduced pressure to give a residue, which was purified by column chromatography on silica gel (eluted with PE:EtOAc=1:1) to provide the title compound (400 mg, yield 36%) as colourless oil.

Example 112

N-isopropyl-2-(3-(4-(pyridin-4-ylamino)pyrimidin-2-yl)phenoxy)acetamide

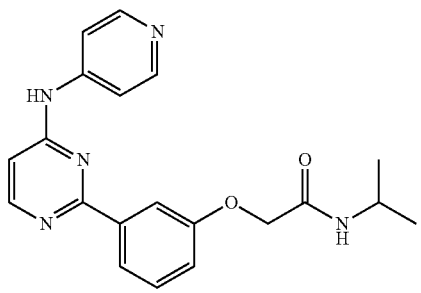 [SMILES: CC(C)NC(=O)COc1cccc(-c2nccc(Nc3ccncc3)n2)c1]

A mixture of compound 2-(3-(4-aminopyrimidin-2-yl)phenoxy)-N-isopropylacetamide
(300 mg, 1.1 mmol), 4-bromopyridine (258 mg, 1.3 mmol), Cs₂CO₃ (1026 mg, 3.3 mmol), Pd₂(dba)₃ (96 mg, 0.1 mmol), and X-Phos (51 mg, 0.1 mmol) in anhydrous dioxane (30 mL) was stirred at 120° C. overnight under N₂. After cooling to room temperature, the mixture was filtered, the filtrate was concentrated, the residue was washed with EtOAc then was filtered to provide the title compound (200 mg, yield 52%) as white solid. ¹H NMR (400 MHz, CD₃OD) δ 10.09 (s, 1H), 8.47-7.92 (m, 8H), 7.45 (t, J=7.6 Hz, 1H), 7.12-6.82 (m, 2H), 4.52 (s, 2H), 3.99-3.92 (m, 1H), 1.06 (d, J=6.8 Hz, 6H); m/e 364 (M+H)+.

Example 113

2-chloro-4-(4-(pyridin-4-yl)piperidin-1-yl)pyrimidine

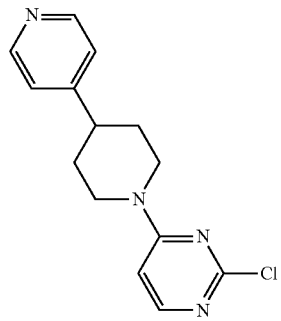 [SMILES: Clc1nccc(N2CCC(c3ccncc3)CC2)n1]

2, 4-Dichloropyrimide (745 mg, 5 mmol), 1,2,3,4,5,6-hexahydro-[4, 4']bipyridinyl (811 mg, 5 mmol), and TEA (758 mg, 7.5 mmol) in EtOH (15 mL) was stirred at reflux overnight. After removing the solvent, the residue was purified by column chromatography on silica gel (eluting with petroleum ether:ethyl acetate=5:1-1:1) to give the title compound (500 mg, yield 36.4%) as a white solid.

Example 114

N-isopropyl-2-(3-(4-(4-(pyridin-4-yl)piperidin-1-yl)pyrimidin-2-yl)phenoxy)acetamide

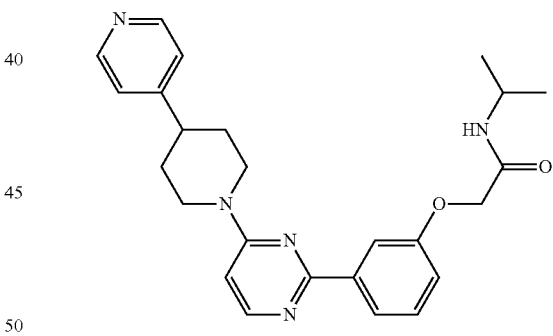

A mixture of 2-chloro-4-(4-(pyridin-4-yl)piperidin-1-yl)pyrimidine (500 mg, 1.82 mmol), Pd(dppf)₂Cl₂ (50 mg), Na₂CO₃ (579 mg, 5.46 mmol) and N-isopropyl-2-(3-(4,4,5,5-tetramethyl-1,3,2-dioxaborolan-2-yl)phenoxy)acetamide (871 mg, 2.73 mmol) in dioxane/water (10:1, 10 mL) was stirred at 100° C. overnight. After removing the solvent, the residue was purified by P-HPLC to give the title compound (300 mg, yield 35.2%) as a solid. ¹H NMR (400 MHz, CD3OD) δ 8.80 (d, J=6.8 Hz, 2H), 8.23 (d, J=7.6 Hz, 1H), 8.10 (d, J=6.4 Hz, 2H), 7.83-7.81 (m, 2H), 7.59 (t, J=8.4 Hz, 1H), 7.37-7.20 (m, 2H), 5.54 (d, J=13.2 Hz, 1H), 4.62 (s, 2H), 4.52 (d, J=14 Hz, 1H), 4.12-4.06 (m, 1H), 3.61-3.47 (m, 4H), 2.26-1.89 (m, 4H), 1.17 (d, J=7.6 Hz, 6H); m/e 432 (M+H)+.

Example 115

4,6-dichloro-2-iodopyrimidine

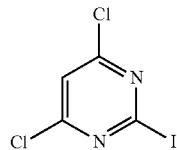

To a solution of compound 4,6-dichloropyrimidin-2-amine (39 g, 237.82 mmol) in CH3CN (300 mL), CH$_2$I2 (1000 mL) was added then t-BuONO (129.3 g, 1.25 mol) was added and the mixture was heated to reflux overnight. The mixture was concentrated under reduced pressure and the residue was purified by column chromatography to give compound the title compound (30 g, yield 46%) as a yellow solid.

Example 116

2-(3-(4,6-dichloropyrimidin-2-yl)phenoxy)-N-isopropylacetamide

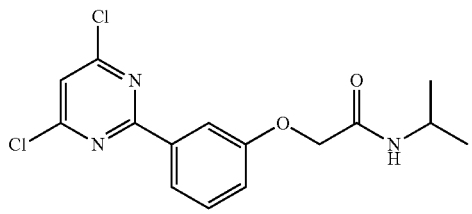 [SMILES: CC(C)NC(=O)COc1cccc(-c2nc(Cl)cc(Cl)n2)c1]

To a mixture of compound 4,6-dichloro-2-iodopyrimidine (13.92 g, 50.64 mmol), N-isopropyl-2-(3-(4,4,5,5-tetramethyl-1,3,2-dioxaborolan-2-yl)phenoxy)acetamide (18 g, 56.39 mmol), Na$_2$CO$_3$ (13.88 g, 130.96) in DME (150 mL) and water (50 mL), Pd(PPh$_3$)$_4$ (5.04 g, 4.36 mmol) was added and the mixture was heated to reflux overnight under N$_2$. Then the reaction mixture was poured into water (100 mL), extracted with EtOAc (150 mL×2) and the organic phase was washed by brine, dried with Na$_2$SO$_4$ and concentrated under reduced pressure and the residue was purified by column chromatography to give the title compound (9.05 g, yield 52%) as white solid.

Example 117

2-(3-(4-((1H-indazol-5-yl)amino)-6-chloropyrimidin-2-yl)phenoxy)-N-isopropylacetamide

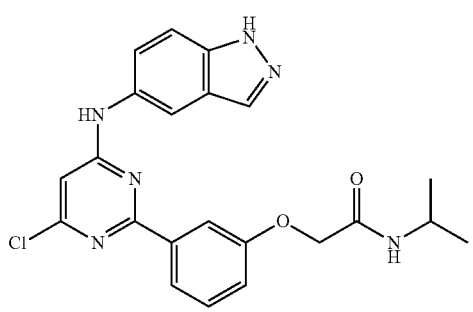 [SMILES: CC(C)NC(=O)COc1cccc(-c2nc(Cl)cc(Nc3ccc4[nH]ncc4c3)n2)c1]

To a solution of compound 2-(3-(4,6-dichloropyrimidin-2-yl)phenoxy)-N-isopropylacetamide (5.7 g, 16.75 mmol) in iPrOH (110 mL), DIPEA (6.5 g, 48.82 mmol) and 1H-indazol-5-amine (2.23 g, 17.25 mmol) were added and the reaction mixture was heated to reflux overnight. The reaction mixture was concentrated under reduced pressure and the residue was purified by column chromatography to give the title compound (3.22 g, yield 44%). $^1$H NMR (400 MHz, DMSO-d$_6$) δ 13.05 (s, 1H), 9.90 (s, H), 8.09 (b, 2H), 7.95-7.89 (m, 3H), 7.59-7.41 (m, 3H), 7.12 (d, J=8.0 Hz, 1H), 6.66 (s, 1H), 4.51 (s, 2H), 4.00-3.94 (m, 1H), 1.08 (d, J=6.4 Hz, 6H); m/e 437 (M+H)$^+$.

Example 118

2-(3-(4-((1H-indazol-5-yl)amino)-6-(piperazin-1-yl)pyrimidin-2-yl)phenoxy)-N-isopropylacetamide

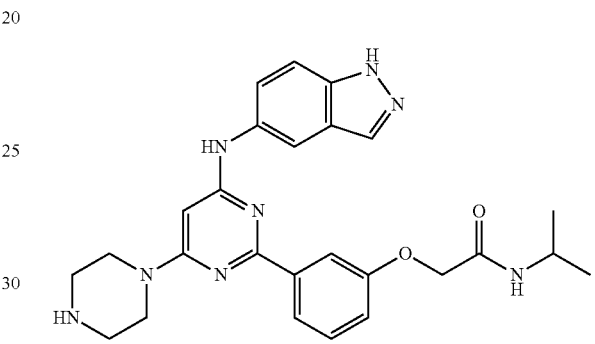

To a stirred solution of 2-(3-(4-((1H-indazol-5-yl)amino)-6-chloropyrimidin-2-yl)phenoxy)-N-isopropylacetamide (300 mg, 0.687 mmol) in iprOH (20 mL), Et$_3$N (3 mL), and piperazine (592 mg, 6.87 mmol) were added at room temperature. The mixture was stirred overnight at 110° C. Then reaction mixture was concentrated under reduced pressure and the residue was purified by pre-HPLC to provide the title compound (114 mg, yield 34%). $^1$H NMR (400 MHz, DMSO-d$_6$) δ 12.91 (s, 1H), 9.01 (s, 1H), 8.08 (s, 1H), 8.02 (s, 1H), 7.94-7.89 (m, 3H), 7.51-7.35 (m, 3H), 7.04 (dd, J=8.0 and 2.0 Hz, 1H), 5.82 (s, 1H), 4.50 (s, 2H), 3.98-3.92 (m, 1H), 3.48 (b, 4H), 2.76 (b, 4H), 1.07 (d, J=6.8 Hz, 6H); m/e 487 (M+H)$^+$.

Example 119

2-(3-(4-((1H-indazol-5-yl)amino)-6-morpholinopyrimidin-2-yl)phenoxy)-N-isopropylacetamide

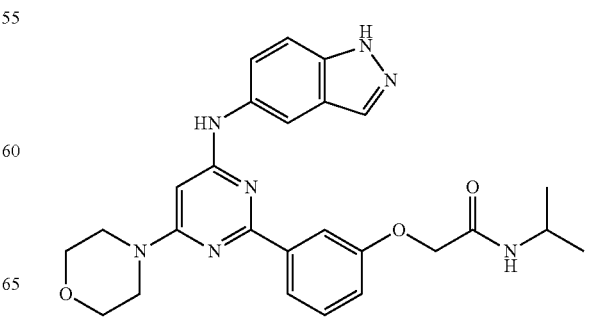

The title compound was synthesized using the same procedure as that for 2-(3-(4-((1H-indazol-5-yl)amino)-6-(piperazin-1-yl)pyrimidin-2-yl)phenoxy)-N-isopropylacetamide (example 118) (112 mg, yield 34%). $^1$H NMR (400 MHz, DMSO-$d_6$) δ 12.93 (s, 1H), 9.09 (s, 1H), 8.08 (s, 1H), 8.03 (s, 1H), 7.95-7.91 (m, 3H), 7.49-7.38 (m, 3H), 7.05 (d, J=8.0 Hz, 1H), 5.84 (s, 1H), 4.50 (s, 2H), 3.94 (b, 1H), 3.69 (s, 4H), 3.52 (s, 4H), 1.06 (d, J=6.8 Hz, 6H); m/e 488 (M+H)$^+$.

Example 120

2-(3-(4-((1H-indazol-5-yl)amino)-6-(4-methyl-1,4-diazepan-1-yl)pyrimidin-2-yl)phenoxy)-N-isopropylacetamide

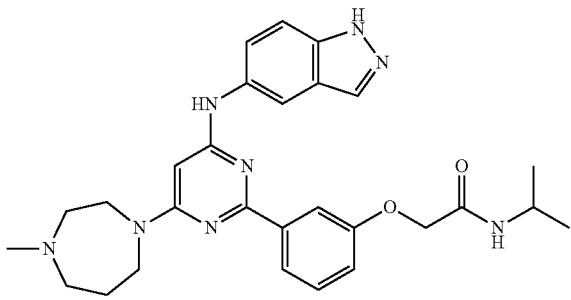 [SMILES: CC(C)NC(=O)COc1cccc(-c2nc(Nc3ccc4[nH]ncc4c3)cc(N3CCCN(C)CC3)n2)c1]

The title compound was synthesized using the same procedure as that for 2-(3-(4-((1H-indazol-5-yl)amino)-6-(piperazin-1-yl)pyrimidin-2-yl)phenoxy)-N-isopropylacetamide (example 118) (100 mg, yield 65%). $^1$H NMR (400 MHz, DMSO-$d_6$) δ 12.94 (s, 1H), 9.00 (s, 1H), 8.13 (s, 1H), 8.05 (s, 1H), 7.97-7.91 (m, 3H), 7.53-7.05 (m, 4H), 5.75 (s, 1H), 4.53 (s, 2H), 4.02-3.62 (m, 5H), 2.64 (b, 2H), 2.50 (b, 2H), 2.26 (s, 3H), 1.92 (b, 2H), 1.09 (d, J=6.8 Hz, 6H); m/e 515 (M+H)$^+$.

Example 121

2-(3-(4-((1H-indazol-5-yl)amino)-6-(1,4-diazepan-1-yl)pyrimidin-2-yl)phenoxy)-N-isopropylacetamide

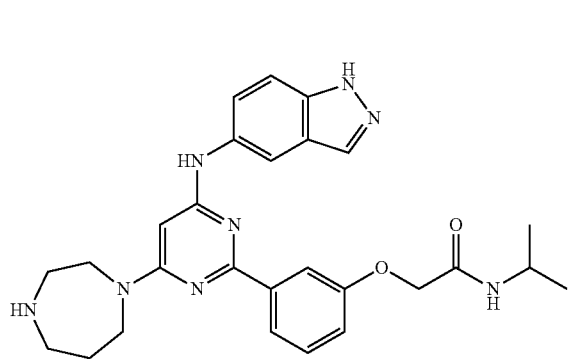 [SMILES: CC(C)NC(=O)COc1cccc(-c2nc(Nc3ccc4[nH]ncc4c3)cc(N3CCCNCC3)n2)c1]

The title compound was synthesized using the same procedure as that for 2-(3-(4-((1H-indazol-5-yl)amino)-6-(piperazin-1-yl)pyrimidin-2-yl)phenoxy)-N-isopropylacetamide (example 118) (110 mg, yield 32%). $^1$H NMR (400 MHz, DMSO-$d_6$) δ 12.90 (s, 1H), 8.96 (s, 1H), 8.11 (s, 1H), 8.02 (s, 1H), 7.92-7.03 (m, 5H), 5.74 (s, 1H), 4.50 (s, 2H), 3.96-3.68 (m, 3H), 2.85 (b, 2H), 2.66 (b, 2H), 2.31 (b, 2H), 1.77 (b, 2H), 1.07 (d, J=6.8 Hz, 6H); m/e 501 (M+H)$^+$.

Example 122

2-(3-(4-((1H-indazol-5-yl)amino)-6-(dimethylamino)pyrimidin-2-yl)phenoxy)-N-isopropylacetamide

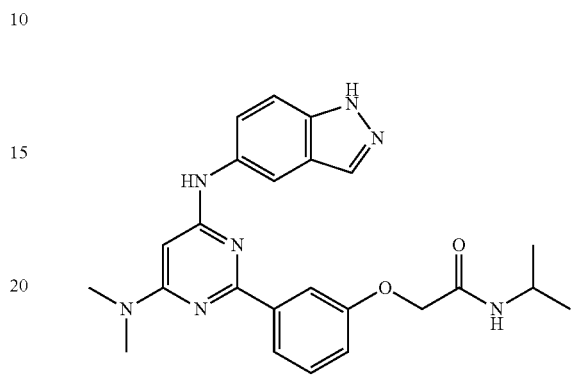

The title compound was synthesized using the same procedure as that for 2-(3-(4-((1H-indazol-5-yl)amino)-6-(piperazin-1-yl)pyrimidin-2-yl)phenoxy)-N-isopropylacetamide (example 118) (101 mg, yield 33%). $^1$H NMR (400 MHz, DMSO-$d_6$) δ 12.90 (s, 1H), 9.00 (s, 1H), 8.10 (s, 1H), 8.02 (s, 1H), 7.97-7.88 (m, 3H), 7.48 (s, 2H), 7.38 (t, J=8.0 Hz, 1H), 7.03 (d, J=7.2 Hz, 1H), 5.73 (s, 1H), 4.50 (s, 2H), 3.98-3.93 (m, 1H), 3.07 (s, 6H), 1.08 (d, J=6.8 Hz, 6H); m/e 446 (M+H)$^+$.

Example 123

2-(3-(4-((1H-indazol-5-yl)amino)-6-(piperidin-1-yl)pyrimidin-2-yl)phenoxy)-N-isopropylacetamide

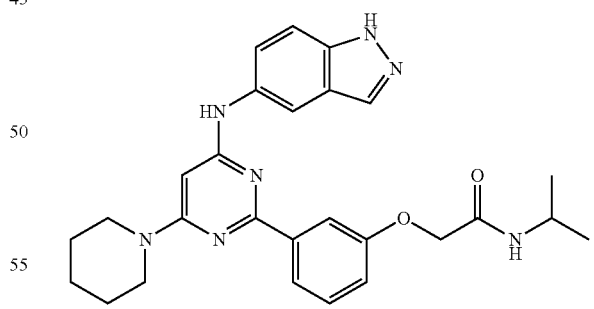

The title compound was synthesized using the same procedure as that for 2-(3-(4-((1H-indazol-5-yl)amino)-6-(piperazin-1-yl)pyrimidin-2-yl)phenoxy)-N-isopropylacetamide (example 118) (110 mg, yield 33%). $^1$H NMR (400 MHz, DMSO-$d_6$) δ 12.91 (s, 1H), 8.98 (s, 1H), 8.09 (s, 1H), 8.02 (s, 1H), 7.94-7.89 (m, 3H), 7.49-7.03 (m, 5H), 5.85 (s, 1H), 5.00 (s, 2H), 3.96-3.93 (m, 1H), 3.58 (b, 4H), 1.55 (b, 6H), 1.07 (d, J=6.8 Hz, 6H); m/e 486 (M+H)$^+$.

Example 124

2-(3-(4-((1H-indazol-5-yl)amino)-6-((2-methoxyethyl)(methyl)amino)pyrimidin-2-yl)phenoxy)-N-isopropylacetamide

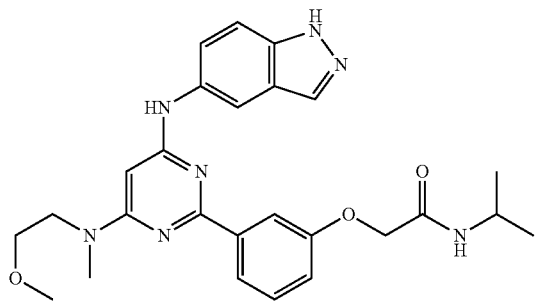 [SMILES: COCCN(C)c1cc(Nc2ccc3[nH]ncc3c2)nc(-c2cccc(OCC(=O)NC(C)C)c2)n1]

The title compound was synthesized using the same procedure as that for 2-(3-(4-((1H-indazol-5-yl)amino)-6-(piperazin-1-yl)pyrimidin-2-yl)phenoxy)-N-isopropylacetamide (example 118) (110 mg, yield 33%). $^1$H NMR (400 MHz, DMSO-d$_6$) δ 13.00 (s, 1H), 9.07 (s, 1H), 8.15 (s, 1H), 8.08 (s, 1H), 8.05-7.92 (m, 3H), 7.53 (s, 1H), 7.42 (t, J=8.0 Hz, 1H), 7.07 (d, J=7.6 Hz, 1H), 5.79 (s, 1H), 4.53 (s, 2H), 4.03-3.95 (m, 1H), 2.78 (b, 2H), 3.59-3.56 (m, 2H), 3.29 (s, 3H), 3.07 (s, 3H), 1.10 (d, J=6.8 Hz, 1H); m/e 490 (M+H)$^+$.

Example 125

2-(3-(4-((1H-indazol-5-yl)amino)-6-((2-(dimethylamino)ethyl)(methyl)amino)pyrimidin-2-yl)phenoxy)-N-isopropylacetamide

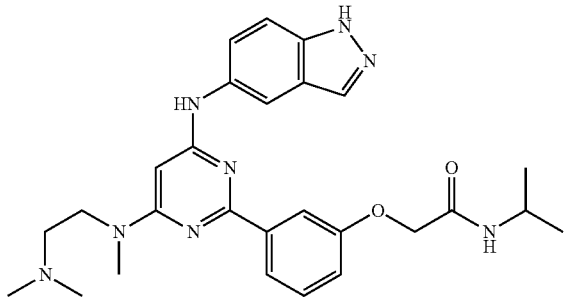 [SMILES: CC(C)NC(=O)COc1cccc(-c2nc(Nc3ccc4[nH]ncc4c3)cc(N(C)CCN(C)C)n2)c1]

The title compound was synthesized using the same procedure as that for 2-(3-(4-((1H-indazol-5-yl)amino)-6-(piperazin-1-yl)pyrimidin-2-yl)phenoxy)-N-isopropylacetamide (example 118) (100 mg, yield 29%). $^1$H NMR (400 MHz, DMSO-d$_6$) δ 12.91 (s, 1H), 8.99 (s, 1H), 8.09 (s, 1H), 8.02 (s, 1H), 7.96-7.86 (m, 3H), 7.49-7.03 (m, 4H), 5.71 (s, 1H), 4.46 (s, 2H), 4.00-3.92 (m, 1H), 3.67 (b, 2H), 3.30 (b, 2H), 3.01 (s, 3H), 2.15 (s, 6H), 1.07 (d, J=6.8 Hz, 6H); m/e 503 (M+H)$^+$.

Example 126

2-(3-(4-chloro-6-(2-(dimethylamino)ethoxy)pyrimidin-2-yl)phenoxy)-N-isopropylacetamide

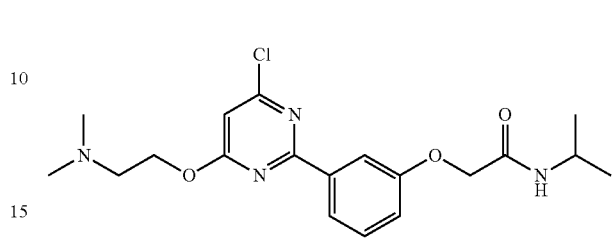

To a solution of compound 2-(3-(4,6-dichloropyrimidin-2-yl)phenoxy)-N-isopropylacetamide (1 g, 2.9 mmol) in toluene (24 mL) were added NaOH (232 mg, 5.8 mmol) and 2-(dimethylamino)ethanol (261 mg, 2.9 mmol). The resulting mixture was stirred for 3 hrs at 110° C. Then the reaction mixture was diluted with water and extracted with DCM. The organic layer was dried over Na$_2$SO$_4$, filtered and concentrated under reduced pressure to give a residue which was purified by column chromatograph on silica gel (eluted with DCM:MeOH=100:1) to give compound the title compound (550 mg, yield 48%) as a solid.

Example 127

2-(3-(4-((1H-indazol-5-yl)amino)-6-(2-(dimethylamino)ethoxy)pyrimidin-2-yl)phenoxy)-N-isopropylacetamide

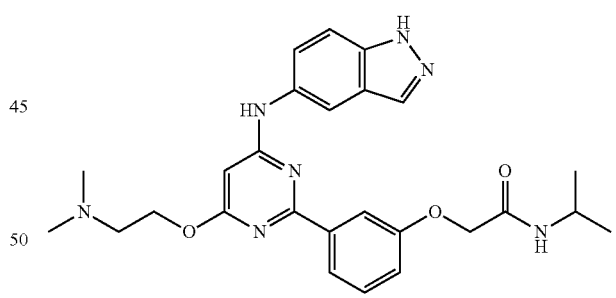

To a solution of compound 2-(3-(4-chloro-6-(2-(dimethylamino)ethoxy)pyrimidin-2-yl)phenoxy)-N-isopropylacetamide (100 mg, 0.25 mmol) in EtOH (1 mL) were added 1H-indozal-5-amine (101.5 mg, 0.76 mmol) and TFA (0.25 mL). The resulting mixture was heated to 80° C. overnight. The mixture was concentrated and purified by chromatography on silica gel column and purified by Prep-TLC again to give the title compound (100 mg, yield 16%) as a light yellow solid. $^1$H NMR (400 MHz, MeOD) δ 8.05-7.96 (m, 4H), 7.54-7.49 (m, 2H), 7.40-7.08 (m, 2H), 5.94 (s, 1H), 4.55 (s, 4H), 4.14-4.06 (m, 1H), 2.79-2.76 (m, 2H), 2.33 (s, 6H), 1.16 (d, J=6.8 Hz, 6H); m/e 490 (M+H)$^+$.

Example 128

3-(4,4,5,5-tetramethyl-1,3,2-dioxaborolan-2-yl)phenyl morpholine-4-carboxylate

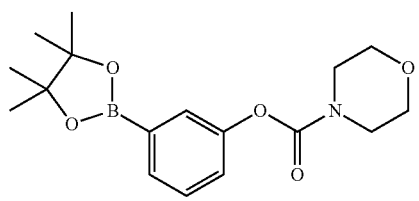 [SMILES: CC1(C)OB(c2cccc(OC(=O)N3CCOCC3)c2)OC1(C)C]

To a mixture of 3-(4,4,5,5-tetramethyl-1,3,2-dioxaborolan-2-yl)phenol (500 mg, 2.27 mmol), DMAP (277.3 mg) and Et$_3$N (450.46 mg, 4.54, mmol) in DCM (10 ml) was added dropwise a solution of morpholine-4-carbonyl chloride (339.5 mg, 2.27 mmol) in DCM (10 ml) at 0° C. Water was added to the mixture and extracted with DCM (40 mL×2). The organic phase was dried with Na$_2$SO$_4$ and concentrated under reduced pressure to give the title compound (600 mg, yield 79%) which was used to next step directly.

Example 129

3-(4-((1H-indazol-5-yl)amino)pyrimidin-2-yl)phenyl morpholine-4-carboxylate

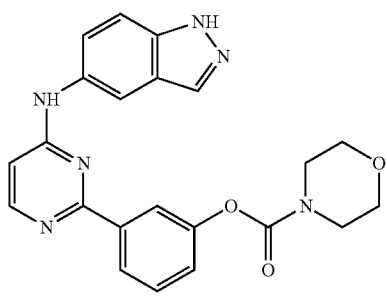 [SMILES: O=C(Oc1cccc(-c2nccc(Nc3ccc4[nH]ncc4c3)n2)c1)N1CCOCC1]

To a stirred solution of tert-butyl 5-((tert-butoxycarbonyl)(2-chloropyrimidin-4-yl)amino)-1H-indazole-1-carboxylate (100 mg, 0.2243 mmol) in EtOH (3 mL) and H$_2$O (0.3 ml) were added Na$_2$CO$_3$ (47.54 mg, 0.4485 mmol), (Boc)$_2$O (93.29 mg, 0.4485 mmol) and 3-(4,4,5,5-tetramethyl-1,3,2-dioxaborolan-2-yl)phenyl morpholine-4-carboxylate (149.44 mg, 0.4485 mmol) at room temperature. The mixture was degassed by budding nitrogen through the solution Pd(PPh$_3$)$_2$Cl$_2$ (15.07 mg, 0.02243 mmol) was added and the mixture was heated under microwave irradiation for 20 minutes at 110° C. The mixture was dried and concentrated under reduced pressure and the residue was purified by column chromatograph on silica gel (DCM:MeOH=50:1) to give the title compound (50 mg, yield 53%). $^1$H NMR (400 MHz, DMSO-d$_6$) δ 13.02 (s, 1H), 9.66 (s, 1H), 8.33-8.18 (m, 4H), 7.55-7.51 (m, 3H), 7.25 (d, J=8.0 Hz, 1H), 6.67 (d, J=5.6 Hz, 1H), 3.64 (b, 6H), 3.45 (b, 2H); m/e 417 (M+H)$^+$.

Example 130

3-(4,4,5,5-tetramethyl-1,3,2-dioxaborolan-2-yl)phenyl dimethylcarbamate

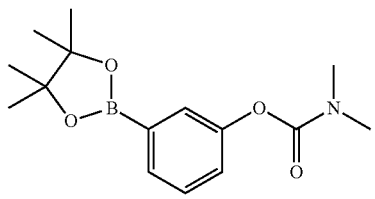

To a mixture of 3-(4,4,5,5-tetramethyl-1,3,2-dioxaborolan-2-yl)phenol (500 mg, 2.23 mmol), DMAP (277.4 mg) and Et$_3$N (450.46 mg, 4.46, mmol) in DCM (15 mL) was added dropwise a solution of dimethylcarbamic chloride (238.6 mg, 2.23 mmol) in DCM (15 ml) at 0° C. and the reaction mixture was stirred overnight at room temperature. Water was added to the mixture and extracted with DCM (40 mL×2). The organic phase was dried with Na$_2$SO$_4$ and concentrated under reduced pressure to give the title compound (500 mg, yield 76%) which was used to next step directly.

Example 131

3-(4-((1H-indazol-5-yl)amino)pyrimidin-2-yl)phenyl dimethylcarbamate

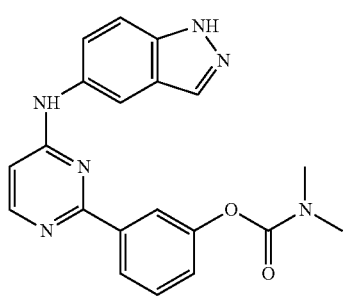 [SMILES: CN(C)C(=O)Oc1cccc(-c2nccc(Nc3ccc4[nH]ncc4c3)n2)c1]

To a stirred solution of tert-butyl 5-((tert-butoxycarbonyl)(2-chloropyrimidin-4-yl)amino)-1H-indazole-1-carboxylate (100 mg, 0.2243 mmol) in EtOH (3 mL) and H$_2$O (0.3 ml) was added Na$_2$CO$_3$ (47.54 mg, 0.4485 mmol), (Boc)$_2$O (93.29 mg, 0.4485 mmol) and 3-(4,4,5,5-tetramethyl-1,3,2-dioxaborolan-2-yl)phenyl dimethylcarbamate (130.58 mg, 0.4485 mmol) at room temperature. The mixture was degassed by budding nitrogen through the solution, Pd(PPh$_3$)$_2$Cl$_2$ (15.07 mg, 0.02243 mmol) was added and the mixture was heated under microwave irradiation for 20 min at 110° C. The mixture was concentrated under reduced pressure and the residue was purified by column chromatograph on silica gel (DCM:MeOH=50:1) to give the title compound (30 mg, yield 37%). $^1$H NMR (400 MHz, DMSO-d$_6$) δ 13.02 (s, 1H), 9.66 (s, 1H), 8.34-8.04 (m, 5H), 7.55-7.47 (m, 3H), 7.21 (d, J=8.0 Hz, 1H), 6.67 (d, J=5.6 Hz, 1H), 3.07 (s, 3H), 2.94 (s, 3H); m/e 375 (M+H)$^+$.

Example 132

3-((3-(4,4,5,5-tetramethyl-1,3,2-dioxaborolan-2-yl)phenoxy)methyl)pyridine

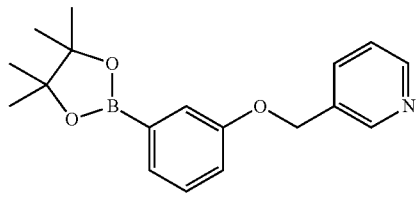 [SMILES: CC1(C)OB(c2cccc(OCc3cccnc3)c2)OC1(C)C]

To a solution of compound 3-(4,4,5,5-tetramethyl-1,3,2-dioxaborolan-2-yl)phenol (1.5 g, 6.8 mmol) in DMF (20 mL) was added NaH (0.82 g, 20.4 mmol) potionwise at 0° C. with stirring. After 30 minutes, compound 3-(chloromethyl)pyridine hydrochloride (1.4 g, 8.9 mmol) was added portionwise at 0° C., and the resulting mixture was allowed to warm to 20° C. and stirred for 16 hrs. It was quenched with water, extracted with EtOAc (100 mL×3), and the extracts were washed with brine, dried over Na₂SO₄, concentrated under reduced pressure, and the residue was purified by chromatography on silica gel column (eluted with PE:EA=10:1 to 2:1) to give the title compound (1 g, yield 50%) as a white solid.

Example 133 tert-butyl 1H-indazol-5-yl(2-(3-(pyridin-3-yl-methoxy)phenyl)pyrimidin-4-yl)carbamate

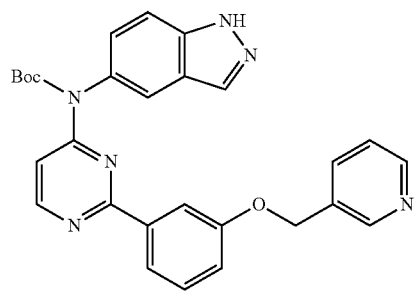 [SMILES: CC(C)(C)OC(=O)N(c1ccc2[nH]ncc2c1)c1ccnc(-c2cccc(OCc3cccnc3)c2)n1]

A mixture of compound 3-((3-(4,4,5,5-tetramethyl-1,3,2-dioxaborolan-2-yl)phenoxy)methyl)pyridine (1 g, 3.2 mmol), compound tert-butyl 5-((tert-butoxycarbonyl)(2-chloropyrimidin-4-yl)amino)-1H-indazole-1-carboxylate (670 mg, 1.5 mmol), K₂CO₃ (414 mg, 3 mmol) and Pd(dppf)₂Cl₂ (109 mg, 0.15 mmol) in dioxane (20 mL) and H₂O (5 mL) was heated at 90° C. for 16 hrs under N₂ atmosphere. Then it was concentrated and the residue was purified by chromatography on silica gel column (eluted with DCM:MeOH=100:1 to 20:1) to give the title compound (370 mg, yield 50%) as a light red oil.

Example 134 tert-butyl 1H-indazol-5-yl(2-(3-(pyridin-3-yl-methoxy)phenyl)pyrimidin-4-yl)carbamate

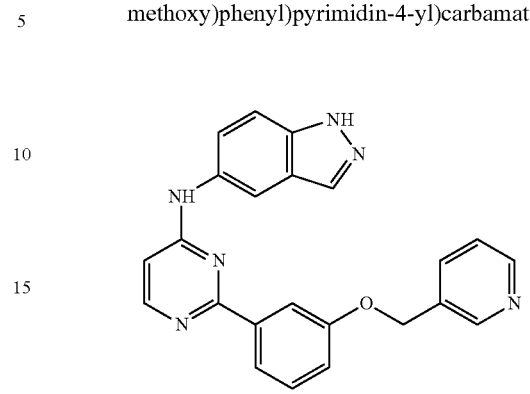

(370 mg, 0.75 mmol) in DCM (5 mL) was added TFA (5 mL), and the resulting solution was stirred at 20° C. for 3 hrs. It was concentrated and the residue was dissolved in DCM/MeOH (10:1, 100 mL), washed with aqueous K₂CO₃ and brine, dried over Na₂SO₄, concentrated and the residue was purified by chromatography on silica gel column (eluted with DCM:MeOH=100:1 to 20:1) and recrystallized from MeOH to afford the title compound (110 mg, yield 37%) as a light yellow solid. ¹H NMR (400 MHz, DMSO-d₆) δ 13.04 (s, 1H), 9.67 (s, 1H), 8.71 (s, 1H), 8.57 (s, 1H), 8.35 (d, J=5.6 Hz, 1H), 8.05 (s, 1H), 8.00-7.89 (m, 4H), 7.56-6.68 (m, 6H), 5.25 (s, 2H).

13.02 (s, 1H), 9.66 (s, 1H), 8.33-8.18 (m, 4H), 7.55-7.51 (m, 3H), 7.25 (d, J=8.0 Hz, 1H), 6.67 (d, J=5.6 Hz, 1H), 3.64 (b, 6H), 3.45 (b, 2H); m/e 417 (M+H)⁺.

Example 135

4-((3-(4,4,5,5-tetramethyl-1,3,2-dioxaborolan-2-yl)phenoxy)methyl)pyridine

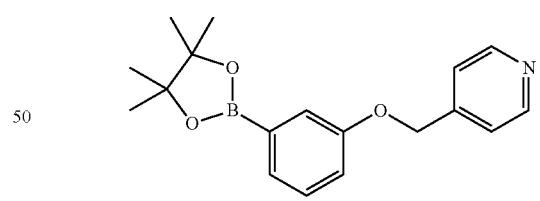

To a solution of compound 3-(4,4,5,5-tetramethyl-1,3,2-dioxaborolan-2-yl)phenol (1.5 g, 6.8 mmol) in DMF (20 mL) was added NaH (0.82 g, 20.4 mmol) potionwise at 0° C. with stirring. After 30 minutes, compound 4-(chloromethyl)pyridine (1.4 g, 8.9 mmol) was added portionwise at 0° C., and the resulting mixture was allowed to warm to 20° C. and stirred for 16 hrs. It was quenched with water, extracted with EtOAc (100 mL×3), and the extracts were washed with brine, dried over Na₂SO₄, concentrated, and the residue was purified by chromatography on silica gel column (eluted with PE:EA=10:1 to 2:1) to give the title compound (1 g, yield 50%) as a white solid.

Example 136

N-(2-(3-(pyridin-4-ylmethoxy)phenyl)pyrimidin-4-yl)-1H-indazol-5-amine

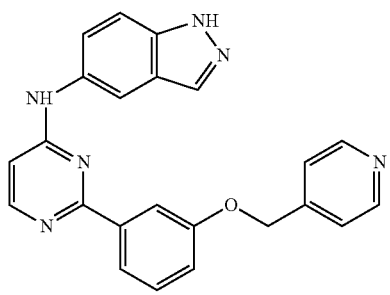 [SMILES: c1cc(OCc2ccncc2)cc(-c2nccc(Nc3ccc4[nH]ncc4c3)n2)c1]

A mixture of compound 4-((3-(4,4,5,5-tetramethyl-1,3,2-dioxaborolan-2-yl)phenoxy)methyl)pyridine (139 mg, 0.44 mmol) (6 batches), compound tert-butyl 5-((tert-butoxycarbonyl)(2-chloropyrimidin-4-yl)amino)-1H-indazole-1-carboxylate (100 mg, 0.22 mmol), Na$_2$CO$_3$ (47 mg, 0.44 mmol), Boc$_2$O (96 mg, 0.44 mmol) and Pd(PPh$_3$)$_2$Cl$_2$ (15.4 mg, 0.022 mmol) in EtOH (2 mL) and H$_2$O (0.2 mL) was heated in microwave reactor at 110° C. for 20 minutes under N$_2$ atmosphere. Then it was cooled, diluted with water, extracted with DCM, the extracts were concentrated and the residue was purified by chromatography on silica gel column (eluted with DCM:MeOH=100:1 to 20:1) and recrystallized from MeOH to afford the title compound (110 mg, yield 23%) as a light yellow solid. $^1$H NMR (400 MHz, MeOD) δ 8.51 (d, J=5.6 Hz, 2H), 8.25 (d, J=6.0 Hz, 1H), 8.15 (s, 1H), 8.05-7.94 (m, 3H), 7.57-7.16 (m, 6H), 6.65 (d, J=6.0 Hz, 1H), 5.26 (s, 2H)); m/e 395 (M+H)$^+$.

Example 137

2-(3-(2-methoxyethoxy)phenyl)-4,4,5,5-tetramethyl-1,3,2-dioxaborolane

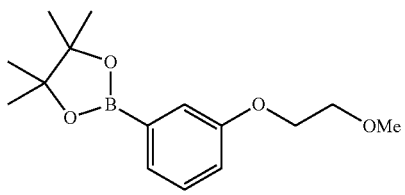 [SMILES: COCCOc1cccc(B2OC(C)(C)C(C)(C)O2)c1]

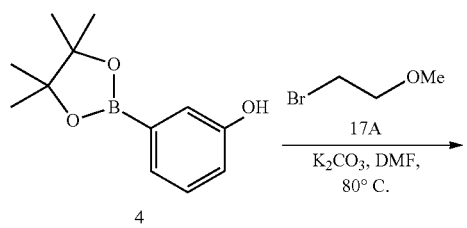

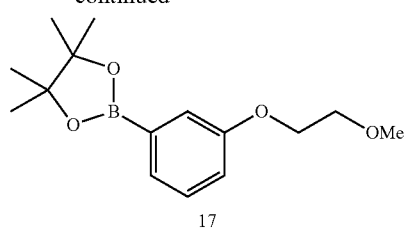

To a mixture of 3-(4,4,5,5-tetramethyl-1,3,2-dioxaborolan-2-yl)phenol (800 mg, 3.636 mmol) in DCM (20 ml) were added KI (1.2 g, 7.273 mmol), K$_2$CO$_3$ (1.307 g 10.091 mmol) and 1-bromo-2-methoxyethane (1.01 g, 7.273 mmol) at room temperature. The mixture was stirred overnight at 80° C. The mixture was extracted with DCM (30 mL×2) and the organic phase was dried with Na$_2$SO$_4$ and concentrated under reduced pressure and the residue was purified by column chromatography to give the title compound (550 mg, yield 50%).

Example 138

N-(2-(3-(2-methoxyethoxy)phenyl)pyrimidin-4-yl)-1H-indazol-5-amine

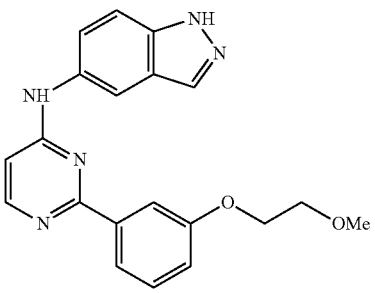 [SMILES: COCCOc1cccc(-c2nccc(Nc3ccc4[nH]ncc4c3)n2)c1]

To a stirred solution of tert-butyl 5-((tert-butoxycarbonyl)(2-chloropyrimidin-4-yl)amino)-1H-indazole-1-carboxylate (100 mg, 0.2243 mmol) in EtOH (3 mL) and H$_2$O (0.3 ml) was added Na$_2$CO$_3$ (47.54 mg, 0.4485 mmol), (Boc)$_2$O (93.29 mg, 0.4485 mmol) and 2-(3-(2-methoxyethoxy)phenyl)-4,4,5,5-tetramethyl-1,3,2-dioxaborolane (124.76 mg, 0.4485 mmol) at room temperature. The mixture was degassed by budding nitrogen through the solution, then Pd(PPh$_3$)$_2$Cl$_2$ (15.07 mg, 0.02243 mmol) was added and the mixture was heated under microwave irradiation for 20 minutes at 110° C. The mixture was concentrated under reduced pressure and the residue was purified by column chromatograph on silica gel (DCM: MeOH=50:1) to give the title compound (40 mg, yield 49%). $^1$H NMR (400 MHz, DMSO-d$_6$) δ 13.01 (s, 1H), 9.61 (s, 1H), 8.32 (d, J=5.6 Hz, 1H), 8.21 (s, 1H), 8.01-7.91 (m, 3H), 7.55-7.36 (m, 3H), 7.04 (d, J=7.6 Hz, 1H), 6.65 (d, J=5.6 Hz, 1H), 4.16 (b, 2H), 3.68 (b, 2H); m/e 362 (M+H)$^+$.

Example 139 tert-butyl 1H-indazol-5-yl(2-(3-methoxyphenyl)pyrimidin-4-yl)carbamate

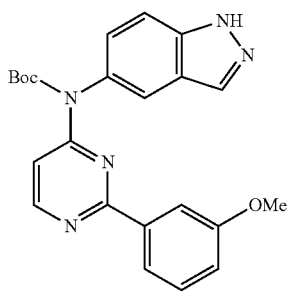 [SMILES: COc1cccc(-c2nccc(N(C(=O)OC(C)(C)C)c3ccc4[nH]ncc4c3)n2)c1]

To a stirred solution of tert-butyl 5-((tert-butoxycarbonyl)(2-chloropyrimidin-4-yl)amino)-1H-indazole-1-carboxylate (100 mg, 0.2243 mmol) in EtOH (3 mL) and H₂O (0.3 ml) were added Na₂CO₃ (47.54 mg, 0.4485 mmol), (Boc)₂O (93.29 mg, 0.4485 mmol) and (3-methoxyphenyl)boronic acid (68.17 mg, 0.4485 mmol) at room temperature. The mixture was degassed by budding nitrogen through the solution, then Pd(PPh₃)₂Cl₂ (15.07 mg, 0.02243 mmol) was added and the mixture was heated under microwave irradiation for 20 min at 110° C. The mixture was concentrated under reduced pressure and the residue was purified by column chromatograph on silica gel to give the title compound (80 mg, yield 85%).

Example 140

N-(2-(3-methoxyphenyl)pyrimidin-4-yl)-1H-indazol-5-amine

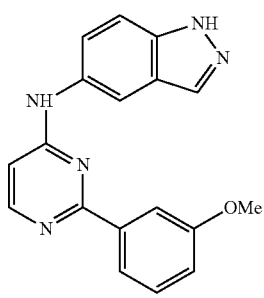 [SMILES: COc1cccc(-c2nccc(Nc3ccc4[nH]ncc4c3)n2)c1]

To a stirred solution of tert-butyl 1H-indazol-5-yl(2-(3-methoxyphenyl)pyrimidin-4-yl)carbamate (1 g, 2.39 mmol) in DCM (20 mL) was added TFA (10 ml) at room temperature and the mixture was stirred overnight at room temperature. Then the mixture was concentrated under reduced pressure and the residue was purified by pre_HPLC to give the title compound (200 mg, yield 26%) as white solid. ¹H NMR (400 MHz, DMSO-d₆) δ 13.05 (s, 1H), 10.02 (s, 1H), 8.32 (d, J=6.0 Hz, 1H), 8.17 (s, 1H), 8.05 (s, 1H), 7.89-7.42 (m, 3H), 7.09 (d, J=7.6 Hz, 1H), 6.72 (d, J=6.0 Hz, 1H), 3.83 (s, 3H); m/e 318 (M+H)⁺.

Example 141

4-(2-(3-bromophenoxy)ethyl)morpholine

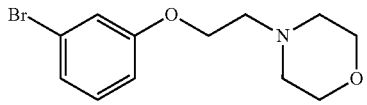 [SMILES: Brc1cccc(OCCN2CCOCC2)c1]

To a solution of 3-bromophenol (7.8 g, 45.2 mmol) in DMF (120 mL) was added 4-(2-chloroethyl)morpholine (8.54 g, 45.2 mmol), K₂CO₃ (414 mg, 3 mmol) and KI (7.5 mg, 45.2 mmol), and the resulting mixture was heated at 20° C. and stirred for 16 hrs. It was quenched with water, extracted with EtOAc (200 mL×3), and the extracts were washed with brine, dried over Na₂SO₄, concentrated, and the residue was purified by chromatography on silica gel column (eluted with DCM:MeOH=100:1 to 20:1) to give compound the title compound (7 g, yield 54%) as a red liquid.

Example 142

4-(2-(3-(4,4,5,5-tetramethyl-1,3,2-dioxaborolan-2-yl)phenoxy)ethyl)morpholine

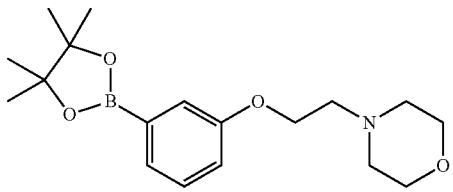 [SMILES: CC1(C)OB(c2cccc(OCCN3CCOCC3)c2)OC1(C)C]

A mixture of compound 4-(2-(3-bromophenoxy)ethyl)morpholine (1.1 g, 3.8 mmol), BIPN (1.47 mg, 5.8 mmol), KOAc (0.83 mg, 8.5 mmol) and Pd(dppf)₂Cl₂ (0.28 mg, 0.38 mmol) in dioxane (15 mL) was heated at 90° C. for 16 hrs under N₂ atmosphere. Then it was concentrated and the residue was purified by chromatography on silica gel column (eluted with DCM:MeOH=100:1 to 20:1) to give compound the title compound (1 g, yield 78%) as a light red oil.

Example 143 tert-butyl 1H-indazol-5-yl(2-(3-(2-morpholinoethoxy)phenyl)pyrimidin-4-yl)carbamate

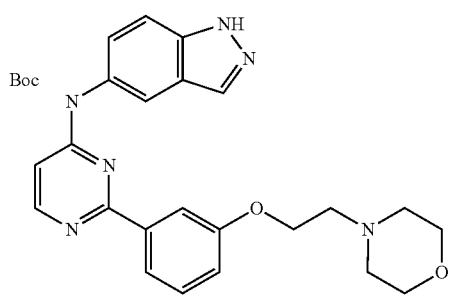 [SMILES: c1cc(OCCN2CCOCC2)cc(-c2nccc(Nc3ccc4[nH]ncc4c3)n2)c1 ; "Boc"]

A mixture of compound 4-(2-(3-(4,4,5,5-tetramethyl-1,3,2-dioxaborolan-2-yl)phenoxy)ethyl)morpholine (1 g, 3.2 mmol), compound tert-butyl 5-((tert-butoxycarbonyl)(2-chloropyrimidin-4-yl)amino)-1H-indazole-1-carboxylate (670 mg, 1.5 mmol), K₂CO₃ (414 mg, 3 mmol) and Pd(dppf)₂Cl₂ (109 mg, 0.15 mmol) in dioxane (20 mL) and H₂O (5 mL) was heated at 90° C. for 16 hrs under N₂ atmosphere. Then it was concentrated and the residue was purified by chromatography on silica gel column (eluted with DCM:MeOH=100:1 to 20:1) to give the tile compound (380 mg, yield 50%) as a light red oil.

Example 144

N-(2-(3-(2-morpholinoethoxy)phenyl)pyrimidin-4-yl)-1H-indazol-5-amine

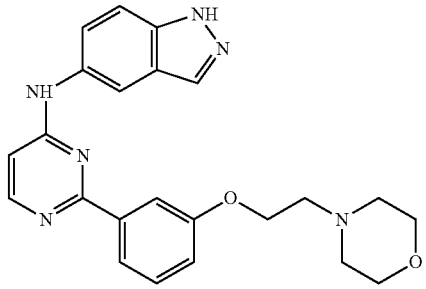 [SMILES: c1cc(OCCN2CCOCC2)cc(-c2nccc(Nc3ccc4[nH]ncc4c3)n2)c1]

To a solution of compound tert-butyl 1H-indazol-5-yl(2-(3-(2-morpholinoethoxy)phenyl)pyrimidin-4-yl)carbamate (380 mg, 0.75 mmol) in DCM (5 mL) was added TFA (5 mL), and the resulting solution was stirred at 20° C. for 3 hrs. It was concentrated and the residue was dissolved in DCM/MeOH (10:1, 100 mL), washed with aqueous K₂CO₃ and brine, dried over Na₂SO₄, concentrated and the residue was purified by chromatography on silica gel column (eluted with DCM:MeOH=80:1 to 15:1) and recrystallized from EtOAc and PE to afford the title compound (120 mg, yield 39%) as a light yellow solid. ¹H NMR (400 MHz, DMSO-d₆) δ 13.04 (s, 1H), 9.65 (s, 1H), 8.36 (m, 3H), 8.08 (s, 1H), 7.94 (s, 1H), 7.57-7.38 (m, 3H), 7.06 (d, J=8.0 Hz, 1H), 6.68 (d, J=5.6 Hz, 1H), 4.17 (t, J=5.6 Hz, 2H), 3.58 (s, 4H), 2.73 (t, J=5.6 Hz, 2H), 2.67 (s, 4H); m/e 417 (M+H)⁺.

Example 145 tert-butyl 5-((2-(3-acetylphenyl)pyrimidin-4-yl)amino)-1H-indazole-1-carboxylate

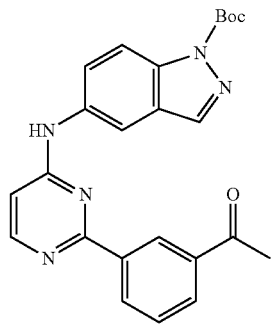 [SMILES: CC(=O)c1cccc(-c2nccc(Nc3ccc4c(cnn4C(=O)OC(C)(C)C)c3)n2)c1]

A mixture of tert-butyl 5-((tert-butoxycarbonyl)(2-chloropyrimidin-4-yl)amino)-1H-indazole-1-carboxylate (100 mg, 0.22 mmol), 3-acetylphenyl)boronic acid (73.7 mg, 0.44 mmol), Na₂CO₃ (47.6 mg, 0.44 mmol), (Boc)₂O (98 mg, 0.44 mmol), Pd(PPh₃)Cl₂ (16 mg, 0.022 mmol) in EtOH:H₂O (3.3 mL, 10:1) was heated under microwave irradiation for 20 min at 110° C. After reaction, it was evaporated, EA and water was added, separated the organic layer, washed with saturated brine, dried over Na₂SO₄, concentrated and purified by silica gel to give the title compound (64 mg, yield 67%).

Example 146 tert-butyl 5-((2-(3-(1-aminoethyl)phenyl)pyrimidin-4-yl)amino)-1H-indazole-1-carboxylate

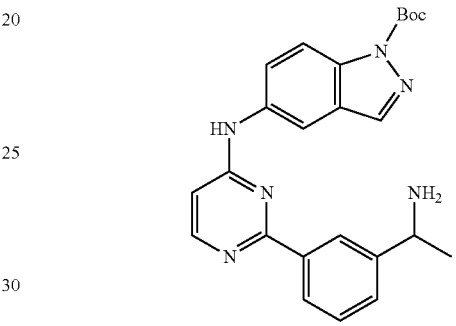

To a stirred solution of tert-butyl 5-((2-(3-acetylphenyl)pyrimidin-4-yl)amino)-1H-indazole-1-carboxylate (500 mg, 1.2 mmol), AcONH₄ (924 mg, 12 mmol) in MeOH (10 mL) was added NaBH₃CN (91 mg, 1.44 mmol), the mixture was stirred 6 hrs at reflux. After reaction, it was evaporated, diluted with water, filtered to give the title compound as a white solid (300 mg, crude).

Example 147

N-(2-(3-(1-aminoethyl)phenyl)pyrimidin-4-yl)-1H-indazol-5-amine

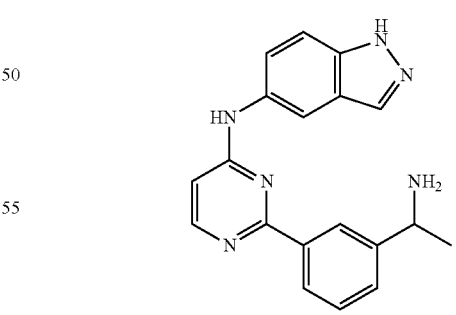

A solution of tert-butyl 5-((2-(3-(1-aminoethyl)phenyl)pyrimidin-4-yl)amino)-1H-indazole-1-carboxylate (300 mg, crude) in HCl/MeOH (20 mL) was stirred at 40° C. for 6 h. After reaction, it was evaporated, then water was added, adjusted the PH to 9 with saturated Na₂CO₃, filtered to give the crude product, which was purified by Pre-HPLC to provide the title compound (100 mg) as a white solid. ¹H NMR (400 MHz, DMSO-d$_6$) δ 13.03 (s, 1H), 9.65 (s, 1H), 8.44 (s, 1H), 8.35 (d, J=5.6 Hz, 2H), 8.18 (d, J=7.2 Hz, 1H), 8.05 (s, 1H), 7.55-7.40 (m, 4H), 6.67 (d, J=5.6 Hz, 1H), 4.12-4.07 (m, 1H), 2.08 (b, 2H), 1.31 (d, J=6.4 Hz, 3H); m/e 331 (M+H)$^+$.

Example 148 tert-butyl 5-((2-(4-acetylphenyl)pyrimidin-4-yl) amino)-1H-indazole-1-carboxylate

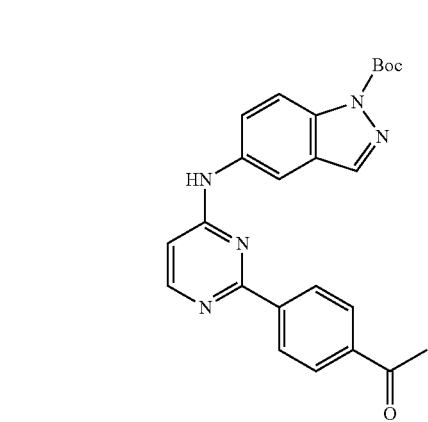 [SMILES: CC(=O)c1ccc(-c2nccc(Nc3ccc4c(cnn4C(=O)OC(C)(C)C)c3)n2)cc1]

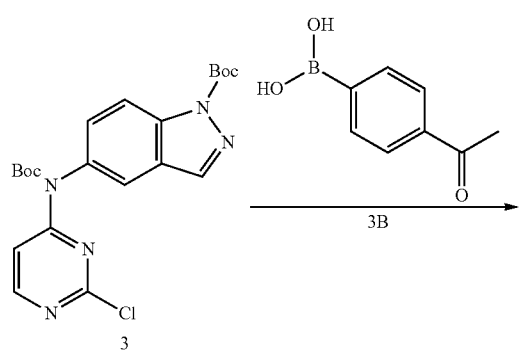

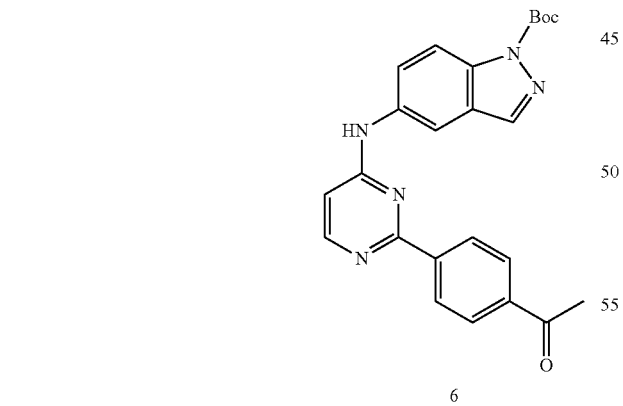

A mixture of tert-butyl 5-((tert-butoxycarbonyl)(2-chloropyrimidin-4-yl)amino)-1H-indazole-1-carboxylate (1.5 g, crude), (4-acetylphenyl)boronic acid (1.12 g, 6.8 mmol), Na$_2$CO$_3$ (721 mg, 6.8 mmol), (Boc)$_2$O (1.48 g, 6.8 mmol), Pd(PPh$_3$)Cl$_2$ (239 mg, 0.34 mmol) in EtOH:H$_2$O (16.5 mL, 10:1) was heated under microwave irradiation for 20 min at 110° C. After reaction, it was evaporated, EA and water was added, separated the organic layer, washed with saturated brine, dried over Na$_2$SO$_4$, concentrated to give the title compound (2.6 g, crude).

Example 149 tert-butyl 5-((2-(4-(1-aminoethyl)phenyl)pyrimidin-4-yl)amino)-1H-indazole-1-carboxylate

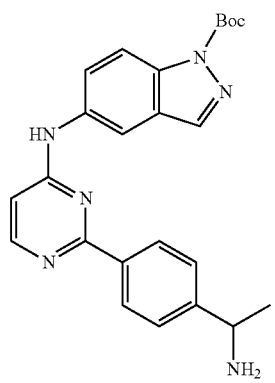 [SMILES: CC(N)c1ccc(-c2nccc(Nc3ccc4c(cnn4C(=O)OC(C)(C)C)c3)n2)cc1]

To a stirred solution of tert-butyl 5-((2-(4-acetylphenyl) pyrimidin-4-yl)amino)-1H-indazole-1-carboxylate (2.6 g, 6.1 mmol), AcONH$_4$ (4.7 g, 61 mmol) in MeOH (60 mL) was added NaBH$_3$CN (461 mg, 7.32 mmol), the mixture was stirred for 10 h at reflux. After reaction, the solvent was evaporated, then water was added, filtered to give the title compound (2.1 g, crude).

Example 150

N-(2-(4-(1-aminoethyl)phenyl)pyrimidin-4-yl)-1H-indazol-5-amine

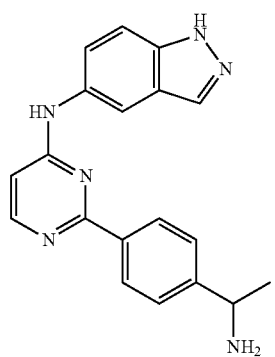 [SMILES: CC(N)c1ccc(-c2nccc(Nc3ccc4[nH]ncc4c3)n2)cc1]

A solution of tert-butyl 5-((2-(4-(1-aminoethyl)phenyl) pyrimidin-4-yl)amino)-1H-indazole-1-carboxylate (2.1 g, crude) in HCl/MeOH (60 mL) was stirred at 40° C. for 6 h. After reaction, the solvent was evaporated, then water was added, adjusted the pH to 9 with saturated Na$_2$CO$_3$, filtered to give the crude product, which was purified by Pre-HPLC to give the title compound (113.5 mg) as a white solid. $^1$H NMR (400 MHz, DMSO-d$_6$) δ 13.02 (s, 1H), 9.58 (s, 1H), 8.34-8.27 (m, 4H), 8.20 (s, 1H), 8.08 (s, 1H), 7.56 (s, 2H), 7.49 (d, J=6.0 Hz, 1H), 4.05-4.03 (m, 1H), 1.27 (d, J=6.4 Hz, 3H); m/e 331 (M+H)$^+$.

Example 151

2-(3-(2,2-diethoxyethoxy)phenyl)-4,4,5,5-tetramethyl-1,3,2-dioxaborolane

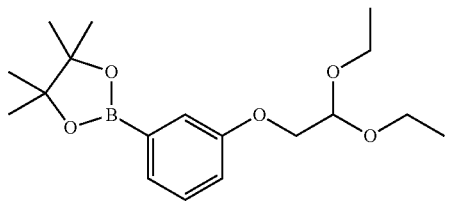 [SMILES: CCOC(COc1cccc(B2OC(C)(C)C(C)(C)O2)c1)OCC]

To a mixture of compound 3-(4,4,5,5-tetramethyl-1,3,2-dioxaborolan-2-yl)phenol (550 mg, 2.5 mmol), 2-bromo-1,1-diethoxyethane (985 mg, 5 mmol), Cs$_2$CO$_3$ (2.43 g, 7.5 mmol) in DMF (25 mL) was added KI (106 mg, 1 mmol), then the mixture was stirred overnight at 110° C. After reaction, water was added, then extracted with EA, washed with saturated brine, dried over Na$_2$SO$_4$, concentrated to give the title compound (360 mg, crude) as a light yellow oil.

Example 152 tert-butyl 5-((2-(3-(2,2-diethoxyethoxy)phenyl)pyrimidin-4-yl)amino)-1H-indazole-1-carboxylate

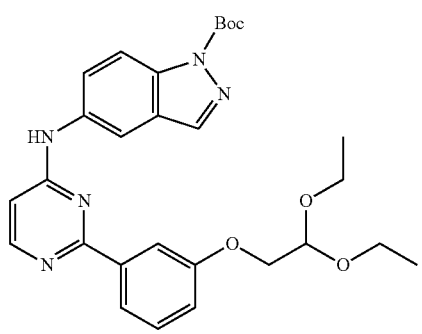 [SMILES: CCOC(COc1cccc(-c2nccc(Nc3ccc4c(cnn4C(=O)OC(C)(C)C)c3)n2)c1)OCC]

A mixture of 2-(3-(2,2-diethoxyethoxy)phenyl)-4,4,5,5-tetramethyl-1,3,2-dioxaborolane (100 mg, crude), tert-butyl 5-((tert-butoxycarbonyl)(2-chloropyrimidin-4-yl)amino)-1H-indazole-1-carboxylate (70 mg, 0.15 mmol), Na$_2$CO$_3$ (65 mg, 0.6 mmol), (Boc)$_2$O (130 mg, 0.6 mmol), Pd(PPh$_3$)$_2$Cl$_2$ (20 mg, 0.03 mmol) in EtOH:H$_2$O (4.4 mL, 10:1) was heated under microwave irradiation for 20 min at 110° C. After reaction, it was evaporated, EA and water was added, separated the organic layer, washed with saturated brine, dried over Na$_2$SO$_4$, concentrated and purified by Pre-TLC to give the title compound (30 mg).

Example 153

2-(3-(4-((1H-indazol-5-yl)amino)pyrimidin-2-yl)phenoxy)acetaldehyde

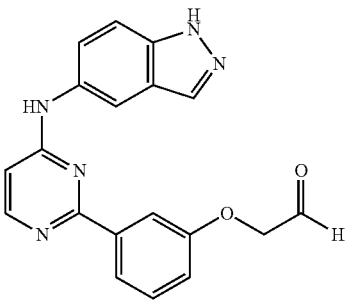 [SMILES: O=CCOc1cccc(-c2nccc(Nc3ccc4[nH]ncc4c3)n2)c1]

To a solution of tert-butyl 5-((2-(3-(2,2-diethoxyethoxy)phenyl)pyrimidin-4-yl)amino)-1H-indazole-1-carboxylate (510 mg, 0.98 mmol) in THF (20 mL) was added dropwise 3M HCl (10 mL), then the mixture was stirred at reflux for 7 h. After reaction, it was evaporated, then water was added, adjusted the pH to 9 with saturated Na$_2$CO$_3$, filtered to give the title compound (420 mg, crude).

Example 154

N-(2-(3-(2-(isopropylamino)ethoxy)phenyl)pyrimidin-4-yl)-1H-indazol-5-amine

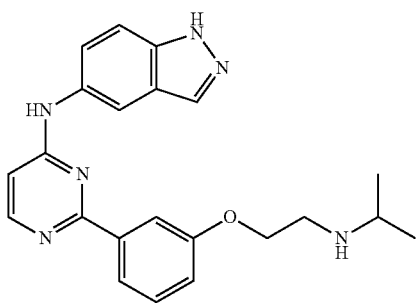 [SMILES: CC(C)NCCOc1cccc(-c2nccc(Nc3ccc4[nH]ncc4c3)n2)c1]

To a stirred solution of 2-(3-(4-((1H-indazol-5-yl)amino)pyrimidin-2-yl)phenoxy)acetaldehyde (420 mg, crude), isopropylamine (245 mg, 4.16 mmol) in MeOH (15 mL) was added NaBH$_3$CN (131 mg, 2.08 mmol), the mixture was stirred 7 h at reflux. After reaction, it was evaporated and purified by Pre-HPLC to give the title compound (90 mg) as a white solid. $^1$H NMR (400 MHz, DMSO-d$_6$) δ 13.02 (s, 1H), 9.65 (s, 1H), 8.34 (d, J=6.0 Hz, 1H), 8.27 (s, 1H), 8.10 (s, 1H), 7.94 (d, J=3.2 Hz, 2H), 7.57-7.38 (m, 3H), 7.05 (d, J=8.0 Hz, 1H), 6.68 (d, J=6.0 Hz, 1H), 4.106-4.079 (m, 1H), 2.91 (s, 2H), 2.80-2.77 (m, 1H), 1.61 (b, 1H), 1.00 (d, J=6.4 Hz, 6H); m/e 389 (M+H)$^+$.

Example 155

N-(2,6-dichloropyrimidin-4-yl)-1H-indazol-5-amine

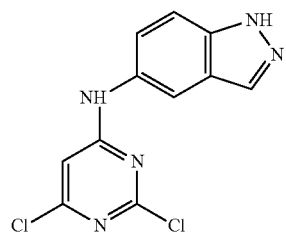 [SMILES: Clc1cc(Nc2ccc3[nH]ncc3c2)nc(Cl)n1]

To a stirred solution of 2,4,6-trichloropyrimidine (5.5 g, 30 mmol) in EtOH (100 mL) were added TEA (1.5 g, 45 mmol) and compound 1H-indazol-5-amine (3.99 g, 30 mmol) at room temperature. The mixture was refluxed overnight. After removing the solvent the residue was re-crystallized in MeOH to give the title compound as a solid (3.4 g, yield 40%).

Example 156 tert-butyl 4-(6-((1H-indazol-5-yl)amino)-2-chloro-pyrimidin-4-yl)piperazine-1-carboxylate

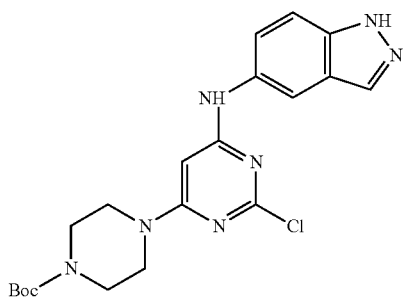 [SMILES: CC(C)(C)OC(=O)N1CCN(c2cc(Nc3ccc4[nH]ncc4c3)nc(Cl)n2)CC1]

To a stirred solution of N-(2,6-dichloropyrimidin-4-yl)-1H-indazol-5-amine (1 g, 3.5 mmol) in EtOH (10 mL) was added TEA (1.4 g, 7 mmol), and compound tert-butyl piperazine-1-carboxylate (0.67 g, 3.5 mmol) at room temperature. The mixture was refluxed overnight. After reaction, water was added, separated the organic layer and saturated brine, dried over $Na_2SO_4$ and concentrated under reduced pressure to give the title compound (1.2 g) which was used directly for next step reaction without further purification.

Example 157 tert-butyl 5-((tert-butoxycarbonyl)(6-(4-(tert-butoxycarbonyl)piperazin-1-yl)-2-chloropyrimidin-4-yl)amino)-1H-indazole-1-carboxylate

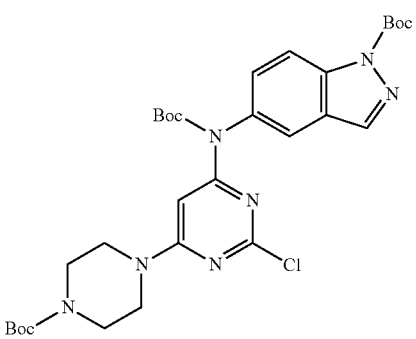 [SMILES: CC(C)(C)OC(=O)N1CCN(c2cc(N(C(=O)OC(C)(C)C)c3ccc4c(cnn4C(=O)OC(C)(C)C)c3)nc(Cl)n2)CC1]

To a stirred solution of tert-butyl 4-(6-((1H-indazol-5-yl)amino)-2-chloropyrimidin-4-yl)piperazine-1-carboxylate (1.2 g, crude) in DCM (10 mL) was added $(Boc)_2O$ (3 g, 14 mmol), TEA (1.4 g, 14 mmol) and DMAP (0.5 g, 3.5 mmol) at room temperature. The mixture was stirred at room temperature for 30 min. After reaction, water was added, separated the organic layer, washed with citric acid monohydrate and saturated brine, dried over $Na_2SO_4$ and concentrated under reduced pressure. The residue was purified by column chromatograph on silica gel to give the title compound (0.6 g).

Example 158 tert-butyl 5-((tert-butoxycarbonyl)(6-(4-(tert-butoxycarbonyl)piperazin-1-yl)-2-(3-methoxyphenyl)pyrimidin-4-yl)amino)-1H-indazole-1-carboxylate

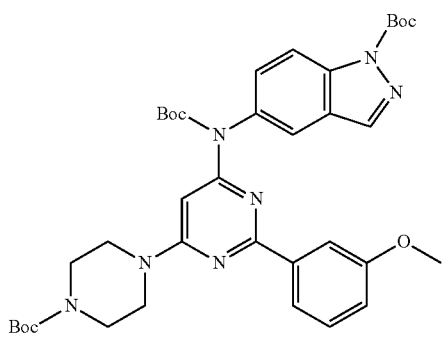 [SMILES: COc1cccc(-c2nc(N3CCN(C(=O)OC(C)(C)C)CC3)cc(N(C(=O)OC(C)(C)C)c3ccc4c(cnn4C(=O)OC(C)(C)C)c3)n2)c1]

A mixture of tert-butyl 5-((tert-butoxycarbonyl)(6-(4-(tert-butoxycarbonyl)piperazin-1-yl)-2-chloropyrimidin-4-yl)amino)-1H-indazole-1-carboxylate (600 mg, 0.95 mmol), (3-methoxyphenyl)boronic acid (160 mg, 1.05 mmol), $Na_2CO_3$ (201 mg, 1.9 mmol), Pd(dppf)$Cl_2$ (70 mg, 0.095 mmol) in dioxane:$H_2O$ (6.6 mL, 10:1) was heated under

Example 159

N-(2-(3-methoxyphenyl)-6-(piperazin-1-yl)pyrimidin-4-yl)-1H-indazol-5-amine

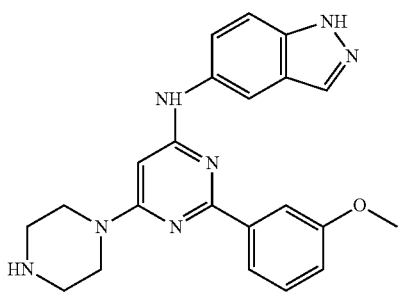 [SMILES: COc1cccc(-c2nc(Nc3ccc4[nH]ncc4c3)cc(N3CCNCC3)n2)c1]

To a solution of tert-butyl 5-((tert-butoxycarbonyl)(6-(4-(tert-butoxycarbonyl)piperazin-1-yl)-2-(3-methoxyphenyl)pyrimidin-4-yl)amino)-1H-indazole-1-carboxylate (250 mg) in DCM (5 mL) was added TFA (1 mL). The mixture was stirred at room temperature for 30 min. it was evaporated, then water was added, adjusted the pH to 9 with saturated Na$_2$CO$_3$, filtered to give the title compound (115 mg, yield 80%) as a white solid. $^1$H NMR (400 MHz, DMSO-d$_6$) δ 12.98 (s, 1H), 9.30 (s, 1H), 8.09 (s, 1H), 8.00 (s, 1H), 7.53-7.37 (m, 6H), 7.03 (d, J=8.8 Hz, 1H), 6.50 (s, 1H), 3.82 (s, 3H), 3.73 (b, 4H), 3.39 (s, 1H), 2.71 (b, 4H); m/e 402 (M+H)$^+$.

Example 160

N-(2-chloro-6-(2-(dimethylamino)ethoxy)pyrimidin-4-yl)-1H-indazol-5-amine

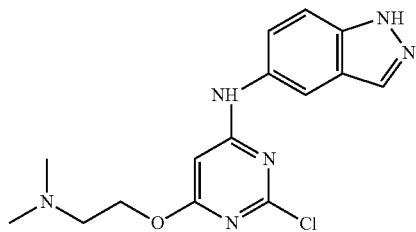 [SMILES: CN(C)CCOc1cc(Nc2ccc3[nH]ncc3c2)nc(Cl)n1]

To a stirred solution of N-(2,6-dichloropyrimidin-4-yl)-1H-indazol-5-amine (2 g, 7 mmol) in EtOH (20 mL) was added TEA (2.8 g, 7 mmol), and 2-(dimethylamino)ethanol (0.64 g, 7 mmol) at room temperature. The mixture was refluxed overnight. After reaction, water was added, separated the organic layer and saturated brine, dried over Na$_2$SO$_4$ and concentrated under reduced pressure to give the title compound (1.5 g). The residue was used into next step.

Example 161

N-(6-(2-(dimethylamino)ethoxy)-2-(3-methoxyphenyl)pyrimidin-4-yl)-1H-indazol-5-amine

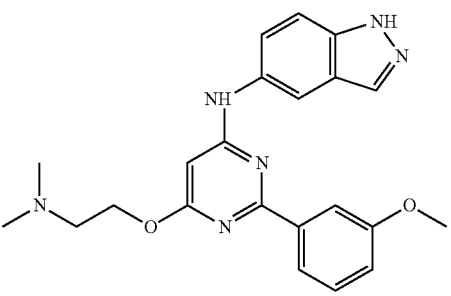

A mixture of N-(2-chloro-6-(2-(dimethylamino)ethoxy)pyrimidin-4-yl)-1H-indazol-5-amine (1.5 g, 4.5 mmol), (3-methoxyphenyl)boronic acid (661 mg, 5 mmol), Na$_2$CO$_3$ (954 mg, 9 mmol), Pd(dppf)Cl$_2$ (300 mg, 0.45 mmol) in dioxane:H$_2$O (22 mL, 10:1) was heated under microwave irradiation for 30 min at 140° C. After reaction, it was evaporated, EA and water was added, separated the organic layer, washed with saturated brine, dried over Na$_2$SO$_4$ and concentrated which was purified by Pre-HPLC to give the title compound as white solid (125 mg). $^1$H NMR (400 MHz, DMSO-d$_6$) δ 13.00 (s, 1H), 9.67 (s, 1H), 8.18 (s, 1H), 8.04 (s, 1H), 7.56-7.41 (m, 5H), 7.08-6.86 (m, 2H), 4.46-4.43 (m, 1H), 3.83 (s, 3H), 2.66-2.63 (m, 2H), 2.22 (s, 6H); m/e 405 (M+H)$^+$.

Example 162

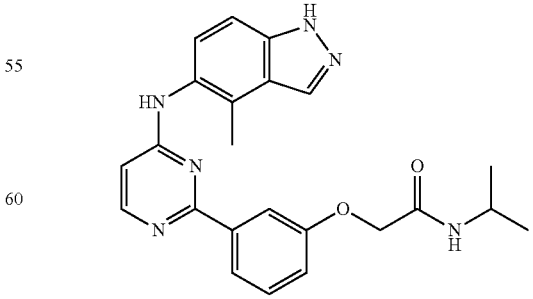

The following compounds were synthesized using the procedures described above:

TABLE 1

| Example No. | Structure | Formula | calc M + H | Observed M + H |
|---|---|---|---|---|
| 163 | 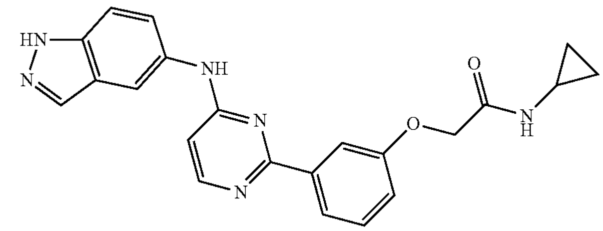 [SMILES: O=C(COc1cccc(-c2nccc(Nc3ccc4[nH]ncc4c3)n2)c1)NC1CC1] | C₂₂H₂₀N₆O₂ | 401 | 401 |
| 164 | 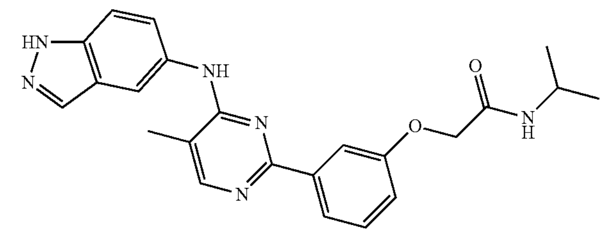 [SMILES: Cc1cnc(-c2cccc(OCC(=O)NC(C)C)c2)nc1Nc1ccc2[nH]ncc2c1] | C₂₃H₂₄N₆O₂ | 417 | 417 |
| 165 | 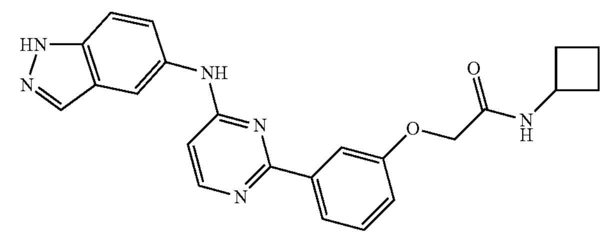 [SMILES: O=C(COc1cccc(-c2nccc(Nc3ccc4[nH]ncc4c3)n2)c1)NC1CCC1] | C₂₃H₂₂N₆O₂ | 415 | 415 |
| 166 | 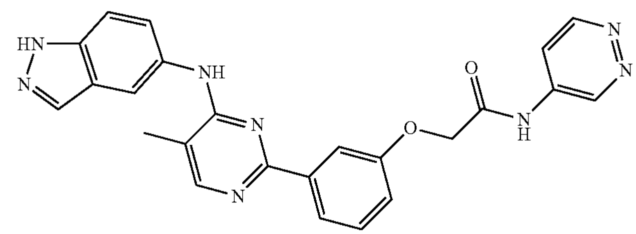 [SMILES: Cc1cnc(-c2cccc(OCC(=O)Nc3ccnnc3)c2)nc1Nc1ccc2[nH]ncc2c1] | C₂₄H₂₀N₈O₂ | 453 | 453 |
| 167 | 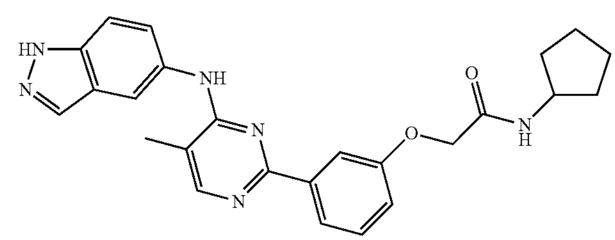 [SMILES: Cc1cnc(-c2cccc(OCC(=O)NC3CCCC3)c2)nc1Nc1ccc2[nH]ncc2c1] | C₂₅H₂₆N₆O₂ | 443 | 443 |
| 168 | 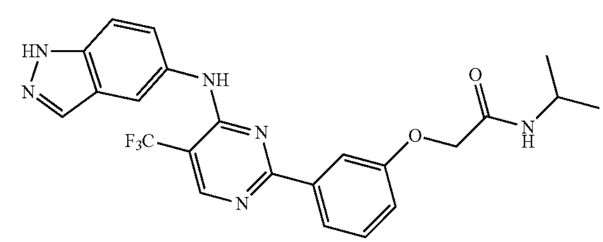 [SMILES: CC(C)NC(=O)COc1cccc(-c2ncc(C(F)(F)F)c(Nc3ccc4[nH]ncc4c3)n2)c1] | C₂₃H₂₁F₃N₆O₂ | 471 | 471 |

TABLE 1-continued
| Example No. | Structure | Formula | calc M + H | Observed M + H |
|---|---|---|---|---|
| 169 | 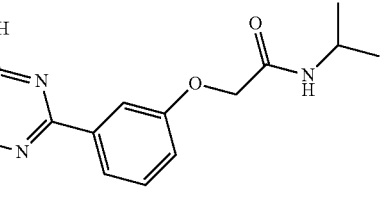 | C$_{23}$H$_{21}$F$_3$N$_6$O$_2$ | 471 | 471 |
| 170 | 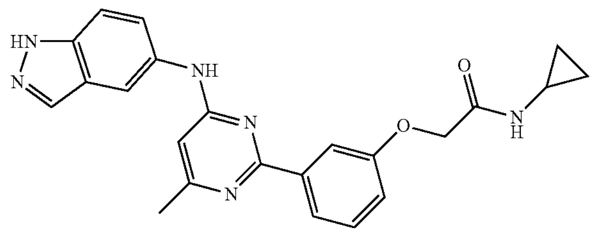 [SMILES: Cc1cc(Nc2ccc3[nH]ncc3c2)nc(-c2cccc(OCC(=O)NC3CC3)c2)n1] | C$_{23}$H$_{22}$N$_6$O$_2$ | 415 | 415 |
| 171 | 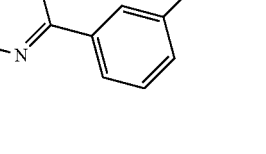 | C$_{24}$H$_{24}$N$_6$O$_2$ | 429 | 429 |
| 172 | 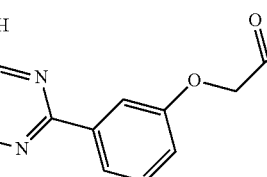 | C$_{24}$H$_{26}$N$_6$O$_2$ | 431 | 431 |
| 173 | 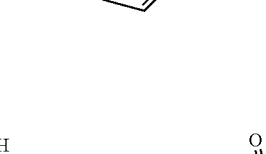 | C$_{25}$H$_{26}$N$_6$O$_2$ | 443 | 443 |
| 174 | 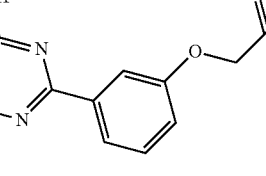 | C$_{23}$H$_{23}$N$_7$O$_2$ | 430 | 430 |

TABLE 1-continued

| Example No. | Structure | Formula | calc M + H | Observed M + H |
|---|---|---|---|---|
| 175 | 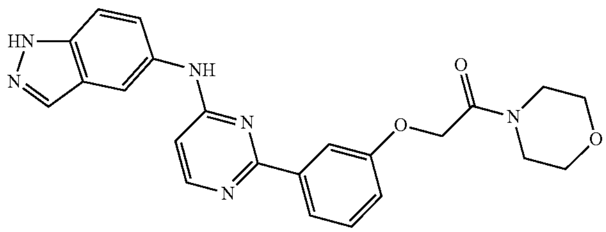 [SMILES: O=C(COc1cccc(-c2nccc(Nc3ccc4[nH]ncc4c3)n2)c1)N1CCOCC1] | C₂₃H₂₂N₆O₃ | 431 | 431 |
| 176 | 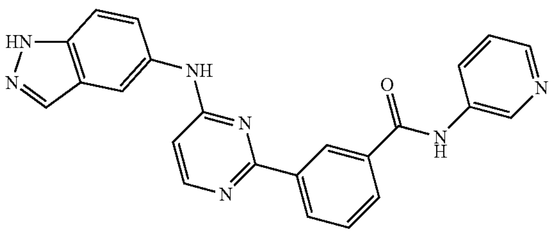 [SMILES: O=C(Nc1cccnc1)c1cccc(-c2nccc(Nc3ccc4[nH]ncc4c3)n2)c1] | C₂₃H₁₇N₇O | 408 | 408 |
| 177 | 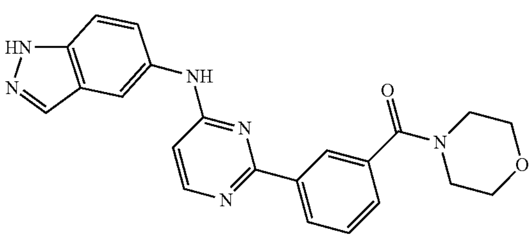 [SMILES: O=C(c1cccc(-c2nccc(Nc3ccc4[nH]ncc4c3)n2)c1)N1CCOCC1] | C₂₂H₂₀N₆O₂ | 401 | 401 |
| 178 | 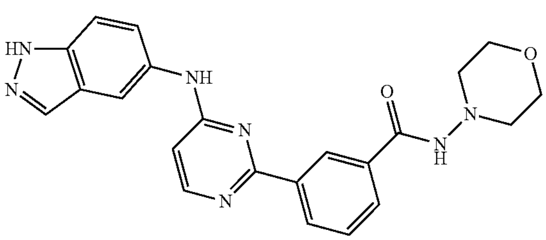 | C₂₂H₂₁N₇O₂ | 416 | 416 |
| 179 | 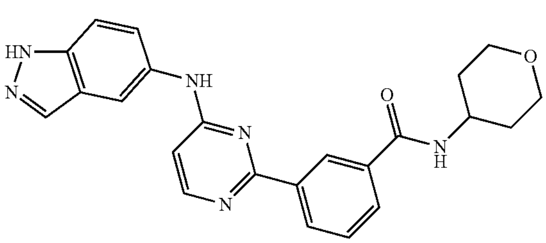 [SMILES: O=C(NN1CCOCC1)c1cccc(-c2nccc(Nc3ccc4[nH]ncc4c3)n2)c1] | C₂₃H₂₂N₆O₂ | 415 | 415 |
| 180 | 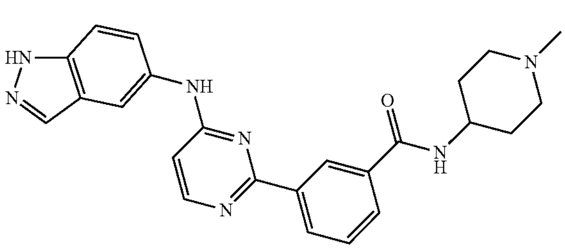 [SMILES: CN1CCC(NC(=O)c2cccc(-c3nccc(Nc4ccc5[nH]ncc5c4)n3)c2)CC1] | C₂₄H₂₅N₇O | 428 | 428 |

Example 181

N-(2-(5-methoxyisoindolin-2-yl)pyrimidin-4-yl)-1H-indazol-5-amine

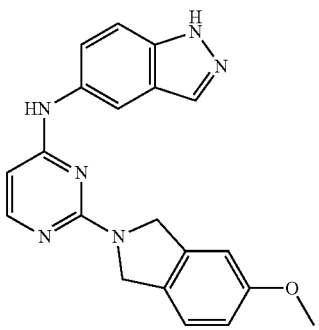 [SMILES: COc1ccc2c(c1)CN(c1nccc(Nc3ccc4[nH]ncc4c3)n1)C2]

N-(2-chloropyrimidin-4-yl)-1H-indazol-5-amine

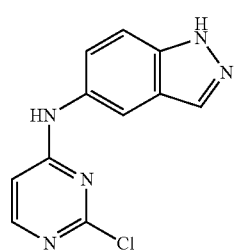

To a solution of 2,4-dichloropyrimidine (2.0 g, 13.4 mmol) in ethanol (67 mL) was added 5-amino-indazole (1.79 g, 13.4 mmol) and triethylamine (2.81 mL, 20.1 mmol). The mixture was heated at reflux overnight. The reaction mixture was concentrated and the residue was recrystallized with methanol to afford the title compound as a pink solid (3.1 g, 97%).

N-(2-(5-methoxyisoindolin-2-yl)pyrimidin-4-yl)-1H-indazol-5-amine

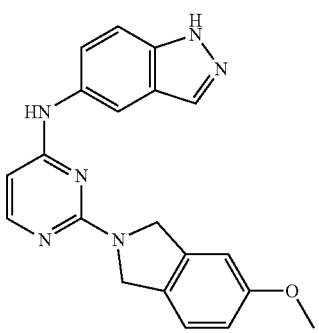 [SMILES: COc1ccc2c(c1)CN(c1nccc(Nc3ccc4[nH]ncc4c3)n1)C2]

A mixture of N-(2-chloropyrimidin-4-yl)-1H-indazol-5-amine (0.500 g, 2.04 mmol), 5-methoxyisoindoline hydrochloride (0.404 g, 2.18 mmol), and $K_2CO_3$ (0.844 g, 6.11 mmol) in DMF (4.07 mL) was stirred at 115° C. overnight. The mixture was diluted with water and extracted with EtOAc twice. The combined organic layers were washed with water and brine, dried over $Na_2SO_4$, concentrated, and purified by chromatography with MeOH in DCM. The product was further purified by recrystallization in EtOAc to provide the title compound as a light orange solid (215 mg, 30%). $^1$H NMR (300 MHz, DMSO-$d_6$) δ 13.15 (s, 1H), 9.45 (s, 1H), 8.52 (s, 1H), 8.29 (s, 1H), 8.16 (d, J=5.8 Hz, 1H), 7.81-7.66 (m, 2H), 7.59 (s, 1H), 7.25 (d, J=19.2 Hz, 1H), 7.10 (d, J=8.4 Hz, 1H), 6.29 (d, J=5.8 Hz, 1H), 5.01 (d, J=16.0 Hz, 4H), 3.99 (s, 3H). MS (ES+) m/e 359 (M+H)$^+$.

Example 182

N-(2-(isoindolin-2-yl)pyrimidin-4-yl)-1H-indazol-5-amine

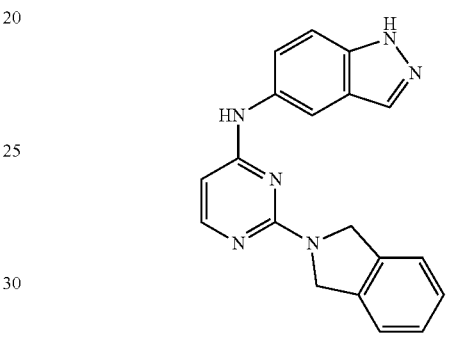

A mixture of N-(2-chloropyrimidin-4-yl)-1H-indazol-5-amine (0.200 g, 1.03 mmol), isoindoline (0.140 g, 1.03 mmol), and $K_2CO_3$ (0.171 g, 1.24 mmol) in DMF (6.89 mL) was stirred 80° C. for 4 h followed by at rt overnight. The mixture was diluted with water and extracted with EtOAc. The organic layer was washed with water, brine and dried over $MgSO_4$ to afford a crude brown oil which was recrystallized from 5% MeOH/DCM followed by further recrystallization in EtOH to afford the title compound as a grey solid (36.1 mg, 11%). $^1$H NMR (300 MHz, DMSO-$d_6$) δ 12.95 (s, 1H), 9.25 (s, 1H), 8.25 (s, 1H), 8.07 (s, 1H), 7.95 (d, J=4.4 Hz, 1H), 7.31-7.51 (m, 6H), 6.08 (d, J=4.4 Hz, 1H), 4.82 (d, J=24.7 Hz, 4H). MS (ES+) m/e 329 (M+H)$^+$.

Example 183

N-(5-fluoro-2-(5-methoxyisoindolin-2-yl)pyrimidin-4-yl)-1H-indazol-5-amine

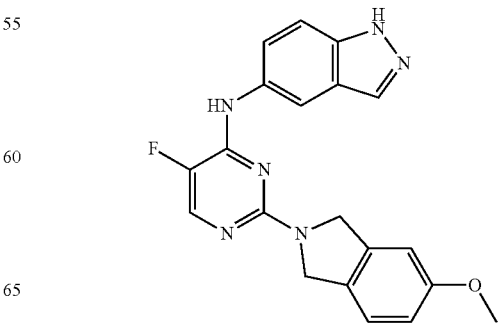

N-(2-chloro-5-fluoropyrimidin-4-yl)-1H-indazol-5-amine

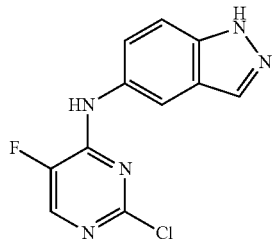 [SMILES: Fc1cnc(Cl)nc1Nc1ccc2[nH]ncc2c1]

To a solution of 2,4-dichloro-5-fluoropyrimidine (0.800 g, 4.55 mmol) in EtOH (40 mL) were added Na$_2$CO$_3$ (6.27 g, 45.5 mmol) and compound 1H-indazol-5-amine (0.605 g, 4.55 mmol). The resulting mixture was stirred for 12 h at 100° C. After LCMS showed the reaction was completed, the solvent was removed under reduced pressure and the residue was put into water (50 mL) and extracted with EtOAc (3×100 mL). The organic phase was dried over Na$_2$SO$_4$, filtered and concentrated under reduced pressure to give a residue which was purified by column chromatograph on silica gel (eluted with PE:EA=1:1) to give the title compound as a solid (120 mg, 9.7%).

N-(5-fluoro-2-(5-methoxyisoindolin-2-yl)pyrimidin-4-yl)-1H-indazol-5-amine

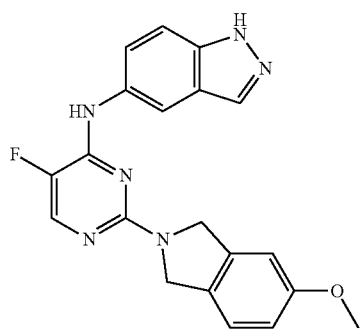 [SMILES: COc1ccc2c(c1)CN(c1ncc(F)c(Nc3ccc4[nH]ncc4c3)n1)C2]

To a solution of N-(2-chloro-5-fluoropyrimidin-4-yl)-1H-indazol-5-amine (300 mg, 1.14 mmol) in acetonitrile (4 mL) were added 5-methoxyisoindoline (170 mg, 1.14 mmol) and DIEA (441 mg, 3.42 mmol). The resulting mixture was heated at 90° C. for 12 h. After LCMS showed the reaction was completed, the mixture was concentrated and dissolved in methanol and purified by preparative HPLC, and lyophilized to give compound the title compound as a white solid (52 mg, 12.1%). $^1$H NMR (300 MHz, DMSO-d$_6$) δ 13.0 (s, 1H), 9.26 (s, 1H), 8.32 (s, 1H), 8.09 (s, 1H), 8.03 (d, J=4.0 Hz, 1H), 7.74 (d, J=8.8 Hz, 1H), 7.50 (d, J=9.2 Hz, 1H), 7.30 (b, 1H), 7.00 (b, 1H), 6.86 (dd, J=8.4 and 2.8 Hz, 1H), 4.72 (s, 2H), 4.69 (s, 2H), 3.76 (s, 3H). MS (ES+) m/e 377 (M+H)$^+$.

Example 184

N-(5-chloro-2-(5-methoxyisoindolin-2-yl)pyrimidin-4-yl)-1H-indazol-5-amine

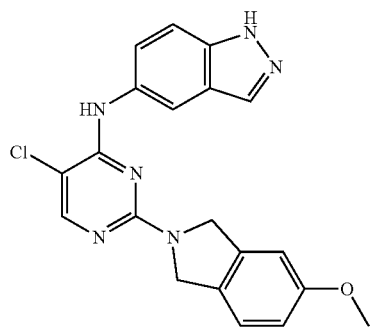 [SMILES: COc1ccc2c(c1)CN(c1ncc(Cl)c(Nc3ccc4[nH]ncc4c3)n1)C2]

N-(2,5-dichloropyrimidin-4-yl)-1H-indazol-5-amine

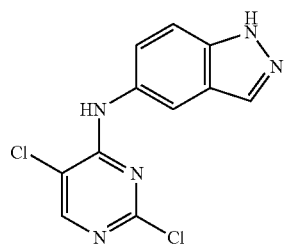 [SMILES: Clc1ncc(Cl)c(Nc2ccc3[nH]ncc3c2)n1]

To a solution of 2,4,5-trichloropyrimidine (1.00 g, 5.49 mmol) in EtOH (20 mL) were added Na$_2$CO$_3$ (3.03 g, 28.6 mmol) and compound 1H-indazol-5-amine (0.657 g, 4.94 mmol). The resulting mixture was stirred for 12 h at 15° C. After LCMS showed the reaction was completed, then the solvent was removed under reduced pressure and the residue was put into water (50 mL) and extracted with EtOAc (3×50 mL). The organic phase was dried over Na$_2$SO$_4$, filtered and concentrated under reduced pressure to give compound the title compound as a solid (800 mg, 52.3%).

N-(5-chloro-2-(5-methoxyisoindolin-2-yl)pyrimidin-4-yl)-1H-indazol-5-amine

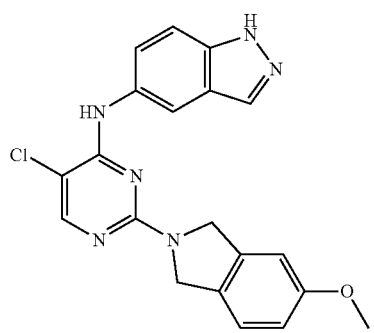 [SMILES: COc1ccc2c(c1)CN(c1ncc(Cl)c(Nc3ccc4[nH]ncc4c3)n1)C2]

To a solution of compound N-(2,5-dichloropyrimidin-4-yl)-1H-indazol-5-amine (281 mg, 1.01 mmol) in acetonitrile (5 mL) were added compound 5-methoxylisoindoline (150 mg, 1.01 mmol) and DIEA (391 mg, 3.03 mmol). The resulting mixture was heated at 90° C. for 12 h. After LCMS showed the reaction was completed, the mixture was concentrated and dissolved in methanol and purified by preparative HPLC, and lyophilized to give compound the title compound as a white solid (115 mg, 29.1%). $^1$H NMR (300 MHz, DMSO-d$_6$) δ 13.00 (s, 1H), 8.73 (s, 1H), 8.14 (s, 1H), 8.08 (s, 2H), 7.69 (d, J=8.8 Hz, 1H), 7.50 (s, J=8.8 Hz, 1H), 7.27 (b, 1H), 6.97 (b, 1H), 6.84 (d, J=8.4 Hz, 1H), 4.67 (t, J=16.4 Hz, 4H), 3.74 (s, 3H). MS (ES+) m/e 393 (M+H)$^+$.

Example 185

N-(2-(5-methoxyisoindolin-2-yl)-5-methylpyrimidin-4-yl)-1H-indazol-5-amine

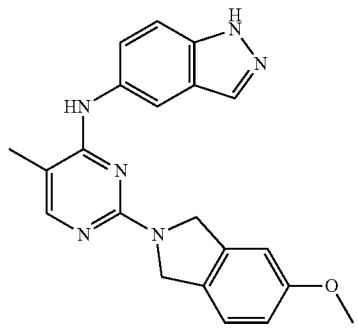

N-(2-chloro-5-methylpyrimidin-4-yl)-1H-indazol-5-amine

To a solution of compound 2,4-dichloro-5-methylpyrimidine (1.00 g, 6.17 mmol) in EtOH (20 mL) were added Na$_2$CO$_3$ (3.27 g, 30.9 mmol) and compound 1H-indazol-5-amine (0.821 g, 6.17 mmol). The resulting mixture was stirred for 12 h at 90° C. After LCMS showed the reaction was completed, then the solvent was removed under reduced pressure and the residue was put into water (50 mL) and extracted with EtOAc (3×50 mL). The organic phase was dried over Na$_2$SO$_4$, filtered and concentrated under reduced pressure to give a residue which was purified by preparative HPLC to give compound the title compound as a solid (400 mg, yield: 25%).

N-(2-(5-methoxyisoindolin-2-yl)-5-methylpyrimidin-4-yl)-1H-indazol-5-amine

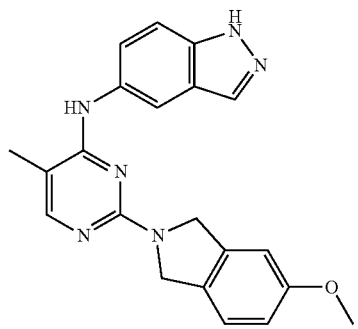

To a solution of compound N-(2-chloro-5-methylpyrimidin-4-yl)-1H-indazol-5-amine (261 mg, 1.01 mmol) in DMF (5 mL) were added compound 5-methoxyisoindoline (150 mg, 1.01 mmol) and DIEA (391 mg, 3.03 mmol). The resulting mixture was heated at 110° C. for 12 h. After LCMS showed the reaction was completed, the mixture was concentrated and dissolved in methanol and purified by preparative HPLC, and lyophilized to give compound the title compound as a white solid (105 mg, 27.0%). $^1$H NMR (300 MHz, DMSO-d$_6$) δ 12.92 (s, 1H), 8.25 (s, 1H), 8.18 (s, 1H), 8.06 (s, 1H), 7.81 (s, 1H), 7.72 (d, J=9.2 Hz, 1H), 7.48 (d, J=8.8 Hz, 1H), 7.25 (d, J=8.0 Hz, 1H), 6.98 (s, 1H), 6.83 (d, J=8.0 Hz, 1H), 4.70 (s, 2H), 4.65 (s, 2H), 3.75 (s, 3H), 2.09 (s, 3H). MS (ES+) m/e 373 (M+H)$^+$.

Example 186

N-(2-(5-methoxyisoindolin-2-yl)-6-methylpyrimidin-4-yl)-1H-indazol-5-amine

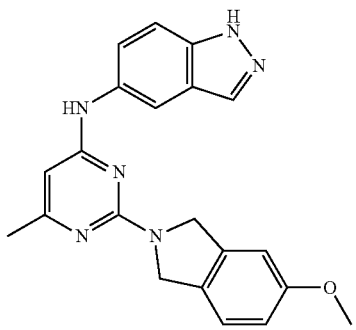

N-(2-chloro-6-methylpyrimidin-4-yl)-1H-indazol-5-amine

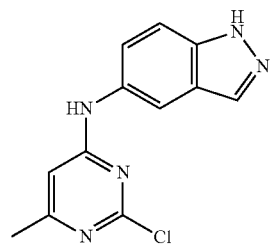 [SMILES: Cc1cc(Nc2ccc3[nH]ncc3c2)nc(Cl)n1]

To a solution of compound 2,4-dichloro-6-methylpyrimidine (1.00 g, 6.17 mmol) in EtOH (20 mL) were added Na$_2$CO$_3$ (3.27 g, 30.9 mmol) and compound 1H-indazol-5-amine (0.821 g, 6.17 mmol). The resulting mixture was stirred for 12 h at 90° C. After LCMS showed the reaction was completed, then the solvent was removed under reduced pressure and the residue was put into water (50 mL) and extracted with EtOAc (3×50 mL). The organic phase was dried over Na$_2$SO$_4$, filtered and concentrated under reduced pressure to give a residue which was purified by preparative HPLC to give compound the title compound as a solid (400 mg, 25%).

N-(2-(5-methoxyisoindolin-2-yl)-6-methylpyrimidin-4-yl)-1H-indazol-5-amine

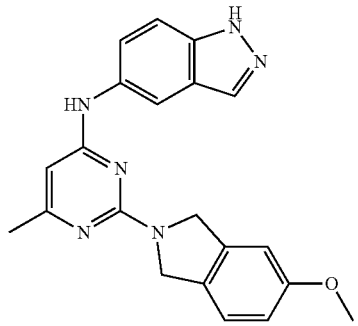

To a solution of compound N-(2-chloro-6-methylpyrimidin-4-yl)-1H-indazol-5-amine (261 mg, 1.01 mmol) in DMF (5 mL) were added compound 5-methoxyisoindoline (150 mg, 1.01 mmol) and DIEA (391 mg, 3.03 mmol). The resulting mixture was heated at 110° C. for 12 h. After LCMS showed the reaction was completed, the mixture was concentrated and dissolved in methanol and purified by preparative HPLC, and lyophilized to give compound the title compound as a white solid (80 mg, 21.4%). $^1$H NMR (300 MHz, DMSO-$d_6$) δ 12.91 (s, 1H), 9.08 (s, 1H), 8.25 (s, 1H), 8.06 (s, 1H), 7.47-7.53 (m, 2H), 7.29 (b, 1H), 7.00-7.05 (m, 1H), 6.87 (d, J=10.4 Hz, 1H), 5.93 (s, 1H), 5.76 (b, 4H), 3.77 (s, 3H), 2.17 (s, 3H). MS (ES+) m/e 373 (M+H)$^+$.

Example 187

N-(1H-indazol-5-yl)-2-(5-methoxyisoindolin-2-yl)-5,7-dihydrofuro[3,4-d]pyrimidin-4-amine

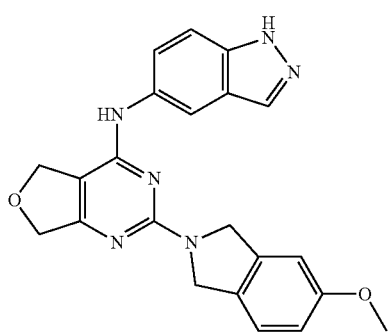 [SMILES: COc1ccc2c(c1)CN(c1nc3c(c(Nc4ccc5[nH]ncc5c4)n1)COC3)C2]

2-chloro-N-(1H-indazol-5-yl)-5,7-dihydrofuro[3,4-d]pyrimidin-4-amine

To a solution of compound 2,4-dichloro-5,7-dihydrofuro[3,4-d]pyrimidine (1.00 g, 5.30 mmol) in EtOH (30 mL) were added Na$_2$CO$_3$ (1.70 g, 15.8 mmol) and compound 1H-indazol-5-amine (711 mg, 5.3 mmol). The resulting mixture was stirred for 12 h at 15° C. After LCMS showed the reaction was completed, the solvent was removed under reduced pressure and the residue was dissolved in EtOAc (100 mL), washed by water (2×50 mL). The organic phase was dried over Na$_2$SO$_4$, filtered and concentrated under reduced pressure to give compound the title compound as a solid (800 mg, yield: 38.3%).

N-(1H-indazol-5-yl)-2-(5-methoxyisoindolin-2-yl)-5,7-dihydrofuro[3,4-d]pyrimidin-4-amine

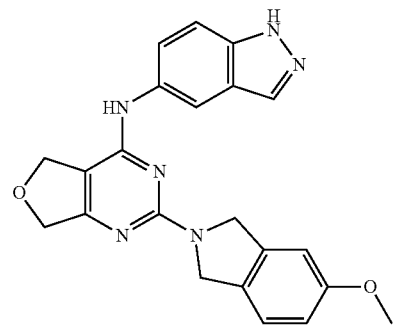 [SMILES: COc1ccc2c(c1)CN(c1nc3c(c(Nc4ccc5[nH]ncc5c4)n1)COC3)C2]

To a solution of compound 2-chloro-N-(1H-indazol-5-yl)-5,7-dihydrofuro[3,4-d]pyrimidin-4-amine (346 mg, 1.21 mmol) in acetonitrile (30 mL) were added compound 5-methoxyisoindoline (150 mg, 1.00 mmol) and DIEA (273 mg, 2.11 mmol). The resulting mixture was heated at 90° C. for 20 h. After LCMS showed the reaction was completed, the mixture was concentrated and dissolved in methanol and purified by preparative HPLC, and lyophilized to give the title compound (69.0 mg, 17.2%). $^1$H NMR (300 MHz, DMSO-$d_6$) δ 12.90 (s, 1H), 8.83 (s, 1H), 8.27 (s, 1H), 8.09 (s, 1H), 7.64 (d, J=8.8 Hz, 1H), 7.50 (d, J=8.8 Hz, 1H), 7.00-7.40 (m, 2H), 6.86 (dd, J=8.4 and 2.8 Hz, 1H), 4.73-4.89 (m, 8H), 3.77 (s, 3H). MS (ES+) m/e 401 (M+H)$^+$.

Example 188

N-(4-(5-methoxyisoindolin-2-yl)pyrimidin-2-yl)-1H-indazol-5-amine

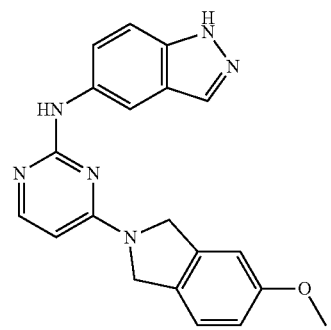 [SMILES: COc1ccc2c(c1)CN(c1ccnc(Nc3ccc4[nH]ncc4c3)n1)C2]

2-(2-chloropyrimidin-4-yl)-5-methoxyisoindoline

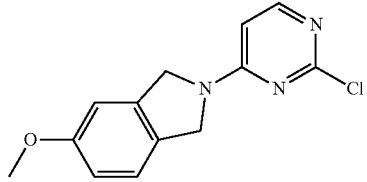 [SMILES: COc1ccc2c(c1)CN(c1ccnc(Cl)n1)C2]

To a solution of compound 2,4-dichloropyrimidine (298 mg, 2.01 mmol) in EtOH (10 mL) were added Na$_2$CO$_3$ (1.11 g, 10.5 mmol) and compound 5-methoxyisoindoline (300 mg, 2.01 mmol). The resulting mixture was stirred for 12 h at 90° C. After LCMS showed the reaction was completed, then the solvent was removed under reduced pressure and the residue was put into water (50 mL) and extracted with EtOAc (3×50 mL). The organic phase was dried over Na$_2$SO$_4$, filtered and concentrated under reduced pressure to give a residue which was purified by preparative TLC to give the title compound as a solid (250 mg, yield: 47.8%).

N-(4-(5-methoxyisoindolin-2-yl)pyrimidin-2-yl)-1H-indazol-5-amine

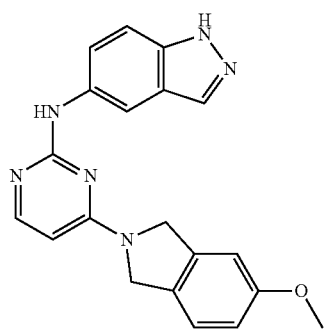 [SMILES: COc1ccc2c(c1)CN(c1ccnc(Nc3ccc4[nH]ncc4c3)n1)C2]

To a solution of compound 2-(2-chloropyrimidin-4-yl)-5-methoxyisoindoline (250 mg, 0.958 mmol) in DMF (20 mL) were added compound 5-aminoindazole (127 mg, 0.958 mmol) and DIEA (370 mg, 2.87 mmol). The resulting mixture was heated at 110° C. for 20 h. After LCMS showed the reaction was completed, the mixture was concentrated and purified by prep-HPLC, and lyophilized to give the title compound (51.7 mg, 17%). $^1$H NMR (300 MHz, DMSO-d$_6$) δ 12.83 (s, 1H), 9.03 (s, 1H), 8.33 (s, 1H), 8.00 (s, 1H), 7.99 (s, 1H), 7.62 (dd, J=9.2 and 2.0 Hz, 1H), 7.42 (d, J=8.8 Hz, 1H), 7.30 (b, 1H), 7.07 (b, 1H), 6.90 (d, J=8.4 Hz, 1H), 6.02 (d, J=6.4 Hz, 1H), 4.83 (d, J=14.4 Hz, 2H), 4.65 (d, J=17.6 Hz, 2H). 3.77 (s, 3H). MS (ES+) m/e 359 (M+H)$^+$.

Example 189

N-(2-(5-fluoroisoindolin-2-yl)pyrimidin-4-yl)-1H-indazol-5-amine

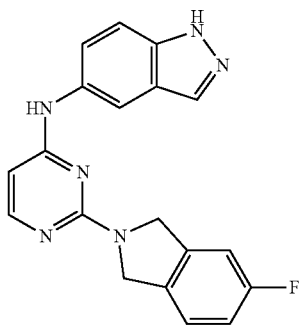 [SMILES: Fc1ccc2c(c1)CN(c1nccc(Nc3ccc4[nH]ncc4c3)n1)C2]

To a solution of N-(2-chloropyrimidin-4-yl)-1H-indazol-5-amine (457 mg, 1.87 mmol) in DMF (5 mL) were added compound 5-fluoroisoindole (250 mg, 1.87 mmol) and DIEA (724 mg, 5.61 mmol). The resulting mixture was heated at 110° C. for 20 h. After LCMS showed the reaction was completed, the mixture was concentrated and purified by prep-HPLC, and lyophilized to give the title compound (200 mg, 31.0%). $^1$H NMR (300 MHz, DMSO-d$_6$) δ 12.92 (s, 1H), 9.24 (s, 1H), 8.28 (s, 1H), 8.06 (s, 1H), 7.94 (d, J=6.0 Hz, 1H), 7.11-7.53 (m, 5H), 6.08 (d, J=6.4 Hz, 1H), 4.80 (b, 4H). MS (ES+) m/e 347 (M+H)$^+$.

Example 190

N-(2-(5-chloroisoindolin-2-yl)pyrimidin-4-yl)-1H-indazol-5-amine

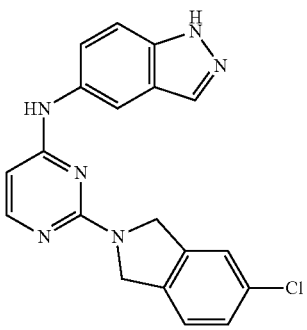 [SMILES: Clc1ccc2c(c1)CN(c1nccc(Nc3ccc4[nH]ncc4c3)n1)C2]

To a solution of N-(2-chloropyrimidin-4-yl)-1H-indazol-5-amine (384 mg, 1.57 mmol) in acetonitrile (5 mL) were added compound 5-chloroisoindoline (240 mg, 157 mmol) and DIEA (608 mg, 4.71 mmol). The resulting mixture was heated at 90° C. for 17 h. After LCMS showed the reaction was completed, the mixture was concentrated and the crude was washed with MeOH to give the title compound as a brown solid (230 mg, yield: 40.5%). $^1$H NMR (300 MHz, DMSO-d$_6$) δ 13.00 (s, 1H), 9.65 (s, 1H), 8.31 (s, 1H), 8.10 (s, 1H), 7.93 (d, J=6.0 Hz, 1H), 7.35-7.57 (m, 5H), 6.18 (d, J=6.0 Hz, 1H), 4.82 (b, 4H). MS (ES+) m/e 363 (M+H)$^+$.

Example 191

N-(2-(6-methoxy-3,4-dihydroisoquinolin-2(1H)-yl)pyrimidin-4-yl)-1H-indazol-5-amine

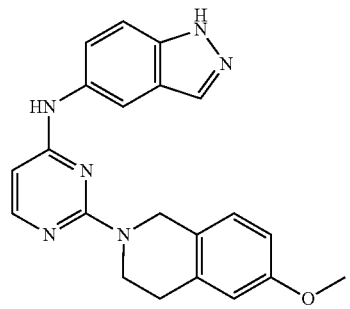 [SMILES: COc1ccc2c(c1)CCN(c1nccc(Nc3ccc4[nH]ncc4c3)n1)C2]

A mixture of N-(2-chloropyrimidin-4-yl)-1H-indazol-5-amine (100 mg, 0.41 mmol), 6-methoxy-1,2,3,4-tetrahydroisoquinoline (81.3 mg, 0.41 mmol), and $K_2CO_3$ (168 mg, 1.22 mmol) in DMF (1.2 mL) was stirred at 120° C. overnight, cooled to rt, diluted with water, and extracted with EtOAc. The organic layer was concentrated and the residue was purified by chromatography with 1-20% MeOH/DCM to provide the title compound as a white solid (42 mg, 28%). $^1$H NMR (300 MHz, DMSO-$d_6$) δ 12.96 (s, 1H), 9.21 (s, 1H), 8.13 (d, J=1.6 Hz, 1H), 8.04 (t, J=1.1 Hz, 1H), 7.93 (d, J=5.7 Hz, 1H), 7.56-7.41 (m, 2H), 7.15 (d, J=8.2 Hz, 1H), 6.84-6.72 (m, 2H), 6.03 (d, J=5.7 Hz, 1H), 4.79 (s, 2H), 3.95 (t, J=5.8 Hz, 2H), 3.73 (s, 3H), 2.85 (t, J=6.0 Hz, 2H). MS (ES+) m/e 373 (M+H)$^+$.

Example 192

N-(2-(6,7-dihydrothieno[3,2-c]pyridin-5(4H)-yl)pyrimidin-4-yl)-1H-indazol-5-amine

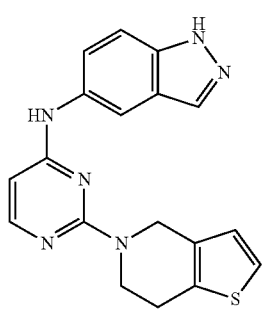 [SMILES: c1cc(Nc2ccc3[nH]ncc3c2)nc(N2CCc3sccc3C2)n1]

A mixture of N-(2-chloropyrimidin-4-yl)-1H-indazol-5-amine (100 mg, 0.41 mmol), 4-H thieno[3,2]pyridine (71.5 mg, 0.41 mmol), and $K_2CO_3$ (168 mg, 1.22 mmol) in DMF (1.2 mL) was stirred at 120° C. overnight, cooled to rt, diluted with water, and extracted with EtOAc. The organic layer was concentrated and the residue was purified by chromatography with 1-20% MeOH/DCM to provide the title compound as a white solid (33 mg, 23%). $^1$H NMR (300 MHz, DMSO-$d_6$) δ 12.97 (s, 1H), 9.23 (s, 1H), 8.12-8.01 (m, 2H), 7.93 (d, J=5.7 Hz, 1H), 7.56-7.40 (m, 2H), 7.34 (d, J=5.1 Hz, 1H), 6.97 (d, J=5.2 Hz, 1H), 6.04 (d, J=5.7 Hz, 1H), 4.80 (s, 2H), 4.07 (t, J=5.6 Hz, 2H), 2.93-2.82 (m, 2H). MS (ES+) m/e 349 (M+H)$^+$.

Example 193

N-(6-(5-methoxyisoindolin-2-yl)pyrimidin-4-yl)-1H-indazol-5-amine

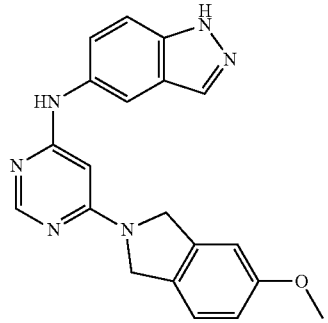 [SMILES: COc1ccc2c(c1)CN(c1cc(Nc3ccc4[nH]ncc4c3)ncn1)C2]

N-(6-chloropyrimidin-4-yl)-1H-indazol-5-amine

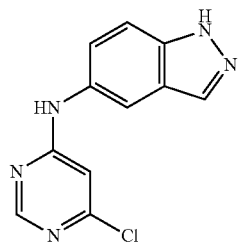 [SMILES: Clc1cc(Nc2ccc3[nH]ncc3c2)ncn1]

A mixture of 4,6-dichloropyrimidine (300 mg, 2.01 mmol), tert-butyl 5-amino-1H-indazole-1-carboxylate (470 mg, 2.01 mmol), diisopropylethylamine (0.74 mL, 3.03 mmol), and DMF (2.01 mL) was stirred at 80° C. overnight followed by 120° C. for 4 h. The mixture was cooled to rt, diluted with water, and extracted with EtOAc. The organic layer was concentrated in vacuo to provide the title compound which was carried out directly for next step reaction without further purification.

N-(6-(5-methoxyisoindolin-2-yl)pyrimidin-4-yl)-1H-indazol-5-amine

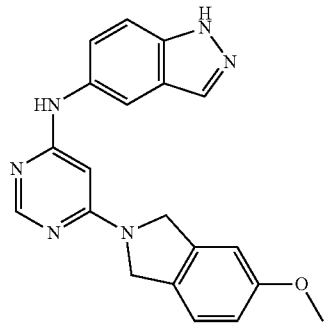 [SMILES: COc1ccc2c(c1)CN(c1cc(Nc3ccc4[nH]ncc4c3)ncn1)C2]

A mixture of N-(6-chloropyrimidin-4-yl)-1H-indazol-5-amine (150 mg, 0.61 mmol), 5-methoxyisoindoline hydrogen chloride (121 mg, 0.65 mmol), $K_2CO_3$ (253 mg, 1.83 mmol) in DMF (1.22 mL) was stirred at 100° C. for 2 h followed by 120° C. for 12 h. The mixture was cooled to rt, diluted with water, and extracted with EtOAc. The organic layer was concentrated and purified by chromatography with 0-20% MeOH in DCM to provide the product which was further purified by trituration with DCM/Hex to provide pure title compound (30 mg, 14%). $^1$H NMR (300 MHz, DMSO-$d_6$) δ 12.95 (s, 1H), 9.02 (s, 1H), 8.22 (d, J=0.9 Hz, 1H), 8.01 (d, J=2.1 Hz, 2H), 7.55-7.36 (m, 2H), 7.31 (d, J=8.4 Hz, 1H), 7.00 (d, J=2.3 Hz, 1H), 6.89 (dd, J=8.4, 2.4 Hz, 1H), 5.74 (d, J=1.1 Hz, 1H), 4.65 (s, 4H), 3.77 (s, 3H). MS (ES+) m/e 359 (M+H)$^+$.

Example 194

N-(6-(5-methoxyisoindolin-2-yl)-2-methylpyrimidin-4-yl)-1H-indazol-5-amine

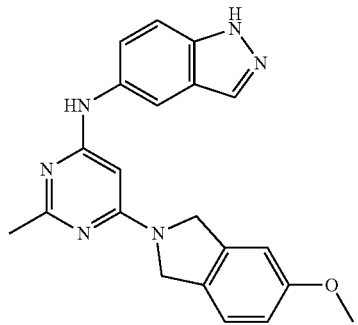

A mixture of N-(6-chloropyrimidin-4-yl)-1H-indazol-5-amine (159 mg, 0.61 mmol), 5-methoxyisoindoline hydrogen chloride (121 mg, 0.65 mmol), K$_2$CO$_3$ (253 mg, 1.83 mmol) in DMF (1.22 mL) was stirred at 100° C. for 2 h followed by 120° C. for 12 h. The mixture was cooled to rt, diluted with water, and extracted with EtOAc. The organic layer was concentrated and purified by chromatography with 0-20% MeOH in DCM to provide the product which was further purified by trituration with DCM/Hex to provide pure title compound (25 mg, 11%). $^1$H NMR (300 MHz, DMSO-$d_6$) δ 12.95 (s, 1H), 8.90 (s, 1H), 7.98 (d, J=15.8 Hz, 2H), 7.54-7.36 (m, 2H), 7.29 (d, J=8.5 Hz, 1H), 6.99 (d, J=2.0 Hz, 1H), 6.88 (dd, J=8.3, 2.4 Hz, 1H), 5.60 (s, 1H), 4.63 (s, 4H), 3.76 (s, 3H), 2.34 (s, 3H). MS (ES+) m/e 373 (M+H)$^+$.

Example 195

N-(2-(1H-pyrrolo[3,4-c]pyridin-2(3H)-yl)pyrimidin-4-yl)-1H-indazol-5-amine

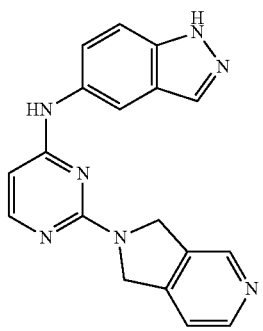 [SMILES: c1cc2c(cn1)CN(c1nccc(Nc3ccc4[nH]ncc4c3)n1)C2]

A mixture of N-(2-chloropyrimidin-4-yl)-1H-indazol-5-amine (100 mg, 0.41 mmol), 2,3-dihydro-1H-pyrrolo[3,4-c]pyridine dihydrogen chloride (102 mg, 0.53 mmol), diisopropylethylamine (0.74 mL, 1.22 mmol) in DMF (0.81 mL) was stirred at 110° C. overnight. The mixture was cooled to rt, diluted with water, and extracted with EtOAc. The organic layer was concentrated and purified by chromatography with 0-20% MeOH in DCM to provide the title compound (13 mg, 10%) as a slightly yellow solid. $^1$H NMR (300 MHz, DMSO-$d_6$) δ 12.95 (s, 1H), 9.29 (s, 1H), 8.69 (s, 1H), 8.52 (d, J=5.0 Hz, 1H), 8.29 (s, 1H), 8.08 (s, 1H), 7.97 (d, J=5.7 Hz, 1H), 7.61-7.46 (m, 3H), 6.11 (d, J=5.8 Hz, 1H), 4.88 (s, 4H). MS (ES+) m/e 330 (M+H)$^+$.

Example 196

N-(2-(5-methoxyisoindolin-2-yl)-5,6-dimethylpyrimidin-4-yl)-1H-indazol-5-amine

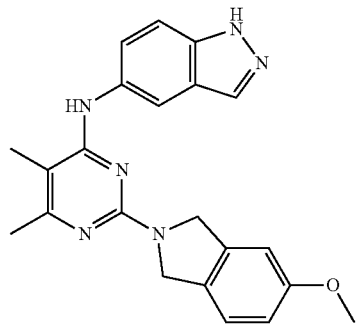

N-(2-chloro-5,6-dimethylpyrimidin-4-yl)-1H-indazol-5-amine

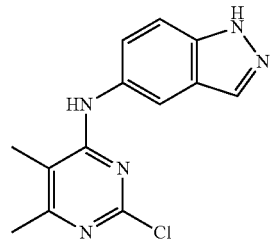

To a solution of 2,4-dichloro-5,6-dimethylpyrimidine (0.800 g, 4.55 mmol) in EtOH (40 mL) were added Na$_2$CO$_3$ (2.42 g, 22.8 mmol) and 1H-indazol-5-amine (0.605 g, 4.55 mmol). The resulting mixture was stirred for 12 h at 100° C. The solvent was removed under reduced pressure and the residue was poured into water (50 mL) and extracted with EtOAc (3×100 mL). The organic phase was dried over Na$_2$SO$_4$, filtered and concentrated under reduced pressure to give a residue which was purified by column chromatograph on silica gel (eluted with PE:EA=1:1) to provide the title compound (120 mg, yield: 9.7%) as a white solid.

N-(2-(5-methoxyisoindolin-2-yl)-5,6-dimethylpy-rimidin-4-yl)-1H-indazol-5-amine

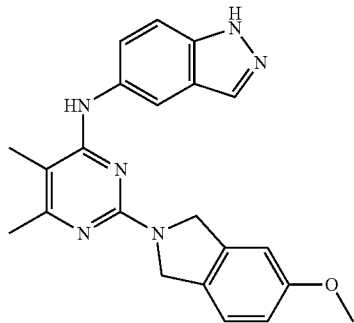

To a solution of N-(2-chloro-5,6-dimethylpyrimidin-4-yl)-1H-indazol-5-amine (1.0 g, 3.66 mmol) in CH$_3$CN (60 mL) were added 5-methoxyisoindoline (545 mg, 3.66 mmol) and K$_2$CO$_3$ (1.01 g, 7.33 mmol). The resulting mixture was heated at 90° C. for 72 h. After LCMS showed the reaction was completed, the mixture was concentrated and the crude was washed with MeOH to provide the title compound (423 mg, yield: 30.0%) as a brown solid. $^1$H NMR (300 MHz, DMSO-d$_6$) δ 12.95 (s, 1H), 8.08 (s, 1H), 8.01 (d, J=8.8 Hz, 1H), 7.30 (d, J=8.0 Hz, 1H), 7.00 (s, 1H), 6.90-6.83 (m, 4H), 4.81 (s, 2H), 4.77 (s, 2H), 3.75 (s, 3H), 2.44 (s, 3H), 2.77 (s, 3H). MS (ES+) m/e 387 (M+H)$^+$.

Example 197

N-(1H-indazol-5-yl)-2-(isoindolin-2-yl)-5,7-dihydro-furo[3,4-d]pyrimidin-4-amine

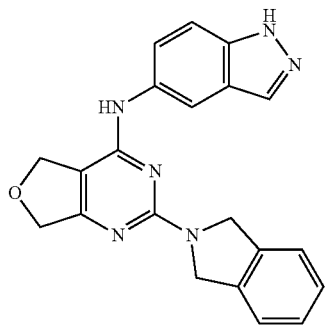 [SMILES: c1ccc2c(c1)CN(c1nc3c(c(Nc4ccc5[nH]ncc5c4)n1)COC3)C2]

The title compound was synthesized using the same procedure as described for the synthesis of Example 7 (KL-00230). $^1$H NMR (400 MHz, DMSO-d$_6$) δ 12.94 (s, 1H), 8.82 (s, 1H), 8.25 (s, 1H), 8.06 (s, 1H), 7.64-7.28 (m, 6H), 4.87-4.72 (m, 8H). MS (ES+) m/e 371 (M+H)$^+$.

Example 198

N-(4-(1H-pyrazol-4-yl)phenyl)-2-(5-methoxyisoin-dolin-2-yl)pyrimidin-4-amine

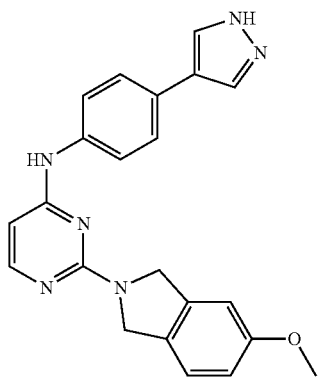 [SMILES: COc1ccc2c(c1)CN(c1nccc(Nc3ccc(-c4cn[nH]c4)cc3)n1)C2]

N-(4-bromophenyl)-2-chloropyrimidin-4-amine

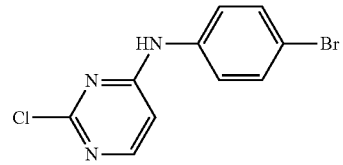 [SMILES: Clc1nccc(Nc2ccc(Br)cc2)n1]

To a solution of compound N-(4-bromophenyl)-2-chloropyrimidin-4-amine (2.00 g, 13.4 mmol) in EtOH (20 mL) were added Na$_2$CO$_3$ (4.26 g, 40.2 mmol) and compound 4-bromoaniline (2.3 g, 13.4 mmol). The resulting mixture was stirred for 12 h at 15° C. After LCMS showed the reaction was completed, then the solvent was removed under reduced pressure and the residue was put into water (50 mL) and extracted with EtOAc (3×50 mL). The organic phase was dried over Na$_2$SO$_4$, filtered and concentrated under reduced pressure to give a residue which was purified by washed with EA to give compound the title compound (1.20 g, yield: 31.6%) as a solid.

N-(4-bromophenyl)-2-(5-methoxyisoindolin-2-yl)pyrimidin-4-amine

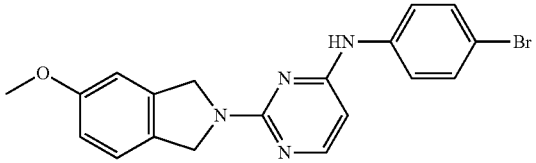 [SMILES: COc1ccc2c(c1)CN(c1nccc(Nc3ccc(Br)cc3)n1)C2]

To a solution of compound N-(4-bromophenyl)-2-chloropyrimidin-4-amine (1.00 g, 3.53 mmol) in acetonitrile (5 mL) were added compound 5-methoxyisoindoline (526 mg, 3.53 mmol) and DIEA (1.36 g, 10.6 mmol). The resulting mixture was heated at 90° C. for 17 h. After LCMS showed the reaction was completed, the mixture was concentrated and the crude was washed with MeOH to give compound the title compound (600 mg, yield: 42.9%) as a brown solid.

2-(5-methoxyisoindolin-2-yl)-N-(4-(1-((2-(trimethyl-silyl)ethoxy)methyl)-1H-pyrazol-4-yl)phenyl)pyrimidin-4-amine

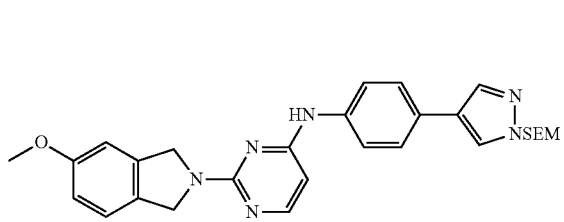 [SMILES: COc1ccc2c(c1)CN(c1nccc(Nc3ccc(-c4cnn(COCC[Si](C)(C)C)c4)cc3)n1)C2]

To the solution of compound N-(4-bromophenyl)-2-(5-methoxyisoindolin-2-yl)pyrimidin-4-amine (300 mg, 0.758 mol), compound 4-(4,4,5,5-tetramethyl-1,3,2-dioxaborolan-2-yl)-1-((2-(trimethylsilyl)ethoxy)methyl)-1H-pyrazole (492 mg, 1.52 mol) and K$_2$CO$_3$ (209 mg, 1.52 mol) were dissolved in dioxane/H$_2$O (2 mL/2 mL) and degassed with nitrogen for 10 minutes. Pd(dppf)Cl2 (27.7 mg, 0.0379 mmol) was added and the reaction mixture was stirred under nitrogen at 85° C. for 17 h. After LCMS showed the reaction was completed, then the mixture was concentrated used to next step.

N-(4-(1H-pyrazol-4-yl)phenyl)-2-(5-methoxyisoindolin-2-yl)pyrimidin-4-amine

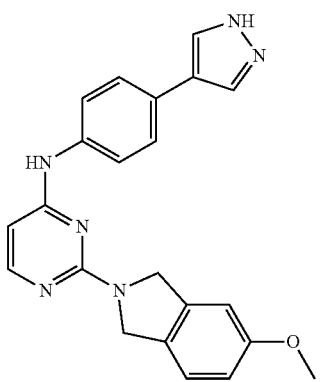 [SMILES: COc1ccc2c(c1)CN(c1nccc(Nc3ccc(-c4cn[nH]c4)cc3)n1)C2]

To the solution of compound 2-(5-methoxyisoindolin-2-yl)-N-(4-(1-((2-(trimethylsilyl)ethoxy)methyl)-1H-pyrazol-4-yl)phenyl)pyrimidin-4-amine (350 mg, 0.0195 mol) was dissolved in TFA (2 mL) and was stirred at 85° C. for 1 h. After LCMS showed the reaction was completed. Then TFA was removed and the residue was purified by prep-HPLC to give the title compound (53.1 mg, yield: 20.3%) as a brown solid. $^1$H NMR (400 MHz, DMSO-d$_6$) δ 9.55 (s, 1H), 7.99 (s, 1H), 7.94 (d, J=6.0, 1H), 7.76 (d, J=8.4, 1H), 7.57 (d, J=8.4, 1H), 7.31 (s, 1H), 7.00 (s, 1H), 6.89 (d, J=8.4, 1H), 6.13 (d, J=5.6, 1H), 4.77 (m, 4H), 3.76 (s, 3H). MS (ES+) m/e 385 (M+H)$^+$.

Example 199

2-(5-methoxyisoindolin-2-yl)-N-(pyridin-4-yl)pyrimidin-4-amine

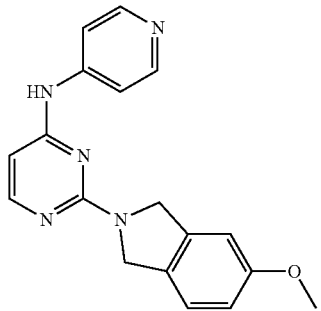 [SMILES: COc1ccc2c(c1)CN(c1nccc(Nc3ccncc3)n1)C2]

2-(5-methoxyisoindolin-2-yl)pyrimidin-4-amine

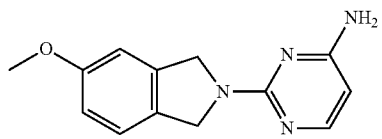 [SMILES: COc1ccc2c(c1)CN(c1nccc(N)n1)C2]

To a solution compound 2-chloropyrimidin-4-amine (381 mg, 2.95 mmol) and DIEA (692 mg, 5.37 mmol) in CH$_3$CN (20 mL) was added compound 5-methoxyisoindoline (400 mg, 2.68 mmol). Then the reaction was stirred at 90° C. for 16 h. After LCMS showed the reaction was complete. The crude product was purified by prep-TLC to give compound the title compound (230 mg, yield: 35.4%).

2-(5-methoxyisoindolin-2-yl)-N-(pyridin-4-yl)pyrimidin-4-amine

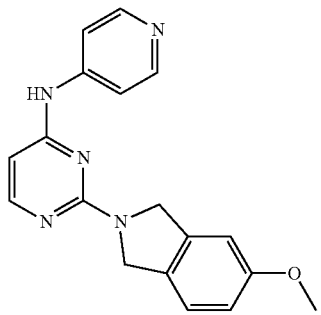 [SMILES: COc1ccc2c(c1)CN(c1nccc(Nc3ccncc3)n1)C2]

To a solution of 2-(5-methoxyisoindolin-2-yl)pyrimidin-4-amine (270 mg, 1.12 mmol) and 4-bromopyridine (193 mg, 1.23 mmol) in dioxane (20 mL) were added Cs$_2$CO$_3$ (1.09 g, 3.35 mmol) and stirred under N$_2$. Then xphos (32.2 mg, 0.0558 mmol) and Pd$_2$(dba)$_3$ (51.1 mg, 0.0558 mmol) were added and the reaction was stirred at 85° C. under N$_2$ for 16 h. After LCMS showed the reaction was completed. The crude product was purified by prep-HPLC to give the title compound (96.0 mg, yield: 26.9%). $^1$H NMR (400

MHz, DMSO-$d_6$) δ 9.69 (s, 1H), 8.38 (dd, J=4.8 and 1.6, 2H), 8.07 (d, J=5.2, 1H), 7.80 (dd, J=4.8 and 1.2, 2H), 7.33-7.89 (m, 1H), 7.04-6.98 (m, 1H), 6.86 (d, J=8.4, 1H), 6.16 (d, J=5.2, 1H), 4.87-4.71 (m, 4H), 3.76 (s, 3H). MS (ES+) m/e 320 (M+H)$^+$.

Example 200

2-(5-methoxyisoindolin-2-yl)-N-(4-(pyridin-4-yl)phenyl)pyrimidin-4-amine

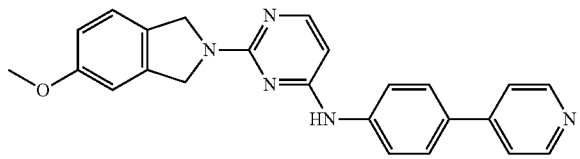 [SMILES: COc1ccc2c(c1)CN(c1nccc(Nc3ccc(-c4ccncc4)cc3)n1)C2]

A mixture of compound N-(4-bromophenyl)-2-(5-methoxyisoindolin-2-yl)pyrimidin-4-amine (297 mg, 0.748 mmol), pyridin-4-ylboronic acid (307 mg, 1.496 mmol), $K_2CO_3$ (206 mg, 1.496 mmol), $PdCl_2$(dppf) (30.5 mg, 0.0374 mmol) and dioxane (20 mL) and $H_2O$ (20 mL) was stirred at 110° C. under $N_2$ for 12 h. After LCMS showed the reaction was completed, the mixture was cooled to 28° C., filtered and the filter cake was washed with MeOH (20 mL), dried to give the title compound (200 mg, yield: 67.6%) as a brown solid. $^1$H NMR (400 MHz, DMSO-$d_6$) δ 9.54 (s, 1H), 8.56 (s, 2H), 8.00-7.69 (m, 7H), 7.29-6.87 (m, 3H), 6.14 (s, 1H), 4.78-4.75 (m, 4H), 3.75 (s, 3H). MS (ES+) m/e 396 (M+H)$^+$.

Example 201

ROCK1 and ROCK2 Compound Selectivity

Dose response curves for Rho-kinase inhibition were derived from a Millipore immuno-based 96 well plate assay (Millipore catalog number CSA001). Purified active ROCK1 and ROCK2 were obtained from Invitrogen (catalog numbers ROCKI, PV3691 and ROCK2, PV3759). The kit components include assay plates, which are pre-coated with recombinant MYPT1, which contains a specifically phosphorylatable Thr696. The inhibitory activities of compounds are measured according to the manufactures protocol. Briefly, decreasing concentrations of test compounds or the known ROCK inhibitor Y-27963, are added, from 50 uM to 0.003 uM to reaction buffer containing 5 mM MgCl2, and 10 mUnits of ROCK1 or ROCK2 in assay dilution buffer. This mixture is overlayed into the 96 well plate and the reaction is initiated with the addition of 2.5 uM ATP. The assay proceeds at 300 Celsius for 30 minutes with gentle shaking at 120 rpm. The assay is terminated by washing of the plate 3 times with Tris-buffered saline and tween wash buffer. Anti-phospho-MYPT1 (Thr696) antibody is added to each well to detect the phosphorylated substrate and incubated for 1 hour at room temperature after which HRP conjugated anti-rabbit IgG secondary is added for 1 hour at room temperature. After washing the assay is developed using a substrate reagent and the absorbance is read at 450 nm on a Tecan Infinite M1000 reflecting the relative remaining ROCK phosphorylation activity.

Data showing inhibition of ROCK1 and ROCK2, and selectivity of certain compounds for ROCK2 inhibition, is presented in Table 1.

TABLE 1

| | IC$_{50}$ and Ki for ROCK1 and ROCK2 | | | |
|---|---|---|---|---|
| Compound | ROCK1 IC$_{50}$ (μM) | ROCK2 IC$_{50}$ (μM) | ROCK1 Ki (μM) | ROCK2 Ki (μM) |
| Ex. 12 | 1.77 | 0.54 | 0.07 | 0.02 |
| Ex. 26 | 53.45 | 0.72 | 2.01 | 0.03 |
| Ex. 28 | 6.69 | 1.96 | 0.26 | 0.08 |
| SLx-2119 | 13.11 | 1.02 | 0.50 | 0.04 |
| Y-27263 | 1.13 | 1.63 | 0.04 | 0.06 |
| Ex. 14 | | 4.25 | | 0.17 |
| Ex. 48 | 0.33 | 0.47 | 0.01 | 0.02 |
| Ex. 13 | 22.53 | 4.64 | 0.87 | 0.18 |

Figure 6:
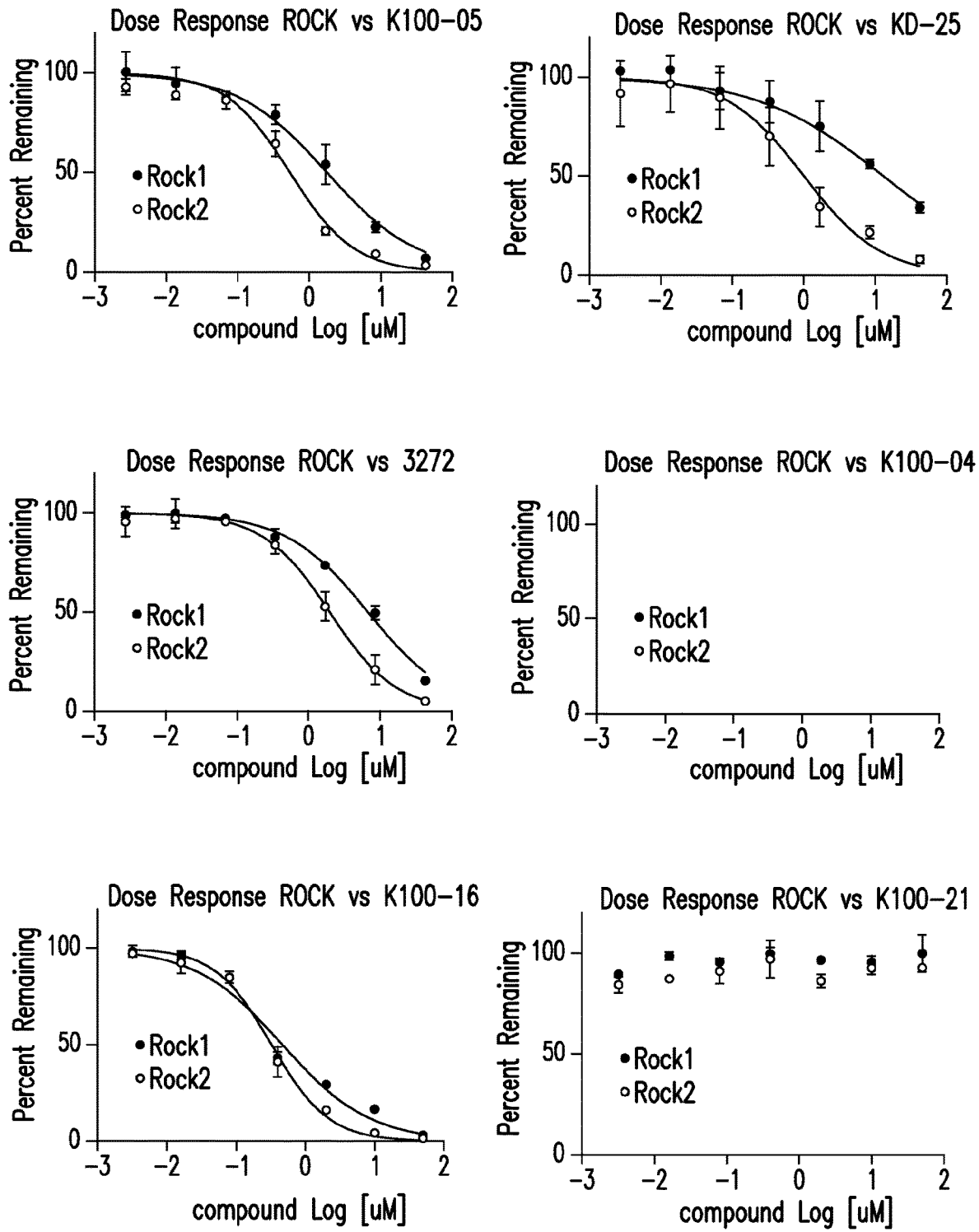
FIG. 6 shows dose response curves for inhibition of ROCK1 vs. ROCK2. Compounds correspond to Examples herein, as follows: K100-5, Ex. 12; KD-25, SLx-2119; 3272, Ex. 28; K100-04, Ex. 14; K100-16, Ex. 43; K100-21; Ex. 38; K100-23 Ex. 52; K100-24, Ex. 111; K100-25, Ex. 56; K100-26, Ex. 13; 3266, Ex. 26.
Figure 6:
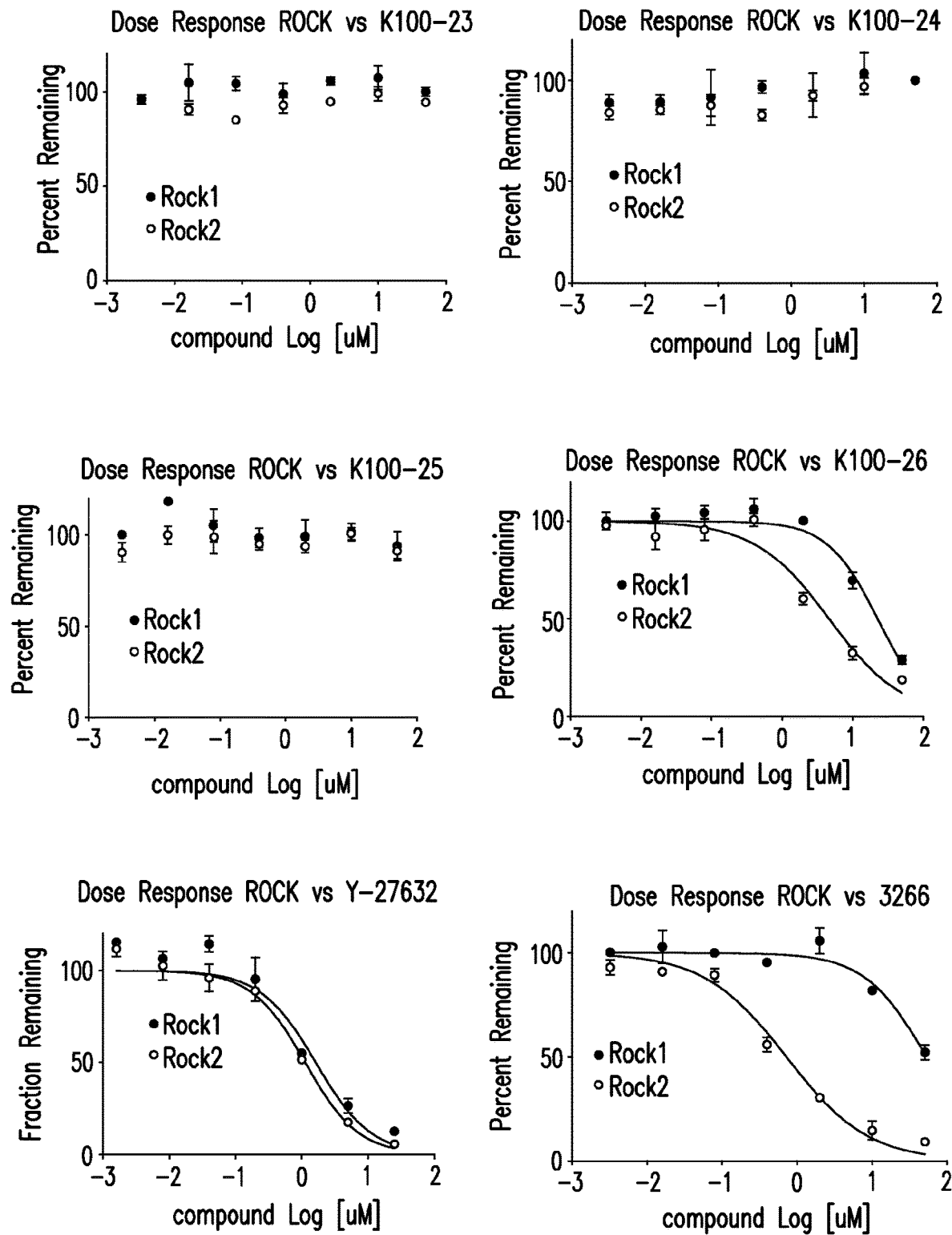
Figure 7:
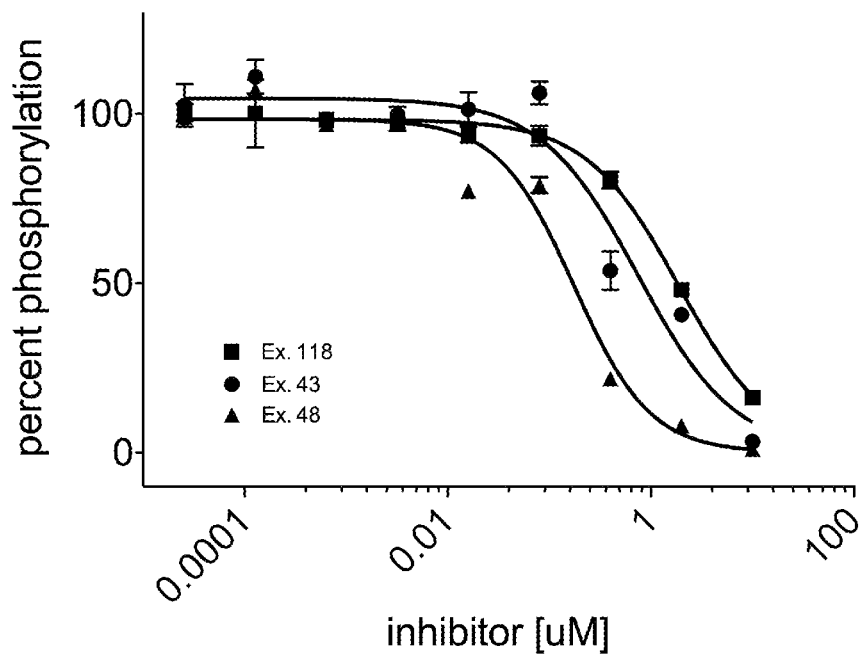
FIG. 7 compares ROCK1 and ROCK2 inhibition among the compounds of Examples 43, 48, and 118.
Figure 7:
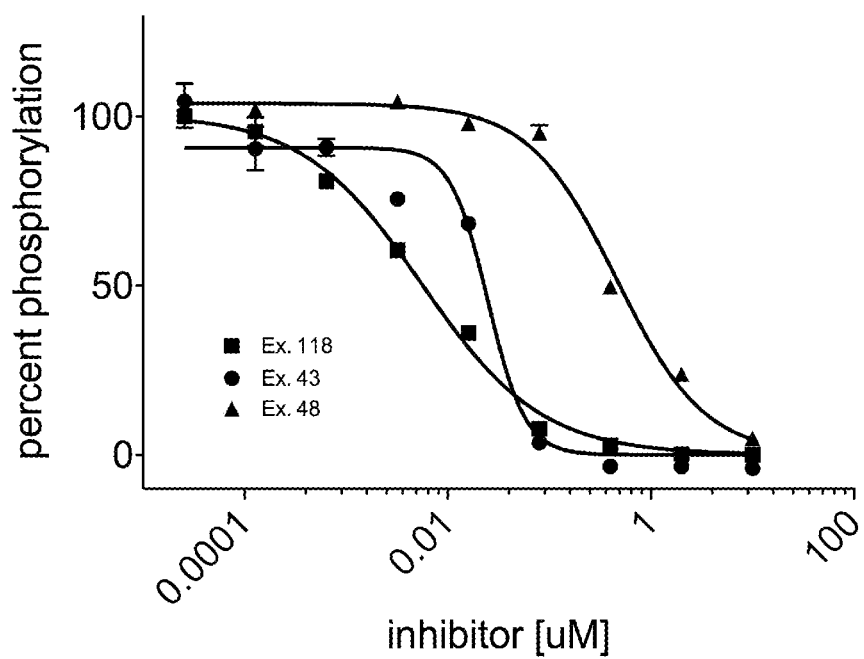

Dose response curves for inhibition of ROCK1 vs ROCK2 are shown in FIG. 6.

Example 202

ROCK1 and ROCK2 Compound Selectivity

Dose response curves for Rho-kinase inhibition were derived from a Invitrogen Z'-LYTE™ Kinase Assay Kit (Invitrogen catalog number PV3793). Purified active ROCK1 and ROCK2 were obtained from Invitrogen (catalog numbers ROCK1, PV3691 and ROCK2, PV3759). The kit components include a coumarin and fluorescein labeled peptide based on myosin light chain 2 (KKRPQRRYSNVF), a proprietary protease containing development reagent and a proprietary Stop buffer used to terminate the development reaction. The inhibitory activities of compounds are measured according to the manufactures protocol. Briefly, decreasing concentrations of test compounds or the known ROCK inhibitor Y-27963, are added, from 10 uM to 2.56× 10$^{-5}$ uM to reaction buffer containing 50 mM HEPES pH 7.5, 10 mM MgCl$_2$, 5 mM EGTA, and 0.05% Brij-35 and of ROCK1 at 0.18 ug/mL or ROCK2 at 0.8 ug/mL in assay dilution buffer. This mixture is overlayed into a white 96-well half area plate and the reaction is initiated with the addition of 5 uM ATP for ROCK1 or 12 uM ATP for ROCK2. The assay proceeds at room temperature for 1 hour followed by the addition of development reagent, and further incubation for 1 hour at room temperature. STOP reagent is then added and the reaction and immediately the coumarin and fluorescein emission signals are read on a Tecan Infinite M1000 fluorescence plate reader (excitation: 400 nm; emission 445 and 520 nm, respectively). By comparing the emission ratios of the test samples against control samples, percent phosphorylation values are calculated and the concentration of inhibitor that produces ½ inhibition of kinase activity (IC$_{50}$) is determined using Prism. Table 2 provides IC$_{50}$ concentrations for compounds of the above examples. Several of the compounds also demonstrated activity in a preliminary assay that measured inhibition of myosin light chain phosphorylation (pMLC). For compounds marked ND, activity was not determinable under the test conditions employed.

TABLE 2

| | ROCK Inhibition | | | | | |
|---|---|---|---|---|---|---|
| Ex. No. | ROCK2 IC$_{50}$ (nM) | ROCK1 IC$_{50}$ (nM) | pMLC inhibition | Ex. No. | ROCK2 IC$_{50}$ (nM) | ROCK1 IC$_{50}$ (nM) | pMLC inhibition |
| 14 | | | + | 91 | | | + |
| 12 | | | ND | 75 | | | ND |

TABLE 2-continued

ROCK Inhibition

| Ex. No. | ROCK2 IC$_{50}$ (nM) | ROCK1 IC$_{50}$ (nM) | pMLC inhibition | Ex. No. | ROCK2 IC$_{50}$ (nM) | ROCK1 IC$_{50}$ (nM) | pMLC inhibition |
|---|---|---|---|---|---|---|---|
| 43 | | | ++ | 79 | | | + |
| 48 | 1000 | 300 | ++ | 95 | | | ND |
| 38 | | | + | 110 | | | |
| 52 | | | | 82 | | | |
| 56 | | | ND | 86 | | | |
| 126 | | | ND | 98 | | | |
| 112 | | | ND | 83 | | | |
| 114 | | | ND | 87 | | | |
| 60 | | | ND | 99 | | | |
| 74 | | | ND | 106 | | | |
| 60 | | | ND | 102 | | | |
| 65 | | | ND | 5 | 70 | >3000 | |
| 71 | | | + | 26 | 30 | 3500 | |
| 117 | | | + | 163 | 80 | 5900 | |
| 118 | 40 | 6600 | + | 164 | 60 | 5000 | |
| 119 | | | + | 165 | 50 | 1700 | |
| 120 | | | | 166 | 20 | 2200 | |
| 121 | | | + | 28 | 70 | 2500 | |
| 122 | | | ND | 167 | 60 | 3400 | |
| 123 | | | ND | 168 | 30 | >10000 | |
| 124 | | | + | 169 | >10000 | >10000 | |
| 125 | | | + | 170 | 70 | 4100 | |
| 127 | | | ++ | 171 | 80 | 7500 | |
| 129 | | | + | 172 | 120 | >10000 | |
| 131 | | | + | 173 | 30 | >10000 | |
| 134 | | | + | 174 | 191 | 2800 | |
| 136 | | | + | 17 | 30 | 1200 | |
| 138 | | | + | 175 | 500 | | |
| 140 | | | + | 176 | 13 | 3500 | |
| 144 | | | + | 177 | 4900 | >10000 | |
| 147 | >5500 | >2000 | | 178 | 700 | 4400 | |
| 150 | 1000 | >3000 | | 179 | 310 | 2400 | |
| 154 | 40 | >10000 | | 22 | 340 | 10000 | |
| 159 | 200 | 100 | ++ | 180 | 380 | >10000 | |
| 161 | 3200 | 1000 | | 20 | 400 | >10000 | |

Example 203

ROCK1 and ROCK2 Compound Selectivity

TABLE 3

ROCK Inhibition

| Ex. No. | ROCK2 IC$_{50}$ (nM) | ROCK1 IC$_{50}$ (nM) | pMLC inhibition | Ex. No. | ROCK2 IC$_{50}$ (nM) | ROCK1 IC$_{50}$ (nM) | pMLC inhibition |
|---|---|---|---|---|---|---|---|
| 181 | 10 | 893 | + | 198 | 2 | 7066 | |
| 181 | 2 | 434 | | 199 | | | |
| 183 | 30 | 8340 | ++ | 200 | 35 | >10000 | |
| 184 | 190 | | | 200 | 40 | >10000 | |
| 184 | 140 | | | 197 | | | |
| 185 | 50 | 8750 | + | 182 | 60 | >10000 | + |
| 186 | 30 | 2370 | + | 191 | 700 | >10000 | + |
| 196 | >10 | | | 192 | 1060 | >10000 | + |
| 187 | 10 | 3750 | ++ | 193 | 130 | >10000 | + |
| 188 | 1170 | >10000 | ND | 194 | 130-180 | >10000 | + |
| 189 | 40 | 2930 | ND | 195 | 340 | >10000 | + |
| 190 | 110 | >10000 | | | | | |

Example 204

ROCK2 siRNA, but not ROCK1 siRNA Inhibits, IL-17 and IL-21 Secretion

Figure 2:
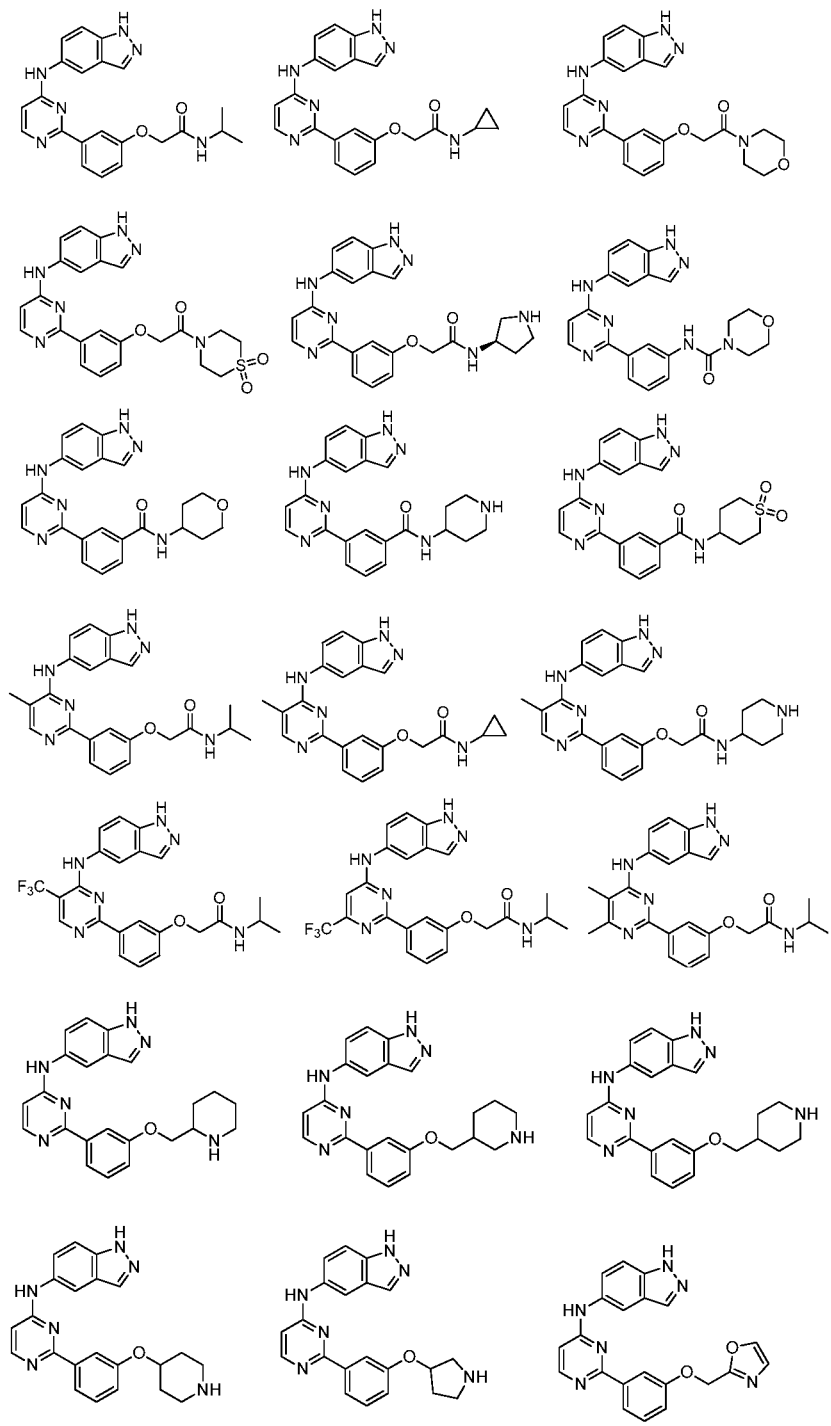
FIG. 2 shows compounds of the invention.
Figure 3:
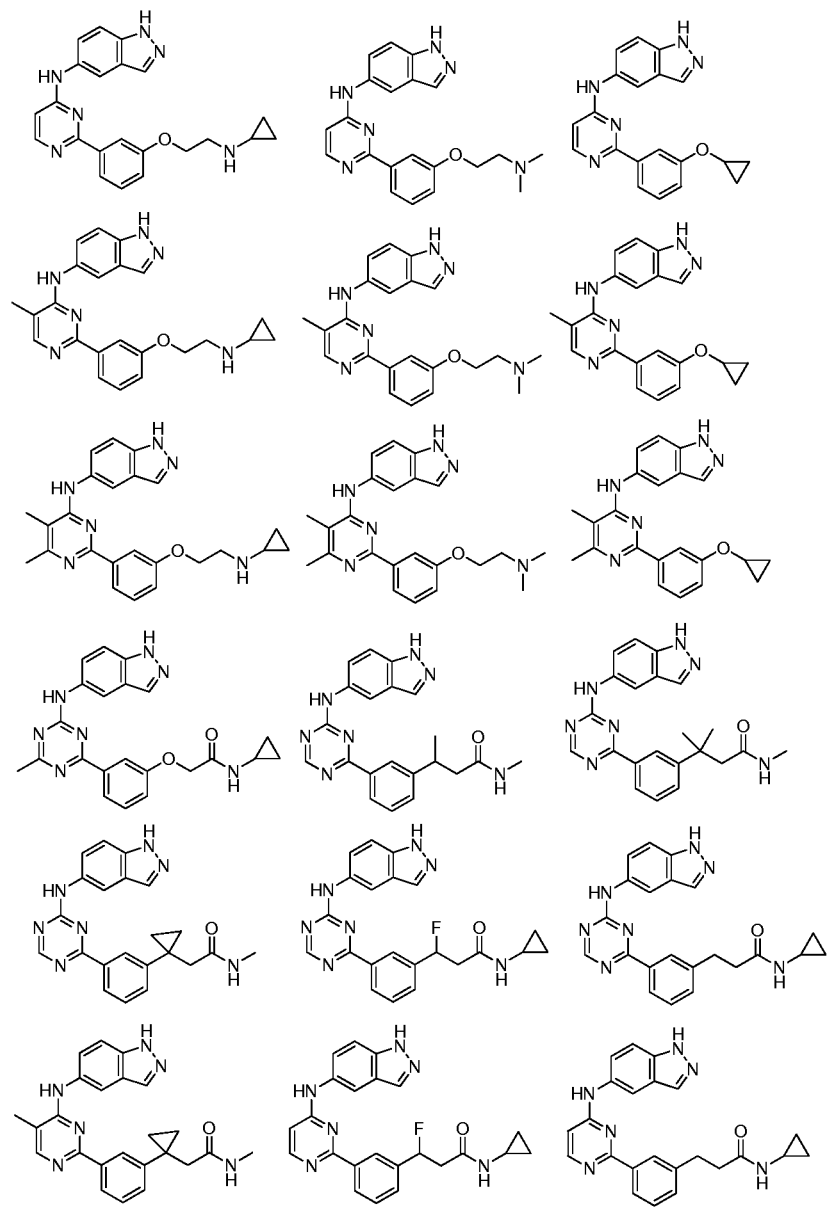
FIG. 3 shows compounds of the invention.
Figure 4:
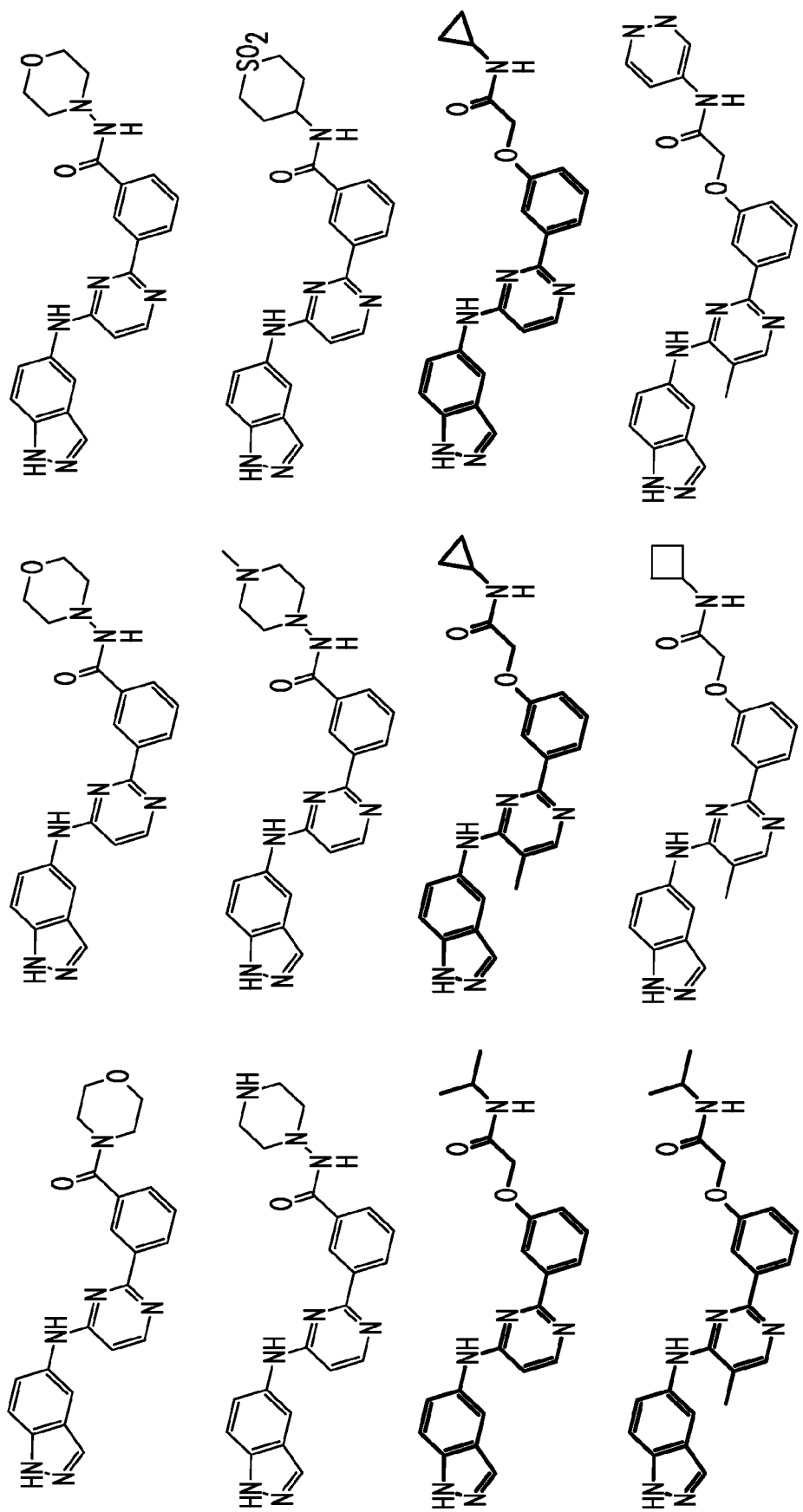
FIG. 4 shows compounds of the invention.
Figure 4:
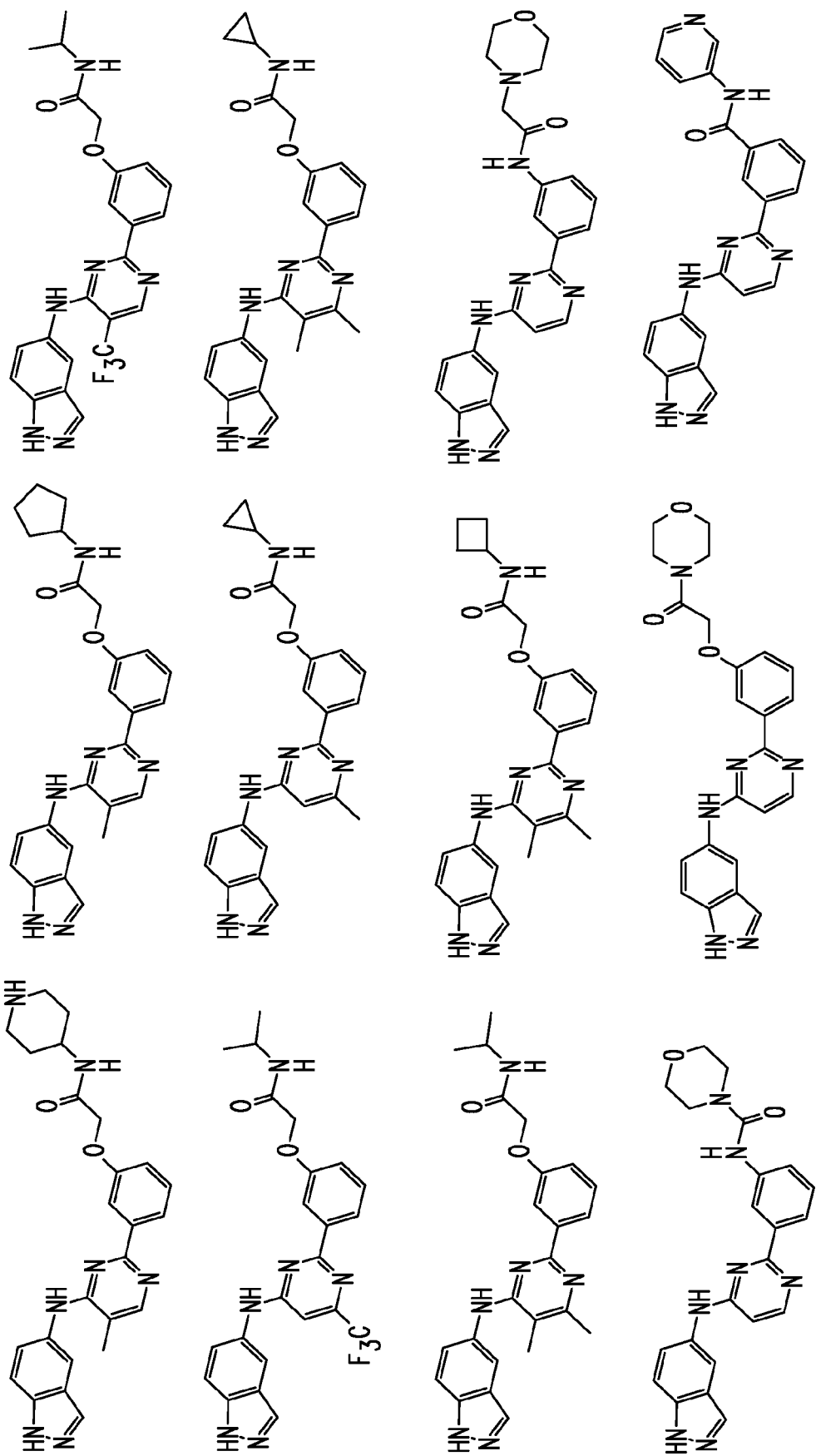
Figure 5:
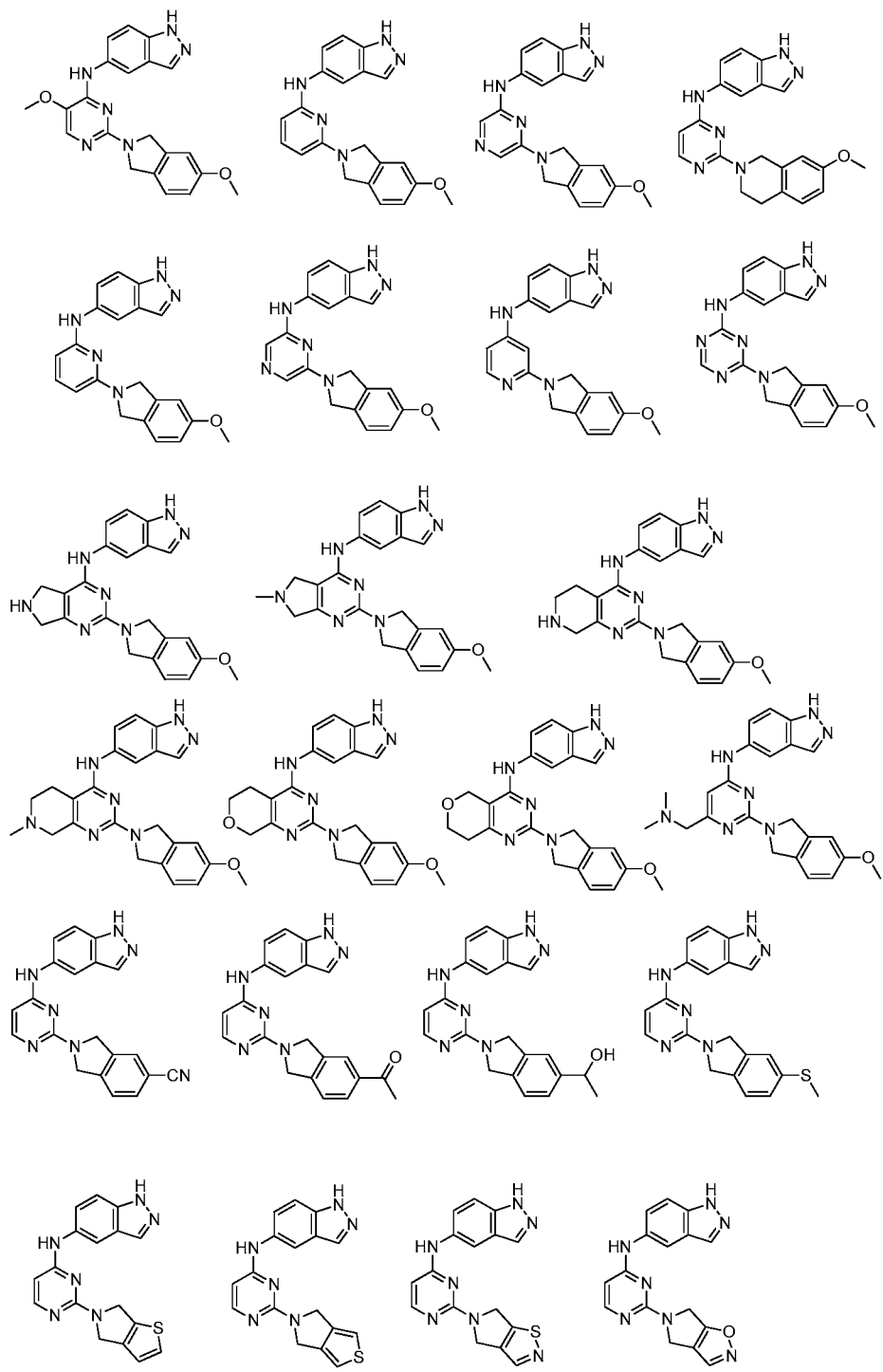
FIG. 5 shows compounds of Formula XXVI of the invention.
Figure 5:
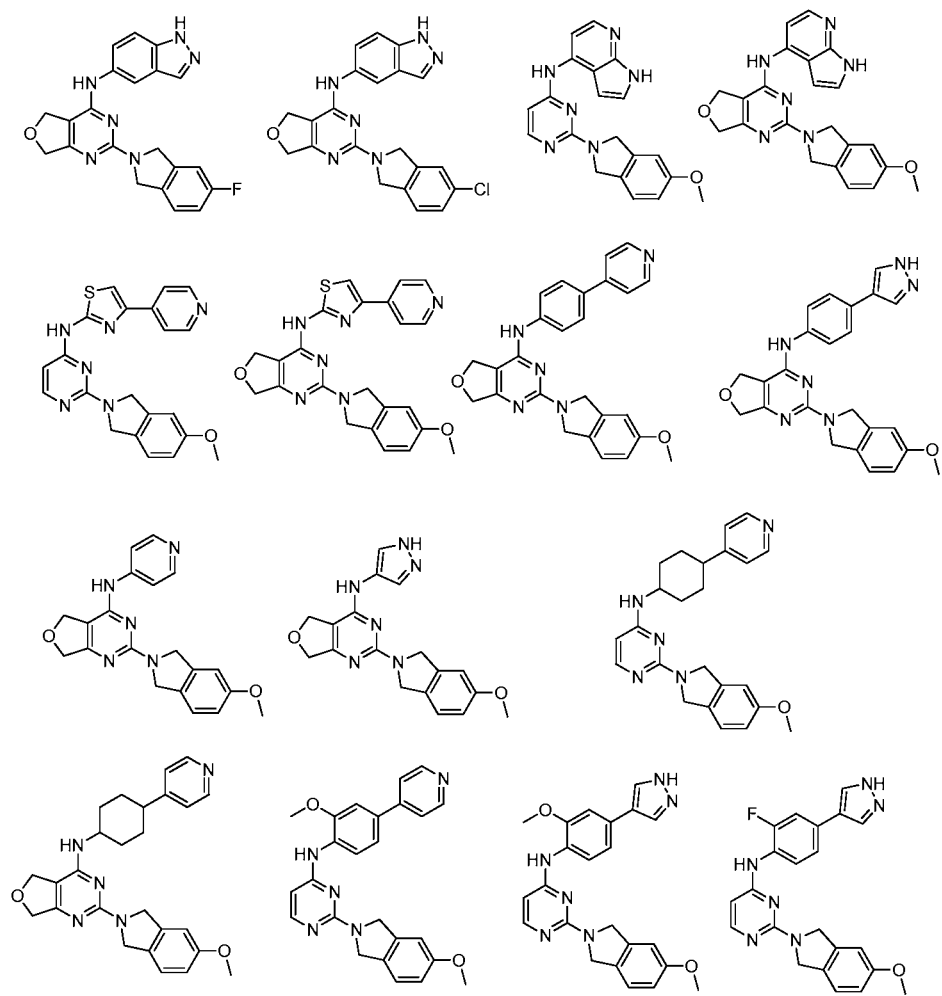

To confirm the role of ROCK2 in regulation of IL-17 and IL-21 secretion in human T cells we specifically silenced ROCK1 and ROCK2 expression by RNA interference. Specific ROCK1 and ROCK2 small interfering RNA (siRNA) reduced the protein expression levels by 72% and 84% respectively. Silencing of ROCK2, but not of ROCK1 significantly reduced the IL-17 and IL-21, with minimal effect on IFN-γ secretion in human T cells (FIG. 2).

Example 205

Figure 8:
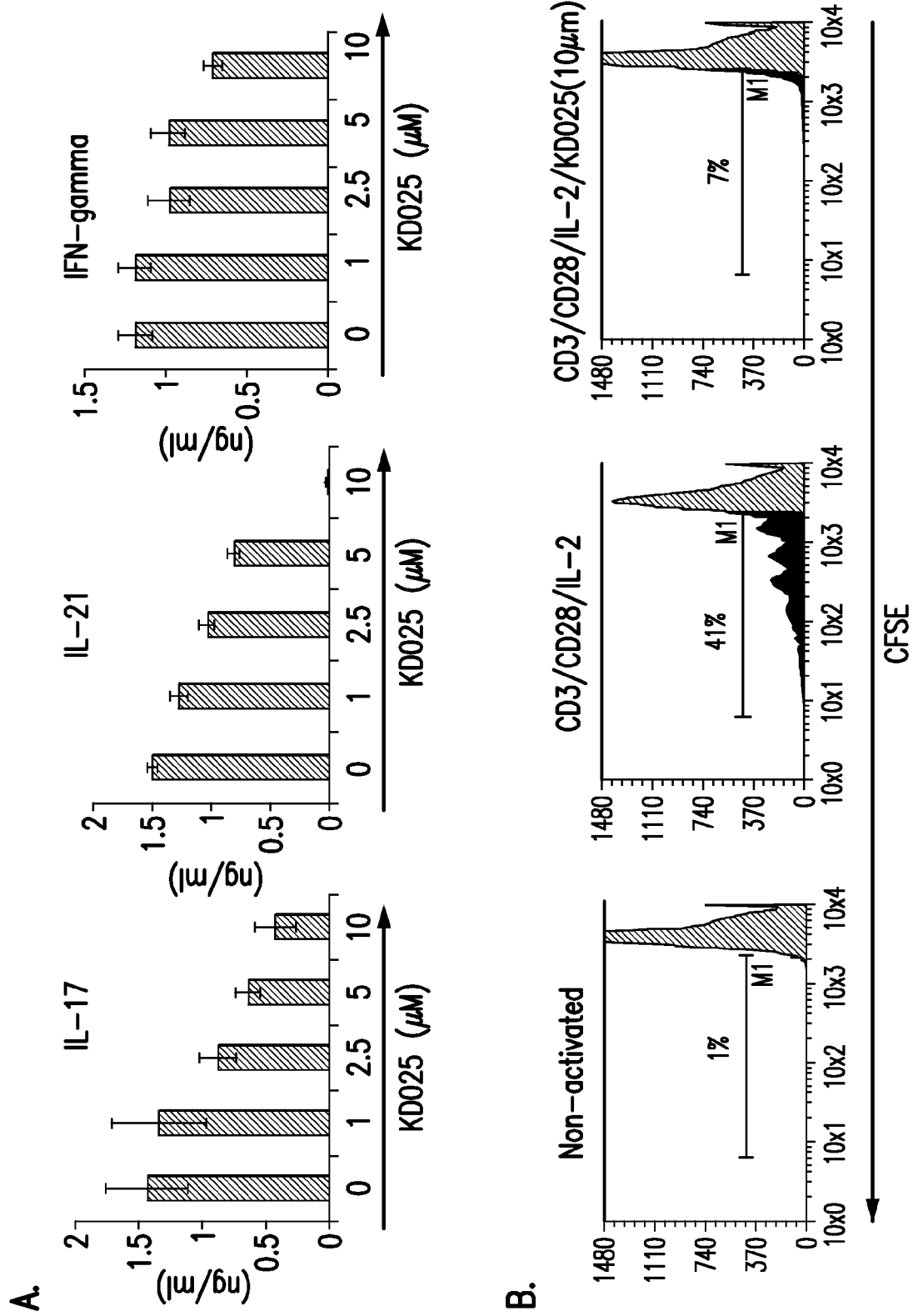
FIG. 8 shows ROCK2 selective inhibitor, KD025 (SLx 2119), inhibits IL-17/IL-21 secretion (A) and proliferation (B) in human CD4$^+$ T cells in vitro.

ROCK2 Selective Inhibitor, KD025, Inhibits IL-17/IL-21 Secretion and Proliferation in Human CD4$^+$ T Cells In Vitro Activation of resting T cells, resulting in cytokine secretion and proliferation, involves two distinct signals from antigen-presenting cells (APCs), mimicked by co-stimulation of the T cell receptor (TCR)/CD3 complex and the CD28 receptor. Using freshly purified CD4$^+$ human T cells and stimulatory antibodies against CD3 and CD28 to stimulate IL-17 and IL-21 secretion in response to TCR activation, it was found that the treatment with ROCK2 selective inhibitor, KD025, significantly inhibited IL-17 and IL-21 secretion in a dose-dependent manner. Under the same conditions, the inhibition of IFN-γ secretion was less robust and significant only at high dose (10 μM) of the inhibitor (FIG. 8A). Similarly, any inhibition of IL-2 secretion was observed only at the highest concentration (10 μM) of KD025. Consistent with the inhibitory effect on cytokine secretion, the treatment of T cells with KD025 down-regulated their ability to proliferate in response to TCR stimulation in vitro (FIG. 8B).

Example 206

ROCK2 siRNA, but not ROCK1 siRNA Inhibits, IL-17 and IL-21 Secretion

Figure 9:
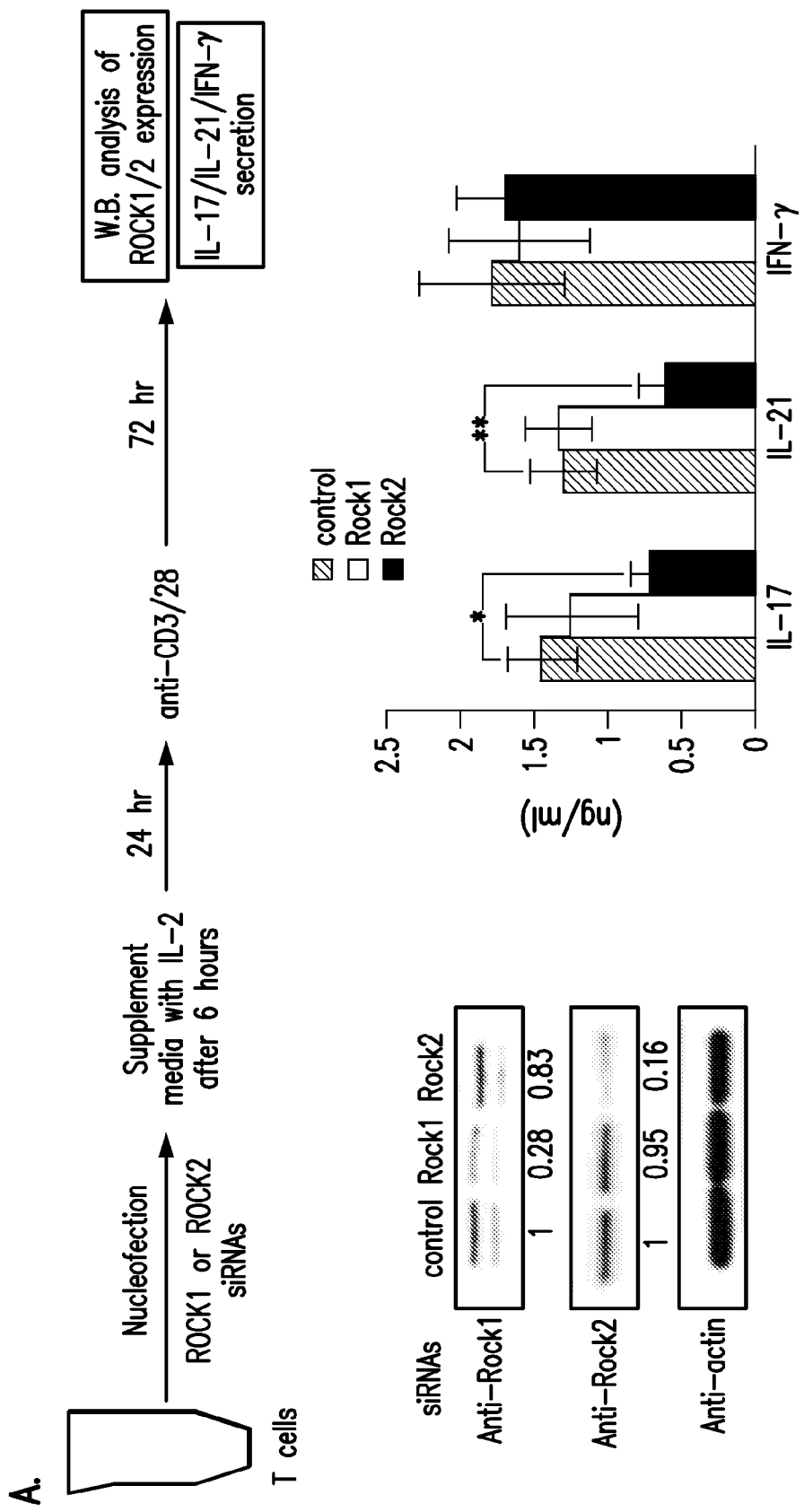
FIG. 9 shows ROCK2 siRNA, but not ROCK1 siRNA, inhibits IL-17 and IL-21 secretion. Panel A, left: Anti-ROCK1 siRNA reduced Rock1 expression by about 75%. Anti-ROCK2 siRNA reduced Rock2 expression by about 85%. Panel A, right: ROCK2 siRNA, but not ROCK1 siRNA, inhibited IL-17 and IL-21 expression. No inhibition of IFN-γ was observed. Panel B: ROCK2 siRNA, but not ROCK1 siRNA, inhibited phosphorylation of Stat3, IRF4, and RORγt. Panel C: ROCK2 siRNA, but not ROCK1 siRNA, inhibited phosphorylation of MLC.
Figure 9:
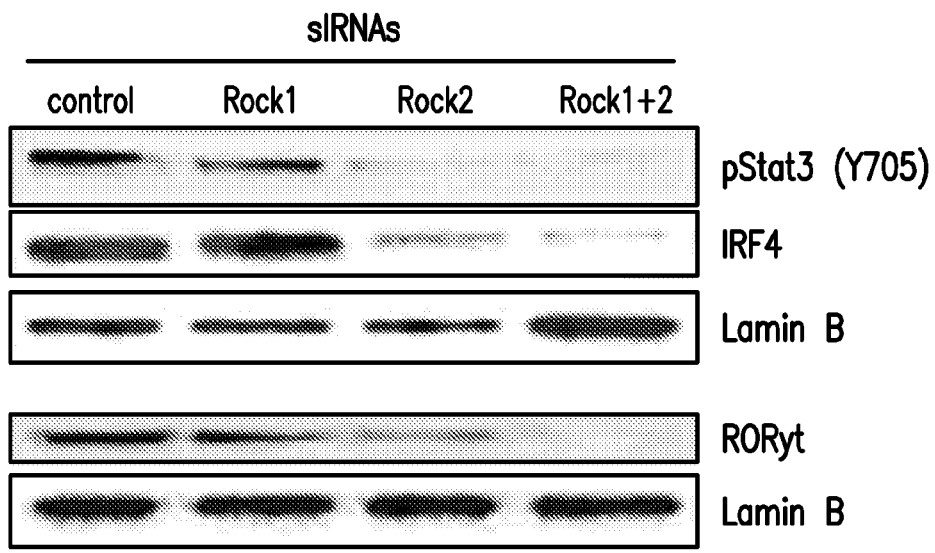
Figure 9:
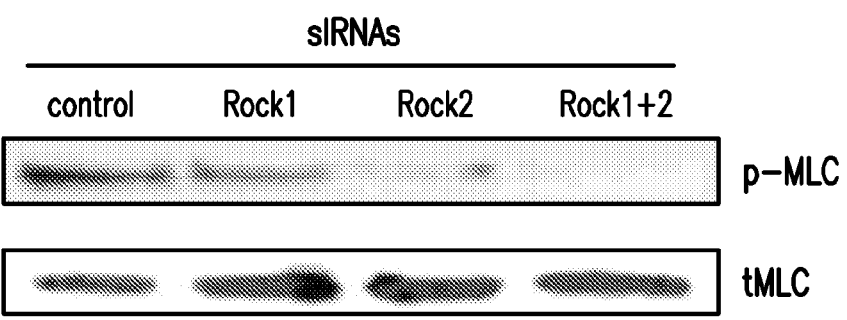
Figure 10:
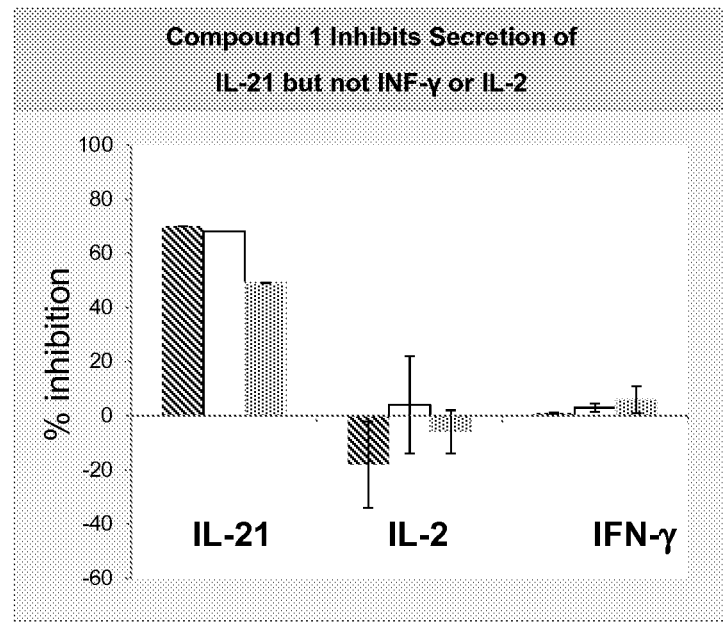
FIG. 10 shows compound 181 of the invention regulates cytokine secretion. Panel A shows the compound of Example 181 inhibits secretion of IL-21, but not INF-γ or IL-2. Panel B shows inhibition of IL-17 secretion is dose-dependent. Legend (A and B): left bars 1: KD025 (a ROCK2 selective inhibitor); center bar: compound of Example 181 dissolved in HCL; right bar; compound of Example 181 dissolved in DMSO.
Figure 10:
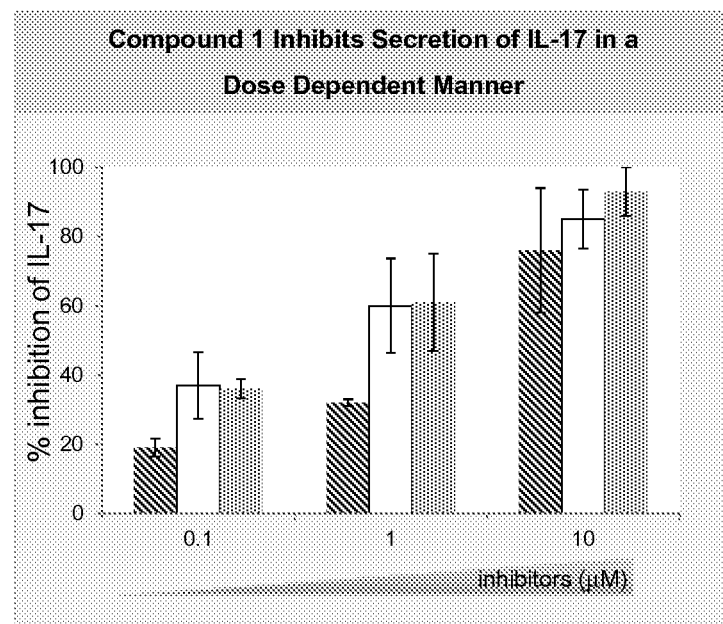

To confirm the role of ROCK2 in regulation of IL-17 and IL-21 secretion in human T cells we specifically silenced ROCK1 and ROCK2 expression by RNA interference. Specific ROCK1 and ROCK2 small interfering RNA (siRNA) reduced the protein expression levels by 72% and 84% respectively. Silencing of ROCK2, but not of ROCK1 significantly reduced the IL-17 and IL-21, with minimal effect on IFN-γ secretion in human T cells (FIG. 9).

Example 207

KD025 Inhibits STAT3 Phosphorylation

Figure 11:
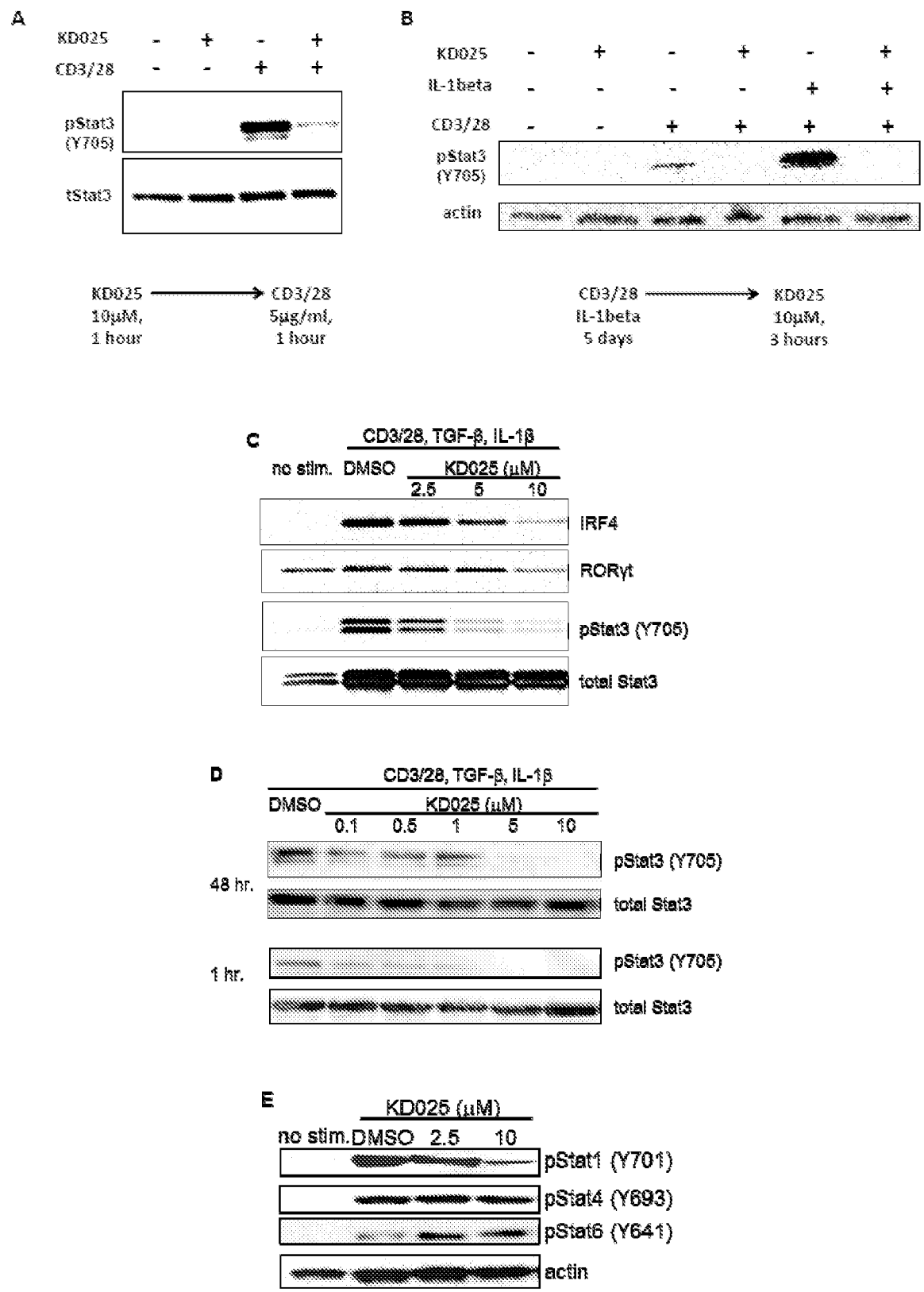
FIG. 11 shows KD025 (SLx 2119) inhibits STAT3 phosphorylation. (A) Pre-treatment of T cells with KD025 followed by stimulation with anti-CD3/CD28 antibodies. (B) Cell culture under Th17-skewing conditions for 5 days followed by treatment with KD025 for 3 hours. (C) CD4$^+$ T cells were activated by anti-CD3/CD28, TGF-β and IL-1β with 0 μM, 2.5 μM, 5 μM, or 10 μM KD025 for 48 hours

STAT3 plays a critical role in Th17 differentiation via regulation of RORγt expression and direct binding to the IL-17 and IL-21 promoters. In addition, recent studies have demonstrated that RhoA-dependent STAT3 stimulation requires ROCK activity and leads to activation of STAT3 phosphorylation on amino acid Y705. Using two different experimental designs, KD025 was demonstrated to significantly down-regulates the phosphorylation of STAT3. In one experiment, T cells were pre-treated with KD025 and then stimulation with anti-CD3/CD28 antibodies. Pre-treatment with KD025 resulted in reduced phosphorylation of STAT3 (FIG. 11A). In a different experiment, cells were cultured under Th17-skewing conditions for 5 days and then treated with the ROCK2 selective inhibitor for 3 hours. STAT3 phosphorylation was reduced by treatment with the ROCK2 inhibitor (FIG. 11B). In a separate experiment, reduced phosphorylation of STAT3, as well as IFR4 and RORγT, was confirmed (FIG. 11C).

Example 208

KD025 Down-Regulates IL-17, IL-21 and IFN-γ Secretion and Reduces the Increased Frequency of IFN-γ and IL-17-Expressing Cells in CD4$^+$ T Cells from RA Patients Rheumatoid arthritis (RA) is a chronic autoimmune inflammatory disease leading to the destruction of joint architecture. The pathogenic events that involved in RA development are not fully understood, although the pivotal role of pro-inflammatory cytokines, such as TNF-α, IL-1β, IFN-β, IL-6 and more recent IL-17 in the induction and maintenance of RA pathogenesis is well documented. Moreover, the frequency of Th17 cells in peripheral blood of RA patients is significantly increased compared to healthy controls and correlates with disease activity score (DAS).

Figure 12:
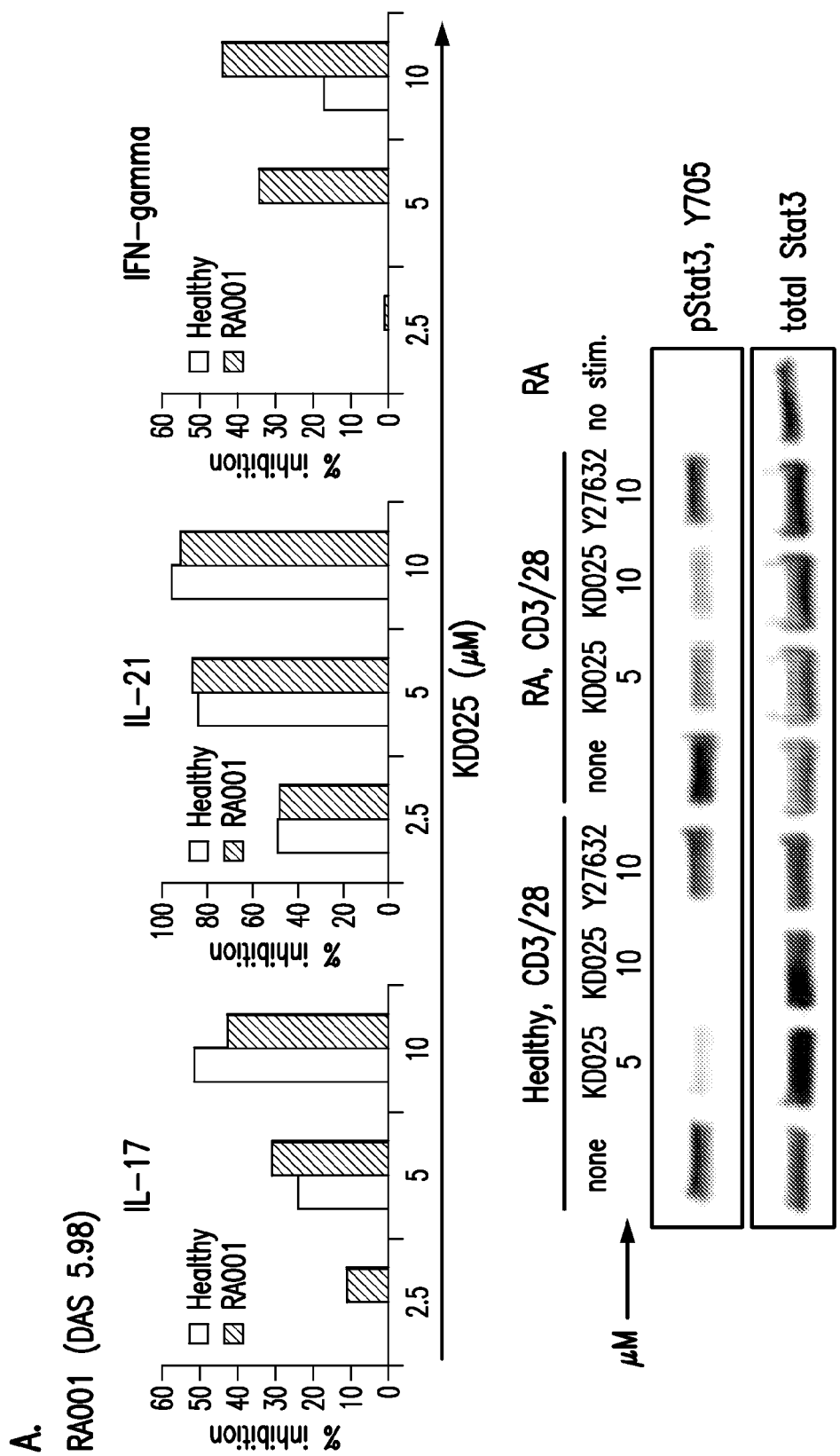
FIG. 12 shows ROCK2 selective inhibitor, KD025, inhibits IL-17, IL-21 and IFN-γ production ex vivo in CD3/CD28 stimulated CD4$^+$ T cells from RA patients. Panel A: In RA patients, KD025 inhibits TCR stimulation of IL-17, and IL-21, as well as IFN-γ. Panel B: Inhibition of IFN-γ production is correlated with disease activity score (DAS). Panel C: Frequency of IL-17 and IFN-γ-producing T cells demonstrated by intracellular staining.
Figure 12:
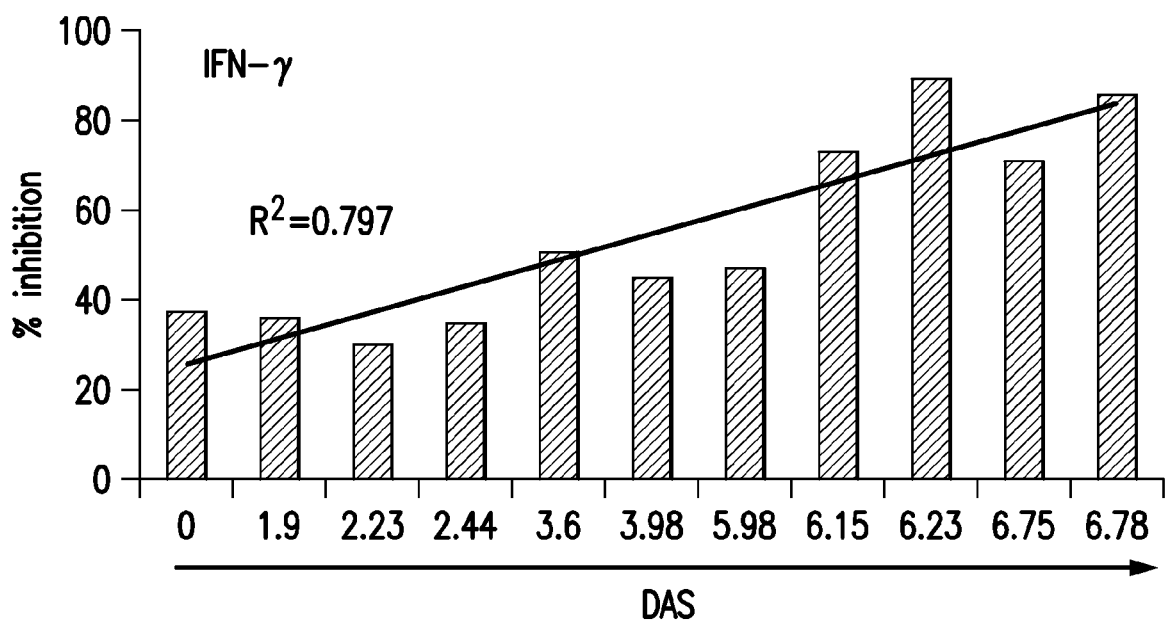
Figure 12:
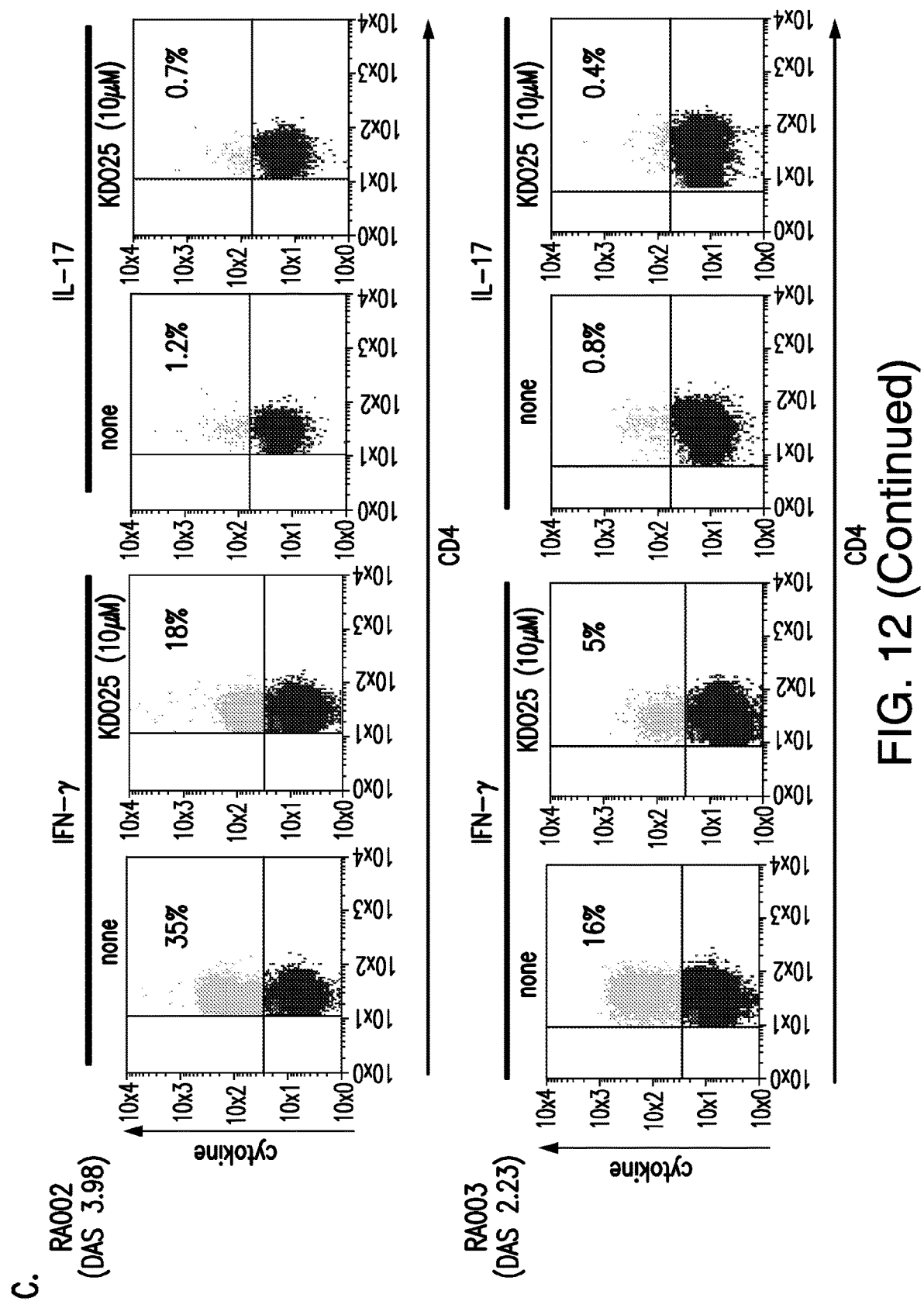
Figure 12:
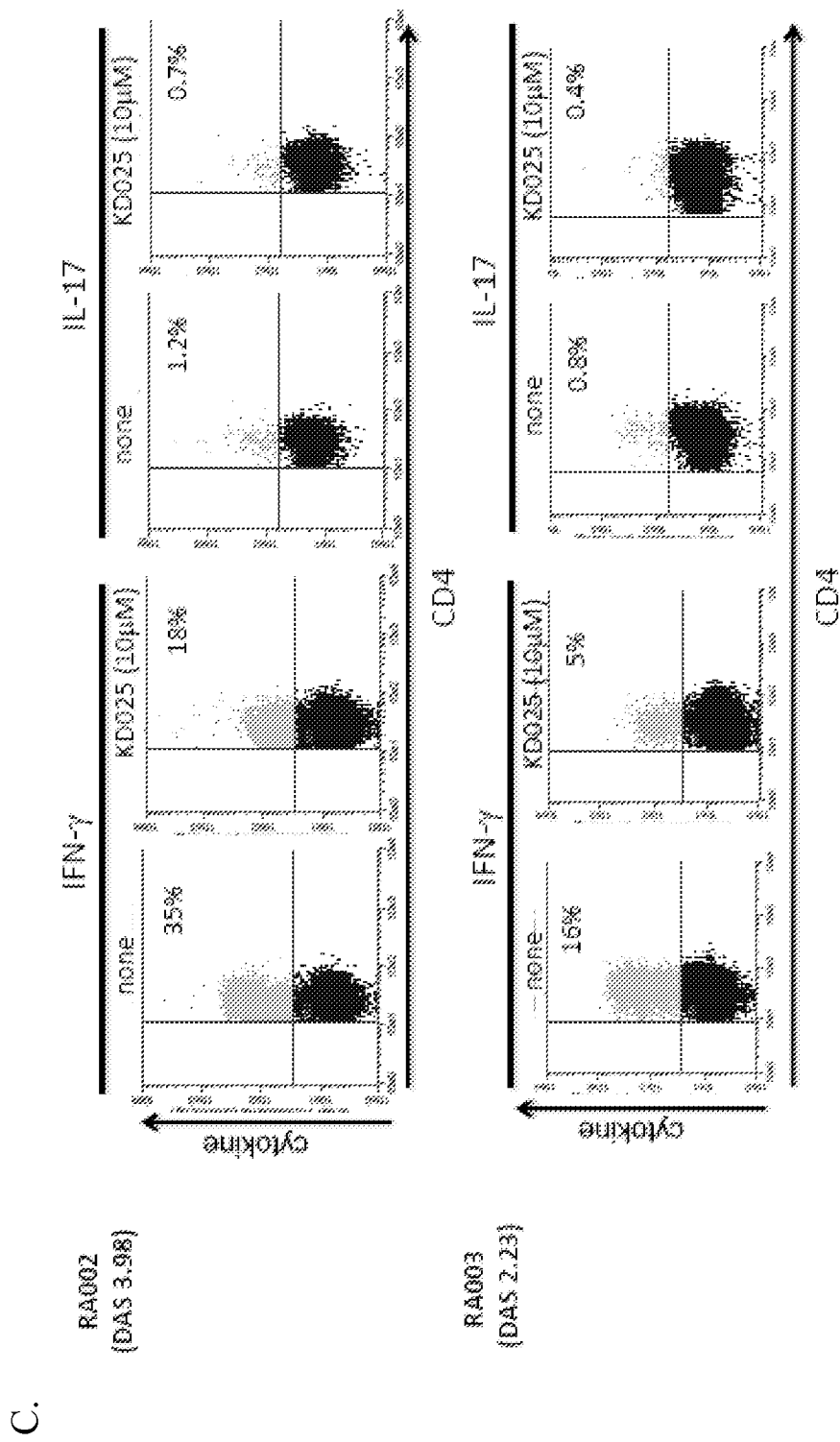

CD4$^+$ T cells were purified from peripheral blood of RA patients at different stages of the disease or from healthy controls and stimulated using anti-CD3/CD28 antibodies in presence of KD025 ex vivo. In CD4$^+$ T cells, the ROCK2 selective inhibitor significantly down-regulated secretion of IL-17, IL-21 and IFN-γ in response to TCR stimulation in a STAT3-dependent manner (FIG. 12A). In contrast to healthy controls, the degree of inhibition of IFN-γ secretion was comparable to inhibition levels of IL-17 and IL-21. Among RA patients, inhibition of IFN-γ production was correlated with disease activity score (DAS). (FIG. 12B). Culture of CD4$^+$ T cells from 2 different RA patients in presence of KD025 significantly reduced the frequencies of both IL-17 and IFN-γ-producing cells as was demonstrated by intracellular staining (FIG. 12C).

Example 209

KD025 Up-Regulates STAT-5 Phosphorylation

Figure 13:
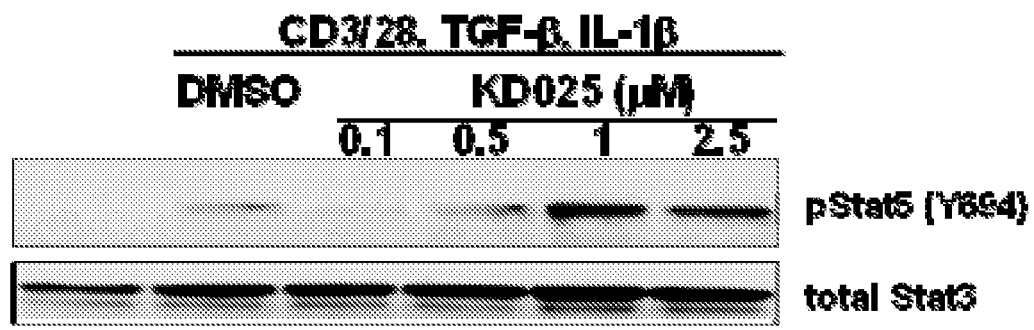
FIG. 13 shows KD025 activates STAT5 phosphorylation. Freshly purified CD4$^+$ T cells were cultured for 2 days with stimulatory antibodies against CD3/CD28 (5 μg/ml), TGF-β (5 ng/ml), IL-1β (50 ng/ml), and the indicated doses of the selective ROCK2 inhibitor KD025.

The presence of cytokines IL-6, TGF-β, IL-113, IL-23 and antigen stimulation of CD4$^+$ T cells leads to induction of IL-17 and IL-21 secretion and development of Th17 effector subset. At the same time, the development and function of Tregs are inhibited. To determine the effect of ROCK2 inhibition on Tregs, freshly purified human CD4$^+$ T cells were activated using stimulatory antibodies against CD3/CD28 (5 µg/ml), TGF-β (5 ng/ml) and IL-113 (50 ng/ml) for 2 days in presence of 0 µM, 0.5 µM, 1 µM, and 2.5 µM concentrations of the selective ROCK2 inhibitor KD025. Western Blot analysis indicates that treatment with KD025 significantly up-regulates phosphorylation of STAT5 on site Y694 in a dose-dependent manner. (FIG. 13). Thus, ROCK2 inhibition down-regulates STAT3 phosphorylation while STAT5 phosphorylation is increased in human CD4$^+$ T cells that are activated under Th17-skewing conditions.

Example 210

KD025 Increases the Proportion of Foxp3$^+$ Cells Among CD4$^+$ T Cells

Figure 14:
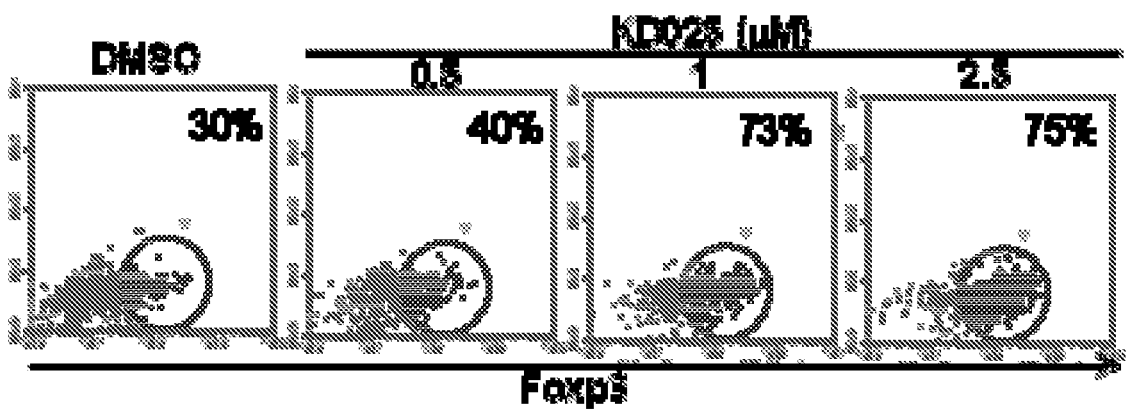
FIG. 14 shows Foxp3 expression in human CD4$^+$ T cells treated with the indicated doses of the selective ROCK2 inhibitor KD025.

Foxp3 is a lineage-specific transcription factor for Tregs and is crucial to the development and inhibitory function of these cells. STAT5 signaling positively regulates the induction and stabilization of Foxp3 expression in T cells in vitro and in vivo. Treatment of human CD4$^+$ T cells with selective ROCK2 inhibitor KD025 significantly increased the percentage of Foxp3$^+$ cells after 5 days of Th17 skewing activation in vitro. (FIG. 14).

Example 211

Figure 15:
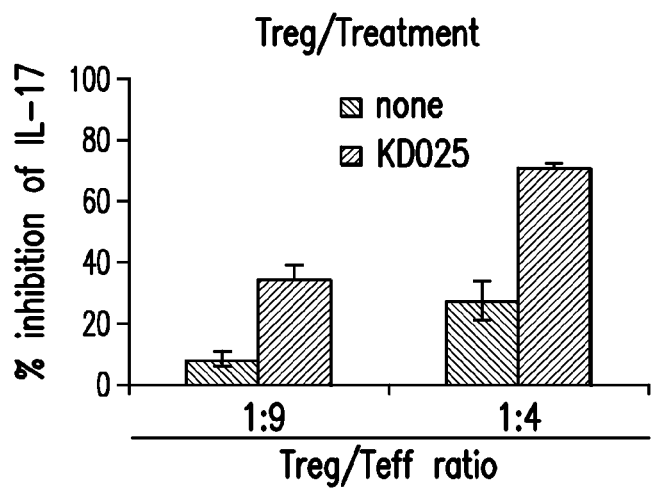
FIG. 15 shows the effect of KD025-mediated ROCK2 inhibition in Tregs on IL-17 secretion by CD4$^+$CD25$^-$ T cells.

KD025 Up-Regulates Treg Inhibition of IL-17 Secretion in CD4$^+$CD25$^-$ T Cells Freshly purified CD4$^+$CD25$^+$ human Tregs were treated with KD025 for 3 hours, washed, mixed with CD4$^+$CD25$^-$ effector T cells at ratio 1:4 and 1:9 (Treg:Teff) and activated by using stimulatory antibodies against CD3 and CD28 for 2 days. KD025-mediated ROCK2 inhibition significantly increased the ability of Tregs to suppress IL-17 secretion in CD4$^+$CD25$^-$ effector T cells. (FIG. 15).

Example 212

Figure 16:
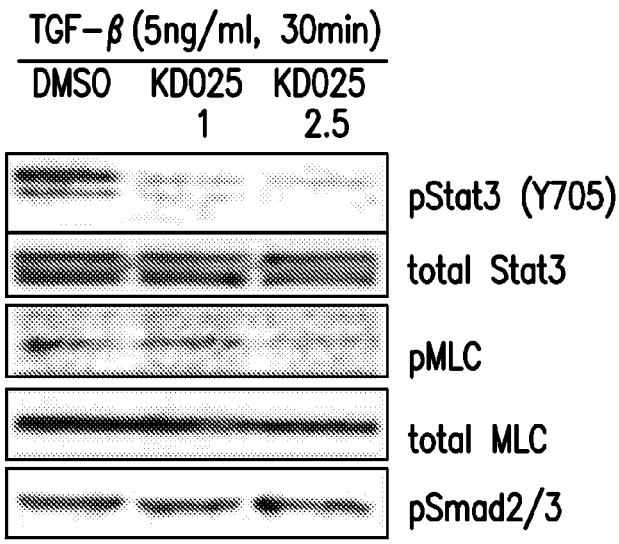
FIG. 16 shows the effect of KD025-mediated ROCK2 inhibition on TGF-3-induced phosphorylation of STAT3, MLC, and SMAD2/3 in Tregs.

KD025 Inhibits TGF-β-Induced STAT3 and MLC Phosphorylation in SMAD2/3-Independent Manner Selective ROCK2 inhibitor KD025 down-regulates TGF-β-induced STAT3 and MLC phosphorylation in a dose-dependent manner, but phosphorylation of SMAD2/3 remains intact. (FIG. 16). TGF-3 is involved in development and function of both Th17 and Treg subsets of T cells. However, when Tregs are regulated in Smad2/3-dependent signaling mechanism, TGF-β regulates Th17 cells in Smad2/3 independent manner that is considered as non-canonical TGF-β-induced signaling. Furthermore, it was demonstrated that ROCK proteins are involved in Smad-independent TGF-β signaling in cancer cells.

Example 213

Figure 17:
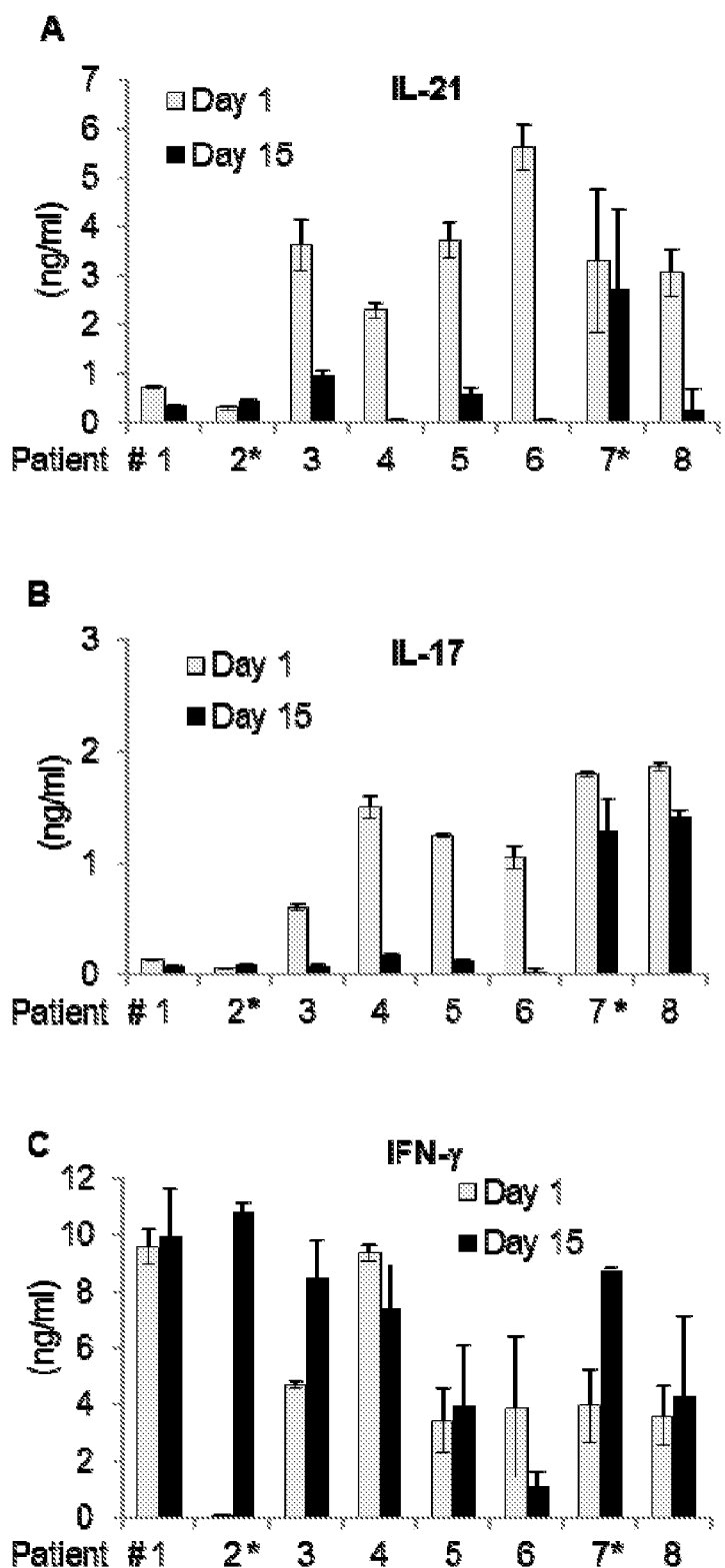
FIG. 17A-C shows the effect of KD025-mediated ROCK2 inhibition on stimulation of (A) IL-17, (B) IL-21, and (C) IFN-γ production in isolated PBMCs. Six patients were treated with 120 mg/day KD025 on days 1 and 8-14, and two patients with placebo. PBMCs were isolated at days 1 and 15 and examined for IL-17 and IL-21 production in response to stimulation by anti-CD3/CD28 antibodies. Patients 2 and 7 received placebo. *=placebo administered to patients 2 and 7. Panels D-F show the effect of increasing doses of KD025 on stimulation of (D) IL-17, (E) IL-21, and (F) IFN-γ production in isolated PBMCs.
Figure 17:
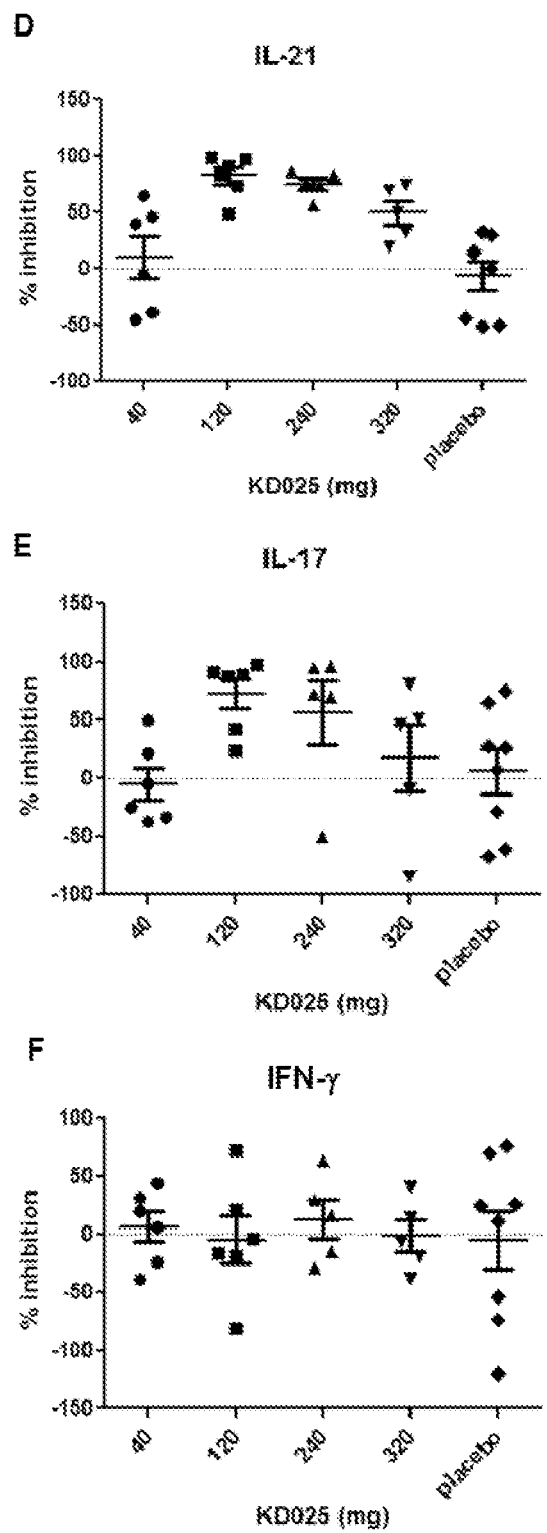

Treatment of Patients with KD025 Inhibits Ex Vivo Stimulation of IL-17 and IL-21 Production in Isolated PBMCs Eight patients were administered 120 mg/day KD025 or placebo on days 1 and 8-14 of the trial. Peripheral blood mononuclear cells (PBMCs) were collected at the start and end of the trial and stimulated by plating on immobilized anti-CD3/CD28 antibodies for 72 hours, and levels of IL-17, IL-21, and IFN-γ were measured. FIG. 17 shows high levels of IL-17 and IL-21 could be induced in PBMCs isolated at day 1 from six of the subjects. Of those six subjects, five received the ROCK2-selective inhibitor KD025, whereas one received placebo. Induction of IL-17 secretion was significantly inhibited in PBMCs isolated from four of five patients treated with KD025 (FIG. 17B), and induction of IL-21 secretion was significantly inhibited in PBMCs from all five patients treated with KD025 (FIG. 17A). No effect on IFN-γ was observed.

Inhibition of cytokine induction was then determined in twenty two patients administered 40 mg/day, 120 mg/day, 240 mg/day, or 320 mg/day KD025. FIG. 17D-F shows the dose-response relationship for IL-21, IL-17, and IFN-γ secretion, respectively.

Example 214

Reversal of Lung Pathology in Murine Model of Chronic GVHD by Selective ROCK2 Inhibitor Chronic GVHD induced by allogeneic HCT after a conditioning regimen of cyclophosphamide and total-body radiation results in pulmonary dysfunction and airway obliteration which leads to bronchiolitis obliterans in patients. KD025 was tested in a previously described murine model of chronic GVHD (Srinivasan M et al. Blood 2012) that involves a wide spectrum of target organs, such lung and liver. Briefly, B10.BR recipients were conditioned with cyclophosphamide (Cy) on days −3 and −2 (120 mg/kg intra-peritoneally). On day −1, recipients received total-body irradiation (TBI) by X-ray (8.5 Gy). Donor bone marrow (BM) was T-cell depleted with anti-Thy 1.2 mAb followed by rabbit complement. On day 0, recipients received $10^7$ BM cells with or without allogeneic splenocytes ($10^6$ cells). Weights of individual mice were recorded twice weekly. Mice (8 per group) were treated intra-peritoneally with KD025 (100 mg/kg) on day 28 (manifestation of decreased lung function and pathology) for 1 month on a daily basis. The analysis of pulmonary function was performed on day 28 (before the treatment) and on day 56. Anesthetized mice were weighed, and lung function was assessed by wholebody plethysmography with the Flexivent system (SCIREQ) and analyzed with Flexivent Version 5.1 software. Survival data were analyzed by life-table methods, and actuarial survival rates are shown. Group comparisons were made by log-rank test. The overall experimental design is provided in the table below:

| Groups | n | TBI Day -1 | Conditioning Treatment Days -2 and -3 | Recipient | Donor Bone Marrow Day 0 | Donor Splenocytes Day 0 |
|---|---|---|---|---|---|---|
| BM | 8 | 850x | Cy | B10.BR | $10^7$ | none |
| BM + Vehicle | 8 | 850x | Cy | B10.BR | $10^7$ | $10^6$ |
| BM + KD025 | 8 | 850x | Cy | B10.BR | $10^7$ | $10^6$ |

Figure 18:
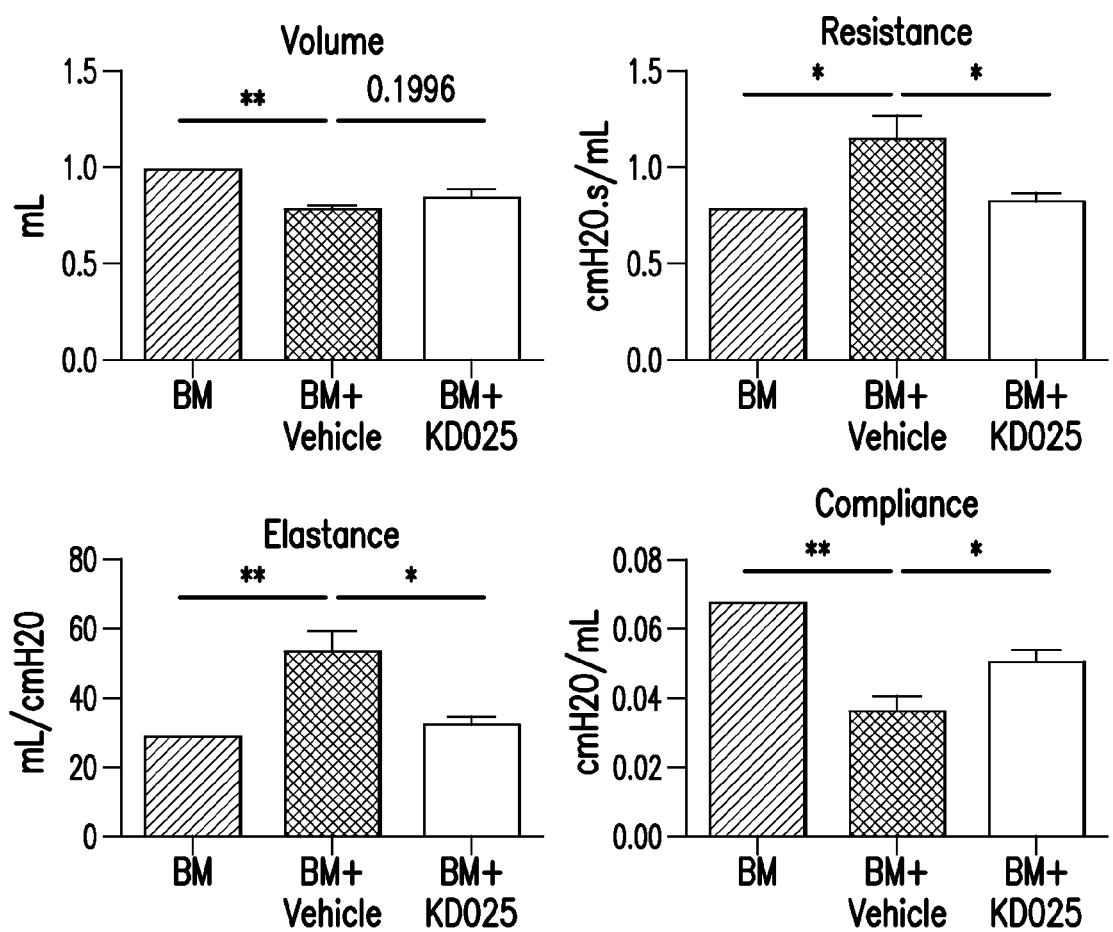
FIG. 18 shows the effect of KD025-mediated ROCK2 inhibition on lung pathology in a mouse model of chronic GVHD. Panel A shows the results of pulmonary function tests of volume, resistance, elastance, and compliance in mice transplanted with bone marrow (BM) cells with or without allogeneic splenocytes ("vehicle"), and treated or untreated with KD025. Panels B and C show that body weight and survival rates between groups of test animals were comparable, thus indicating that KD025 has no effect on body weight and survival rates.
Figure 18:
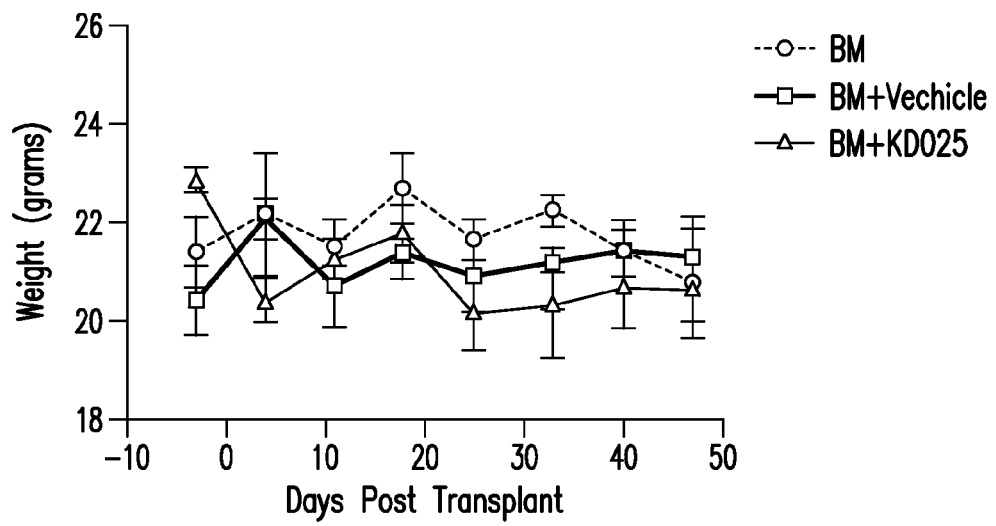
Figure 18:
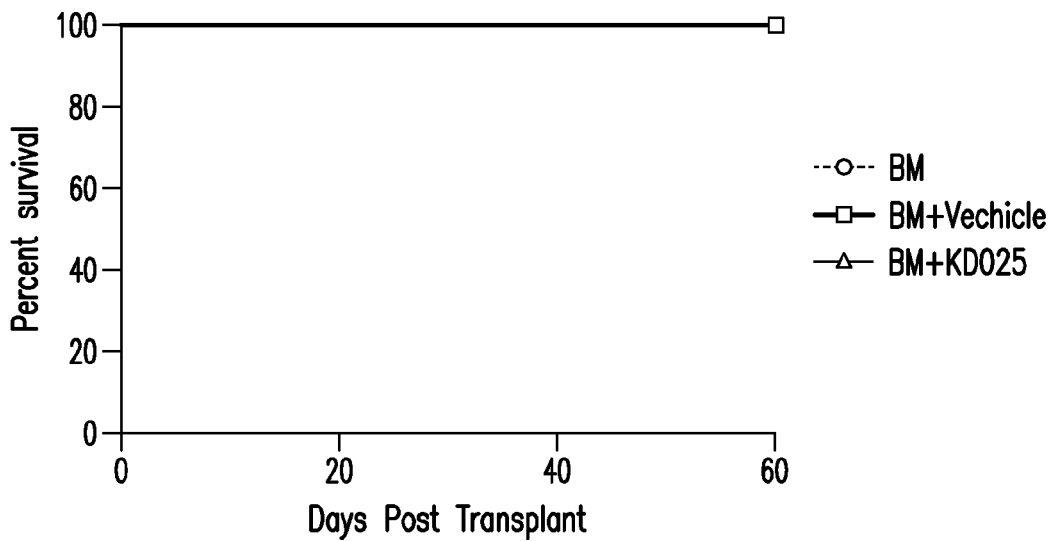
Figure 19:
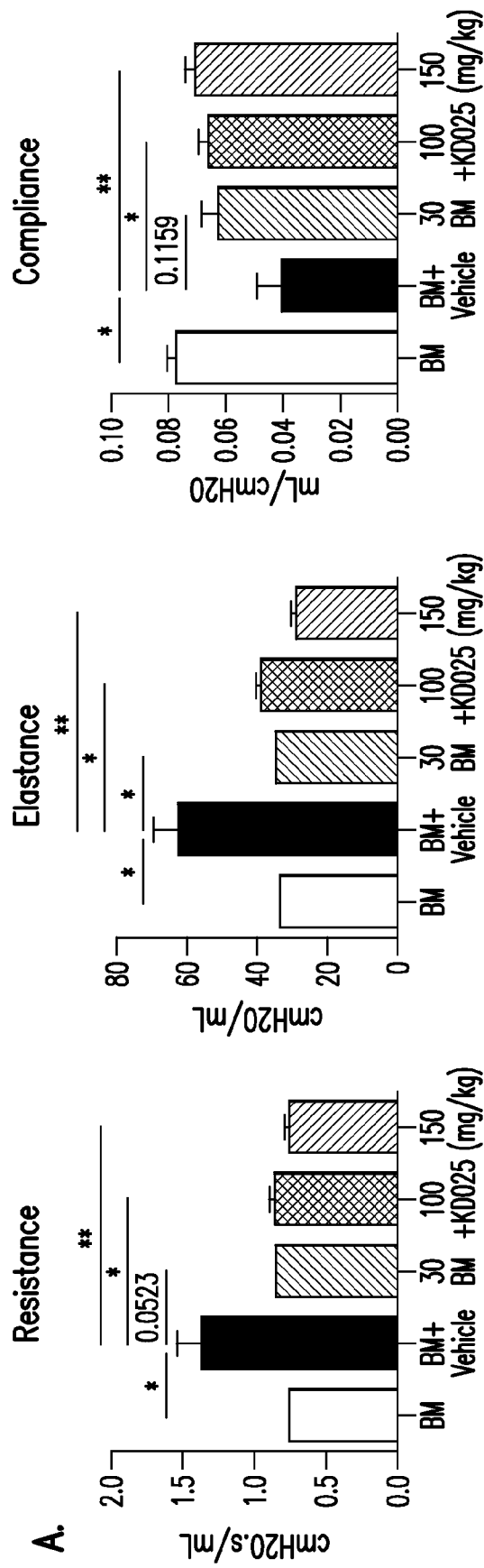
FIG. 19, Panel A, shows KD025 dose dependence of reversal of cGVHD-associated lung pathology. Mice transplanted with bone marrow (BM) cells and allogeneic splenocytes ("vehicle") were treated with 30 mg/kg, 100 mg/kg, or 150 mg/kg of KD025 and evaluated for pulmonary resistance, elastance, and compliance. Panel B shows that body weights between groups of test animals were comparable, thus indicating that KD025 has no effect on body weight.
Figure 19:
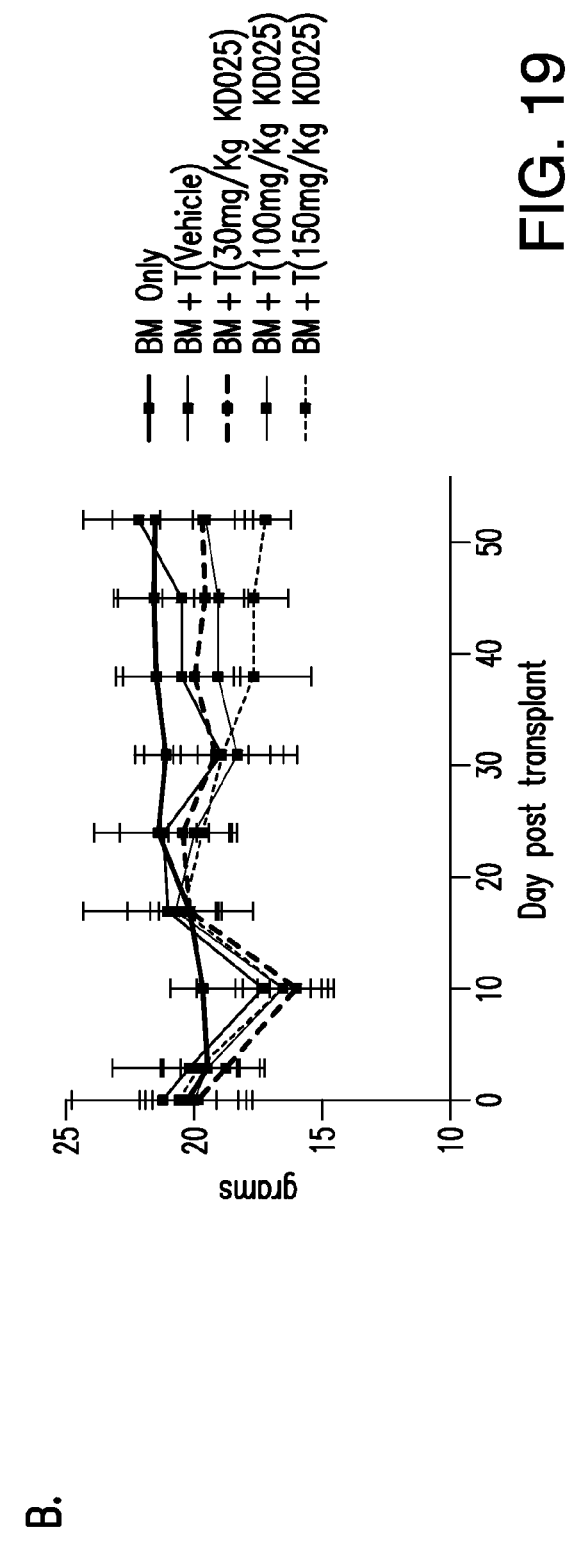

As shown in FIG. 18, Panel A, in mice transplanted with BM cells and allogeneic splenocytes ("vehicle"), pulmonary function tests (PFTs) on day 56 after transplantation showed an increase in airway resistance, increased lung constriction, increases elastance, and decreased compliance. These measures indicate increased stiffness or rigidity of the lungs. Treatment with KD025 significantly improved and normalized pulmonary function, i.e., resulted in decrease in resistance and elastance, and increase in lung compliance compared to vehicle treated group. A decrease in pulmonary function in mice not treated with KD025 was noticed as early as 28 days after transplantation. FIG. 19, Panel A, shows that the effect of KD025 on cGVHD is dose dependent. Panels B and C of FIG. 18 and Panel B of FIG. 19 show that body weight and survival rates between groups of test animals were comparable, thus indicating that KD025 has no effect on body weight and survival rates. Survival data were analyzed by life-table methods, and actuarial survival rates are shown. Group comparisons were made by log-rank test.

cGVHD is characterized by fibrosis and increased collagen deposition around bronchioles and blood vessels in lungs. In addition, elevated antibody deposition is also observed in lungs. Organs from mice treated with donor bone marrow (BM) cells, with or without allogeneic splenocytes ("vehicle"), and with or without 150 mg/kg of KD025 were harvested, embedded in optimal cutting temperature compound, snap-frozen in liquid nitrogen, and stored at −80° C. Lungs were inflated by infusion of 1 mL of optimal cutting temperature compound:PBS (3:1) intratracheally prior to harvest. Six-micrometer cryosections were fixed for 5 minutes in acetone and stained with mMasson's trichrome staining kit (Sigma-Aldrich) for detection of collagen deposition. Collagen deposition was quantified on trichrome-stained sections as a ratio of area of blue staining to area of total staining by use of the Adobe mPhotoshop CS3 analysis tool (Adobe Systems). For measuring Ig deposition, acetone-fixed 6-m lung cryosections were blocked with horse serum and streptavidin-biotin blocking kit (Vector) and stained with fluorescein isothiocyanate (FITC)-labeled anti-mouse-Ig (BD Pharmingen). Antibody deposition was quantified by area of Ig staining per 100-µm section.

Figure 20:
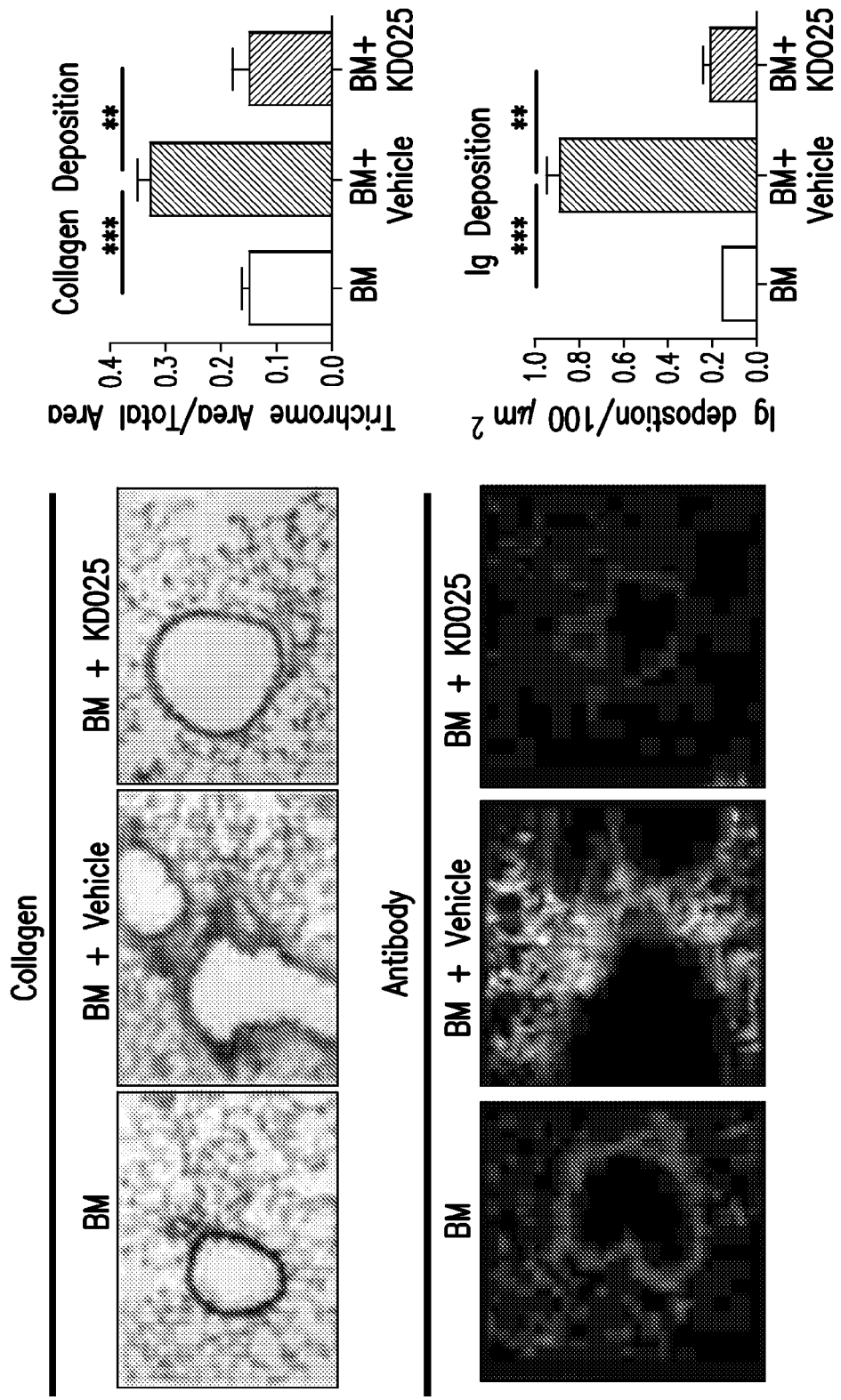
FIG. 20 shows collagen deposition and antibody deposition in mice resulting from transplantation with donor bone marrow (BM) cells, induction with allogeneic splenocytes ("vehicle"), and KD025-mediated ROCK2 inhibition.

FIG. 20 shows collagen deposition and antibody deposition in lungs of test mice following transplantation with donor bone marrow (BM) cells, with or without induction by allogeneic splenocytes ("vehicle"), and with or without KD025-mediated ROCK2 inhibition. Tissue samples from KD025 treated mice were essentially indistinguishable from samples from uninduced mice that did not receive allogeneic splenocytes.

Example 215

Reduction of Number of Germinal Centers and Frequency of T Follicular Helper (Tfh) Cells in Spleen of Murine Model of Chronic GVHD by Selective ROCK2 Inhibitor Germinal centers (GCs) in the spleen are sites of interaction between proliferating antigen-specific B cells and T follicular helper (Tfh) cells, where mature B cells rapidly proliferate, differentiate, and undergo somatic hypermutation and selection that results in the production of class-switched antibody. Tfh cells are critical for the formation and function of B cell responses. Tfh cells are commonly identified by high surface expression of the chemokine receptor CXCR5, and the inhibitory receptor programmed cell death-1 (PD-1). CXCR5 expression allows Tfh cells to migrate from the T cell zone to the B cell follicle where they localize to the GC, and mediate B cell help via cell-cell contact and secretion of the cytokines, such IL-21 and IL-4. Robust GC reactions are present at the time of cGVHD disease initiation and blockade of GC formation has been observed to suppress cGVHD.

Mice were administered 150 mg/kg of KD025 and otherwise treated as described above. Fixed 6-µm spleen cryosections of mice were stained with rhodamine-conjugated peanut agglutinin (PNA; Vector Laboratories), and the size of the PNA-positive sections was measured and defined as germinal centers. For flow cytometric analysis of Tfh cells and GC B cells, single-cell suspensions from spleens were obtained and labeled with anti-CD4, anti-CXCR5, and anti-PD1 antibodies (eBioscience). Cells were analyzed on a BD LSRFortessa cell analyzer.

Figure 21:
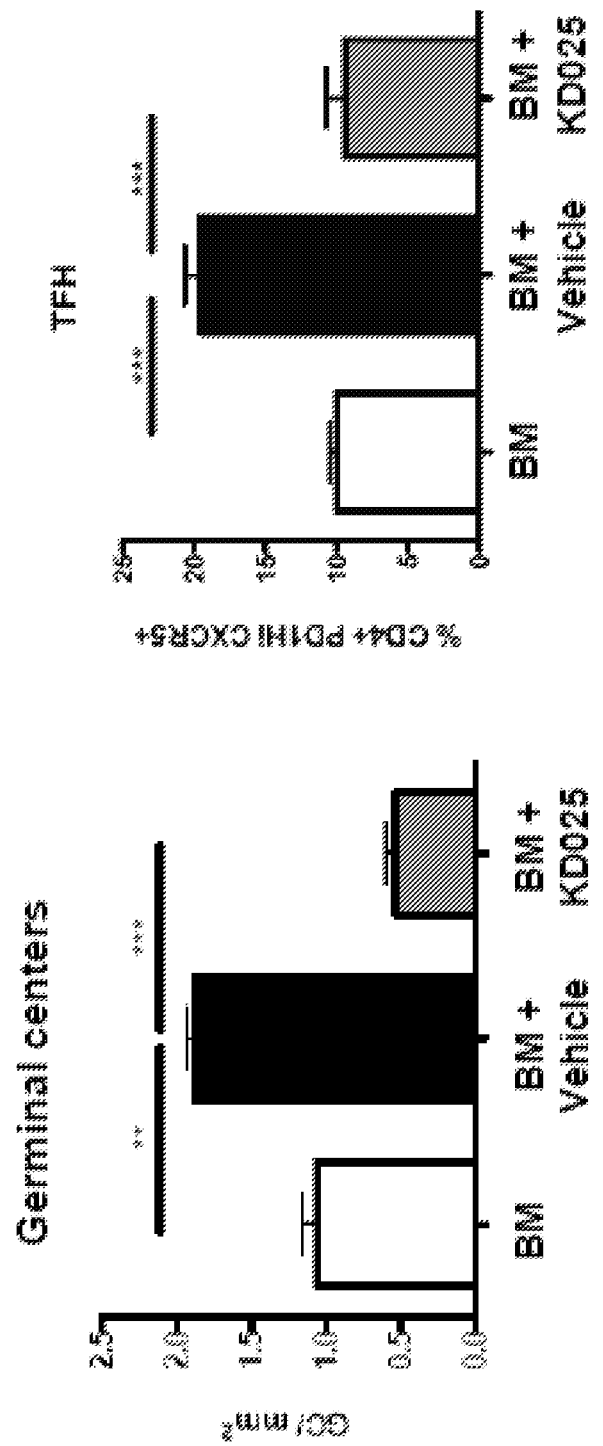
FIG. 21 shows germinal center (GC) formation and T helper cell (Tfh) activity in mice induced to chronic GVHD and reduction of GC activity by KD025-mediated ROCK2 inhibition.

Spleens of mice transplanted with BM cells and allogeneic splenocytes demonstrated increased numbers of GCs, as well as increased numbers of CD4$^+$PD1$^{Hi}$CXCR5 Tfh cells. Both effects were reversed by administration of KD025 (FIG. 21).

Example 216

KD025 Concurrently Regulates STAT3/STAT5 Phosphorylation and Down-Regulates Protein Levels of RORγt, IRF4 and Bcl6 in a Murine Model of cGVHD Mice were treated as described above, except that twelve animals per group were tested. Blood was collected on day 56 before or after the last dose of KD025 by cardiac puncture, and plasma was prepared and stored at −80° C. (n=3/group). Spleens were also collected for analysis on day 56. Pulmonary function tests were performed on day 98 (42 days post KD025 treatment). Pulmonary function tests and analysis of body weight were performed as described above.

Single cell suspensions were prepared from the isolated spleens. Cells were lysed in RIPA buffer and analyzed for protein content. Sample buffer was then added, and, after boiling, the samples, containing equal amounts of proteins, were separated by SDS-PAGE gel electrophoresis and transferred to a nitrocellulose membrane. Membranes were blocked and probed with specific antibodies overnight. Actin was used as a loading control. Anti-pSTAT3 pSTAT5 and Bcl6 antibodies were purchased from Cell Signaling Technologies (Beverly, Mass.). Anti-IRF4 (sc-48338) and anti-RORγt (14-6988) were obtained from Santa Cruz Biotechnology Inc. and eBioscience respectively. Immunoreactive protein bands were visualized using an HRP-conjugated secondary antibodies and an enhanced ECL system.

Figure 22:
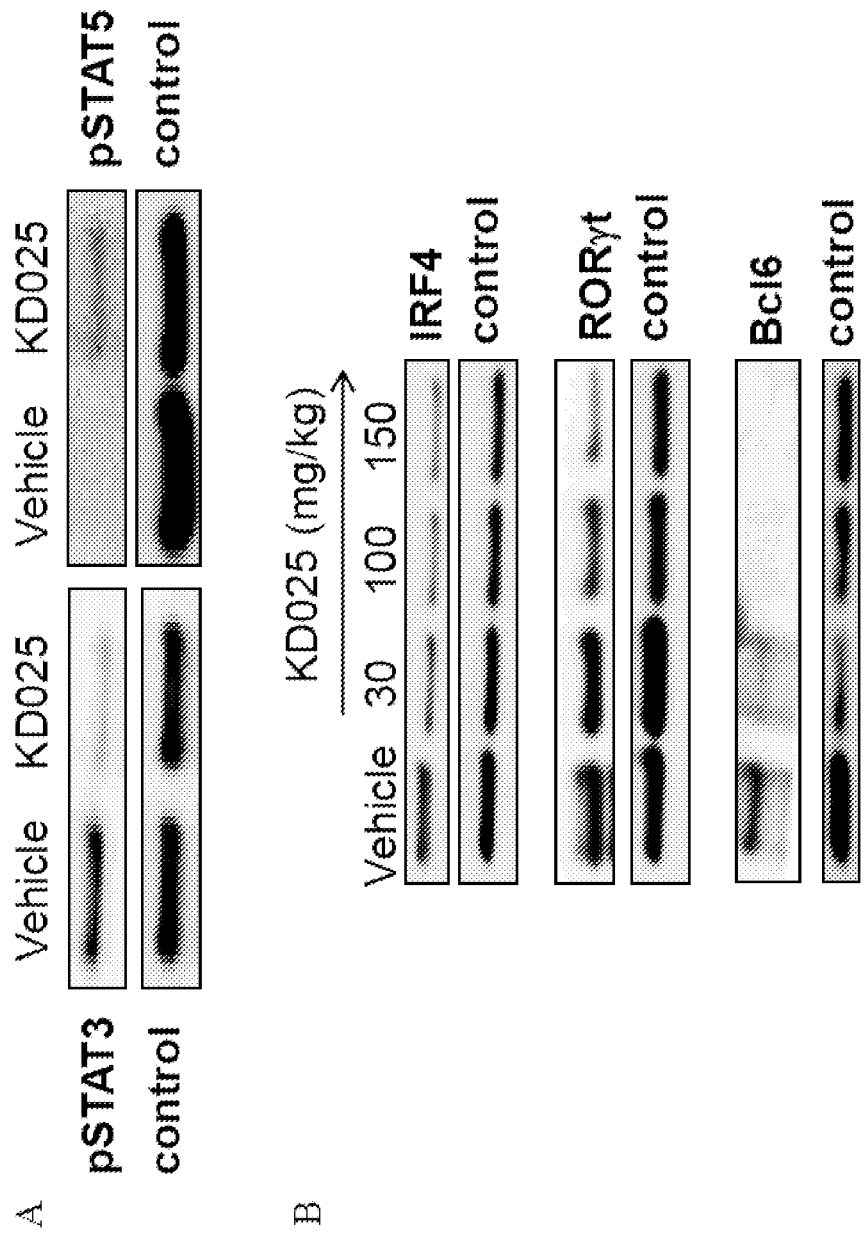
FIG. 22 shows that treatment with KD025 from days 28-56 down-regulated STAT3 phosphorylation and up-regulated STAT5 phosphorylation. This effect was followed by dose-dependent reduction in protein levels of RORγt, IRF4 and Bcl6 transcription factors in spleens.
Figure 23:
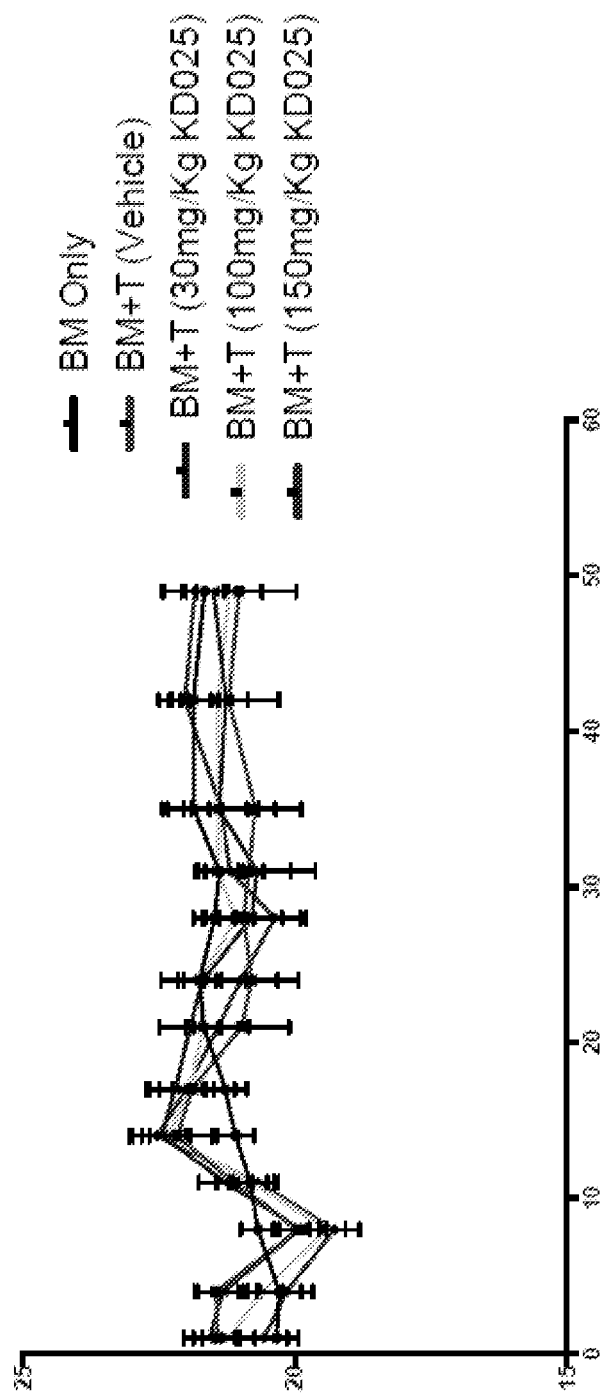
FIG. 23 shows that body weights between groups of test animals were comparable, thus indicating that KD025 has no effect on body weight.
Figure 24:
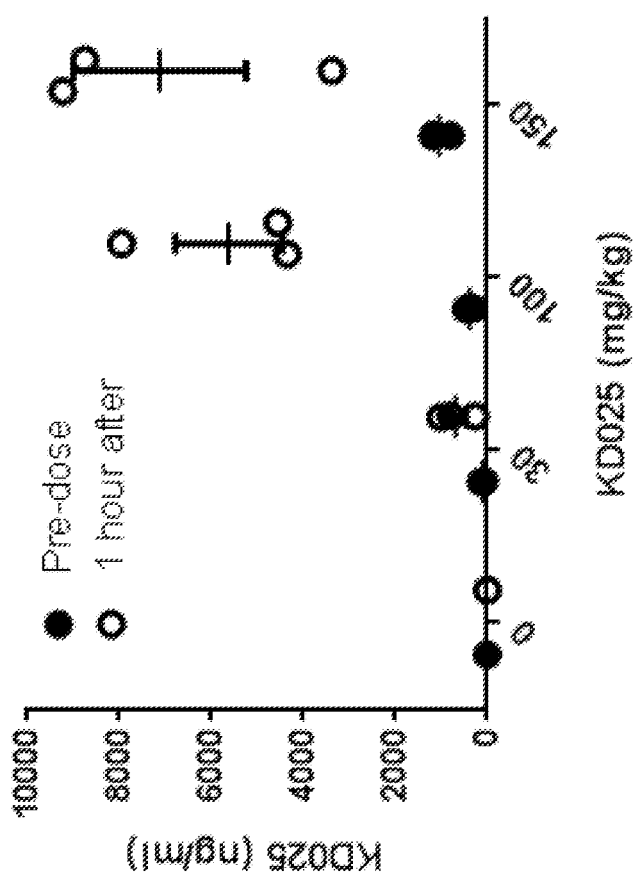
FIG. 24 shows a pharmacokinetic analysis of KD025 in murine chronic GVHD, demonstrating that KD025 is detectable in the blood of treated mice and in a dose depended fashion.

Treatment of mice with the selective ROCK2 inhibitor KD025 from days 28-56 after transplantation lead to a significant reduction in STAT3 phosphorylation and concurrent increase in STAT5 phosphorylation in spleens (FIG. 22, Panel A). In addition, targeted ROCK2 inhibition resulted in a dose-dependent decrease in protein levels of transcription factors such as RORγt, IRF4 and Bcl6 in spleenocytes (FIG. 22, Panel B). Body weight curves were comparable between groups (FIG. 23). Plasma KD025 concentrations values were measurable and generally dose dependent (day 56 1-hr pre-dose), and increased with increasing doses and were generally at levels consistent with previous experiments (day 56, 1-hr post-dose) (FIG. 24).

Figure 25:
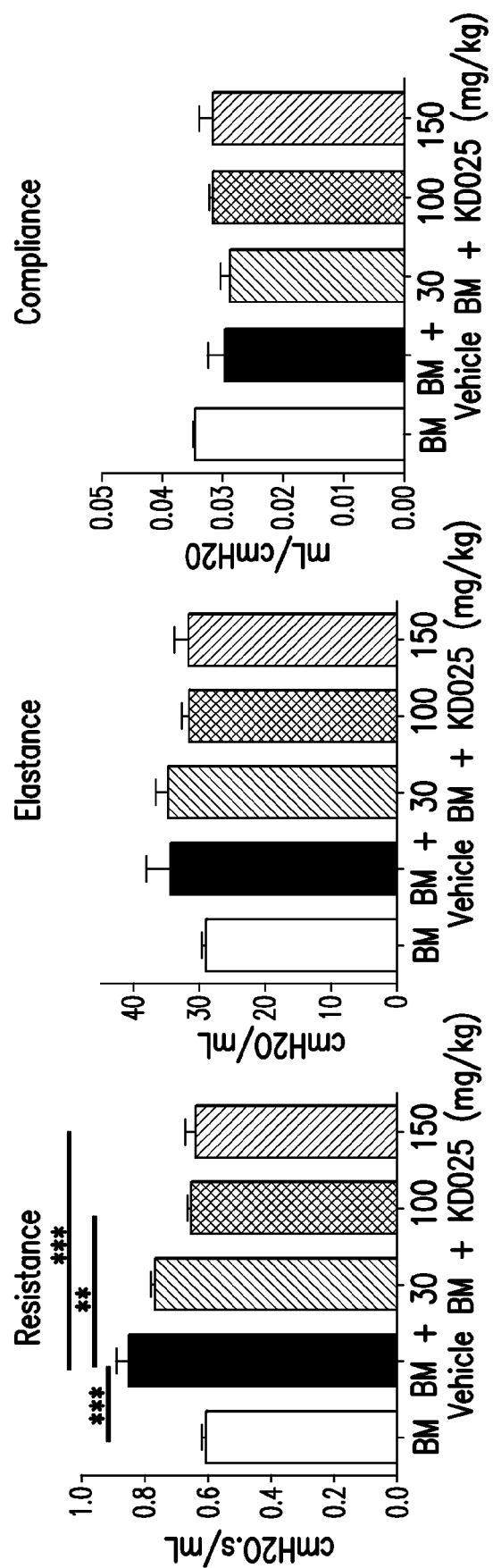
FIG. 25 shows the effect of KD025-mediated ROCK2 inhibition on lung pathology in a mouse model of chronic GVHD. Partial improvement in the respiratory function was detectable 42 days after the last administration of KD025 in mice with cGVHD.

The pulmonary function tests performed on day 98 revealed that KD025 treatment leads to long-lasting improvement of respiratory function and dose-dependent decrease in lung resistance was observed 42 days after the last administration of KD025 (FIG. 25).

Example 217

Figure 26:
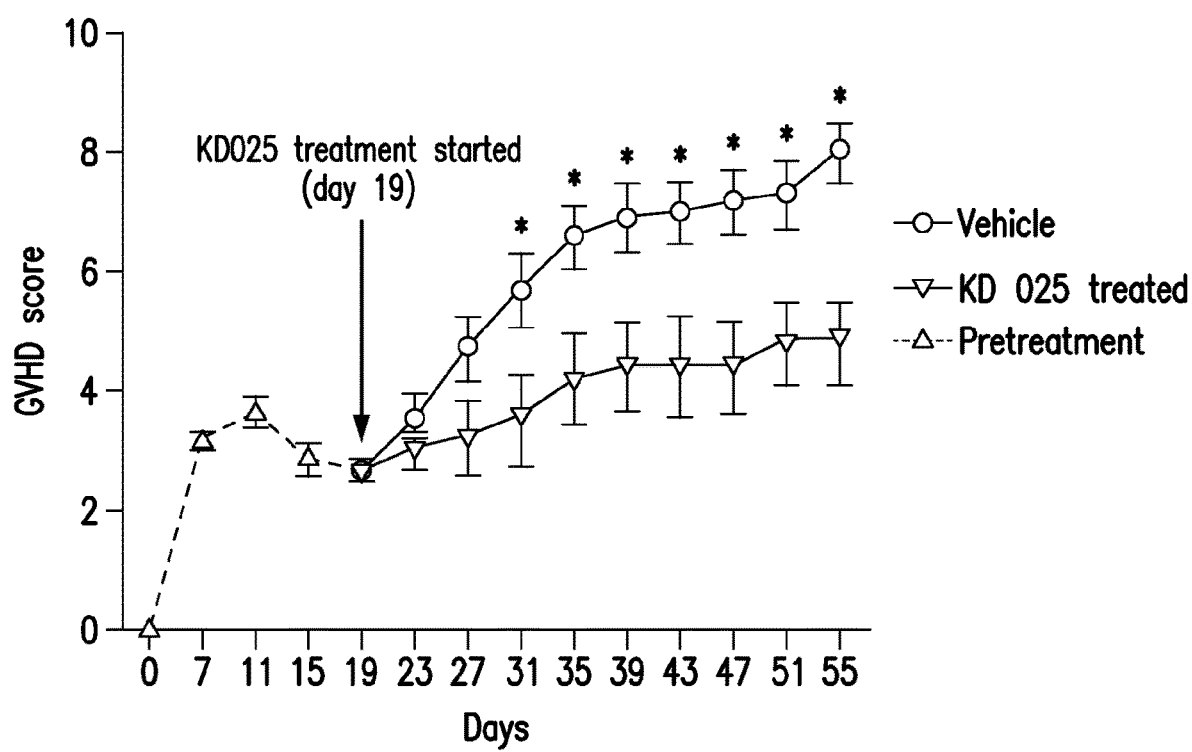
FIG. 26 shows that KD025 significantly decreases the GVHD score in a mouse model for sclerodermatous cGVHD.
Figure 27:
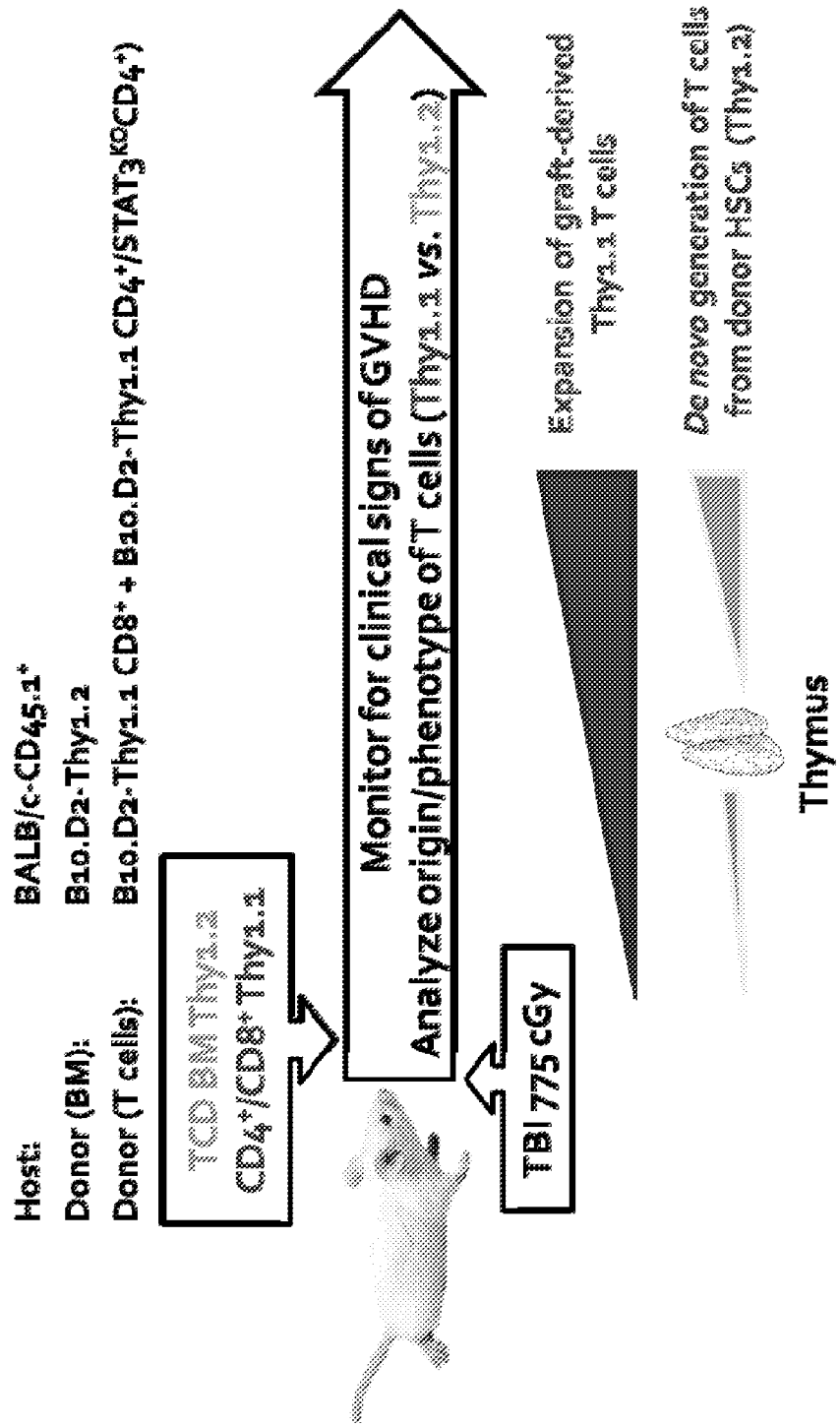
FIG. 27 shows an illustration of a sclerodermatous cGVHD mouse model.
Figure 28:
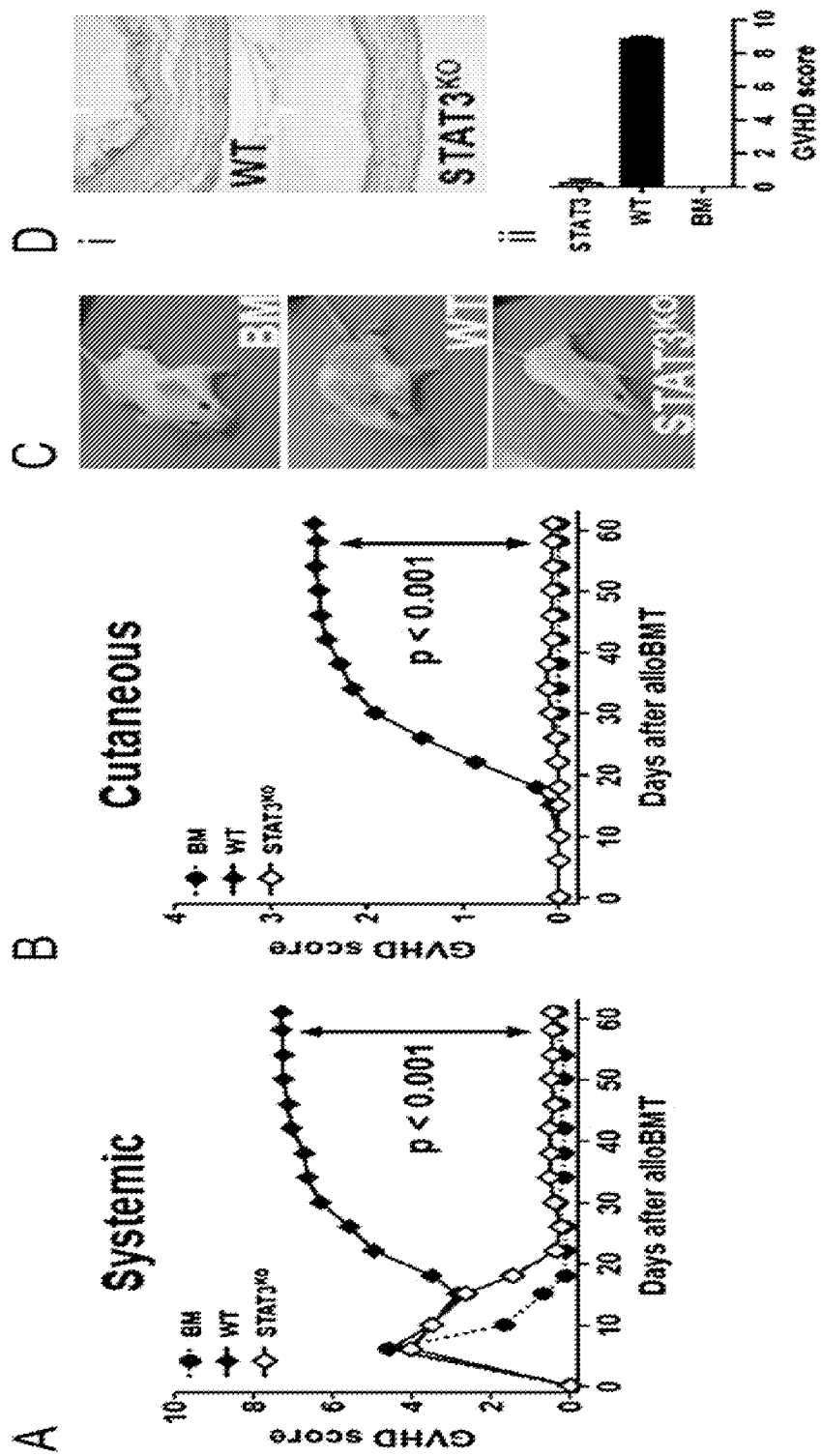
FIG. 28 shows data indicating role of CD4+ T cells expressing STAT3 in manifestation of scleroderma.
Figure 29:
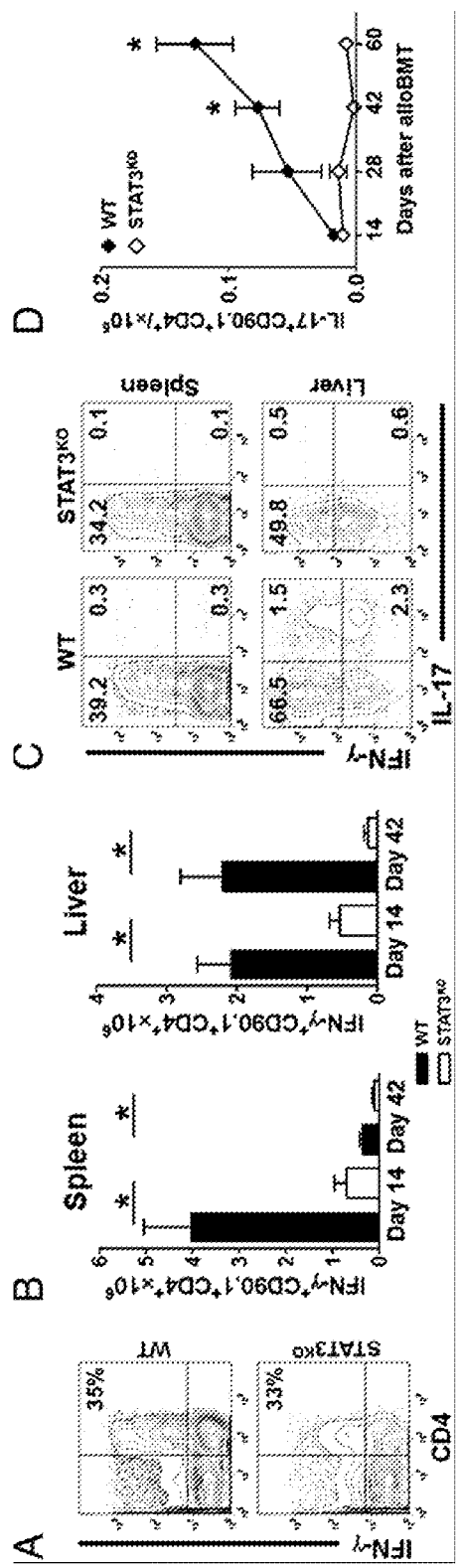
FIG. 29 shows reduced Th1 and Th17 cell numbers in a mouse model of sclerodermatous chronic GVHD receiving CD4+ STAT3 KO T cells.
Figure 30:
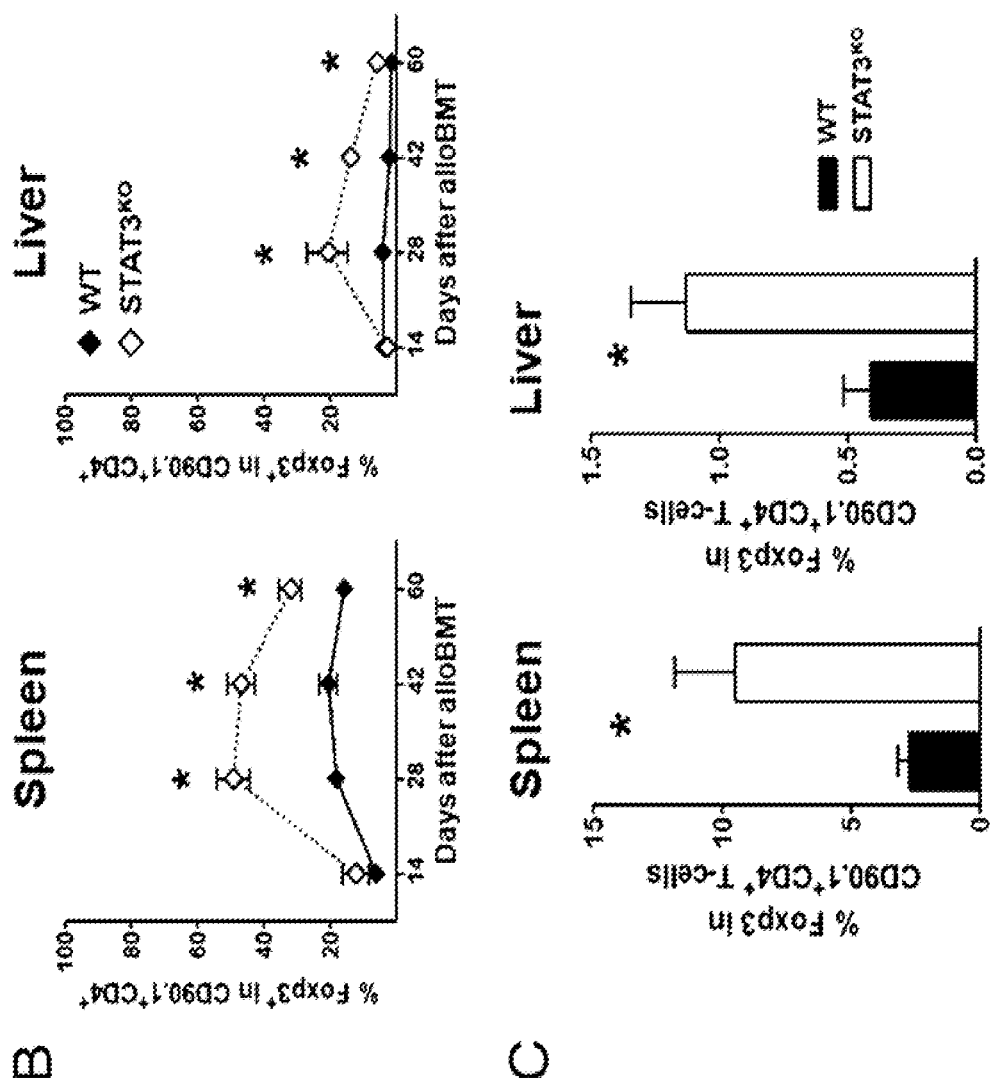
FIG. 30 shows increased amount of Tregs in a mouse model of sclerodermatous chronic GVHD receiving CD4+ STAT3 KO T cells.
Figure 31:
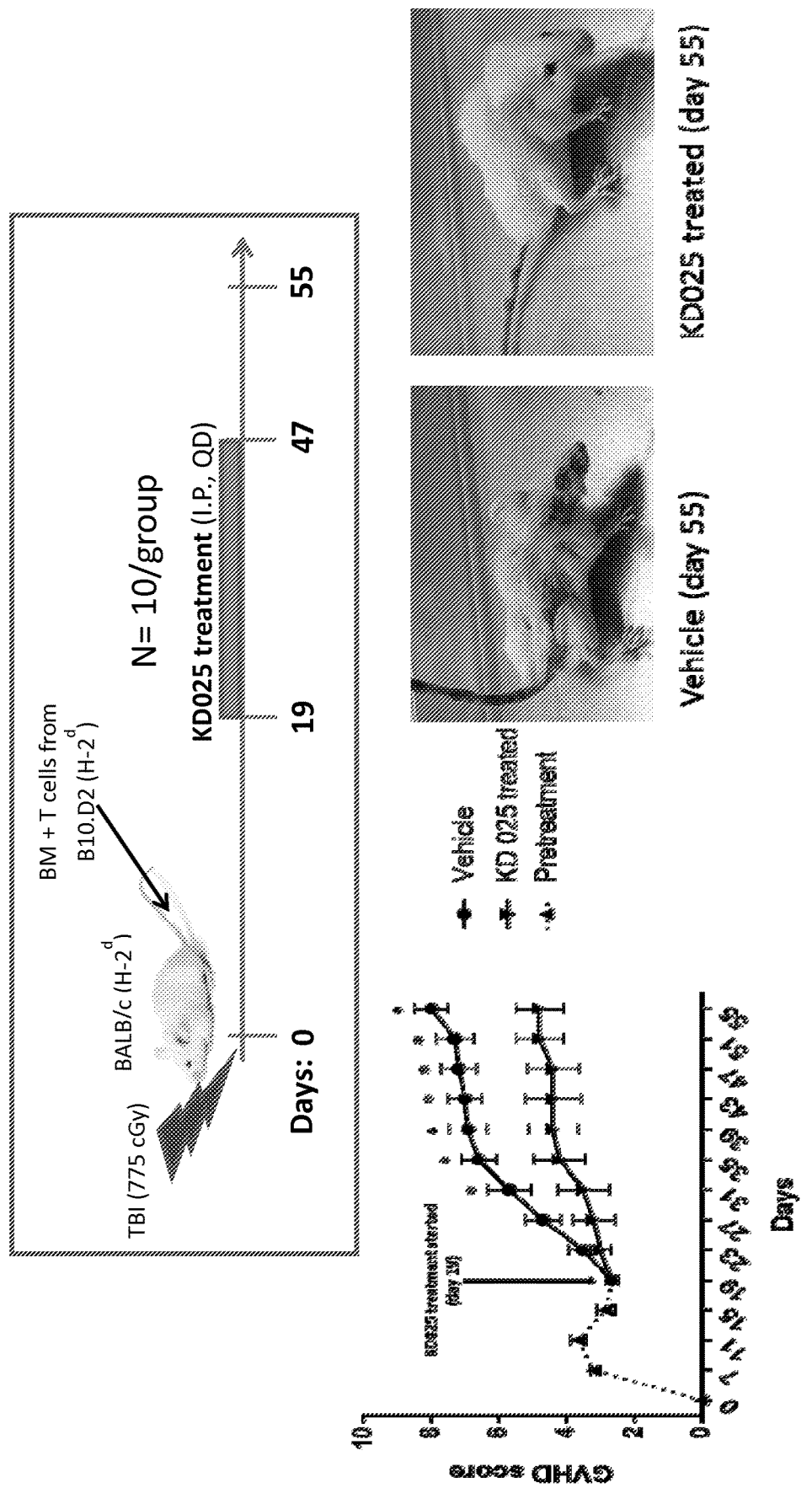
FIG. 31 shows that KD025 treatment blocks progression of sclerodermatous chronic GVHD in mice.
Figure 32:
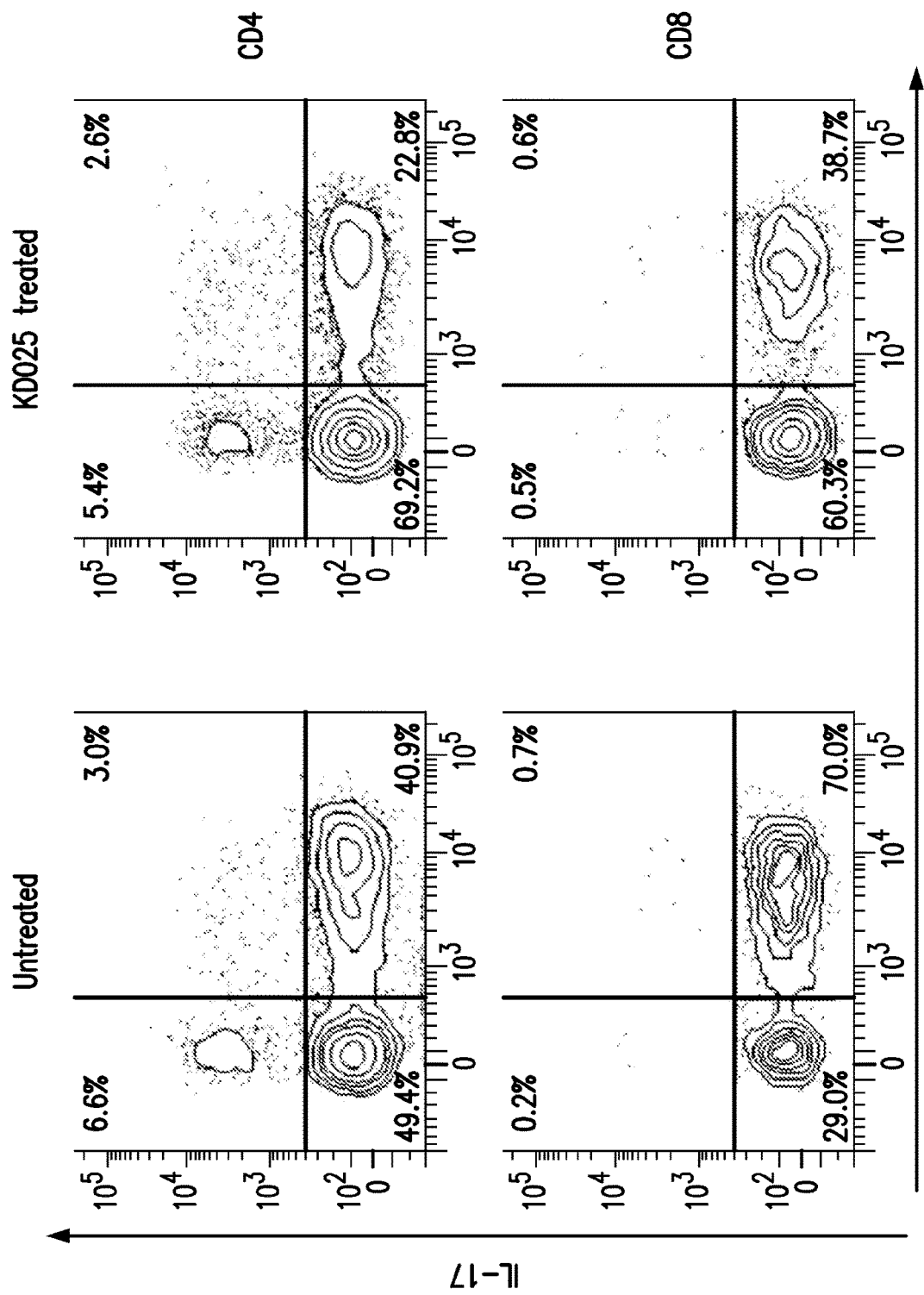
FIG. 32 shows decreased cervical LN T Cell IFNg in KD025 treated scleroderma mice.
Figure 33:
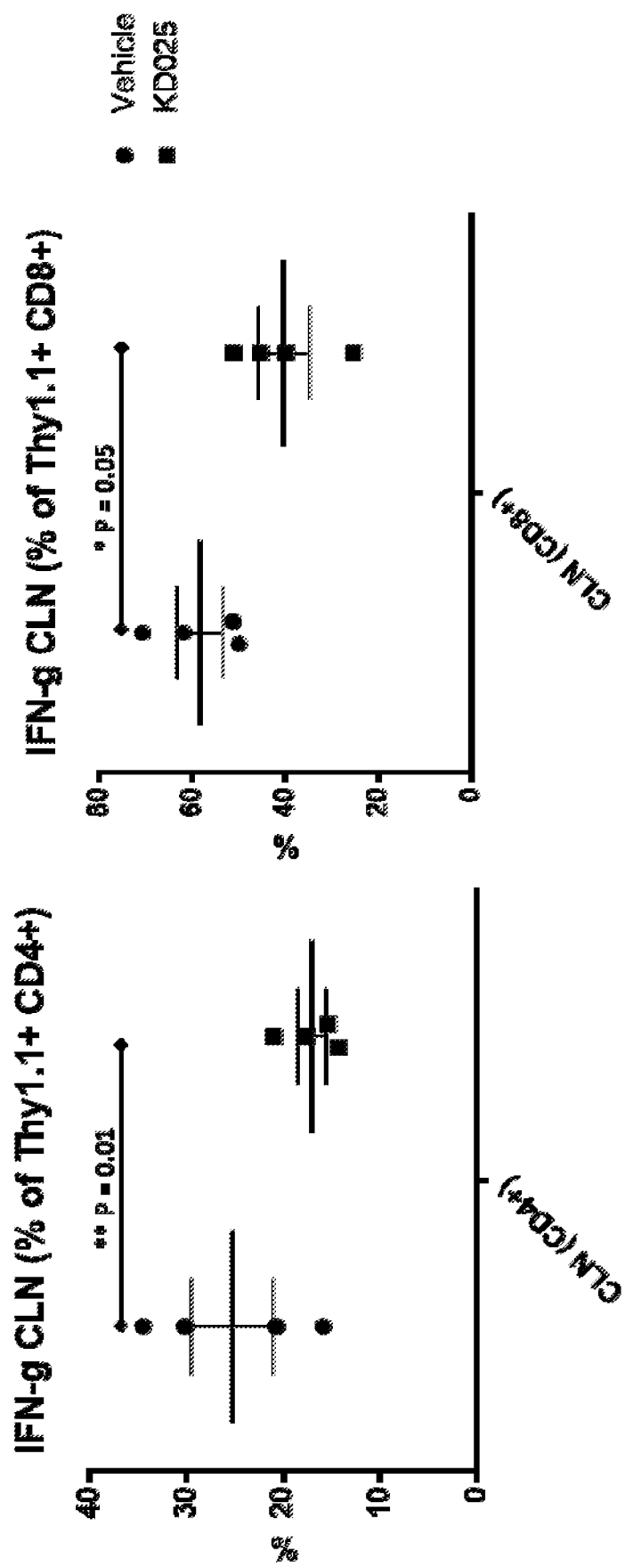
FIG. 33 shows IFNg in donor T Cells within the cervical lymph node (CLN) in KD025 treated scleroderma mice with chronic GVHD.
Figure 34:
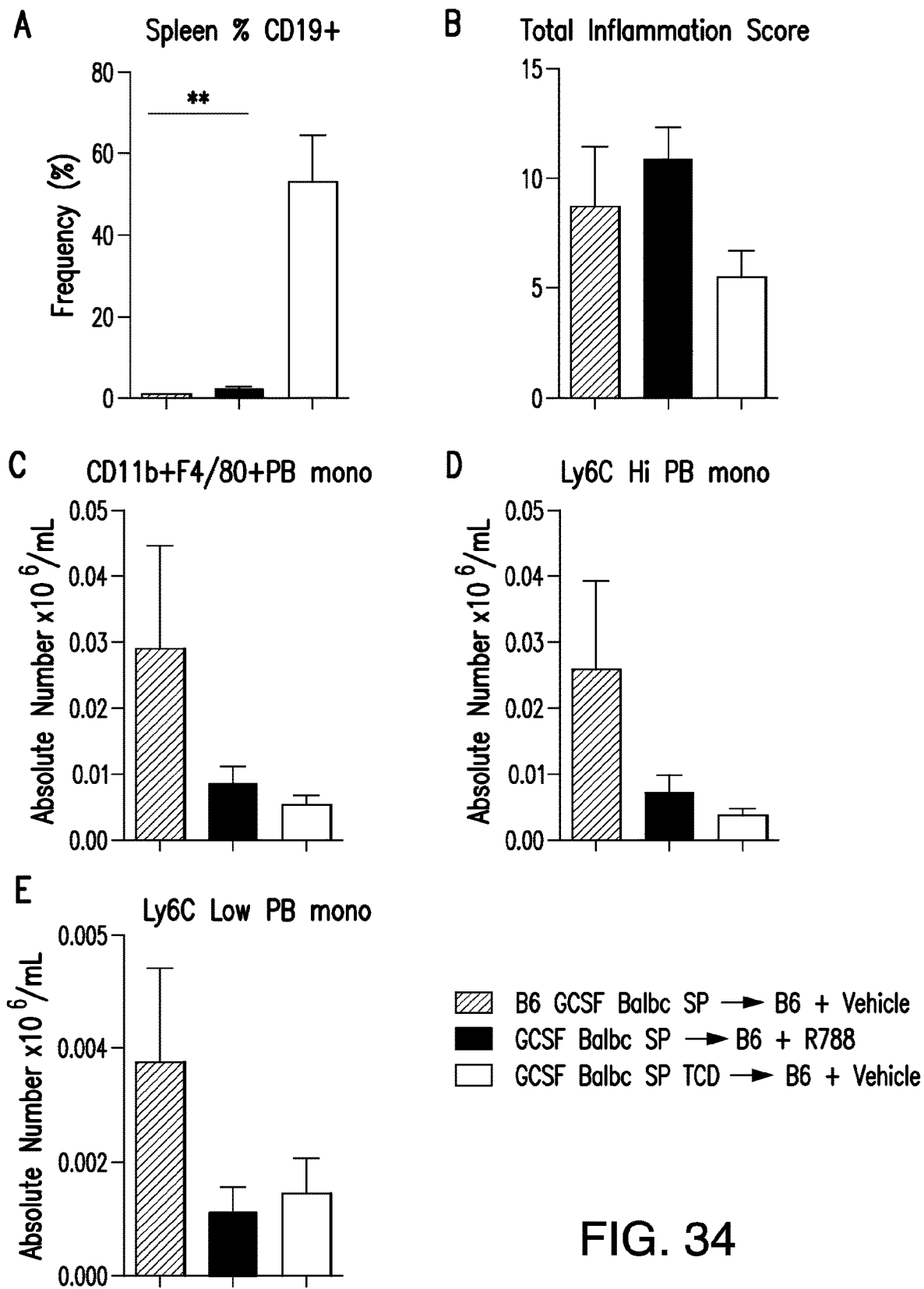
FIG. 34 shows the analysis of inflammation in KD025 treated scleroderma mice.
Figure 35:
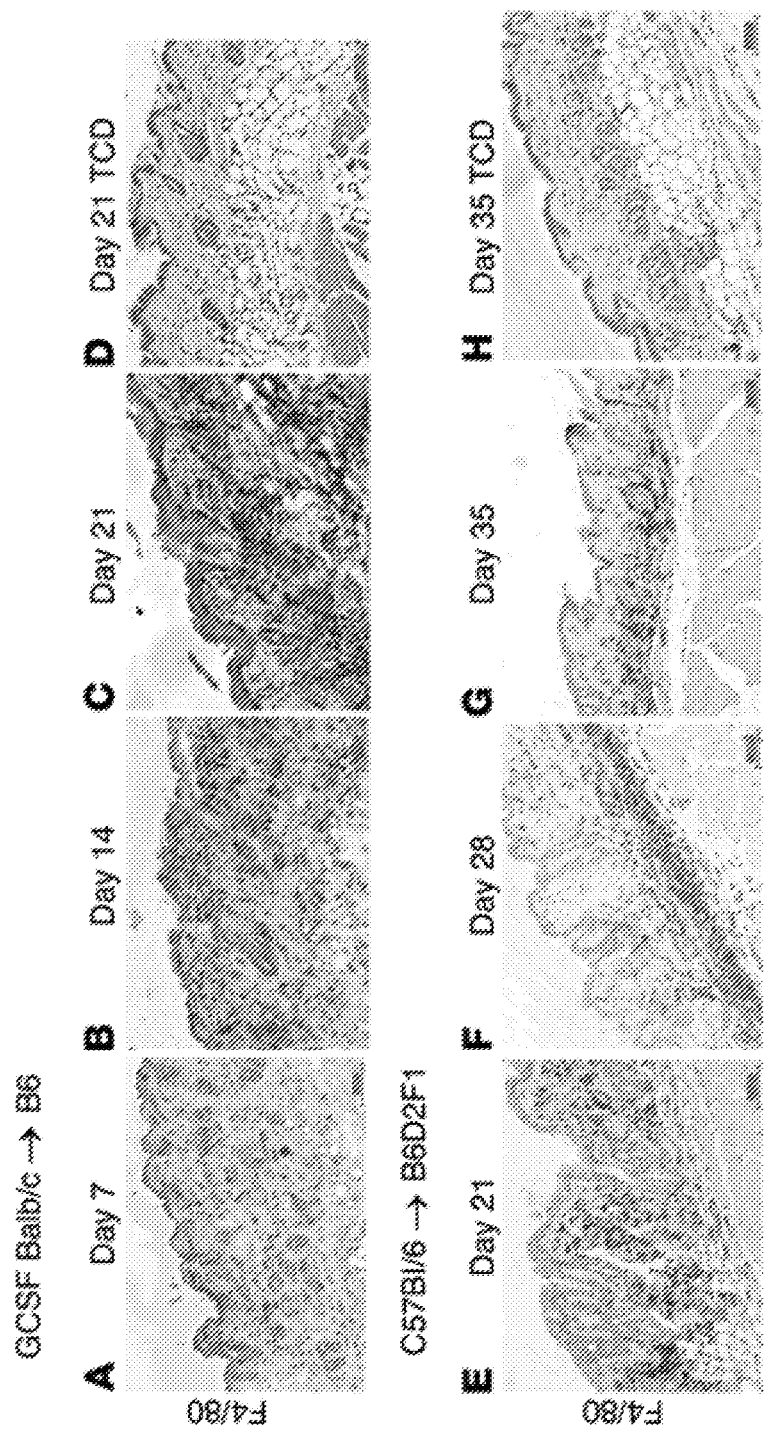
FIG. 35 shows macrophage infiltration and scleroderma in lethally irradiated recipients of G-CSF mobilized fully allogeneic splenocytes or non-mobilized semi-allogeneic splenocytes.

Therapeutic Administration of KD025 Blocks Progression of Sclerodermatous cGVHD in Mice To assess the efficacy of KD025 as a therapeutic intervention for cGVHD a well-characterized B10.D2 (H-2$^d$) into BALB/c (H-2d) MHC-matched, minor histocompatibility Ag-mismatched model was used that recapitulates the pathopsysiology of cGVHD, especially the sclerodermatous form of the disease. In this model, BALB/c (H-2$^d$) mice received 775 cGy of total body radiation on day 0 and were transplanted with bone marrow and T-cells from B10.D2 (H-2$^d$) mice. KD025 was administered intraperitoneally once daily from days 19-47. Compared to vehicle treated mice, KD025 treatment blocked the development of chronic sclerodermatous cGVHD and significantly decreased the GVHD score in this mouse model. The GVHD score in this model combined changes in weight lost, posture, activity, fur texture, and skin integrity (FIG. 26). Sclerodermatous cGVHD mice were further analyzed as depicted in FIGS. 27-35.

We claim:

1. A method of treating sclerodermatous chronic graft versus host disease in a subject in need thereof, which comprises administering to the subject an effective amount of a compound of Formula:

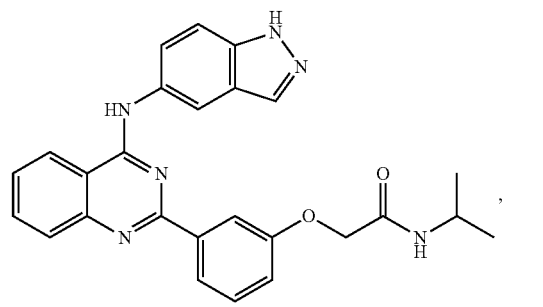

(SLx-2119)

or pharmaceutically acceptable salt thereof.

2. The method of claim 1, wherein the compound is administered to the subject with a second agent.

* * * * *